United States Patent
Schrimpf et al.

(10) Patent No.: US 7,598,236 B2
(45) Date of Patent: Oct. 6, 2009

(54) DIAZABICYCLIC CENTRAL NERVOUS SYSTEM ACTIVE AGENTS

(75) Inventors: Michael R. Schrimpf, Grayslake, IL (US); Karin R. Tietje, Mundelein, IL (US); Richard B. Toupence, West Milford, NJ (US); Jianguo Ji, Libertyville, IL (US); Anwer Basha, Lake Forest, IL (US); William H. Bunnelle, Mundelein, IL (US); Jerome F. Daanen, Racine, WI (US); Jennifer M. Frost, Grayslake, IL (US); Kevin B. Sippy, Antioch, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/957,424

(22) Filed: Dec. 15, 2007

(65) Prior Publication Data

US 2008/0097094 A1   Apr. 24, 2008

Related U.S. Application Data

(62) Division of application No. 10/810,999, filed on Mar. 26, 2004, now Pat. No. 7,319,106.

(51) Int. Cl.
| | |
|---|---|
| A61P 25/00 | (2006.01) |
| A61K 31/397 | (2006.01) |
| C07D 205/00 | (2006.01) |
| C07D 471/00 | (2006.01) |
| C07D 487/00 | (2006.01) |
| C07D 237/30 | (2006.01) |
| C07D 401/00 | (2006.01) |
| C07D 421/00 | (2006.01) |
| C07D 241/00 | (2006.01) |
| C07D 239/00 | (2006.01) |
| C07D 403/00 | (2006.01) |
| C07D 215/00 | (2006.01) |
| C07D 275/00 | (2006.01) |
| C07D 417/00 | (2006.01) |
| C07D 261/00 | (2006.01) |

(52) U.S. Cl. .................. 514/210.16; 514/300; 514/314; 514/338; 544/237; 544/238; 544/242; 544/316; 544/330; 544/334; 544/335; 544/336; 544/406; 544/407; 544/408; 544/409; 546/113; 546/114; 546/115; 546/116; 546/168; 546/169; 546/170; 546/171; 546/172; 546/175; 546/176; 546/268.1; 546/276.7; 548/213; 548/214; 548/243; 548/246; 548/247; 548/248; 548/453; 548/950; 548/953

(58) Field of Classification Search ............ 514/210.16; 546/113; 548/453, 950, 953
See application file for complete search history.

(56) References Cited

U.S. PATENT DOCUMENTS

| | | | |
|---|---|---|---|
| 5,071,999 A | 12/1991 | Schenke et al. | 548/453 |
| 5,382,584 A | 1/1995 | Balasubramanian | 514/254.02 |
| 5,472,958 A | 12/1995 | Gunn et al. | 514/210.01 |
| 5,478,939 A | 12/1995 | Trybulski et al. | 544/336 |
| 5,773,912 A | 6/1998 | Saeki et al. | 310/326 |
| 5,914,328 A | 6/1999 | Lin et al. | 514/252.03 |
| 5,948,793 A | 9/1999 | Abreo et al. | 514/318 |

FOREIGN PATENT DOCUMENTS

| | | |
|---|---|---|
| EP | 0 324 543 | 7/1989 |
| EP | 0 400 661 | 12/1990 |
| EP | 0 603 887 | 9/1994 |
| EP | 0 345 808 | 1/1995 |
| WO | 94/08922 | 4/1994 |
| WO | 95/23152 | 8/1995 |
| WO | 96/06093 | 2/1996 |
| WO | 96/31475 | 10/1996 |
| WO | 97/05139 | 2/1997 |
| WO | 97/17961 | 5/1997 |
| WO | 99/21834 | 5/1999 |
| WO | 99/32117 | 7/1999 |
| WO | 99/51602 | 10/1999 |
| WO | 00/34284 | 6/2000 |
| WO | 00/44755 | 8/2000 |
| WO | 00/66586 | 11/2000 |
| WO | 00/71534 | 11/2000 |
| WO | 01/44243 | 6/2001 |

OTHER PUBLICATIONS

Arneric et al., "Cholingeric channel modulators as a novel therapeutic strategy for alzheimer's disease," Exp. Opin. Invest. Drugs 5(1):79-100 (1996).

Arneric. et al., "Neuronal Nicotinic Acetylcholine Receptors," Psychopharmacology: The fourth Generation of Progress 95-109 (1995).

(Continued)

*Primary Examiner*—Brenda L Coleman
(74) *Attorney, Agent, or Firm*—Portia Chen; Antonia M. Holland

(57) ABSTRACT

Compounds of formula I

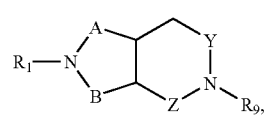

pharmaceutical compositions of these compounds, and use of said compositions to control synaptic transmission in mammals.

19 Claims, No Drawings

OTHER PUBLICATIONS

Barlocco et al., J. Med. Chem. 41:674-681 (1998).
Benowitz, et al., "Pharmacokinetics, metabolism, and pharmacodynamics of nicotine," Nicotine Psychopharmacology 112-157 (1990).
Berge, et al., "Pharmaceutical Salts," Journal of Pharmaceutical Sciences 66(1): 1-19 (1977).
Brehm et al., "Glycine antagonists, synthesis, structure. and biological effects of some bicyclic 5-isoxazolol zwitterions," J. Med. Chem. 269:224-229 (1986).
Chem Pharm Bull. 6:408-411 (1958).
Cherny. "Opioid Analgesics," Drug 51(5): 713-737 (1996).
Clayton, et al., "A total synthesis of (±)-Epibatidine." Tetrahedron Letters 36(46): 7493-7496 (1993).
Cope et al., "Syntheses of D-and L-2,6-diheterobicyclo [3.3.0]octanes." JACS 78:5916-5920 (1956).
Corey, et al., "A synthetic method for formyl-ehtynyl conversion (RCHO-RC=CH or CR)," Tetrahedron Letters 36:3769-3772 (1972).
Davidson, et al., "Cholinergic Agonists in alzheimer's Disease Patients," Current Research in Alzheimer Therapy 333-336 (1988).
Decker et al., "Therapeutic potential of Neuronal Nicotine Acetylcholine Receptor Agonists As Novel Analgesics." Biochemical Pharmacology 58:917-923 (1999).
Dormoy. "Syntheses Industrielle en serie ellipticine." Tetrahedron 49(14): 2885-2914 (1993).
Dray et al., "New pharmacological strategies for pain relief," Annu. Rev. Pharmacol. Toxicol 36:253-80 (1996).
Dray, et al.. Trends in Pharmacol. Sci. 15:190-197 (1994.
Ghelardini et al.. "Antinociceptive profile of the new nicotinic agonists DBO-83," Drug Development Research 40:251-258 (1997).
Gribble. et al.. "Regioselective ortho lithiation of halopyridines." Tetrahedron letters 21:4137-4140 (1980).
Hands, et al., "A convenient method for the preparation of 5-,6 and 7-azaindoles and their derivates," Synthesis 877-882 (1996).
IUPAC. Pure and Applied Chemistry 45:13-30, 1976.
Jacquet et al., Tetrahedron Letters 32(12): 1565-1568 (1991).
Knight et al., "6-Hydroxypiperidinecarboxylates: additions to the chiral pool from bakers' yeast reduction of beta-ketopiperidinecarboxylates," J. Chem. Soc. Perkins Trans. 1:3673-3683 (1998).
Korczyn, "Parkinson's Disease" Psychopharmacology: The Fourth Generation of Progress 126:1479-1484, 1995.
Lazar, et al.. "Saturated heterocycles. Part 172. Synthesis of 2,6-disubstituted-5,6,7,8-tetrahydropyrido[4.3-d]pyrimidine derivates." J. Heterocyclic Chem. 27:1885-1892 (1990).
Linstrom, "Nicotinic Acetylcholine Receptors in Health and disease," Molecular Neurobiology 15:193-222 (1997).
Lloyd et al, "The potential of subtype-selective neuronal nicotinic acetylcholine receptor agonists as therapeutics agents," Life Sciences 62(17/18): 1601-1606 (1998).
Numata, et al., "General synthetic method for naphthyridines and their n-oxides containing isoquinolinic nitrogen," Synthesis 2:306-311 (1999).
Organic Mass Spectrometry 19(9): 459-490 (1984).
Padwa, et al., Organic Synthesis 67:133-140 (1988).
Pebreza et al., Molecuar Pharmacology 39:9-12 (1990).
Poste et al. Methods in Cell Biology XIV: 33-71 (1976).
Reimschussel. et al., "Studies on new derivatives of caprolactam," Journal of Organic Chemistry 34(4): 959-963 (1969).
Ronn. et al., "Palladium(II)-Catalyzed Cyclization Using Molecual Oxygen as reoxidant," Tetrahedron Letters 36(42): 7749-7752 (1995).
Roth, et al, "Biochemical Pharmacology of Midbrain dopamine Neurons," Psychopharmacology: The Fourth Generation of Progress 227-243 (1995).
Salin-Pascual, et al., "Antidepressant effect of transdermal nicotine patches in nonsmoking patients with major depression," J. Clin. Psychiatry 57:387-389 (1996).
Sirisoma, et al., Alpha-Iodocyloalkenones: synthesis of (±)-Epibatidine.: Tetrahedron Letters 39:2059-2062 (1998).
Wagaw. et al., "The synthesis of aminopyridines: A method employing palladium-catalyzed carbon-nitrogen bond formation." J. Org. Chem. 61:7240-4241 (1996).
Williams et al, "Beyond the tobacco debate: dissecting out the therapeutic potential of nicotine," Exp. Opin. Invest Drugs 5(8): 1035-1045 (1996).
Williams. et al., J. Med. Chem. 42(9): 1481-1500 (1999).
Wittenberger, et al., "Dialkyltin Oxide mediated addition of trimethylsilyl azide to nitriles. A novel preparation of 5-substituted tetrazoles," J. Org. Chem. 58:4139-4141 (1993).

DIAZABICYCLIC CENTRAL NERVOUS SYSTEM ACTIVE AGENTS

CROSS-REFERENCE TO RELATED APPLICATIONS

This application is a divisional patent application of U.S. patent application Ser. No. 10/810,999, filed Mar. 26, 2006, which is a divisional application of U.S. patent application Ser. No. 09/833,914, filed Apr. 12, 2001 and issued as U.S. Pat. No. 6,809,105, which claims the benefit of U.S. Provisional Patent Application Ser. No. 60/200,111, filed on Apr. 27, 2000, now abandoned.

FIELD OF THE INVENTION

The present invention is directed to a series of N-substituted diazabicyclic compounds, a method for selectively controlling neurotransmitter release in mammals using these compounds, and pharmaceutical compositions including those compounds.

BACKGROUND OF THE INVENTION

Compounds that selectively control chemical synaptic transmission offer therapeutic utility in treating disorders that are associated with dysfunctions in synaptic transmission. This utility may arise from controlling either pre-synaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For example, a fuller explanation of chemical synaptic transmission Hoffman et al., "Neuro-transmission: The autonomic and somatic motor nervous systems." in Goodman and Gilman's. The Pharmacological Basis of Therapeutics. 9th ed., J. G. Hardman. L. E. Limbird, P. B. Molinoff. R. W. Ruddon, and A. Goodman Gilman, eds., Pergamon Press, New York. (1996), pp. 105-139).

Typically, chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See Goodman and Gilman's, The Pharmacological Basis of Therapeutics, op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition As indicated above, the two principal sites to which drug compounds that affect chemical synaptic transmission may be directed are the presynaptic membrane and the post-synaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system (CNS), postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. The more that is understood about chemical synaptic transmission in CNS disorders, the easier it would be to design drugs to treat such disorders.

Knowing how specific neurotransmitters act in the CNS allows one to predict the disorders that may be treatable with certain CNS active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons" Psychopharmacology: The Fourth Generation of Progress, F. E. Bloom and D. J. Kupfer. Eds. Raven Press, NY, 1995, pp 227-243). Patients with Parkinson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", Psychopharmacology: The Fourth Generation of Progress. op. cit., pp 1479-1484).

New and selective neurotransmitter controlling agents are still being sought, in the hope that one or more will be useful in important, but as yet poorly controlled, disease states or behavior models. For example, prior to the present invention dementia, such as is seen with Alzheimer's disease or Parkinsonism, remained largely untreatable. Symptoms of chronic alcoholism and nicotine withdrawal involve aspects of the central nervous system, as does the behavioral disorder Attention Deficit Disorder (ADD). Specific agents for treatment of these and related disorders are few in number or nonexistent.

A more complete discussion of the possible utility as CNS active agents of compounds with activity as cholinergic ligands selective for neuronal nicotinic receptors, (i.e., for controlling chemical synaptic transmission) may be found in U.S. Pat. No. 5,472,958 the disclosure of which is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in Nicotine Psychopharmacology, S. Wonnacott, M. A. H. Russell, & I. P. Stolerman, eds., Oxford University Press. Oxford, 1990, pp. 112-157; and M. Davidson, et al., in Current Research in Alzheimer Therapy, E. Giacobini and R. Becker, ed.; Taylor & Francis: New York, 1988; pp 333-336).

The use of cholinergic channel modulators to treat Parkinson's and Alzheimer's Diseases is described by M. Williams et al. "Beyond the Tobacco Debate: Dissecting Out the Therapeutic Potential of Nicotine", Exp. Opin. Invest. Drugs 5, pp. 1035-1045 (1996). Short-term improvement of nonsmoking patients suffering from depression by treatment with nicotine patches is described by R. J. Salin-Pascual et al., "Antidepressant Effect of Transdermal Nicotine Patches in Non-Smoking Patients with Major Depression", J. Clin. Psychiatry, v. 57 pp. 387-389 (1996).

WO 94/08922 describes pyridyl ether compounds which enhance cognitive function. U.S. patent application Ser. Nos. 08/474,873 and 08/485,537 describe certain substituted pyridyl ether compounds as well as other compounds which also act at the nicotinic acetylcholine receptor to stimulate or inhibit neurotransmitter release. WO 96/31475 describes certain 3-substituted pyridine derivatives which are described as being useful for a variety of disorders as modulators of acetylcholine receptors. While some of these references have alluded to pain control as a potential use of the compounds or analogs recited therein, the Applicants have discovered that compounds of formula I shown below have a surprising and unexpected analgesic effect.

In addition, cholinergic channel modulators may be useful in treating pain. The search for more potent and more effective pain controllers or analgesics continues to be a significant research goal in the medical community. A substantial number of medical disorders and conditions produce pain as part of the disorder or condition. Relief of this pain is a major aspect of ameliorating or treating the overall disease or condition. Pain and the possible alleviation thereof is also attributable to the individual patient's mental condition and physical condition. One pain reliever, or a class, may not be effective for a particular patient, or group of patients, which leads to a need for finding additional compounds or pharmaceuticals which are effective analgesics. Opioid and non-opioid drugs are the two major classes of analgesics (Dray, A. and Urban, L., Ann. Rev. Pharmacol. Toxicol., 36: 253-280, 1996). Opioids, such as morphine, act at opioid receptors in the brain to block transmission of the pain signals in the brain and spinal cord (Cherney, N. I. Drug, 51:713-737, 1996). Opioids such as morphine have abuse and addiction liability. Non-opioids such as non-steroid anti-inflammatory agents (NSAIDs) typically, but not exclusively, block the production of prostaglandins to prevent sensitization of nerve endings that facilitate the pain signal to the brain (Dray, et al, Trends in Pharmacol. Sci., 15: 190-197, 1994; Carty, T. J. and Marfat. A., "COX-2 Inhibitors. Potential for reducing NSAID side-effects in treating inflammatory diseases", Emerging Drugs: Prospect for Improved Medicines. (W. C. Bowman, J. D. Fitzgerald, and J. B. Taylor, eds.). Ashley Publications Ltd., London. Chap. 19., pp. 391411). Most of the commonly prescribed over-the-counter (OTC) NSAIDs are also commonly associated with at least one side effect or another, such as stomach ulceration or pain. For example, NSAIDs such as aspirin are also known to cause irritation and ulceration of the stomach and duodenum.

Certain compounds, with primary therapeutic indications other than analgesia, have been shown to be effective in some types of pain control. These are classified as analgesic adjuvants, and include tricyclic antidepressants (TCAs) and some anticonvulsants such as gabapentin (Williams et al., J. Med. Chem. (1999), 42, 1481-1500). The exact mechanism of action of these drugs is not fully understood, but they are used increasingly for treatment, especially for pain resulting from nerve injury due to trauma, radiation, or disease.

The compounds of the present invention are novel, have utility in treating pain and may also have utility in treating disorders and medical conditions listed herein. The compounds of the present invention may also have utility when administered in combination with an opioid such as morphine, a non-steroid anti-inflammatory agent such as aspirin, a tricyclic antidepressant, or an anticonvulsant such as gabapentin or pregabalin for treating disorders and medical conditions listed herein.

SUMMARY OF THE INVENTION

The present invention discloses N-substituted diazabicyclic compounds, a method for selectively controlling neurotransmitter release in mammals using these compounds, a method for controlling pain in mammals, and pharmaceutical compositions including those compounds. More particularly, the present invention is directed to compounds of formula I

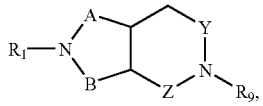

or pharmaceutically acceptable salts and prodrugs thereof, wherein

A is selected from the group consisting of a covalent bond, $CH_2$, $CH_2CH_2$, and $CH_2CH_2CH_2$;

B is selected from the group consisting of $CH_2$ and $CH_2CH_2$, provided that when A is $CH_2CH_2CH_2$, then B is $CH_2$;

Y is selected from the group consisting of a covalent bond, $CH_2$, and $CH_2CH_2$;

Z is selected from the group consisting of a covalent bond, $CH_2$, and $CH_2CH_2$, provided that when Y is $CH_2CH_2$, then Z is a covalent bond and further provided that when Z is $CH_2CH_2$, then Y is a covalent bond;

$R_1$ is selected from the group consisting of

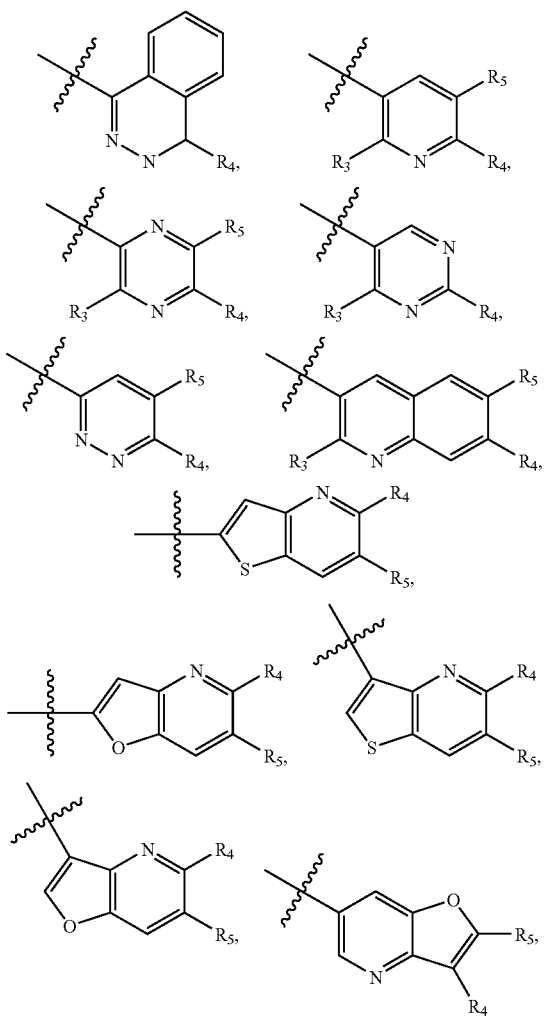

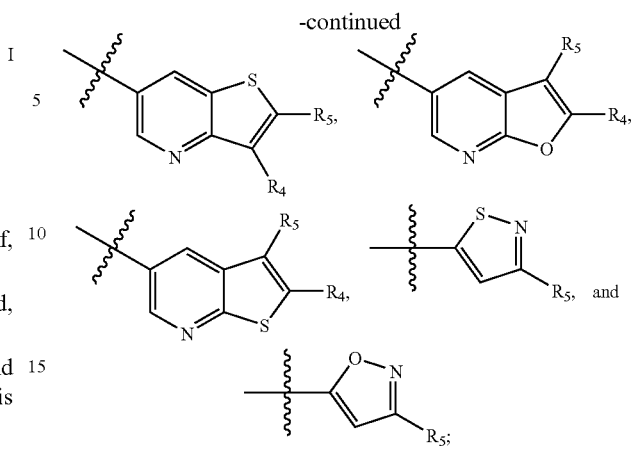

$R_3$ is selected from the group consisting of hydrogen, alkyl, and halogen;

$R_4$ is selected from the group consisting of hydrogen, alkoxy, alkyl, amino, halogen, and nitro;

$R_5$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, $-NR_6S(O)_2R_7$, $-C(NR_6)NR_7R_8$, $-CH_2C(NR_6)NR_7R_8$, $-C(NOR_6)R_7$, $-C(NCN)R_6$, $-C(NNR_6R_7)R_8$, $S(O)_2OR_6$, and $-S(O)_2R_6$;

$R_6$, $R_7$, and $R_8$ are independently selected from the group consisting of hydrogen and alkyl; and $R_9$ is selected from the group consisting of hydrogen, alkoxycarbonyl, alkyl, amino, aminoalkyl, aminocarbonylalkyl, benzyloxycarbonyl, cyanoalkyl, dihydro-3-pyridinylcarbonyl, hydroxy, hydroxyalkyl, and phenoxycarbonyl.

DETAILED DESCRIPTION OF THE INVENTION

In one embodiment of the present invention, compounds of formula I are disclosed wherein $R_1$ is selected from

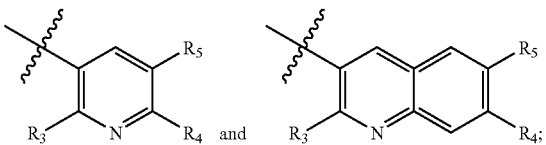

and A, B, Y, Z, $R_3$, $R_4$, $R_5$ and $R_9$ are as defined in formula I.

In another embodiment of the present invention, compounds of formula II are disclosed

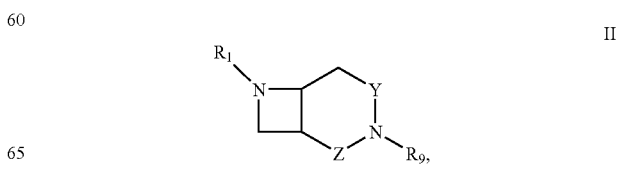

or pharmaceutically acceptable salts and prodrugs thereof wherein Y, Z, $R_1$ and $R_9$ are as defined in formula I.

In another embodiment, compounds of formula II are disclosed wherein Y is a covalent bond; Z is $CH_2$); and $R_1$ and $R_9$ are as defined in formula I.

In another embodiment, compounds of formula II are disclosed wherein Y is a covalent bond; Z is $CH_2$;

$R_1$ is

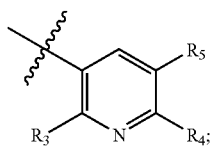

and $R_3$, $R_4$, $R_5$ and $R_9$ are as defined in formula I.

In another embodiment, compounds of formula II are disclosed wherein Y is $CH_2$; Z is a covalent bond; and $R_1$ and $R_9$ are as defined in formula I.

In another embodiment, compounds of formula II are disclosed wherein Y is $CH_2$; Z is a covalent bond;

$R_1$ is

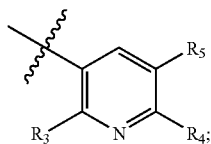

and $R_3$, $R_4$, $R_5$ and $R_9$ are as defined in formula I.

In another embodiment, compounds of formula II are disclosed wherein Y is $CH_2CH_2$; Z is a covalent bond; and $R_1$ and $R_9$ are as defined in formula I.

In another embodiment, compounds of formula II are disclosed wherein Y is $CH_2$; Z is $CH_2$; and $R_1$ and $R_9$ are as defined in formula I.

In another embodiment, compounds of formula II are disclosed wherein Y is a covalent bond; Z is $CH_2CH_2$; and $R_1$ and $R_9$ are as defined in formula I.

In another embodiment, compounds of formula II are disclosed wherein Y is a covalent bond; Z is $CH_2CH_2$;

$R_1$ is

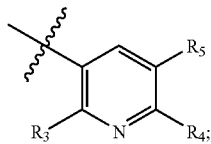

and $R_3$, $R_4$, $R_5$ and $R_9$ are as defined in formula I.

In another embodiment, compounds of formula II are disclosed wherein Y and Z are as defined in formula I; $R_9$ is selected from hydrogen and lower alkyl wherein hydrogen and methyl are preferred;

$R_1$ is

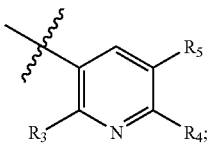

$R_3$ is selected from hydrogen or halogen; $R_4$ is selected from hydrogen, halogen, and lower alkyl; $R_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

Representative compounds of formula II include, but are not limited to:
(1R,5R)-6-(6-chloro-3-pyridinyl)-2,6-diazabicyclo[3.2.0]heptane;
(1R,5R)-6-(3-pyridinyl)-2,6-diazabicyclo[3.2.0]heptane;
(cis)-6-(3-pyridinyl)-3,6-diazabicyclo[3.2.0]heptane;
(cis)-6-(6-chloro-3-pyridinyl)-3,6-diazabicyclo[3.2.0]heptane;
(1R,5S)-6-(3-pyridinyl)-3,6-diazabicyclo[3.2.0]heptane;
(1R,5S)-6-(5-bromo-3-pyridinyl)-3,6-diazabicyclo[3.2.0]heptane;
(1S,5R)-6-(6-chloro-3-pyridinyl)-3,6-diazabicyclo[3.2.0]heptane;
(1S,5R)-6-(3-pyridinyl)-3,6-diazabicyclo[3.2.0]heptane;
(1R,5S)-6-(6-chloro-3-pyridinyl)-3,6-diazabicyclo[3.2.0]heptane;
(1S,5R)-6-(5-ethynyl-3-pyridinyl)-3,6-diazabicyclo[3.2.0]heptane;
(1S,5R)-6-(5-vinyl-3-pyridinyl)-3,6-diazabicyclo[3.2.0]heptane;
5-[(1S,5R)-3,6-diazabicyclo[3.2.0]hept-6-yl]nicotinonitrile;
(1S,5R)-6-(5-bromo-3-pyridinyl)-3,6-diazabicyclo[3.2.0]heptane;
(1S,5R)-6-(6-bromo-5-vinyl-3-pyridinyl)-3,6-diazabicyclo[3.2.0]heptane;
2-bromo-5-[(1R,5S)-3,6-diazabicyclo[3.2.0)]hept-6-yl]nicotinonitrile;
(1R,5S)-6-(5-ethynyl-3-pyridinyl)-3,6-diazabicyclo[3.2.0]heptane;
5-[(1R,5S)-3,6-diazabicyclo[3.2.0]hept-6-yl]nicotinonitrile;
(cis)-8-(3-pyridinyl)-3,8-diazabicyclo[4.2.0]octane;
(cis)-8-(6-chloro-3-pyridinyl)-3,8-diazabicyclo[4.2.0]octane;
(1S,6R) (cis)-8-(6-chloro-3-pyridinyl)-3,8-diazabicyclo[4.2.0]octane;
(−) (cis)-8-(6-chloro-3-pyridinyl)-3,8-diazabicyclo[4.2.0]octane;
5-[(1R,6S)-3,8-diazabicyclo[4.2.0]oct-8-yl]nicotinonitrile;
(1S,6R)-5-[3,8-diazabicyclo[4.2.0]oct-8-yl]nicotinonitrile;
(1R,5S)-6-(5,6-dichloro-3-pyridinyl)-3,6-diazabicyclo[3.2.0]heptane;
(1S,5R)-6-(5,6-dichloro-3-pyridinyl)-3,6-diazabicyclo[3.2.0]heptane;
(cis)-6-(5,6-dichloro-3-pyridinyl)-3,6-diazabicyclo[3.2.0]heptane;
(cis)-8-(5-methoxy-3-pyridinyl)-3,8-diazabicyclo[4.2.0]octane;
(1R,5S)-6-(5-methoxy-3-pyridinyl)-3,6-diazabicyclo[3.2.0]heptane;
(1S,5R)-6-(5-methoxy-3-pyridinyl)-3,6-diazabicyclo[3.2.0]heptane;

(cis)-6-(6-bromo-5-methoxy-3-pyridinyl)-3,6-diazabicyclo[3.2.0]heptane;
(1R,5S)-6-(6-chloro-5-methyl-3-pyridinyl)-3,6-diazabicyclo[3.2.0]heptane;
(1S,5R)-6-(6-chloro-5-methyl-3-pyridinyl)-3,6-diazabicyclo[3.2.0]heptane;
(1S,6R) (cis)-8-(5-methoxy-3-pyridinyl)-3,8-diazabicyclo[4.2.0]octane;
(1R,6S)-8-(5-methoxy-3-pyridinyl)-3,8-diazabicyclo[4.2.0]octane;
(cis)-8-(6-chloro-5-methyl-3-pyridinyl)-3,8-diazabicyclo[4.2.0]octane;
(1S,6R)-8-(6-chloro-5-methyl-3-pyridinyl)-3,8-diazabicyclo[4.2.0]octane;
(1R,6S)-8-(6-chloro-5-methyl-3-pyridinyl)-3,8-diazabicyclo[4.2.0]octane;
(1S,6R)-8-(3-pyridinyl)-3,8-diazabicyclo[4.2.0]octane;
(1R,6S)-8-(3-pyridinyl)-3,8-diazabicyclo[4.2.0]octane;
(cis)-8-(5,6-dichloro-3-pyridinyl)-3,8-diazabicyclo[4.2.0]octane
(1S,6R)-8-(5,6-dichloro-3-pyridinyl)-3,8-diazabicyclo[4.2.0]octane;
(1R,6S)-8-(5,6-dichloro-3-pyridinyl)-3,8-diazabicyclo[4.2.0]octane;
(cis)-6-(6-bromo-5-methoxy-3-pyridinyl)-3,6-diazabicyclo[3.2.0]heptane;
(1R,5S)-6-(6-bromo-5-methoxy-3-pyridinyl)-3,6-diazabicyclo[3.2.0]heptane;
(1S,5R)-6-(6-bromo-5-methoxy-3-pyridinyl)-3,6-diazabicyclo[3.2.0]heptane;
(cis)-6-(5-azido-3-pyridinyl)-3,6-diazabicyclo[3.2.0]heptane;
(1R,5S)-6-(5-azido-3-pyridinyl)-3,6-diazabicyclo[3.2.0]heptane; and
(1R,5S)-6-(5-azido-3-pyridinyl)-3,6-diazabicyclo[3.2.0]heptane.

The following additional compounds representative of formula II, may be prepared by one skilled in the art using known synthetic chemistry methodology or by using synthetic chemistry methodology described in the Schemes and Examples contained herein.

(cis)-6-(6-chloro-5-methyl-3-pyridinyl)-3,6-diazabicyclo[3.2.0]heptane;
(cis)-6-(6-chloro-5-fluoro-3-pyridinyl)-3,6-diazabicyclo[3.2.0]heptane;
(cis)-6-(5-fluoro-3-pyridinyl)-3,6-diazabicyclo[3.2.0]heptane;
(cis)-6-(6-methyl-3-pyridinyl)-3,6-diazabicyclo[3.2.0]heptane;
(cis)-6-(furo[3,2-b]pyridin-6-yl)-3,6-diazabicyclo[3.2.0]heptane;
(cis)-8-(6-chloro-5-fluoro-3-pyridinyl)-3,8-diazabicyclo[4.2.0]octane;
(cis)-8-(5-fluoro-3-pyridinyl)-3,8-diazabicyclo[4.2.0]octane;
(cis)-8-(6-methyl-3-pyridinyl)-3,8-diazabicyclo[4.2.0]octane;
(cis)-8-(furo[3,2-b]pyridin-6-yl)-3,8-diazabicyclo[4.2.0]octane;
(cis)-7-(3-pyridinyl)-3,7-diazabicyclo[4.2.0]octane;
(cis)-7-(6-chloro-3-pyridinyl)-3,7-diazabicyclo[4.2.0]octane;
(cis)-7-(5,6-dichloro-3-pyridinyl)-3,7-diazabicyclo[4.2.0]octane;
(cis)-7-(6-chloro-5-methyl-3-pyridinyl)-3,7-diazabicyclo[4.2.0]octane;
(cis)-7-(6-chloro-5-fluoro-3-pyridinyl)-3,7-diazabicyclo[4.2.0]octane;
(cis)-7-(5-fluoro-3-pyridinyl)-3,7-diazabicyclo[4.2.0]octane;
(cis)-7-(6-methyl-3-pyridinyl)-3,7-diazabicyclo[4.2.0]octane; and
(cis)-7-(furo[3,2-b]pyridin-6-yl)-3,7-diazabicyclo[4.2.0]octane.

In another embodiment of the present invention, compounds of formula III are disclosed

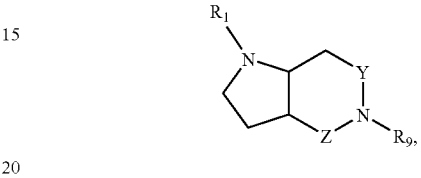

or pharmaceutically acceptable salts and prodrugs thereof wherein Y, Z, $R_1$ and $R_9$ are as defined in formula I.

In another embodiment of the present invention compounds of formula III are disclosed wherein Y is a covalent bond; Z is a covalent bond; and $R_1$ and $R_9$ are as defined in formula I.

In another embodiment of the present invention, compounds of formula III are disclosed wherein Y is a covalent bond; Z is a covalent bond;

$R_1$ is

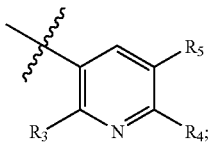

and $R_3$, $R_4$, $R_5$ and $R_9$ are as defined in formula I.

In another embodiment of the present invention, compounds of formula III are disclosed wherein Y is $CH_2$; Z is a covalent bond; and $R_1$ and $R_9$ are as defined in formula I.

In another embodiment of the present invention, compounds of formula III are disclosed wherein Y is a covalent bond; Z is $CH_2$; and $R_1$ and $R_9$ are as defined in formula I.

In another embodiment of the present invention, compounds of formula III are disclosed wherein Y is a covalent bond; Z is $CH_2$;

$R_1$ is

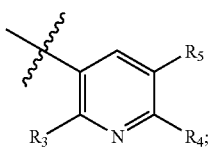

and $R_3$, $R_4$, $R_5$ and $R_9$ are as defined in formula I.

In another embodiment of the present invention, compounds of formula III are disclosed wherein Y is $CH_2CH_2$; Z is a covalent bond; and $R_1$ and $R_9$ are as defined in formula I.

In another embodiment of the present invention, compounds of formula III are disclosed wherein Y is $CH_2$; Z is $CH_2$; and $R_1$ and $R_9$ are as defined in formula I.

In another embodiment of the present invention, compounds of formula III are disclosed wherein Y is a covalent bond; Z is $CH_2CH_2$; and $R_1$ and $R_9$ are as defined in formula I.

In another embodiment of the present invention, compounds of formula III are disclosed wherein Y and Z are as defined in formula I; $R_9$ is selected from hydrogen and lower alkyl wherein hydrogen and methyl are preferred; $R_1$ is

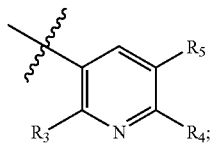

$R_3$ is selected from hydrogen or halogen; $R_4$ is selected from hydrogen, halogen, and lower alkyl; $R_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

Representative compounds of formula III include, but are not limited to:

(1R,5R)-2-(3-pyridinyl)-2,6-diazabicyclo[3.2.0]heptane;
(cis)-1-(6-chloro-3-pyridinyl)octahydropyrrolo[3,4-b]pyrrole;
(cis)-1-(6-chloro-3-pyridinyl)-5-methyloctahydropyrrolo[3,4-b]pyrrole;
(3aR,6aR)-1-(6-chloro-3-pyridinyl)octahydropyrrolo[3,4-b]pyrrole;
(3aR,6aR)-1-(3-pyridinyl)octahydropyrrolo[3,4-b]pyrrole;
(3aS,6aS)-1-(6-chloro-3-pyridinyl)octahydropyrrolo[3,4-b]pyrrole;
(3aS,6aS)-1-(3-pyridinyl)octahydropyrrolo[3,4-b]pyrrole;
5-((3aR,6aR)-hexahydropyrrolo[3,4-b]pyrrol-1(2H)-yl)nicotinonitrile;
(3aS,6aS)-1-(5-hydroxy-3-pyridinyl)octahydropyrrolo[3,4-b]pyrrole; and
5-((3aS,6aS)-hexahydropyrrolo[3,4-b]pyrrol-1(2H)-yl)nicotinonitrile.

The following additional compounds, representative of formula III, may be prepared by one skilled in the art using known synthetic chemistry methodology or by using synthetic chemistry methodology described in the Schemes and Examples contained herein.

(cis)-1-(5,6-dichloro-3-pyridinyl)octahydropyrrolo[3,4-b]pyrrole;
(cis)-1-(6-chloro-5-methyl-3-pyridinyl)octahydropyrrolo[3,4-b]pyrrole;
(cis)-1-(6-chloro-5-fluoro-3-pyridinyl)octahydropyrrolo[3,4-b]pyrrole;
(cis)-1-(5-fluoro-3-pyridinyl)octahydropyrrolo[3,4-b]pyrrole;
(cis)-1-(6-methyl-3-pyridinyl)octahydropyrrolo[3,4-b]pyrrole; and
(cis)-1-(furo[3,2-b]pyridin-6-yl)octahydropyrrolo[3,4-b]pyrrole.

In another embodiment of the present invention, compounds of formula IV are disclosed

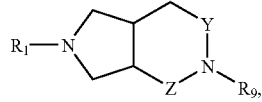

or pharmaceutically acceptable salts and prodrugs thereof wherein Y, Z, $R_1$ and $R_9$ are as defined in formula I.

In another embodiment of the present invention, compounds of formula IV are disclosed wherein Y is a covalent bond; Z is a covalent bond; and $R_1$ and $R_9$ are as defined in formula I.

In another embodiment of the present invention, compounds of formula IV are disclosed wherein Y is a covalent bond; Z is a covalent bond;

$R_1$ is

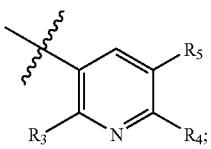

and $R_3$, $R_4$, $R_5$ and $R_9$ are as defined in formula I.

In another embodiment of the present invention, compounds of formula IV are disclosed wherein Y is $CH_2$; Z is a covalent bond; and $R_1$ and $R_9$ are as defined in formula I.

In another embodiment of the present invention, compounds of formula IV are disclosed wherein Y is $CH_2$; Z is a covalent bond;

$R_1$ is

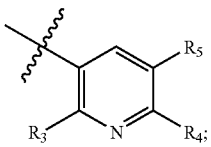

and $R_3$, $R_4$, $R_5$ and $R_9$ are as defined in formula I.

In another embodiment of the present invention, compounds of formula IV are disclosed wherein Y is a covalent bond; Z is $CH_2$; and $R_1$ and $R_9$ are as defined in formula I.

In another embodiment of the present invention, compounds of formula IV are disclosed wherein Y is a covalent bond; Z is $CH_2$;

$R_1$ is selected from

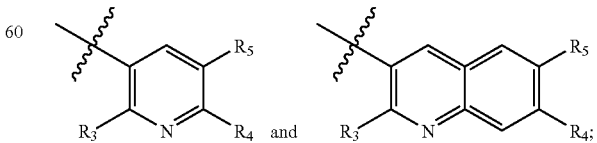

and $R_3$, $R_4$, $R_5$ and $R_9$ are as defined in formula I.

In another embodiment of the present invention, compounds of formula IV are disclosed wherein Y is CH$_2$CH$_2$; Z is a covalent bond; and R$_1$ and R$_9$ are as defined in formula I.

In another embodiment of the present invention, compounds of formula IV are disclosed wherein Y is CH$_2$CH$_2$; Z is a covalent bond:

R$_1$ is

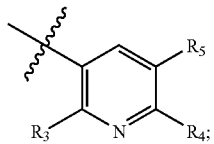

and R$_3$, R$_4$, R$_5$ and R$_9$ are as defined in formula I.

In another embodiment of the present invention, compounds of formula IV are disclosed wherein Y is CH$_2$; Z is CH$_2$; and R$_1$ and R$_9$ are as defined in formula I.

In another embodiment of the present invention, compounds of formula IV are disclosed wherein Y and Z are as defined in formula I; R$_9$ is selected from hydrogen and lower alkyl wherein hydrogen and methyl are preferred; R$_1$ is

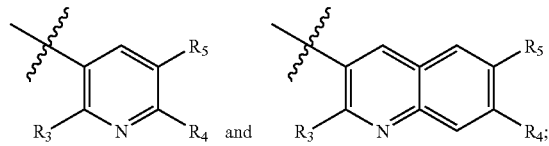

R$_3$ is selected from hydrogen or halogen; R$_4$ is selected from hydrogen, halogen, and lower alkyl; R$_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

Representative compounds of formula IV include, but are not limited to:
(cis)-5-(6-chloro-3-pyridinyl)octahydropyrrolo[3,4-b]pyrrole;
(3aR,6aR)-5-(6-chloro-3-pyridinyl)octahydropyrrolo[3,4-b]pyrrole;
(3aS,6aS)-5-(6-chloro-3-pyridinyl)octahydropyrrolo[3,4-b]pyrrole;
(3aR,6aR)-5-(5,6-dichloro-3-pyridinyl)octahydropyrrolo[3,4-b]pyrrole;
(3aS,6aS)-5-(5,6-dichloro-3-pyridinyl)octahydropyrrolo[3,4-b]pyrrole;
(3aS,6aS)-5-(6-chloro-5-methyl-3-pyridinyl)octahydropyrrolo[3,4-b]pyrrole;
(3aR,6aR)-5-(6-chloro-5-methyl-3-pyridinyl)octahydropyrrolo[3,4-b]pyrrole;
(3aR,6aR)-5-(3-pyridinyl)octahydropyrrolo[3,4-b]pyrrole;
(3aR,6aR)-5-(5-methoxy-3-pyridinyl)octahydropyrrolo[3,4-b]pyrrole;
(3aS,6aS)-5-(3-pyridinyl)octahydropyrrolo[3,4-b]pyrrole;
(3aS,6aS)-5-(5-bromo-3-pyridinyl)octahydropyrrolo[3,4-b]pyrrole;
(3aS,6aS)-5-(5-methoxy-3-pyridinyl)octahydropyrrolo[3,4-b]pyrrole;
(cis)-2-(3-pyridinyl)octahydropyrrolo[3,4-c]pyrrole;
(cis)-2-methyl-5-(3-pyridinyl)octahydropyrrolo[3,4-c]pyrrole;
(cis)-2-(6-chloro-3-pyridinyl)octahydropyrrolo[3,4-c]pyrrole;
(cis)-2-(6-chloro-3-pyridinyl)-5-methyloctahydropyrrolo[3,4-c]pyrrole;
(cis)-2-(3-quinolinyl)octahydropyrrolo[3,4-c]pyrrole;
(cis)-2-(5-hydroxy-3-pyridinyl)octahydropyrrolo[3,4-c]pyrrole;
(cis)-2-(5-methoxy-3-pyridinyl)octahydropyrrolo[3,4-c]pyrrole;
(cis)-2-(5-ethoxy-3-pyridinyl)octahydropyrrolo[3,4-c]pyrrole;
(cis)-2-(5-propoxy-3-pyridinyl)octahydropyrrolo[3,4-c]pyrrole;
(cis)-2-(6-chloro-5-methoxy-3-pyridinyl)octahydropyrrolo[3,4-c]pyrrole;
(cis)-2-(6-chloro-5-methyl-3-pyridinyl)octahydropyrrolo[3,4-c]pyrrole;
(cis)-2-[5-(2,2,2-trifluoroethoxy)-3-pyridinyl]octahydropyrrolo[3,4-c]pyrrole;
(cis)-6-(6-chloro-3-pyridinyl)octahydro-1H-pyrrolo[3,4-b]pyridine;
(cis)-6-(3-pyridinyl)octahydro-1H-pyrrolo[3,4-b]pyridine;
(cis)-3-(3-pyridinyl)-3,6-diazabicyclo[3.2.0]heptane;
(cis)-3-(6-chloro-3-pyridinyl)-3,6-diazabicyclo[3.2.0]heptane;
5-[(1R,5R)-3,6-diazabicyclo[3.2.0]hept-3-yl]nicotinonitrile;
(1R,5R)-3-(6-chloro-3-pyridinyl)-3,6-diazabicyclo[3.2.0]heptane;
(3aR,6aR)-5-(5-pyridinyl-3-pyridinyl)octahydropyrrolo[3,4-b]pyrrole;
(3aR,6aR)-5-(5-bromo-3-pyridinyl)octahydropyrrolo[3,4-b]pyrrole;
5-((3aR,6aR)-hexahydropyrrolo[3,4-b]pyrrol-5(1H)-yl)nicotinonitrile;
(3aR,6aR)-5-(6-bromo-5-methoxy-3-pyridinyl)octahydropyrrolo[3,4-b]pyrrole;
5-((3aR,6aR)-hexahydropyrrolo[3,4-b]pyrrol-5(1H)-yl)-2-bromonicotinonitrile;
(3aR,6aR)-5-(5-vinyl-3-pyridinyl)octahydropyrrolo[3,4-b]pyrrole;
(3aR,6aR)-5-(5-methyl-3-pyridinyl)octahydropyrrolo[3,4-b]pyrrole;
(3aR,6aR)-5-(6-bromo-5-chloro-3-pyridinyl)octahydropyrrolo[3,4-b]pyrrole;
(3aR,6aR)-5-(6-bromo-5-methyl-3-pyridinyl)octahydropyrrolo[3,4-b]pyrrole;
(3aR,6aR)-5-(5-ethyl-3-pyridinyl)octahydropyrrolo[3,4-b]pyrrole;
[5-((3aR,6aR)-hexahydropyrrolo[3,4-b]pyrrol-5(1H)-yl)-2-bromo-3-pyridinyl]methanol;
(3aR,6aR)-5-(6-bromo-5-vinyl-3-pyridinyl)octahydropyrrolo[3,4-b]pyrrole;
[5-((3aR,6aR)-hexahydropyrrolo[3,4-b]pyrrol-5(1H)-yl)-2-bromo-3-pyridinyl]acetonitrile; and
(3aR,6aR)-5-[6-bromo-5-(methoxymethyl)-3-pyridinyl]octahydropyrrolo[3,4-b]pyrrole.

The following additional compounds, representative of formula IV, may be prepared by one skilled in the art using known synthetic chemistry methodology or by using synthetic chemistry methodology described in the Schemes and Examples contained herein.
(cis)-3-(5,6-dichloro-3-pyridinyl)-3,6-diazabicyclo[3.2.0]heptane;
(cis)-3-(6-chloro-5-methyl-3-pyridinyl)-3,6-diazabicyclo[3.2.0]heptane;
(cis)-3-(6-chloro-5-fluoro-3-pyridinyl)-3,6-diazabicyclo[3.2.0]heptane;

(cis)-3-(5-fluoro-3-pyridinyl)-3,6-diazabicyclo[3.2.0]heptane;

(cis)-3-(6-methyl-3-pyridinyl)-3,6-diazabicyclo[3.2.0]heptane;

(cis)-3-(furo[3,2-b]pyridin-6-yl)-3,6-diazabicyclo[3.2.0]heptane;

(cis)-2-(5,6-dichloro-3-pyridinyl)octahydropyrrolo[3,4-c]pyrrole;

(cis)-2-(6-dichloro-5-fluoro-3-pyridinyl)octahydropyrrolo[3,4-c]pyrrole;

(cis)-2-(5-fluoro-3-pyridinyl)octahydropyrrolo[3,4-c]pyrrole;

(cis)-2-(6-methyl-3-pyridinyl)octahydropyrrolo[3,4-c]pyrrole;

(cis)-2-(furo[3,2-b]pyridin-6-yl)octahydropyrrolo[3,4-c]pyrrole;

(cis)-5-(6-chloro-5-fluoro-3-pyridinyl)octahydropyrrolo[3,4-b]pyrrole;

(cis)-5-(-5-fluoro-3-pyridinyl)octahydropyrrolo[3,4-b]pyrrole;

(cis)-5-(6-methyl-3-pyridinyl)octahydropyrrolo[3,4-b]pyrrole; and (cis)-5-(furo[3,2-b]pyridin-6-yl)octahydropyrrolo[3,4-b]pyrrole.

In another embodiment of the present invention, compounds of formula V are disclosed

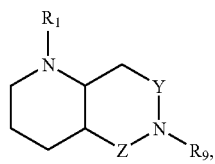

V or pharmaceutically acceptable salts and prodrugs thereof wherein Y, Z, $R_1$ and $R_9$ are as defined in formula I.

In another embodiment of the present invention, compounds of formula V are disclosed wherein Y is a covalent bond; Z is a covalent bond; and $R_1$ and $R_9$ are as defined in formula I.

In another embodiment of the present invention, compounds of formula V are disclosed wherein Y is $CH_2$; Z is a covalent bond; and $R_1$ and $R_9$ are as defined in formula I.

In another embodiment of the present invention, compounds of formula V are disclosed wherein Y is a covalent bond; Z is $CH_2$; and $R_1$ and $R_9$ are as defined in formula I.

In another embodiment of the present invention, compounds of formula V are disclosed wherein Y is $CH_2CH_2$; Z is a covalent bond; and $R_1$ and $R_9$ are as defined in formula I.

In another embodiment of the present invention, compounds of formula V are disclosed wherein Y is $CH_2$; Z is $CH_2$; and $R_1$ and $R_9$ are as defined in formula I.

In another embodiment of the present invention, compounds of formula V are disclosed wherein Y is a covalent bond; Z is $CH_2C_2$; and $R_1$ and $R_9$ are as defined in formula I.

In another embodiment of the present invention, compounds of formula V are disclosed wherein Y and Z are as defined in formula I; $R_9$ is selected from hydrogen and lower alkyl wherein hydrogen and methyl are preferred; $R_1$ is

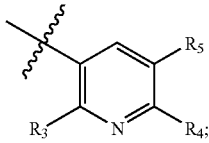

$R_3$ is selected from hydrogen or halogen; $R_4$ is selected from hydrogen, halogen, and lower alkyl; $R_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

The following compounds, representative of formula V, may be prepared by one skilled in the art using known synthetic chemistry methodology or by using synthetic chemistry methodology described in the Schemes and Examples contained herein.

(cis)-1-(3-pyridinyl)octahydro-1H-pyrrolo[3,4-b]pyridine;
(cis)-1-(6-chloro-3-pyridinyl)octahydro-1H-pyrrolo[3,4-b]pyridine;
(cis)-1-(5,6-dichloro-3-pyridinyl)octahydro-1H-pyrrolo[3,4-b]pyridine;
(cis)-1-(6-chloro-5-methyl-3-pyridinyl)octahydro-1H-pyrrolo[3,4-b]pyridine;
(cis)-1-(6-chloro-5-fluoro-3-pyridinyl)octahydro-1H-pyrrolo[3,4-b]pyridine;
(cis)-1-(5-fluoro-3-pyridinyl)octahydro-1H-pyrrolo[3,4-b]pyridine;
(cis)-1-(6-methyl-3-pyridinyl)octahydro-1H-pyrrolo[3,4-b]pyridine;
(cis)-1-(furo[3,2-b]pyridin-6-yl)octahydro-1H-pyrrolo[3,4-b]pyridine;
(cis)-4-(3-pyridinyl)octahydro-1H-pyrrolo[3,2-b]pyridine;
(cis)-4-(6-chloro-3-pyridinyl)octahydro-1H-pyrrolo[3,2-b]pyridine;
(cis)-4-(5,6-dichloro-3-pyridinyl)octahydro-1H-pyrrolo[3,2-b]pyridine;
(cis)-4-(6-chloro-5-methyl-3-pyridinyl)octahydro-1H-pyrrolo[3,2-b]pyridine;
(cis)-4-(6-chloro-5-fluoro-3-pyridinyl)octahydro-1H-pyrrolo[3,2-b]pyridine;
(cis)-4-(5-fluoro-3-pyridinyl)octahydro-1H-pyrrolo[3,2-b]pyridine;
(cis)-4-(6-methyl-3-pyridinyl)octahydro-1H-pyrrolo[3,2-b]pyridine; and
(cis)-4-(furo[3,2-b]pyridin-6-yl)octahydro-1H-pyrrolo[3,2-b]pyridine.

In another embodiment of the present invention, compounds of formula VI are disclosed

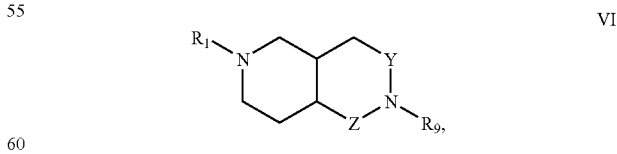

VI or pharmaceutically acceptable salts and prodrugs thereof wherein Y, Z, $R_1$ and $R_9$ are as defined in formula I.

In another embodiment of the present invention, compounds of formula VI are disclosed wherein Y is a covalent bond; Z is a covalent bond; and $R_1$ and $R_9$ are as defined in formula I.

In another embodiment of the present invention, compounds of formula VI are disclosed wherein Y is $CH_2$; Z is a covalent bond; and $R_1$ and $R_9$ are as defined in formula I.

In another embodiment of the present invention, compounds of formula VI are disclosed wherein Y is a covalent bond; Z is $CH_2$; and $R_1$ and $R_9$ are as defined in formula I.

In another embodiment of the present invention, compounds of formula VI are disclosed wherein Y is $CH_2CH_2$; Z is a covalent bond, and $R_1$ and $R_9$ are as defined in formula I.

In another embodiment of the present invention, compounds of formula VI are disclosed wherein Y is $CH_2$; Z is $CH_2$; and $R_1$ and $R_9$ are as defined in formula I.

In another embodiment of the present invention, compounds of formula VI are disclosed wherein Y is a covalent bond; Z is $CH_2CH_2$; and $R_1$ and $R_9$ are as defined in formula I.

In another embodiment of the present invention, compounds of formula VI are disclosed wherein Y and Z are as defined in formula I; $R_9$ is selected from hydrogen and lower alkyl wherein hydrogen and methyl are preferred; $R_1$ is

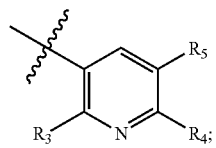

$R_3$ is selected from hydrogen or halogen; $R_4$ is selected from hydrogen, halogen, and lower alkyl; $R_5$ is selected from hydrogen, cyano, cyanoalkyl, haloalkoxy haloalkyl, halogen, hydroxy, hydroxyalkyl, lower alkenyl, lower alkoxyalkyl, lower alkoxy, lower alkyl, lower alkynyl, and nitro.

The following compounds, representative of formula VI, may be prepared by one skilled in the art using known synthetic chemistry methodology or by using synthetic chemistry methodology described in the Schemes and Examples contained herein.

(cis)-5-(3-pyridinyl)octahydro-1H-pyrrolo[3,2-c]pyridine;
(cis)-5-(6-chloro-3-pyridinyl)octahydro-1H-pyrrolo[3,2-c]pyridine;
(cis)-5-(5,6-dichloro-3-pyridinyl)octahydro-1H-pyrrolo[3,2-c]pyridine;
(cis)-5-(6-chloro-5-methyl-3-pyridinyl)octahydro-1H-pyrrolo[3,2-c]pyridine;
(cis)-5-(6-chloro-5-fluoro-3-pyridinyl)octahydro-1H-pyrrolo[3,2-c]pyridine;
(cis)-5-(5-fluoro-3-pyridinyl)octahydro-1H-pyrrolo[3,2-c]pyridine;
(cis)-5-(6-methyl-3-pyridinyl)octahydro-1H-pyrrolo[3,2-c]pyridine;
(cis)-5-(furo[3,2-b]pyridin-6-yl)octahydro-1H-pyrrolo[3,2-c]pyridine;
(cis)-5-(3-pyridinyl)octahydro-1H-pyrrolo[3,4-c]pyridine;
(cis)-5-(6-chloro-3-pyridinyl)octahydro-1H-pyrrolo[3,4-c]pyridine;
(cis)-5-(5,6-dichloro-3-pyridinyl)octahydro-1H-pyrrolo[3,4-c]pyridine;
(cis)-5-(6-chloro-5-methyl-3-pyridinyl)octahydro-1H-pyrrolo[3,4-c]pyridine;
(cis)-5-(6-chloro-5-fluoro-3-pyridinyl)octahydro-1H-pyrrolo[3,4-c]pyridine;
(cis)-5-(5-fluoro-3-pyridinyl)octahydro-1H-pyrrolo[3,4-c]pyridine;
(cis)-5-(6-methyl-3-pyridinyl)octahydro-1H-pyrrolo[3,4-c]pyridine;
(cis)-5-(furo[3,2-b]pyridin-6-yl)octahydro-1H-pyrrolo[3,4-c]pyridine;
(cis)-2-(3-pyridinyl)decahydro[2,6]naphthyridine;
(cis)-2-(6-chloro-3-pyridinyl)decahydro[2,6]naphthyridine;
(cis)-2-(5,6-dichloro-3-pyridinyl)decahydro[2,6]naphthyridine;
(cis)-2-(6-chloro-5-methyl-3-pyridinyl)decahydro[2,6]naphthyridine;
(cis)-2-(6-chloro-5-fluoro-3-pyridinyl)decahydro[2,6]naphthyridine;
(cis)-2-(5-fluoro-3-pyridinyl)decahydro[2,6]naphthyridine;
(cis)-2-(6-methyl-3-pyridinyl)decahydro[2,6]naphthyridine; and
(cis)-2-(furo[3,2-b]pyridin-6-yl)decahydro[2,6]napthyridine.

In another embodiment of the present invention, compounds of formula VII are disclosed

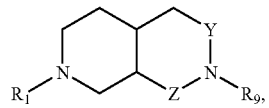

or pharmaceutically acceptable salts and prodrugs thereof wherein Y, Z, $R_1$ and $R_9$ are as defined in formula I.

In another embodiment of the present invention, compounds of formula VII are disclosed wherein Y is a covalent bond; Z is a covalent bond, and $R_1$ and $R_9$ are as defined in formula I.

In another embodiment of the present invention compounds of formula VII are disclosed wherein Y is a covalent bond; Z is a covalent bond;

$R_1$ is

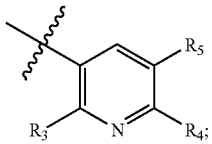

and $R_3$, $R_4$, $R_5$ and $R_9$ are as defined in formula I.

In another embodiment of the present invention, compounds of formula VII are disclosed wherein Y is $CH_2$; Z is a covalent bond; and $R_1$ and $R_9$ are as defined in formula I.

In another embodiment of the present invention, compounds of formula VII are disclosed wherein Y is a covalent bond; Z is a covalent bond;

$R_1$ is

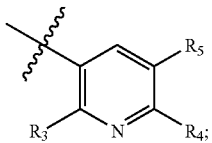

and $R_3$, $R_4$, $R_5$ and $R_9$ are as defined in formula I.

In another embodiment of the present invention, compounds of formula VII are disclosed wherein Y is CH$_2$CH$_2$; Z is a covalent bond; and R$_1$ and R$_9$ are as defined in formula I.

In another embodiment of the present invention, compounds of formula VII are disclosed wherein Y and Z are as defined in formula I; R$_9$ is selected from hydrogen and lower alkyl wherein hydrogen and methyl are preferred; R$_1$ is

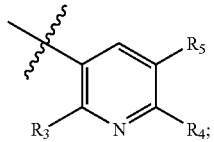

R$_3$ is selected from hydrogen or halogen; R$_4$ is selected from hydrogen, halogen, and lower alkyl; R$_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

Representative compounds of formula VII include, but are not limited to:
(cis)-3-(3-pyridinyl)-3,8-diazabicyclo[4.2.0]octane;
(cis)-3-(6-chloro-3-pyridinyl)-3,8-diazabicyclo[4.2.0]octane;
(1R,6S)-3-(6-chloro-3-pyridinyl)-3,8-diazabicyclo[4.2.0]octane;
(cis)-5-[3,8-diazabicyclo[4.2.0]oct-3-yl]nicotinonitrile; and
(cis)-6-(3-pyridinyl)octahydro-1H-pyrrolo[2,3-c]pyridine.

The following additional compounds, representative of formula VIII, may be prepared by one skilled in the art using known synthetic chemistry methodology or by using synthetic chemistry methodology described in the Schemes and Examples contained herein.
(cis)-3-(5,6-dichloro-3-pyridinyl)-3,8-diazabicyclo[4.2.0]octane;
(cis)-3-(6-chloro-5-methyl-3-pyridinyl)-3,8-diazabicyclo[4.2.0]octane;
(cis)-3-(6-chloro-5-fluoro-3-pyridinyl)-3,8-diazabicyclo[4.2.0]octane;
(cis)-3-(5-methyl-3-pyridinyl)-3,8-diazabicyclo[4.2.0]octane;
(cis)-3-(6-methyl-3-pyridinyl)-3,8-diazabicyclo[4.2.0]octane;
(cis)-3-(furo[3,2-b]pyridin-6-yl)-3,8-diazabicyclo[4.2.0]octane;
(cis)-6-(6-chloro-3-pyridinyl)octahydro-1H-pyrrolo[2,3-c]pyridine;
(cis)-6-(5,6-dichloro-3-pyridinyl)octahydro-1H-pyrrolo[2,3-c]pyridine;
(cis)-6-(6-chloro-5-methyl-3-pyridinyl)octahydro-1H-pyrrolo[2,3-c]pyridine;
(cis)-6-(6-chloro-5-fluoro-3-pyridinyl)octahydro-1H-pyrrolo[2,3-c]pyridine;
(cis)-6-(5-fluoro-3-pyridinyl)octahydro-1H-pyrrolo[2,3-c]pyridine;
(cis)-6-(6-methyl-3-pyridinyl)octahydro-1H-pyrrolo[2,3-c]pyridine; and
(cis)-6-(furo[3,2-b]pyridin-6-yl)octahydro-1H-pyrrolo[2,3-c]pyridine.

In another embodiment of the present invention, compounds of formula VIII are disclosed

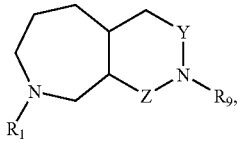

or pharmaceutically acceptable salts and prodrugs thereof wherein Y, Z, R$_1$ and R$_9$ are as defined in formula I.

In another embodiment of the present invention, compounds of formula VII are disclosed wherein Y is a covalent bond; Z is a covalent bond; and R$_1$ and R$_9$ are as defined in formula I.

In another embodiment of the present invention, compounds of formula VIII are disclosed wherein Y is CH$_2$; Z is a covalent bond; and R$_1$ and R$_9$ are as defined in formula I.

In another embodiment of the present invention, compounds of formula VIII are disclosed wherein Y is a covalent bond; Z is CH$_2$; and R$_1$ and R$_9$ are as defined in formula I.

In another embodiment of the present invention, compounds of formula VIII are disclosed wherein Y and Z are as defined in formula I; R$_9$ is selected from hydrogen and lower alkyl wherein hydrogen and methyl are preferred; R$_1$ is

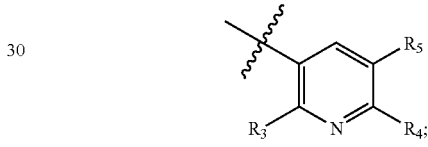

R$_3$ is selected from hydrogen or halogen; R$_4$ is selected from hydrogen, halogen, and lower alkyl; R$_5$ is selected from hydrogen, cyano, cyanoalkyl, haloalkoxy, haloalkyl, halogen, hydroxy, hydroxyalkyl, lower alkenyl, lower alkoxyalkyl, lower alkoxy, lower alkyl, lower alkynyl, and nitro.

The following compounds, representative of formula VIII, may be prepared by one skilled in the art using known chemistry methodology or by using chemistry methodology described in the Schemes and Examples contained herein.
(cis)-3-(3-pyridinyl)-3,9-diazabicyclo[5.2.0]nonane;
(cis)-3-(6-chloro-3-pyridinyl)-3,9-diazabicyclo[5.2.0]nonane;
(cis)-3-(5,6-dichloro-3-pyridinyl)-3,9-diazabicyclo[5.2.0]nonane;
(cis)-3-(6-chloro-5-ethyl-3-pyridinyl)-3,9-diazabicyclo[5.2.0]nonane;
(cis)-3-(6-chloro-5-fluoro-3-pyridinyl)-3,9-diazabicyclo[5.2.0]nonane;
(cis)-3-(5-fluoro-3-pyridinyl)-3,9-diazabicyclo[5.2.0]nonane;
(cis)-3-(6-methyl-3-pyridinyl)-3,9-diazabicyclo[5.2.0]nonane;
(cis)-3-(furo[3,2-b]pyridin-6-yl)-3,9-diazabicyclo[5.2.0]nonane;
(cis)-7-(3-pyridinyl)decahydropyrrolo[2,3-c]azepine;
(cis)-7-(6-chloro-3-pyridinyl)decahydropyrrolo[2,3-c]azepine;
(cis)-7-(5,6-dichloro-3-pyridinyl)decahydropyrrolo[2,3-c]azepine;
(cis)-7-(6-chloro-5-methyl-3-pyridinyl)decahydropyrrolo[2,3-c]azepine;

(cis)-7-(6-chloro-5-fluoro-3-pyridinyl)decahydropyrrolo[2,3-c]azepine;
(cis)-7-(5-fluoro-3-pyridinyl)decahydropyrrolo[2,3-c]azepine;
(cis)-7-(6-methyl-3-pyridinyl)decahydropyrrolo[2,3-c]azepine; and
(cis)-7-(furo[3,2-b]pyridin-6-yl)decahydropyrrolo[2,3-c]azepine.

In another embodiment of the present invention compounds of formula IX are disclosed

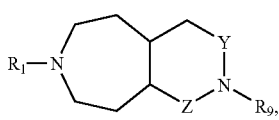

IX or pharmaceutically acceptable salts and prodrugs thereof wherein Y, Z, $R_1$ and $R_9$ are as defined in formula I.

In another embodiment of the present invention, compounds of formula IX are disclosed wherein Y is a covalent bond; Z is a covalent bond; and $R_1$ and $R_9$ are as defined in formula I.

In another embodiment of the present invention, compounds of formula IX are disclosed wherein Y is $CH_2$; Z is a covalent bond; and $R_1$ and $R_9$ are as defined in formula I.

In another embodiment of the present invention, compounds of formula IX are disclosed wherein Y is a covalent bond; Z is $CH_2$; and $R_1$ and $R_9$ are as defined in formula I.

In another embodiment of the present invention compounds of formula IX are disclosed wherein Y and Z are as defined in formula I; $R_9$ is selected from hydrogen and lower alkyl wherein hydrogen and methyl are preferred; $R_1$ is

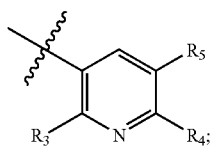

$R_3$ is selected from hydrogen or halogen; $R_4$ is selected from hydrogen, halogen, and lower alkyl; $R_5$ is selected from hydrogen, cyano, haloalkoxy, haloalkyl, halogen, hydroxy, lower alkoxy, lower alkyl, lower alkynyl, and nitro.

The following compounds, representative of formula IX, may be prepared by one skilled in the art using known chemistry methodology or by using chemistry methodology described in the Schemes and Examples contained herein.
(cis)-4-(3-pyridinyl)-4,8-diazabicyclo[5.2.0]nonane;
(cis)-4-(6-chloro-3-pyridinyl)-4,8-diazabicyclo[5.2.0]nonane;
(cis)-4-(5,6-dichloro-3-pyridinyl)-4,8-diazabicyclo[5.2.0]nonane;
(cis)-4-(6-chloro-5-methyl-3-pyridinyl)-4,8-diazabicyclo[5.2.0]nonane;
(cis)-4-(6-chloro-5-fluoro-3-pyridinyl)-4,8-diazabicyclo[5.2.0]nonane;
(cis)-4-(5-fluoro-3-pyridinyl)-4,8-diazabicyclo[5.2.0]nonane;
(cis)-4-(6-methyl-3-pyridinyl)-4,8-diazabicyclo[5.2.0]nonane;
(cis)-4-(furo[3,2-b]pyridin-6-yl)-4,8-diazabicyclo[5.2.0]nonane;
(cis)-6-(3-pyridinyl)decahydropyrrolo[2,3-d]azepine;
(cis)-6-(6-chloro-3-pyridinyl)decahydropyrrolo[2,3-d]azepine;
(cis)-6-(5,6-dichloro-3-pyridinyl)decahydropyrrolo[2,3-d]azepine;
(cis)-6-(6-chloro-5-methyl-3-pyridinyl)decahydropyrrolo[2,3-d]azepine;
(cis)-6-(6-chloro-5-fluoro-3-pyridinyl)decahydropyrrolo[2,3-d]azepine;
(cis)-6-(5-fluoro-3-pyridinyl)decahydropyrrolo[2,3-d]azepine;
(cis)-6-(6-methyl-3-pyridinyl)decahydropyrrolo[2,3-d]azepine; and
(cis)-6-(furo[3,2-b]pyridin-6-yl)decahydropyrrolo[2,3-d]azepine.

The compounds of formula I-IX may be in either the cis or trans configuration.

Another embodiment of the present invention relates to pharmaceutical compositions comprising a therapeutically effective amount of a compound of formula I or a pharmaceutically acceptable salt thereof in combination with a pharmaceutically acceptable carrier.

Another embodiment of the present invention relates to a method for selectively controlling neurotransmitter release in a mammal comprising administering to a mammal in need of such treatment a therapeutically effective amount of a compound of formula I.

Another embodiment of the present invention relates to a method of treating a disorder, such as Alzheimer's disease, Parkinson's disease, memory dysfunction, Tourette's syndrome, sleep disorders, attention deficit hyperactivity disorder, neurodegeneration, inflammation, neuroprotection, amyotrophic atral sclerosis, anxiety, depression, mania, schizophrenia, anorexia and other eating disorders, AIDS-induced dementia, epilepsy, urinary incontinence, Crohn's disease, migraines, premenstrual syndrome, erectile dysfunction, substance abuse, smoking cessation and inflammatory bowel syndrome, in a host mammal in need of such treatment comprising administering a therapeutically effective amount of a compound of formula I.

Another embodiment of the present invention relates to a method for controlling pain in a mammal in need of such treatment comprising administering a therapeutically effective amount of a compound of formula I in combination with a pharmaceutically acceptable carrier.

Another embodiment of the present invention relates to a method for controlling pain in a mammal in need of such treatment comprising administering a therapeutically effective amount of a compound of formula I in combination with an opioid and a pharmaceutically acceptable carrier.

Another embodiment of the present invention relates to a method for controlling pain in a mammal in need of such treatment comprising administering a therapeutically effective amount of a compound of formula I in combination with a non-steroid anti-inflammatory agent and a pharmaceutically acceptable carrier.

Another embodiment of the present invention relates to a method for controlling pain in a mammal in need of such treatment comprising administering a therapeutically effective amount of a compound of formula I in combination with a tricyclic antidepressant and a pharmaceutically acceptable carrier.

Another embodiment of the present invention relates to a method for controlling pain in a mammal in need of such treatment comprising administering a therapeutically effective amount of a compound of formula I in combination with an anticonvulsant such as gabapentin or pregabalin and a pharmaceutically acceptable carrier.

DEFINITIONS OF TERMS

As used throughout this specification and the appended claims, the following terms have the following meanings.

The term "alkenyl," as used herein, refers to a straight or branched chain hydrocarbon containing from 2 to 10 carbons, preferably 2 to 6 carbon atoms, preferably in a straight chain, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl 2-heptenyl, 2-methyl-1-heptenyl, and 3-decenyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to tert-butoxymethoxy, 2-ethoxyethoxy, 2-methoxyethoxy, and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl," as used herein, refers to a straight or branched chain hydrocarbon containing from 1 to 10 carbon atoms, preferably 1 to 6 carbon atoms, and preferably in a straight chain. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and tert-butylcarbonyloxy.

The term "alkylthio," as used herein, refers to an alkyl group, as defined herein, appended to the parent molecular moiety through a thio moiety, as defined herein. Representative examples of alkylthio include, but are not limited, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms, preferably 2 to 6 carbon atoms, preferably in a straight chain, and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino," as used herein, refers to a —$NR_{20}R_{21}$ group wherein $R_{20}$ and $R_{21}$ are independently selected from hydrogen, alkyl, and alkylcarbonyl as defined herein. Representative examples of amino include, but are not limited, acetylamino, amino, methylamino, dimethylamino, ethylamino, and methylcarbonylamino.

The term "aminoalkyl," as used herein, refers to an amino group, as defined herein, appended to the parent molecular moiety through an alkyl group, as defined herein. Representative examples of aminoalkyl include, but are not limited, aminomethyl, (methylamino)methyl, 2-aminoethyl, and (dimethylamino)methyl.

The term "aminocarbonyl," as used herein, refers to an amino group, as defined herein, appended to the parent molecular moiety through a carbonyl group, as defined herein. Representative examples of aminocarbonyl include, but are not limited, aminocarbonyl, dimethylaminocarbonyl, methylaminocarbonyl, and ethylaminocarbonyl.

The term "aminocarbonylalkyl," as used herein, refers to an aminocarbonyl group, as defined herein, appended to the parent molecular moiety through an alkyl group, as defined herein. Representative examples of aminocarbonylalkyl include, but are not limited to, 2-amino-2-oxoethyl, 2-(methylamino)-2-oxoethyl, 4-amino-4-oxobutyl, and 4-(dimethylamino)-4-oxobutyl.

The term "aminosulfonyl," as used herein, refers to an amino group, as defined herein, appended to the parent molecular moiety through a sulfonyl group, as defined herein. Representative examples of aminosulfonyl include, but are not limited, aminosulfonyl, dimethylaminosulfonyl, methylaminosulfonyl, and ethylaminosulfonyl.

The term "aryl," as used herein, refers to a monocyclic-ring system, or a fused bicyclic-ring system wherein one or more of the fused rings are aromatic. Representative examples of aryl include, but are not limited to, azulenyl, indanyl, indenyl, naphthyl, phenyl, and tetrahydronaphthyl.

The aryl groups of the present invention can be substituted with 1, 2, or 3 substituents independently selected from alkenyl, alkoxy, alkoxyalkoxy, alkoxyalkyl, alkoxycarbonyl, alkoxycarbonyl alkyl, alkyl, alkylcarbonyl, alkylcarbonyloxy, alkylthio, alkynyl, amino, aminosulfonyl, carboxy, carboxyalkyl, cyano, cyanoalkyl, formyl, formylalkyl, halogen, haloalkyl, hydroxy, hydroxyalkyl, mercapto, and nitro.

The term "carbonyl," as used herein, refers to a —C(O)— group.

The term "carboxy," as used herein, refers to a —$CO_2H$ group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "formyl," as used herein, refers to a —C(O)H group.

The term "formylalkyl," as used herein, refers to a formyl group, as defined herein, appended to the parent molecular moiety through an alkyl group, as defined herein. Representative examples of formylalkyl include, but are not limited to, formylmethyl and 2-formylethyl.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzofuranyl dibenzothiophenyl, naphthofuranyl, naphthothiophenyl, oxanthrenyl, phenazinyl, phenoxathiinyl, phenoxazinyl, phenothiazinyl, thianthrenyl, thioxanthenyl, and xanthenyl.

The heterocycles of the present invention can be substituted with 1, 2, or 3 substitutents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminosulfonyl, carboxy, carboxyalkyl, cyano, cyanoalkyl, formyl, formylalkyl, halogen, haloalkyl, hydroxy, hydroxyalkyl, mercapto, and nitro.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "lower alkenyl," as used herein, is a subset of alkenyl as defined herein and refers to a straight or branched chain hydrocarbon group containing from 2 to 4 carbon atoms and containing at least one carbon-carbon double bond. Representative examples of lower alkenyl include, but are not limited, to ethenyl, vinyl, allyl, 1-propenyl and 3-butenyl.

The term "lower alkoxy," as used herein, is a subset of alkoxy as defined herein and refers to a lower alkyl group, as defined herein, appended to the parent molecular moiety through an oxy group, as defined herein. Representative examples of lower alkoxy include, but are not limited to, methoxy, ethoxy, propoxy, 2-propoxy, butoxy, and tert-butoxy.

The term "lower alkoxyalkyl," as used herein, is a subset of alkoxyalkyl as defined herein and refers to a lower alkoxy group, as defined herein, appended to the parent molecular moiety through a lower alkyl group, as defined herein. Representative examples of lower alkoxyalkyl include, but are not limited to, methoxymethyl, ethoxymethyl, propoxymethyl, 2-propoxyethyl, butoxymethyl, and tert-butoxymethyl.

The term "lower alkyl," as used herein, is a subset of alkyl as defined herein and refers to a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower alkynyl," as used herein, is a subset of alkynyl as defined herein and refers to a straight or branched chain hydrocarbon group containing from 2 to 4 carbon atoms and containing at least one carbon-carbon triple bond. Representative examples of lower alkynyl include, but are not limited, to acetylenyl, 1-propynyl, 2-propynyl, and 3-butynyl.

The term "mercapto," as used herein, refers to a —SH group.

The term "mercaptoalkyl," as used herein refers to a mercapto group, as defined herein, appended to the parent molecular moiety through an alkyl group, as defined herein. Representative examples of mercaptoalkyl include, but are not limited to, sulfanylmethyl, 2-sulfanylethyl and 3-sulfanylpropyl.

The term "nitrogen protecting group" or "N-protecting group," as used herein, refers to those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), trifluoroacetyl, and triphenylmethyl (trityl). Commonly used N-protecting groups are disclosed in T. W. Greene and P. G. M. Wuts, Protective Groups in Organic Synthesis, 3rd edition, John Wiley & Sons, New York (1999).

The term "nitro," as used herein, refers to a —$NO_2$ group.

The term "oxo," as used herein, refers to a =O moiety.

The term "oxy," as used herein, refers to a —O— moiety.

The term "sulfonyl," as used herein, refers to a —$SO_2$— group.

The term "thio," as used herein, refers to a —S— moiety.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in (IUPAC 1974 Recommendations for Section E, Fundamental Stereochemistry. Pure Appl. Chem., (1976), 45: 13-30). In particular, the stereochemistry at the two bridgehead carbon atoms, shown in formula I, may independently be either (R) or (S), resulting in a cis or trans configuration, unless specifically noted otherwise.

The present invention contemplates various stereoisomers and mixtures thereof which are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; aralkyl halides like benzyl and phenethyl bromides and others.

Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of the present invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to cations based on alkali metals or alkaline earth metals such as lithium, sodium, potassium, calcium, magnesium and aluminum salts and the like and nontoxic quaternary ammonia and amine cations including ammonium, tetramethylammonium, tetraethyl ammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

In Vitro Data

Determination of Nicotinic Acetylcholine Receptor Binding Potencies

Compounds of the invention were subjected to in vitro assays against the nicotinic acetylcholine receptor as described below and were found to be effective binders to the receptor. The In Vitro protocols for determination of nicotinic acetylcholine channel receptor binding potencies of ligands were determined as follows.

Binding of [$^3$H]-cytisine ([$^3$H]-CYT) to neuronal nicotinic acetylcholine receptors was accomplished using crude synaptic membrane preparations from whole rat brain (Pabreza et al., Molecular Pharmacol., 1990, 39:9). Washed membranes were stored at −80° C. prior to use. Frozen aliquots were slowly thawed and resuspended in 20 volumes of buffer (containing: 120 mM NaCl, 5 mM KCl, 2 mM $MgCl_2$, 2 mM $CaCl_2$ and 50 mM Tris-Cl, pH 7.4@4° C.). After centrifuging at 20,000×g for 15 minutes, the pellets were resuspended in 30 volumes of buffer.

The test compounds were dissolved in water to make 10 mM stock solutions. Each solution was then diluted (1:100) with buffer (as above) and further taken through seven serial log dilutions to produce test solutions from $10^{-5}$ to $10^{-11}$ M.

Homogenate (containing 125-150 μg protein) was added to triplicate tubes containing the range of concentrations of test compound described above and [$^3$H]-CYT (1.25 nM) in a final volume of 500 μL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 μM (−)-nicotine and values were expressed as a percentage of total binding. $IC_{50}$ values were determined with the RS-1 (BBN) nonlinear least squares curve-fitting program and $IC_{50}$ values were converted to Ki values using the Cheng and Prusoff correction ($K_i=IC_{50}/(1+[ligand]/Kd$ of ligand).

The results are detailed in Table 1.

TABLE 1

Binding Data

| Example Number | Average $K_i$ (nM) |
|---|---|
| 1 | 0.12 |
| 2 | 26 |
| 3 | 0.20 |
| 4 | 36 |
| 5 | 1.7 |
| 6 | 0.75 |
| 7 | 0.08 |
| 8 | 0.04 |
| 9 | 0.04 |
| 10 | 0.03 |
| 11 | 0.04 |
| 12 | 0.05 |
| 13 | 1.5 |
| 14 | 1.1 |
| 15 | 6.3 |
| 16 | 23 |
| 17 | 31 |
| 18 | 154 |
| 19 | 576 |
| 20 | 122 |
| 22 | 11 |
| 23 | 4.1 |
| 24 | 0.16 |
| 25 | 1.4 |
| 26 | 0.62 |
| 27 | 0.10 |
| 28 | 0.34 |
| 29 | 0.35 |
| 30 | 2.9 |
| 31 | 14 |
| 32 | 5.3 |
| 33 | 0.02 |
| 35 | 0.13 |
| 36 | 0.17 |
| 37 | 1.2 |
| 38 | 0.16 |
| 39 | 0.54 |
| 40 | 6.2 |
| 41 | 1.9 |
| 42 | 0.03 |
| 43 | 0.30 |
| 44 | 0.23 |
| 45 | 0.88 |
| 46 | 0.73 |
| 47 | 0.80 |
| 48 | 0.10 |
| 49 | 0.02 |
| 50 | 0.51 |
| 51 | 0.12 |
| 52 | 1.3 |
| 53 | 3.1 |
| 54 | 1.3 |
| 55 | 0.72 |
| 56 | 0.62 |
| 57 | 1.2 |
| 58 | 0.53 |
| 59 | 0.35 |
| 60 | 0.11 |
| 61 | 2.5 |
| 62 | 0.10 |
| 63 | 0.56 |
| 64 | 1.1 |
| 65 | 3.1 |
| 66 | 0.26 |
| 67 | 1.0 |
| 68 | 0.61 |
| 69 | 3.2 |
| 70 | 0.86 |
| 71 | 1.5 |
| 72 | 0.60 |
| 73 | 24 |
| 74 | 3.2 |

TABLE 1-continued

Binding Data

| Example Number | Average $K_i$ (nM) |
|---|---|
| 75 | 6.9 |
| 76 | 0.28 |
| 77 | 19 |
| 78 | 25 |
| 79 | 0.12 |
| 80 | 0.17 |
| 81 | 11 |
| 82 | 363 |
| 83 | 97 |
| 84 | 2.4 |
| 85 | 0.27 |
| 86 | 0.75 |
| 87 | 0.20 |
| 88 | 0.56 |
| 89 | 0.24 |
| 90 | 0.04 |
| 91 | 1.1 |
| 92 | 0.12 |
| 93 | 0.30 |
| 94 | 0.12 |
| 95 | 0.12 |
| 96 | 1.9 |

In Vivo Data

Determination of Effectiveness of Nicotinic Acetylcholine Receptor Ligands as Analgesic Agents in the Mouse Hot Plate Paradigm An in vivo protocol was utilized to determine the effectiveness of nicotinic acetylcholine receptor ligands as analgesic agents in the mouse hot plate paradigm.

Separate groups of mice, (n=8/group) were utilized for each dose group. All drugs were administered by the intraperitoneal route of administration. Test drugs were dissolved in water to make a 6.2 mM stock solution. Animals were dosed with this solution (10 mL/kg body weight) for a 62 micromol/kg dose. Lower doses were administered similarly, following serial dilution of the stock solution in half-log increments. Animals were dosed 30 minutes prior to testing in the hot plate. The hot-plate utilized was an automated analgesia monitor (Model #AHP16AN, Omnitech Electronics, Inc. of Columbus, Ohio). The temperature of the hot plate was maintained at 55° C. and a cut-off time of 180 seconds was utilized. Latency until the tenth jump was recorded as the dependent measure. An increase in the tenth jump latency relative to the control was considered an effect.

Table 2 shows the minimally effective dose (MED), among the doses tested, at which a significant effect, as defined above, was observed for compounds of the present invention. The data shows that selected compounds of the invention show a significant antinociceptive effect at doses ranging from 1.9 to 62 μmol/kg.

TABLE 2

Mouse Hot Plate Data

| Example Number | (MED) μmol/kg |
|---|---|
| 1 | 19 |
| 3 | 6.2 |
| 7 | 19 |

TABLE 2-continued

Mouse Hot Plate Data

| Example Number | (MED) μmol/kg |
|---|---|
| 8 | 6.2 |
| 9 | 19 |
| 10 | 6.2 |
| 11 | 6.2 |
| 12 | 62 |
| 13 | 6.2 |
| 14 | 1.9 |
| 15 | 19 |
| 22 | 19 |
| 23 | 62 |
| 24 | 6.2 |
| 26 | 19 |
| 27 | 1.9 |
| 28 | 6.2 |
| 29 | 19 |
| 33 | 1.9 |

Determination of Effectiveness of Nicotinic Acetylcholine Receptor Ligands as Analgesic Agents in the Formalin Test Another in vivo protocol utilized to determine the effectiveness of nicotinic acetylcholine receptor ligands as analgesic agents was the formalin test.

Male Sprague-Dawley rats (Charles River, Portage, Mich.) weighing 200 to 400 grams were used for all experiments. After a 20 minute period of acclimation to individual cages, 50 μL of a 5% formalin solution was injected subcutaneous into the dorsal aspect of one of the rear paws and the rats were then returned to the clear observation cages suspended above mirror panels. Rats were observed for either a continuous periods of 60 minutes or for periods of time corresponding to phase 1 and phase 2 of the formalin test. Phase 1 of the formalin test was defined as the period of time immediately after injection of formalin until 10 minutes after the formalin injection (i.e., 0-10 minutes after formalin). Phase 2 was defined as the 20 minute period from 30 to 50 minutes after formalin injection. The investigator recorded nocifensive behaviors in the injected paw of four animals during the session by observing each animal for one 15 second observation period during each 1 minute interval. Nocifensive behavior recorded included flinching, licking or biting the injected paw. In dose-response studies, the test compound (or saline) was administered intraperitoneally 5 minutes before injection of formalin.

Table 3 shows the minimally effective dose (MED) at which a statistically significant effect was observed for compounds of the present invention. The data shows that selected compounds of the present invention show antinociceptive effect at doses ranging from 0.19 to >19 μmol/kg.

TABLE 3

Formalin Test Data

| Example Number | (MED) μmol/kg |
|---|---|
| 1 | 0.62 |
| 7 | 6.2 |
| 10 | 1.9 |
| 13 | 0.62 |
| 14 | 0.62 |
| 15 | >6.2 |
| 22 | 1.9 |
| 23 | 0.62 |
| 24 | 6.2 |
| 28 | 1.9 |
| 29 | 6.2 |
| 33 | 0.62 |
| 35 | 1.9 |
| 36 | 6.2 |
| 37 | 6.2 |
| 38 | >6.2 |
| 40 | 1.9 |
| 41 | >1.9 |
| 43 | 6.2 |
| 44 | 6.2 |
| 45 | 0.62 |
| 46 | 0.62 |
| 47 | 1.9 |
| 48 | 0.19 |
| 50 | 6.2 |
| 51 | 0.62 |
| 52 | 19 |
| 53 | >19 |
| 54 | 1.9 |
| 55 | >19 |
| 56 | 1.9 |
| 57 | 6.2 |
| 58 | 1.9 |
| 60 | 0.62 |
| 62 | 0.19 |
| 63 | >19 |
| 64 | >19 |
| 65 | >19 |
| 67 | 19 |
| 68 | >19 |
| 69 | >19 |
| 70 | >19 |
| 71 | >19 |
| 72 | >19 |
| 74 | 1.9 |
| 76 | 1.9 |
| 85 | >19 |
| 86 | >19 |
| 87 | 6.2 |

The data in Tables 1, 2 and 3 demonstrates that compounds of the present invention bind to the nicotinic acetylcholine receptor and are useful for treating pain. Compounds of the present invention may also be useful for ameliorating or preventing additional disorders affected by nicotinic acetylcholine receptors such as Alzheimer's disease, Parkinson's disease, memory dysfunction, Tourette's syndrome, sleep disorders, attention deficit hyperactivity disorder, neurodegeneration, inflammation, neuroprotection, amyotrophic atral sclerosis, anxiety, depression, mania, schizophrenia, anorexia and other eating disorders, AIDS-induced dementia, epilepsy, urinary incontinence, Crohn's disease, migraines, PMS, erectile disfunction, substance abuse, smoking cessation and inflammatory bowel syndrome.

Dosage forms for topical administration of a compound of the present invention include powders, sprays, ointments and inhalants. The active compound is mixed under sterile conditions with pharmaceutically acceptable carrier and any needed preservatives, buffers or propellants which can be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention administered to a human or lower animal may range from about 0.001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Compounds of the present invention that are formed by in vivo conversion of a different compound that was administered to a mammal are intended to be included within the scope of the present invention.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula I, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design American Pharmaceutical Association and Pergamon Press (1987).

The term "pharmaceutically acceptable ester" or "ester." as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I may be prepared according to conventional methods.

The compounds of the present invention may have activity against disorders which are mediated through the central nervous system. The following references describe various disorders affected by nicotinic acetylcholine receptors; 1) Williams, M.; Arneric, S. P.; Beyond the Tobacco Debate; dissecting out the therapeutic potential of nicotine. Exp. Opin. Invest. Drugs (1996)5(8): 1035-1045; 2) Arneric, S. P.; Sullivan, J. P.; Williams, W.; Neuronal nicotinic acetylcholine receptors. Novel targets for central nervous system therapeutics. In: Psychopharmacology: The Fourth Generation of Progress. Bloom F E, Kupfer D J (Eds.), Raven Press, New York (1995): 95-109:3) Arneric, S. P.; Holladay. M. W.; Sullivan, J. P.; Cholinergic channel modulators as a novel therapeutic strategy for Alzheimer's disease. Exp. Opin. Invest. Drugs (1996) 5(1): 79-100; 4) Lindstrom, J.; Nicotinic Acetylcholine Receptors in Health and Disease. Molecular Neurobiology (1997) 15: 193-222; and 5) Lloyd. G K; Menzaghi, F; Bontempi B; Suto, C; Siegel. R; Akong, M; Stauderman. K; Velicelebi, G; Johnson, E; Harpold, M M; Rao, T S; Sacaan, A I; Chavez-Noriega, L E; Washburn, M S; Vernier, J M; Cosford, N D P; McDonald, L A; The potential of subtype selective neuronal nicotinic acetylcholine receptor agonists as therapeutic agents. Life Sciences (1998)62(17/18): 1601-1606. These disorders include, but are not limited to the following: pain (references 1 and 2), Alzheimer's disease (references 1-5), Parkinson's disease (references 1, 4 and 5), memory dysfunction, Tourette's syndrome (references 1, 2 and 4), sleep disorders (reference 1), attention deficit hyperactivity disorder (references 1 and 3), neurodegeneration, inflammation, neuroprotection (references 2 and 3), amyotrophic atral sclerosis, anxiety (references 1, 2 and 3), depression (reference 2), mania, schizophrenia (references 1, 2 and 4), anorexia and other eating disorders, AIDS-induced dementia, epilepsy (references 1, 2 and 4), urinary incontinence (reference 1), Crohn's disease, migraines, PMS, erectile disfunction, substance abuse, smoking cessation (references 1 and 2) and inflammatory bowel syndrome (references 1 and 4) among others.

Abbreviations

Abbreviations which have been used in the descriptions of the Schemes and the Examples that follow are: Ac for acetyl; AcOH for acetic acid; BINAP for 2,2'-bis(diphenylphosphino)-1,1'-binaphthyl; Boc for tert-butoxycarbonyl; (Boc)$_2$O for di-tert-butyl dicarbonate; dba for dibenzylideneacetone; DMF for N,N-dimethylformamide; dppf for 1,1'-bis(diphenylphosphino)ferrocene; EtOAc for ethyl acetate; Et$_2$O for diethyl ether; EtOH for ethanol; eq for equivalents; formalin for a solution of formaldehyde (37% by weight) in water; HPLC for high pressure liquid chromatography; LAH for lithium aluminum hydride; MeOH for methanol; Ms for mesylate (SO$_2$CH$_3$); Tf for triflate (SO$_2$CF$_3$); TFA for trifluoroacetic acid; THF for tetrahydrofuran; TMS for trimethylsilyl; Ts for tosylate; and TsOH for para-toluenesulfonic acid.

Preparation of Compounds of the Present Invention

The compounds and processes of the present invention will be better understood in connection with the following synthetic Schemes and Examples which illustrate a means by which the compounds of the present invention can be prepared.

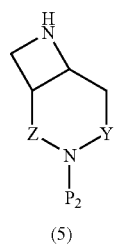

(5)

Bicyclic diamines of general formula (5), wherein Y and Z are as defined in formula I and P$_2$ is a nitrogen protecting group such as tert-butoxycarbonyl (Boc), can be prepared as described in Scheme 1. β-Keto esters of general formula (1), wherein R is lower alkyl such as methyl or ethyl, can be purchased commercially or prepared as described in (J. Chem. Soc. Perkin I (1998) 3673-3689; J. Heterocyclic Chem. (1990) 27(7), 1885-1892; and J. Med. Chem. (1986) 29(2), 224-229). β-Keto esters of general formula (1) can be treated with benzylamine and then sodium borohydride in the presence of acetic acid to provide aminoalcohols of general formula (2). Aminoalcohols of general formula (2) can be treated with a palladium catalyst such as palladium on carbon under a hydrogen atmosphere to provide aminoalcohols of general formula (3). Aminoalcohols of general formula (3), can be treated with 2.0 equivalents of 2-nitrobenzenesulfonyl chloride in the presence of a base such as triethylamine to provide sulfonamides of general formula (4). Sulfonamides of general formula (4) can be treated with alkyl or aryl mercaptans such as thiophenol to provide monoprotected bicyclic diamines of general formula (5).

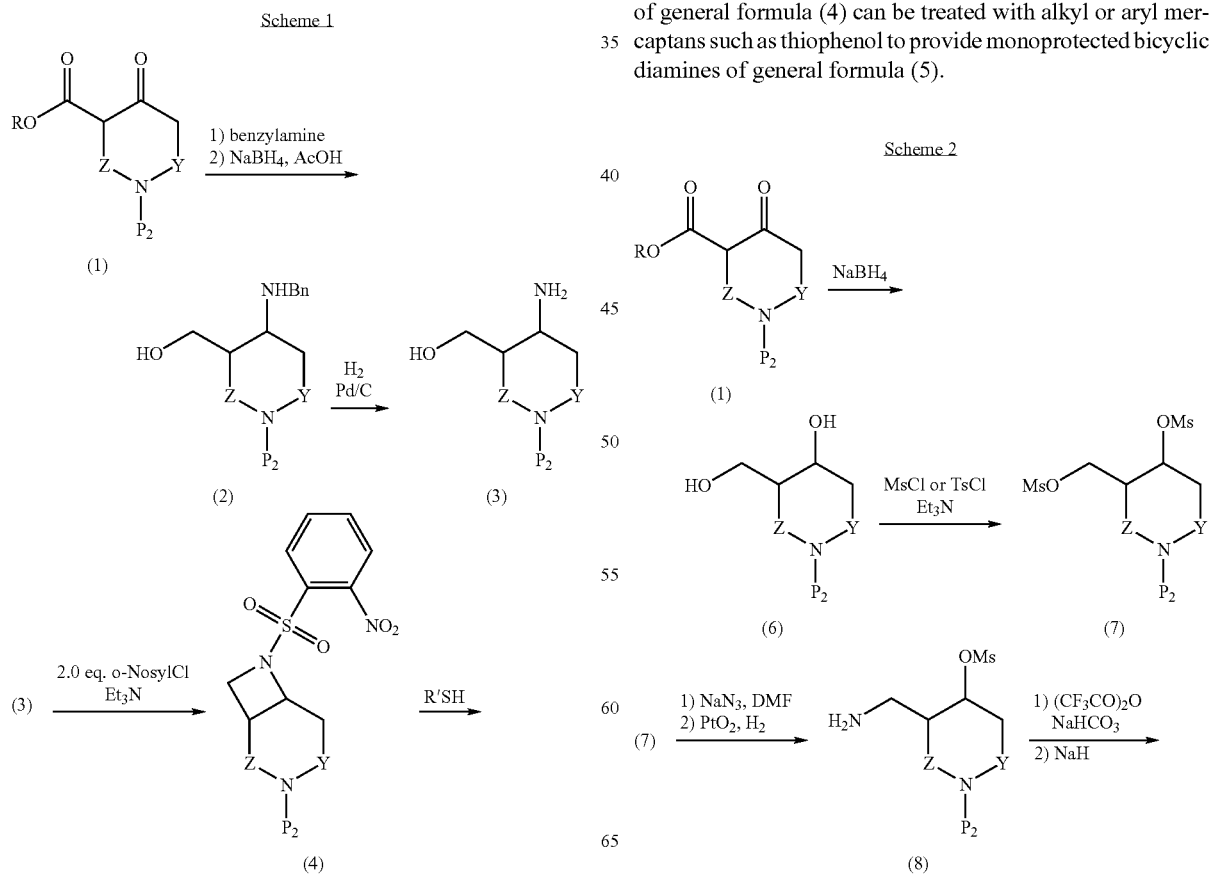

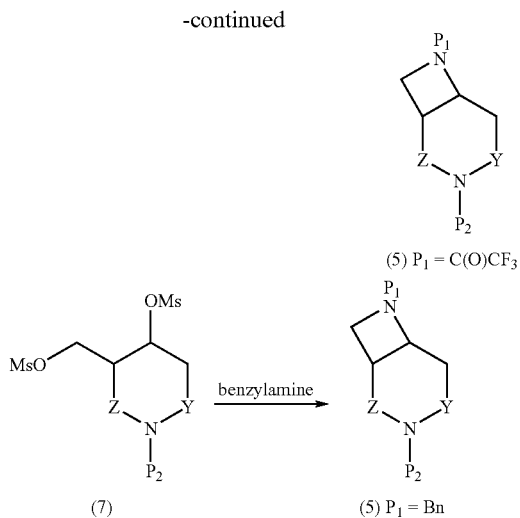

An alternative method of preparing bicyclic diamines of general formula (5), wherein Y and Z are as defined in formula I and $P_2$ is a nitrogen protecting group such as benzyl, can be used as described in (Jacquet et. al., Tetrahedron Lett. (1991) 32(12), 1565-1568). β-Keto esters of general formula (1) can be treated with sodium borohydride to provide diols of general formula (6). Diols of general formula (6) can be treated with methanesulfonyl chloride or para-toluenesulfonyl chloride to provide bis sulfonates of general formula (7). Bis sulfonates of general formula (7) can be treated with sodium azide and then hydrogenated in the presence of a platinum catalyst such as platinum (IV) oxide to provide amines of general formula (8). Amines of general formula (8) can be treated with a nitrogen protecting group such as trifluoroacetic anhydride and then treated with sodium hydride to effect ring closure to provide bicyclic diamines of general formula (5).

Alternatively, bis sulfonates of general formula (7) can be treated with amines such as benzyl amine to provide bicyclic amines of general formula (5).

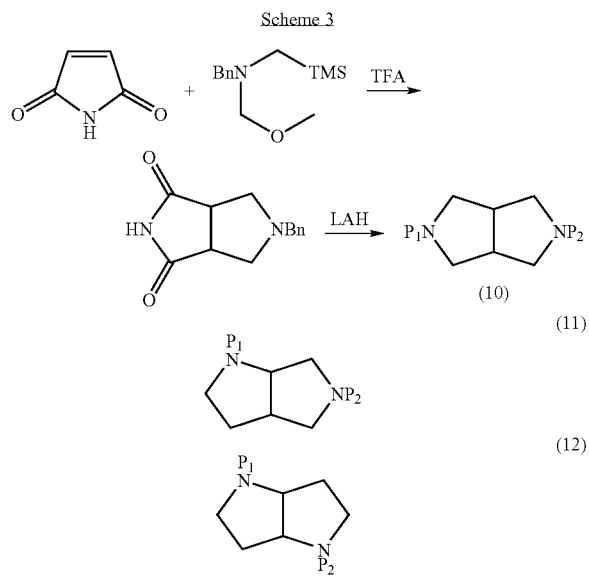

Octahydropyrrolo[3,4-c]pyrroles of general formula (10), wherein $P_1$ and $P_2$ are independently selected from hydrogen or a nitrogen protecting group, can be prepared as described in Scheme 3. 1H-Pyrrole-2,5-dione can be treated with N-benzyl-N-(methoxymethyl)-N-[(trimethylsilyl)methyl] amine in the presence of a catalytic amount of acid such as trifluoroacetic acid to provide 5-benzyltetrahydropyrrolo[3,4-c]pyrrole-1,3(2H,3aH)-dione. The tetrahydropyrrolo[3,4-c]pyrrole can be treated with lithium aluminum hydride to provide octahydropyrrolo[3,4-c]pyrroles of general formula (10).

Octahydropyrrolo[3,2-b]pyrroles of general formula (11), wherein $P_1$ and $P_2$ are independently selected from hydrogen or a nitrogen protecting group can be prepared as described in (U.S. Pat. No. 5,071,999).

Octahydropyrrolo[3,4-b]pyrroles of general formula (12), wherein $P_1$ and $P_2$ are independently selected from hydrogen or a nitrogen protecting group, can be prepared as described in (Cope and Shen, JACS (1956) 78, 5916-5920).

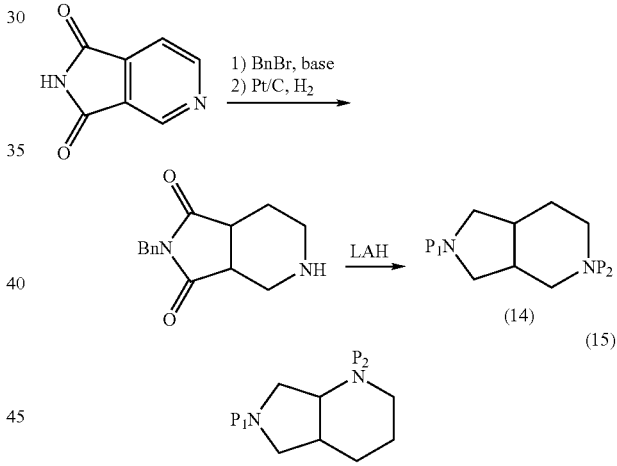

Octahydro-1H-pyrrolo[3,4-c]pyridines of general formula (14), wherein $P_1$ and $P_2$ are independently selected from hydrogen or a nitrogen protecting group, can be prepared as described in Scheme 4. 1H-Pyrrolo[3,4-c]pyridine-1,3(2H)-dione, commercially available, can be treated with a base and a nitrogen protecting group such as benzyl bromide and then treated with a transition metal catalyst such as a platinum catalyst, platinum on carbon for example, under a hydrogen atmosphere to provide 2-benzylhexahydro-1H-pyrrolo[3,4-c]pyridine-1,3(2H)-dione. The dione can then be treated with a reducing agent such as lithium aluminum hydride to provide octahydro-1H-pyrrolo[3,4-c]pyridines of general formula (14).

Octahydro-1H-pyrrolo[3,4-b]pyridines of general formula (15), wherein $P_1$ and $P_2$ are independently selected from hydrogen or a nitrogen protecting group, can be prepared as described in (EP 0603887 A2).

Scheme 5

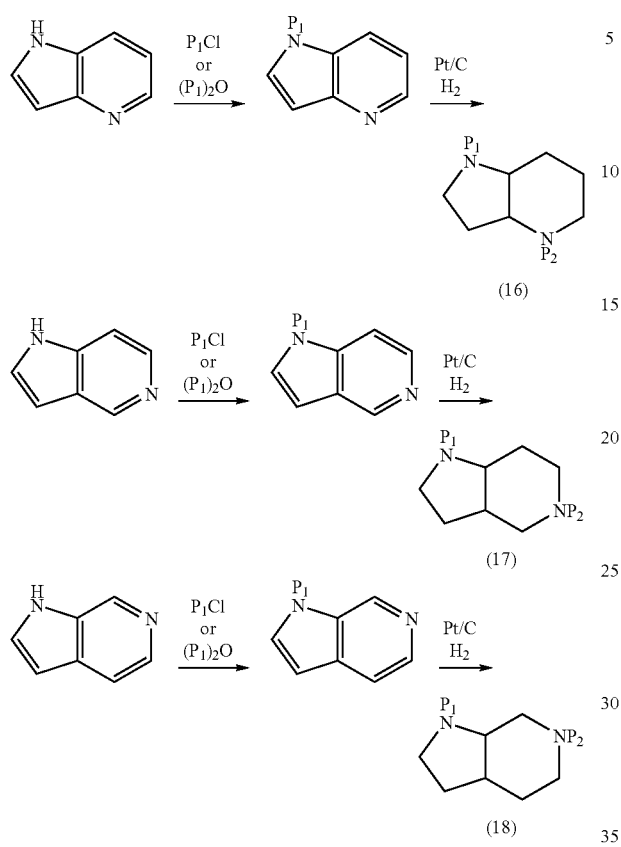

Octahydro-1H-pyrrolo[3,2-b]pyridines of general formula (16), wherein P₁ and P₂ are independently selected from hydrogen or a nitrogen protecting group, can be prepared as described in Scheme 5. 1H-Pyrrolo[3,2-b]pyridine prepared as described in (J. Chem. Soc. (1948) 198), can be treated with a nitrogen protecting reagent such as benzyl bromide or di-tert-butyl dicarbonate to provide N-protected pyrrolopyridines which can then be treated with a platinum catalyst such as platinum on carbon under a hydrogen atmosphere to provide octahydro-1H-pyrrolo[3,2-b]pyridines of general formula (16).

1H-Pyrrolo[3,2-c]pyridine, prepared as described in (Tetrahedron (1993) 49(4), 2885-2914) can be processed as described above to provide octahydro-1H-pyrrolo[3,2-c]pyridines of general formula (17).

1H-Pyrrolo[2,3-c]pyridine, prepared as described in (Synthesis (1996) 877-882) can be processed as described above to provide octahydro-1H-pyrrolo[2,3-c]pyridines of general formula (18).

Scheme 6

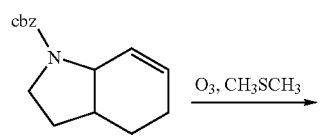

Decahydropyrrolo[2,3-c]azepines of general formula (20), wherein P₁ and P₂ are independently selected from hydrogen or a nitrogen protecting group, can be prepared as described in Scheme 6. Benzyl 2,3,3a,4,5,7a-hexahydro-1H-indole-1-carboxylate, prepared as described in (Ronn and Andersson, Tetrahedron Lett., (1995) 36(42) 7749-7752), can be treated with ozone and methyl sulfide to provide the dialdehyde. The dialdehyde can be treated with amines such as benzyl amine in the presence of acetic acid and sodium cyanoborohydride to provide decahydropyrrolo[2,3-c]azepines of general formula (20).

Decahydropyrrolo[3,4-c]azepines of general formula (22), wherein P₁ and P₂ are independently selected from hydrogen or a nitrogen protecting group, can be prepared as described in Scheme 6. 1,5,6,7-Tetrahydro-2H-azepin-2-one, prepared as described in (Reimschuessel and Pascale, JOC (1969) 34(4) 959-963), can be treated with a nitrogen protecting reagent and then treated with N-benzyl-N-(methoxymethyl)-N—[(trimethylsilyl)methyl]amine in the presence of a catalytic amount of acid such as trifluoroacetic acid to provide octahydropyrrolo[3,4-c]azepinones of general formula (21).

Octahydropyrrolo[3,4-c]azepinones of general formula (21) can be treated with a reducing agent such as lithium aluminum hydride to provide decahydropyrrolo[3,4-c]azepines of general formula (22).

Scheme 7

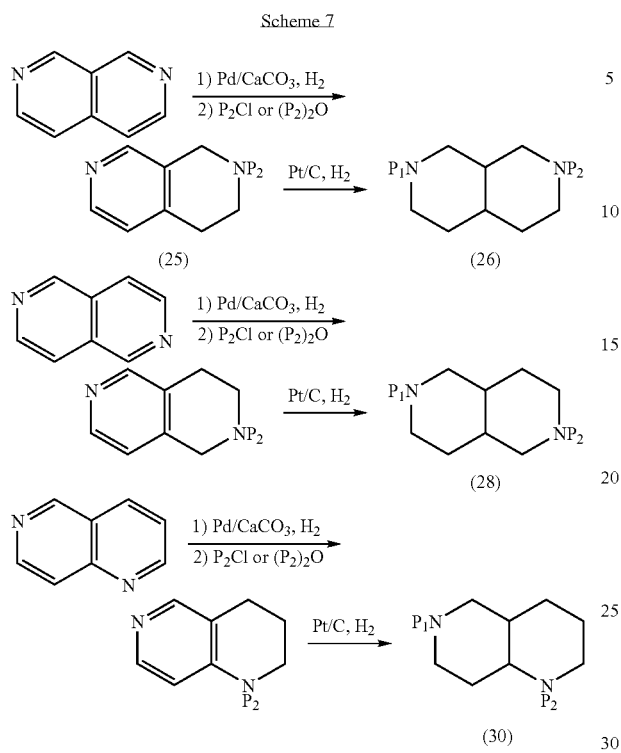

Bicyclic diamines of general formula (26), (28), and (30), wherein $P_1$ and $P_2$ are independently selected from hydrogen or a nitrogen protecting group, can be prepared as described in Scheme 7. [2,7]Naphthyridine, prepared as described in (Numata, et. al., Synthesis (1999) 2, 306-311) can be treated with palladium such as palladium on calcium carbonate under a hydrogen atmosphere as described in (Chem. Pharm. Bull., (1958) 6, 408) and then treated with a nitrogen protecting reagent to provide tetrahydro[2,7]naphthyridines of general formula (25).

Tetrahydro[2,7]naphthyridines of general formula (25) can be further reduced with platinum on carbon under a hydrogen atmosphere to provide bicyclic diamines of general formula (26).

[2,6]Naphthyridine and [1,6]naphthyridine, prepared as described in (Numata. et. al., Synthesis (1999) 2, 306-311;) can be processed as described above to provide bicyclic diamines of general formula (28) and general formula (30) respectively.

Scheme 8

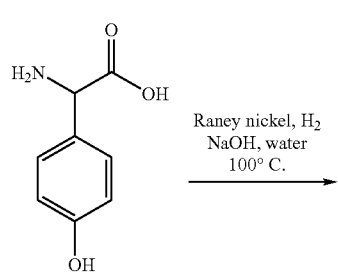

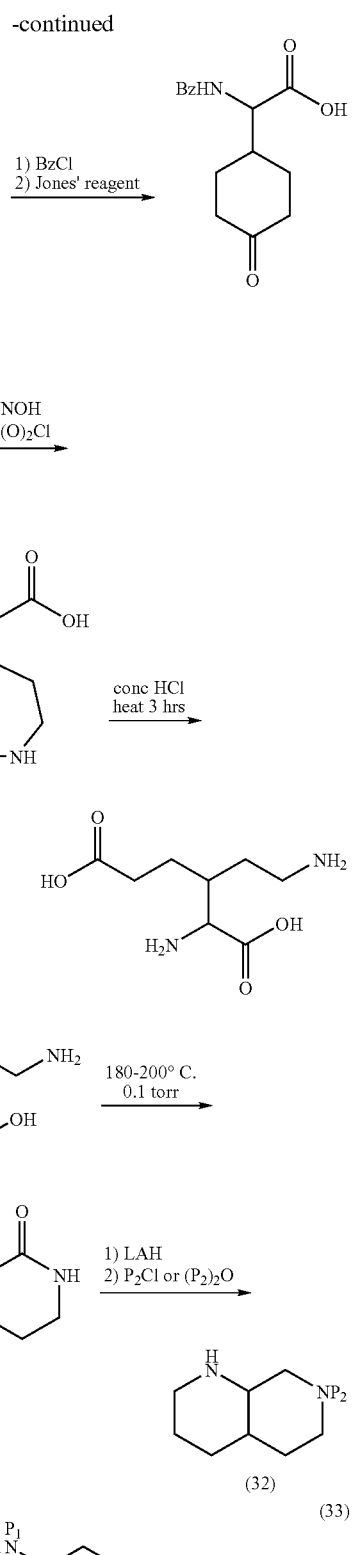

Bicyclic diamines of general formula (32), wherein $P_2$ is a nitrogen protecting group, can be prepared as described in (Org. Mass Spectrum. (1984) 19(9), 459-460). Amino(4-hydroxyphenyl)acetic acid, purchased commercially, can be treated with Raney nickel and heat to provide amino(4-hydroxycyclohexyl)acetic acid. Amino(4-hydroxycyclohexyl) acetic acid can be treated with benzoyl chloride and then oxidized with Jones' reagent to provide (benzoylamino)(4-oxocyclohexyl)acetic acid. (Benzoylamino)(4-oxocyclohexyl)acetic acid can be subjected to a Beckmann rearrangement using hydroxylamine and a sulfonyl chloride such as phenyl sulfonyl chloride to provide (benzoylamino)(7-oxo-4-azepanyl)acetic acid. (Benzoylamino)(7-oxo-4-azepanyl) acetic acid can be treated with concentrated HCl and heat to provide 2-amino-3-(2-aminoethyl)hexanedioic acid. 2-Amino-3-(2-aminoethyl)hexanedioic acid can be distilled at 180-200° C./0.1 torr to provide octahydro[1,7]naphthyridine-2,8-dione. Octahydro[1,7]naphthyridine-2,8-dione can be treated with lithium aluminum hydride and monoprotected with a nitrogen protecting reagent such as acetyl chloride/acetic anhydride, di-tert-butyl dicarbonate, benzyloxycarbonyl chloride, or benzyl bromide to provide bicyclic diamines of general formula (32).

Bicyclic amines of general formula (33), wherein $P_1$ and $P_2$ are independently selected from hydrogen or a nitrogen protecting group, can be prepared as described in (Frydman, et. al., JOC (1971) 36(3), 450-454.

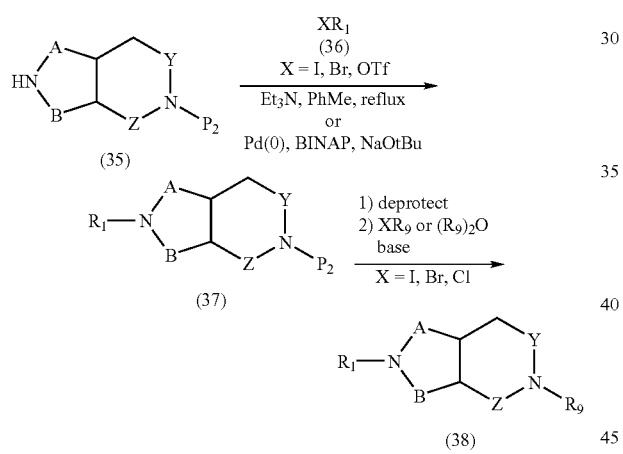

Bicyclic diamines of general formula (38), wherein A, B, Y, Z, $R_1$, and $R_9$ are as defined in formula I, can be prepared as described in Scheme 9. Bicyclic diamines of general formula (35) from Schemes 1-8, wherein $P_2$ is a nitrogen protecting group, can be treated with a heterocyclic halide of general formula (36) and a base such as triethyl amine to provide compounds of general formula (37). Alternatively, bicyclic diamines of general (Formula (35) can be treated with heterocyclic halides of general formula (36), a palladium catalyst, BINAP, and a base such as sodium tert-butoxide as described in (Wagaw and Buchwald, JOC (1996) 61, 7240-7241) to provide compounds of general formula (37). Compounds of general formula (37) can be deprotected and then optionally treated with alkylating or acylating agents to provide bicyclic diamines of general formula (38).

It may be preferable to effect transformations of the $R_3$, $R_4$, and $R_5$ substituents of $R_1$, wherein $R_1$, $R_3$, $R_4$, and $R_5$ are as defined in formula I, after $R_1$ has been coupled to a bicyclic diamine. As such, compounds of the present invention may be further transformed to other distinct compounds of the present invention. These transformations involve Stille, Suzuki, Heck, and Negishi coupling reactions all of which are well known to those skilled in the art of organic chemistry. Shown below in Schemes 10-12 are representative methods of such transformations of compounds of the present invention to other compounds of the present invention.

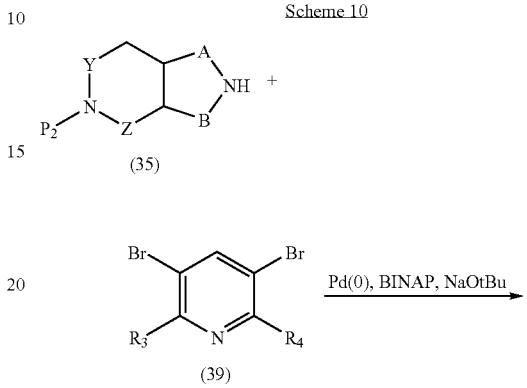

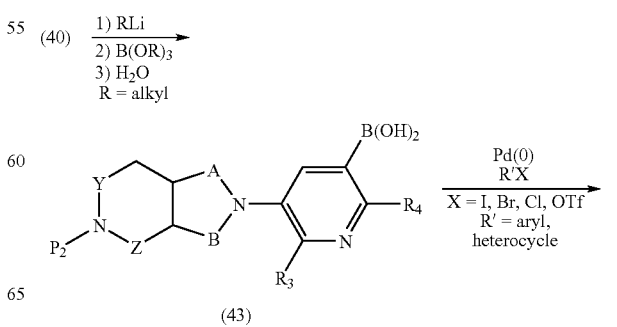

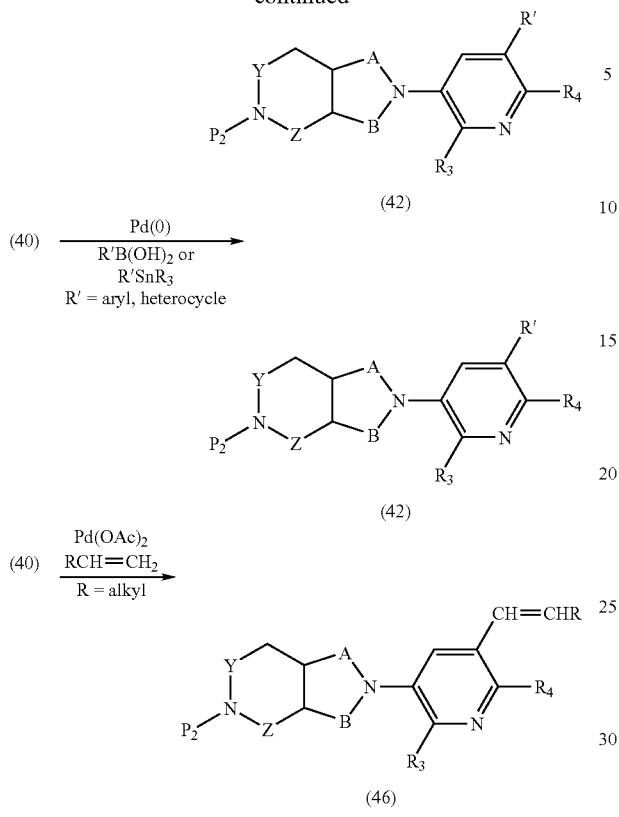

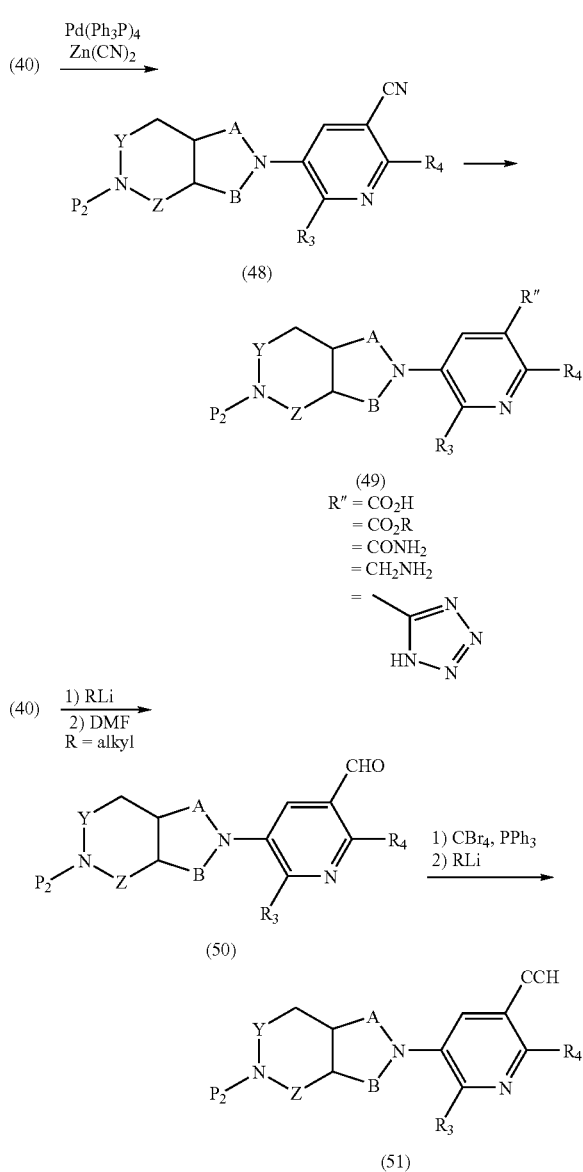

electrophiles to afford intermediates which can be further elaborated as described in Schemes 10-12.

Compounds of general formula (40), (42), and (46), wherein A, B, Y, Z, $R_3$, and $R_4$ are as defined in formula I, R is alkyl, and R' is an aryl group or a heterocycle, can be prepared as described in Scheme 10. Bicyclic diamines of general formula (35) from Schemes 1-8, wherein $P_2$ is a nitrogen protecting group, can be treated with BINAP, a palladium catalyst, sodium tert-butoxide, and a dibromoheterocycle such as a compound of general formula (39), to provide bromides of general formula (40). Bromides of general formula (40) can be treated with an organolithium reagent and trialkyltin chloride to provide stannanes of general formula (41). Stannanes of general formula (41) can be treated with a palladium catalyst and an aryl or heterocyclic halide (or triflate) to provide compounds of general formula (42).

Bromides of general formula (40) can also be treated with an organolitilium reagent, trialkoxy boranes, and water to provide boronic acids of general formula (43). Boronic acids of general formula (43) can be treated with a palladium catalyst and an aryl or heterocyclic halide (or triflate) to provide compounds of general formula (42).

Bromides of general formula (40) can also be treated with a palladium catalyst and aryl or heterocyclic boronic acids (or aryl or heterocyclic stannanes) to provide compounds of general formula (42).

Bromides of general formula (40) can also be treated with a palladium catalyst and alkenes or alkynes to provide compounds of general formula (46).

An alternate method for functionalizing heterocycles, defined as $R_1$ in formula I, that are coupled to bicyclic diamines from Schemes 1-8 involves ortho-directed metalation as described in (Gribble et al., Tetrahedron Lett. (1980) 21, 4137). The metalated species can be trapped with various Bromides of general formula (40) from Scheme 10, can be further elaborated to nitrites of general formula (48). Nitriles of general formula (48) can be subjected to conditions well known to those skilled in the art of organic chemistry to provide carboxylic acids, esters, amides, and aminomethyl compounds of general formula (49). Aminomethyl compounds of general formula (49) can be treated with trimethylsilyl azide as described in (Wittenberger and Donner, JOC (1993) 58, 4139) to provide tetrazoles of general formula (49).

Bromides of general formula (40) from Scheme 10, can also be further elaborated to aldehydes of general formula (50). Aldehydes of general formula (50) can be treated with carbon tetrabromide, triphenylphosphine, and butyllithium as described in (Tetrahedron Lett. (1972) 3769-3772) to provide terminal alkynes of general formula (51). Aldehydes of general formula (50) can also be elaborated in ways well known to those skilled in the art of organic chemistry such as formation of oximes, hydrazones, olefins, and mono and disubstituted amino compounds. Grignard reagents can also be added to aldehydes of general formula (50) to provide secondary alcohols which can be oxidized to ketones.

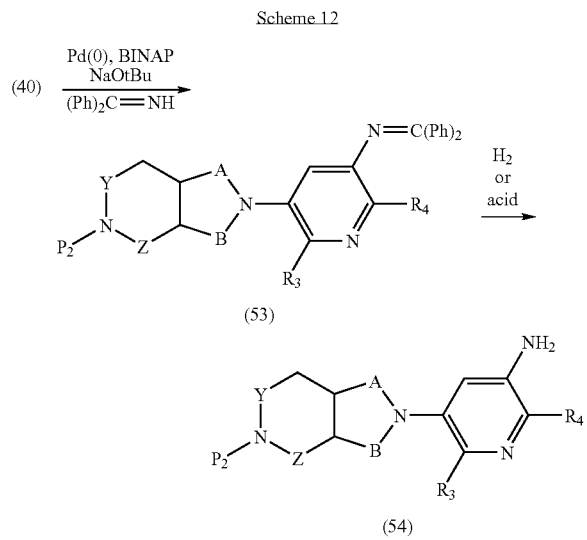

Scheme 12

Bromides of general formula (40) from Scheme (10), can be treated with diphenylmethanimine and then treated with acid or treated with a palladium catalyst under a hydrogen atmosphere to provide amines of general formula (54). Amines of general formula (54) can be engaged in acylation, sulfonylation, and/or alkylation processes well known to those skilled in the art of organic chemistry. Combinations of alkylations, sufonylations, and acylations may be employed to prepare other compounds of the present invention.

The compounds and processes of the present invention will be better understood in connection with the following Examples which are intended as an illustration of and not a limitation upon the scope of the invention.

Example 1 cis-2-(3-pyridinyl)octahydropyrrolo[3,4-c]pyrrole dihydrochloride

Example 1A cis-5-benzyltetrahydropyrrolo[3,4-c]-pyrrole-1,3(2H,3aH)-dione

1H-Pyrrole-2,5-dione (8.0 g, 82 mmol) in dichloromethane (220 mL) at 0° C. was treated with trifluoroacetic acid (0.93 g, 8.2 mmol) and then treated with N-benzyl-N-(methoxymethyl)-N-[(trimethylsilyl)methyl]amine (26 g, 110 mmol) prepared according to (Organic Synthesis (1988), 67, 133-135) in dichloromethane (15 mL) dropwise over 30 minutes. The mixture was allowed to stir at ambient temperature overnight and then concentrated under reduced pressure. The residue was triturated with ethyl acetate:hexane (3:7, 50 mL), cooled to 0° C. and filtered to provide the title compound as a white solid (5.86 g, 31% yield). MS (DCI/NH$_3$) m/z 231 (M+H)$^+$.

Example 1B cis-2-benzyloctahydropyrrolo[3,4-c]pyrrole

A suspension of lithium aluminum hydride (2.87 g, 76 mmol) in dry tetrahydrofuran (250 mL) was treated with the product from Example 1A (5.80 g, 25 mmol) portionwise. The mixture was heated at reflux for 3.5 hours, cooled in ice, and quenched by successive addition of water (2.9 mL), 15% NaOH (2.9 mL), and water (8.7 mL). The mixture was filtered and the solids rinsed with ether (200 mL). The filtrate was concentrated under reduced pressure to provide the title compound as a colorless oil (4.59 g, 90% yield). MS (DCI/NH$_3$) m/z 203 (M+H)$^+$.

Example 1C tert-butyl cis-5-benzylhexahydropyrrolo[3,4-c]pyrrole-2(1H)-carboxylate The product from Example 1B (4.59 g, 23 mmol) in dichloromethane (80 mL) was treated with di-tert-butyl dicarbonate (5.2 g 24 mmol). The mixture was stirred at ambient temperature for 1.5 hours and then concentrated under reduced pressure. The residue was purified by chromatography (SiO$_2$, hexane:ethyl acetate (7:3)) to provide the title compound as a colorless oil (4.89 g, 71% yield). MS (DCI/NH$_3$) m/z 303 (M+H)$^+$.

Example 1D tert-butyl cis-hexahydropyrrolo[3,4-c]pyrrole-2(1H)-carboxylate

The product from Example 1C (4.89 g, 16.2 mmol) in ethanol (150 mL) was treated with 10% Pd/C (0.45 g) at ambient temperature under a hydrogen (1 atm) overnight. The catalyst was removed by filtration through diatomaceous earth and the filtrate was concentrated under reduced pressure. The residue was passed through a small plug of silica gel with ether to provide the title compound as a white solid (3.01 g, 88% yield). $^1$H NMR (CDCl$_3$, 300 MHz) δ 1.46 (s, 9H), 2.75 (m, 4H), 3.09 (m, 2H), 3.20 (br d, J=11 Hz, 2H), 3.54 (m, 2H); MS (DCI/NH$_3$) m/z 213 (M+H)$^+$.

Example 1E tert-butyl cis-5-(3-pyridinyl)hexahydropyrrolo[3,4-c]pyrrole-2(1H)-carboxylate The product from Example 1D (0.52 g, 2.45 mmol) in toluene (30 mL) was concentrated by distillation under N$_2$ (1 atm) to a volume of ~20 mL. The solution was cooled to 35° C. and treated with tris(dibenzylideneacetone)dipalladium (0) (Pd$_2$(dba)$_3$) (45 mg, 0.049 mmol) available from Alfa Aesar and 2,2'-bis(diphenylphosphino)-1,1'-binaphthyl (BINAP) (75 mg, 0.12 mmol) available from Strem Chemicals. The mixture was warmed to 85° C. for 10 minutes and then cooled to 35° C. Sodium tert-butoxide (371 mg, 3.86 mmol) and 3-bromopyridine (426 mg, 2.70 mmol), both obtained from the Aldrich Chemical Co. were added, and the mixture warmed to 85° C. under N$_2$ for 2 hours. The mixture was cooled to 30° C. and filtered through diatomaceous earth with an ethyl acetate (100 mL) rinse. The filtrate was concentrated under reduced pressure to provide a red oil, which was purified by chromatography (SiO$_2$, 6% MeOH/CH$_2$Cl$_2$) to provide the title compound as a pale yellow solid (0.62 g, 87% yield). MS (DCI/NH$_3$) m/z 290 (M+H)$^+$.

Example 1F cis-2-(3-pyridinyl)octahydropyrrolo[3,4-c]pyrrole dihydrochloride The product from Example 1E (310 mg, 1.07 mmol) in ethanol (5 mL) was treated with a solution of HCl in 1,4-dioxane (4M, 2 mL, 8 mmol) at ambient temperature for 4 hours. The solution was concentrated under reduced pressure, and the residual solid was crystallized from ethanol:ethyl acetate (1:5) to provide the title compound as a white solid (203 mg, 72% yield). mp 250-252° C. (dec); $^1$H NMR (CD$_3$OD, 300 MHz) δ 3.32 (m, 4H), 3.57 (dd, J=11, 3 Hz, 2H), 3.65 (m, 4H), 7.78 (m, 1H), 7.83 (dd, J=8, 5 Hz, 1H), 8.09 (d, J=5 Hz, 1H), 8.12 (d, J=3 Hz, 1H); MS (DCI/NH$_3$) m/z 190 (M+H)$^+$; Anal. calculated for C$_{11}$H$_{15}$N$_3$.2HCl: C, 50.39; H, 6.54; N, 16.03. Found: C, 50.25; H, 6.36; N, 15.95.

Example 2 cis-2-methyl-5-(3-pyridinyl)octahydropyrrolo[3,4-c] pyrrole hydrochloride

The product from Example 1E (200 mg, 0.69 mmol) was treated with 88% formic acid (1.8 mL) and 37% formalin (3.5 mL) and then warmed to 95° C. for 3 hours. The solution was concentrated under reduced pressure and the resulting pale yellow solid was taken up in 20% aqueous KOH (5 mL) and extracted into ethyl acetate (2×20 mL). The organic phases were combined, dried (MgSO$_4$), and concentrated under reduced pressure. The residue was dissolved in ethanol (10 mL), treated with HCl/1,4-dioxane (4M, 2 mL), and concentrated under reduced pressure to leave an oily solid. The oily solid was crystallized from ethanol:ethyl acetate (1:20) to provide the title compound as an off-white, hygroscopic solid. mp 207-209° C.; $^1$H NMR (free base, CDCl$_3$, 300 MHz) δ 2.35 (s, 3H), 2.48 (dd, J=9, 3 Hz, 2H), 2.72 (dd, J=10, 8 Hz, 2H), 3.00 (m, 2H), 3.23 (dd, J=10, 3 Hz, 2H), 3.44 (m, 2H), 6.90 (br d, J=9 Hz, 1H), 7.11 (dd, J=8.4 Hz, 1H), 7.98 (d, J=4 Hz, 1H), 8.06 (d, J=3 Hz, 1H); MS (DCI/NH$_3$) m/z 190 (M+H)$^+$; Anal. calculated for C$_{12}$H$_{17}$N$_3$.2HCl.0.8H$_2$O: C, 49.59; H, 7.14; N, 14.46. Found: C, 49.44; H, 6.79; N, 14.29.

Example 3 cis-2-(6-chloro-3-pyridinyl)octahydropyrrolo[3,4-c] pyrrole hydrochloride

Example 3A tert-butyl cis-5-(6-chloro-3-pyridinyl)hexahydropyrrolo[3,4-c]pyrrole-2(1H)-carboxylate The product from Example 1D (1.70 g, 8 mmol) and 2-chloro-5-iodopyridine (2.11 g, 8.8 mmol) prepared as described in (Tetrahedron Lett. (1993), 34, 7493-7496) were processed as described in Example 1E to provide the title compound as a yellow solid (1.18 g, 46% yield). MS (DCI/NH$_3$) m/z 324, 326 (M+H)$^+$.

Example 3B cis-2-(6-chloro-3-pyridinyl)octahydropyrrolo[3,4-c] pyrrole hydrochloride The product from Example 3A (360 mg, 1.11 mmol) in dichloromethane (20 mL) was treated with a solution of HCl in 1,4-dioxane (4M, 2 mL, 8 mmol). After stirring at ambient temperature for 2 hours, the mixture was concentrated under reduced pressure. The yellow solid was crystallized from ethanol:ethyl acetate (2:1) after carbon treatment to provide the title compound as a white solid (198 mg, 69% yield). mp 230-236° C. (dec); $^1$H NMR (CD$_3$OD, 300 MHz) δ 3.28 (m, 4H), 3.49 (m, 4H), 3.62 (m, 2H), 7.45 (dd, J=9, 3 Hz, 1H), 7.52 (d, J=9 Hz, 1H), 7.90 (d, J=3 Hz, 1H); MS (DCI/NH$_3$) m/z 224/226 (M+H)$^+$; Anal. calculated for C$_{11}$H$_{14}$N$_3$Cl.HCl: C, 50.78; H, 5.81; N, 16.15. Found: C, 50.54; H, 5.86; N, 16.03.

Example 4 cis-2-(6-chloro-3-pyridinyl)-5-methyloctahydropyrrolo[3,4-c]pyrrole dihydrochloride

Example 4A cis-2-(6-chloro-3-pyridinyl)-5-methyloctahydropyrrolo[3,4-c]pyrrole The product from Example 3A (207 mg, 0.64 mmol) was treated with 88% formic acid (1.8 mL) and formalin (3.5 mL) and then heated at 95° C. for 2 hours. The solution was concentrated under reduced pressure and the resulting solid was purified by chromatography (SiO$_2$, CH$_2$Cl$_2$:MeOH: Et$_2$NH, 94:5:1) to provide the title compound (135 mg, 88% yield). (DCI/NH$_3$) m/z 238/240 (M+H)$^+$.

Example 4B cis-2-(6-chloro-3-pyridinyl)-5-methyloctahydropyrrolo[3,4-c]pyrrole dihydrochloride The product from Example 4A (30 mg, 0.12 mmol) in ethyl acetate (2 mL) was treated with excess HCl/1,4-dioxane (4M, 0.7 mL). Additional ethyl acetate (2 mL) was added and after a few minutes solids began to separate. The mixture was cooled in ice and filtered to provide the title compound as a hygroscopic white solid (25 mg, 64% yield). $^1$H NMR (CD$_3$OD, 300 MHz) δ 2.92 & 2.96 (two s, 3H, endo and exo salts), 3.25 (m, 2H), 3.41 (m, 4H), 3.62 (m, 3H), 3.98 (m, 1H), 7.48 (m, 2H), 7.89 (t, J=3 Hz, 1H); MS (DCI/NH$_3$) m/z 238/240 (M+H)$^+$; Anal. calculated for C$_{12}$H$_{16}$N$_3$Cl.1.8HCl: C, 47.51; H, 5.91; N, 13.85. Found: C, 47.88; H, 5.81; N, 13.68.

Example 5 cis-2-(3-quinolinyl)octahydropyrrolo[3,4-c]pyrrole dihydrochloride

Example 5A tert-butyl cis-5-(3-quinolinyl)hexahydropyrrolo[3,4-c]pyrrole-2(1H)-carboxylate The product from Example 1D (250 mg, 1.18 mmol) and 3-bromoquinoline (270 mg, 1.3 mmol), available from the Aldrich Chemical Co., were processed as described in

Example 5B cis-2-(3-quinolinyl)octahydropyrrolo[3,4-c]pyrrole dihydrochloride The product from Example 5A (360 mg, 1.06 mmol) in ethyl acetate:ethanol (1:1, 20 mL) was treated with HCl/1,4-dioxane (4M, 3 mL, 12 mmol). After stirring at ambient temperature for 2 hours, the mixture was concentrated under reduced pressure. The resulting solid was crystallized from ethanol:diethyl ether to provide the title compound as a white solid (198 mg, 68% yield). mp>260° C.; $^1$H NMR ($CD_3OD$, 300 MHz) δ 3.38 (m, 4H), 3.70 (m, 6H), 7.69 (m, 2H), 8.08 (m, 2H), 8.15 (br s, 1H), 8.82 (d, J=3 Hz, 1H); MS (DCI/$NH_3$) m/z 240 (M+H)$^+$; Anal. calculated for $C_{15}H_{17}N_3$·2HCl: C, 56.88; H, 6.28; N, 13.27. Found: C, 57.18; H, 6.11; N, 13.46.

Example 6 cis-2-(5-hydroxy-3-pyridinyl)octahydropyrrolo[3,4-c]pyrrole dihydrochloride

Example 6A tert-butyl cis-5-[5-(benzyloxy)-3-pyridinyl]hexahydropyrrolo[3,4-c]pyrrole-2(1H)-carboxylate The product from Example 1D (1.0 g, 4.7 mmol) and 3-(benzyloxy)-5-bromopyridine (1.37 g, 5.2 mmol), prepared according to (U.S. Pat. No. 5,733,912), were processed as described in Example 1E to provide the title compound as a solid (1.5 g, 81% yield). MS (DCI/$NH_3$) m/z 396 (M+H)$^+$.

Example 6B tert-butyl cis-5-(5-hydroxy-3-pyridinyl)hexahydropyrrolo[3,4-c]pyrrole-2(1H)-carboxylate The product from Example 6A (1.3 g, 3.8 mmol) in 2-propanol (100 mL) was treated with 10% Pd/C (0.65 g) and then shaken under a hydrogen (4 atm) at ambient temperature for 18 hours. The catalyst was removed by filtration, and the filtrate was concentrated under reduced pressure. The residue was triturated with a minimum amount of ethyl acetate and filtered to provide the title compound as a solid (0.76 g, 66% yield). $^1$H NMR ($CD_3OD$, 300 MHz) δ 3.05 (m, 2H), 3.20 (dd, J=10, 5 Hz, 2H), 3.28 (m, 2H), 3.51 (dd, J=10, 7 Hz, 2H), 3.64 (m, 2H), 6.42 (t, J=3 Hz, 1H), 7.40 (d, J=3 Hz, 1H), 7.43 (d, J=3 Hz, 1H).

Example 6C cis-2-(5-hydroxy-3-pyridinyl)octahydropyrrolo[3,4-c]pyrrole dihydrochloride The product from Example 6B (150 mg, 0.49 mmol) in ethyl acetate:methanol (1:2, 15 mL) was treated with HCl/1,4-dioxane (4M, 1 mL, 4 mmol). The mixture was stirred at ambient temperature overnight and then cooled in ice to complete precipitation. The mixture was filtered to provide the title compound as a white solid (136 mg, 99% yield). $^1$H NMR ($CD_3OD$, 300 MHz) δ 3.30 (m, 4H), 3.51 (dd, J=10, 3 Hz, 2H), 3.60 (m, 4H), 7.06 (t, J=3 Hz, 1H), 7.62 (d, J=3 Hz, 1H), 7.69 (d, J=3 Hz, 1H); MS (DCI/$NH_3$) m/z 206 (M+H)$^+$; Anal. calculated for $C_{11}H_{15}N_3O$·2HCl·0.5$H_2O$: C, 46.01; H, 6.32; N, 14.63. Found: C, 46.29; H, 6.49; N, 14.33.

Example 7 cis-2-(5-methoxy-3-pyridinyl)octahydropyrrolo[3,4-c]pyrrole dihydrochloride

Example 7A 3-bromo-5-methoxypyridine

A solution of methanol (180 mL) was treated with sodium spheres (4.7 g, 0.20 mol) portionwise, evaporated to dryness, azeotroped with toluene (100 mL), and then concentrated under reduced pressure. The sodium methoxide in dry DMF (130 mL) was treated with 3,5-dibromopyridine (32 g, 135 mmol), from Avocado Chemicals. After heating at 70° C. for 4 hours, the mixture was poured onto ice/water (300 g) and filtered. The filter cake was dried under reduced pressure to provide the title compound (15.6 g, 62% yield). MS (DCI/$NH_3$) m/z 188/190 (M+H)$^+$.

Example 7B tert-butyl cis-5-(5-methoxy-3-pyridinyl)hexahydropyrrolo[3,4-c]pyrrole-2(1H)-carboxylate The product from Example 1D (300 mg, 1.4 mmol) and the product from Example 7A (290 mg, 1.5 mmol) were processed as described in Example 1E to provide the title compound (310 mg, 69% yield). MS (DCI/$NH_3$) m/z 320 (M+H)$^+$.

Example 7C cis-2-(5-methoxy-3-pyridinyl)octahydropyrrolo[3,4-c]pyrrole dihydrochloride The product from Example 7B (310 mg, 0.97 mmol) was processed as described in Example 5B to provide the title compound as a white crystalline solid (150 mg, 53% yield). $^1$H NMR ($CD_3OD$, 300 MHz) δ 3.32 (m, 4H), 3.58 (dd, J=10, 3 Hz, 2H), 3.63 (m, 4H), 4.00 (s, 3H), 7.21 (t, J=3 Hz, 1H), 7.78 (d, J=3 Hz, 1H), 7.85 (d, J=3 Hz, 1H); MS (DCI/$NH_3$) m/z 220 (M+H)$^+$; Anal. calculated for $C_{12}H_{17}N_3O$·2HCl: C, 49.33; H, 6.55; N, 14.38. Found: C, 49.06; H, 6.48; N, 14.19.

Example 8 cis-2-(5-ethoxy-3-pyridinyl)octahydropyrrolo[3,4-c]pyrrole dihydrochloride

Example 8A 3-bromo-5-ethoxypyridine

Ethanol and 3,5-dibromopyridine were processed as described in Example 7A to provide the title compound (69% yield). MS (DCI/$NH_3$) m/z 202/204 (M+H)$^+$.

Example 8B tert-butyl cis-5-(5-ethoxy-3-pyridinyl)hexahydropyrrolo[3,4-c]pyrrole-2(1H)-carboxylate The product from Example 1D (600 mg, 2.8 mmol) and the product from Example 8A (625 mg, 3.1 mmol) were processed as described in Example 1E to provide the title compound (600 mg, 64% yield). MS (DCI/NH$_3$) m/z 334 (M+H)$^+$.

Example 8C cis-2-(5-ethoxy-3-pyridinyl)octahydropyrrolo[3,4-c]pyrrole dihydrochloride The product from Example 8B (600 mg, 1.8 mmol) in ethyl acetate:ethanol (3:1, 20 mL) was treated with HCl/1,4-dioxane (4M, 3 mL, 12 mmol). After heating to reflux for 1.5 hours, the mixture was cooled in ice and filtered to provide the title compound as a white crystalline solid (435 mg, 79% yield). mp 226-227° C.; $^1$H NMR (CD$_3$OD, 300 MHz) δ 1.57 (t, J=7 Hz, 3H), 3.30 (m, 4H), 3.55 (dd, J=10, 3 Hz, 2H), 3.61 (m, 4H), 4.25 (q, J=7 Hz, 2H), 7.19 (t, J=3 Hz, 1H), 7.78 (d, J=3 Hz, 1H), 7.84 (d, J=3 Hz, 1H); MS (DCI/NH$_3$) m/z 234 (M+H)$^+$; Anal. calculated for C$_{13}$H$_{19}$N$_3$O.2 HCl.0.5H$_2$O: C, 49.53; H, 7.03; N, 13.33. Found: C, 49.37; H, 6.90; N, 13.35.

Example 9 cis-2-(5-propoxy-3-pyridinyl)octahydropyrrolo[3,4-c]pyrrole semi(fumarate)

Example 9A 3-bromo-5-propoxypyridine n-Propanol and 3,5-dibromopyridine were processed as described in Example 7A except that the heating time was extended to 4 hours. The reaction mixture was quenched onto ice/water, extracted with ethyl ether, and concentrated under reduced pressure. The residue was purified on silica gel (hexanes:ethyl acetate, 8:2) to provide the title compound as a colorless oil (25% yield). MS (DCI/NH$_3$) m/z 216/218 (M+H)$^+$.

Example 9B tert-butyl cis-5-(5-propoxy-3-pyridinyl)hexahydropyrrolo[3,4-c]pyrrole-2(1H)-carboxylate The product from Example 1D (300 mg, 1.4 mmol) and the product from Example 9A (333 mg, 1.5 mmol) were processed as described in Example 1E to provide the title compound (130 mg, 27% yield). MS (DCI/NH$_3$) m/z 348 (M+H)$^+$.

Example 9C cis-3-(5-propyloxy-3-pyridinyl)-3,7-diazabicyclo[3.3.0]octane semi(fumarate)

The product from Example 9B (130 mg, 0.38 mmol) in ethyl acetate (8 mL) and ethanol (2 mL) was treated with HCl/1,4-dioxane (4M, 1 mL, 1 mmol). After heating at reflux for 3 hours, the mixture was concentrated under reduced pressure to provide a hygroscopic oil. The oil was coated onto silica gel and eluted with CH$_2$Cl$_2$:EtOH:NH$_4$OH (96:3:0.5) to provide the free base (70 mg). The free base in ethyl acetate (8 mL) and methanol (1 mL) was treated with a solution of fumaric acid (34 mg, 1 eq) in methanol (1.2 mL) dropwise. The solution was diluted with diethyl ether and scratched to induce crystallization. The mixture was filtered and the filter cake dried under reduced pressure to provide the title compound (50 mg, 31% yield). $^1$H NMR (CD$_3$OD, 300 MHz) δ 1.06 (t, J=7 Hz, 3H), 1.81 (m, 2H), 3.20 (m, 4H), 3.40 (m, 4H), 3.54 (m, 2H), 3.99 (t, J=7 Hz, 2H), 6.65 (s, 1H), 6.68 (t, J=3 Hz, 1H), 7.62 (m, 2H); MS (DCI/NH$_3$) m/z 248 (M+H)$^+$; Anal. calculated for C$_{14}$H$_{21}$N$_3$O.0.5C$_4$H$_4$O$_4$: C, 62.93; H, 7.59; N, 13.76. Found: C, 62.81; H, 7.57; N, 13.99.

Example 10 cis-2-(6-chloro-5-methoxy-3-pyridinyl)octahydropyrrolo[3,4-c]pyrrole dihydrochloride

Example 10A 3-bromo-5-hydroxypyridine 3-(Benzyloxy)-5-bromopyridine (15.0 g, 56.8 mmol), prepared as described in (U.S. Pat. No. 5,733,912), in 30% HBr/acetic acid (200 mL) was stirred at room temperature for 16 hours. The reaction mixture was diluted with diethyl ether (500 mL) and the resulting white solid (12.9 g) was isolated by filtration. The solid in methanol (300 mL) was treated with concentrated NH$_4$OH (50 mL). After stirring at ambient temperature for 12 hours, the reaction mixture was concentrated in under reduced pressure to provide the title compound as a white solid (9.8 g, 89%). MS (DCI/NH$_3$) m/e 174/176 (M+H)$^+$.

Example 10B 5-bromo-2-chloro-3-hydroxypyridine

The product from Example 10A (9.8 g, 56.3 mmol) was treated with aqueous NaOCl (35 mL of 10% solution), water (100 mL), and NaOH (2.40 g, 100 mmol), The reaction mixture was stirred at ambient temperature for 16 hours, quenched with acetic acid (5 ml), and then extracted with ethyl acetate (500 mL). The organic phase was dried (MgSO$_4$) and concentrated under reduced pressure. The residue was purified on SiO$_2$ (3% MeOH/CH$_2$Cl$_2$) to provide the title compound as a yellow solid (11.20 g, 96%). MS (DCI/NH$_3$) m/e 208, 210 (M+H)$^+$.

Example 10C 5-bromo-2-chloro-3-methoxypyridine

A suspension of sodium hydride (181 mg, 7.5 mmol) in dry DMF (30 mL) and diethyl ether (6 mL) was treated with the product from Example 10B (1.2 g, 5.8 mmol) in diethyl ether (5 mL). After stirring at ambient temperature for 30 minutes, the reaction mixture was treated with a solution of iodomethane (1.06 g, 7.5 mmol) in diethyl ether (3 mL) and stirring was continued for 30 minutes longer. The mixture was quenched with water (20 mL), extracted with diethyl ether (100 mL), dried (MgSO$_4$), and concentrated under reduced pressure. The residue was purified on SiO$_2$ (ethyl acetate: hexane, 1:4) to provide the title compound as a colorless oil (0.83 g, 65% yield). MS (DCI/NH$_3$) m/z 222/224/226 (M+H)$^+$.

Example 10D tert-butyl cis-5-(6-chloro-5-methoxy-3-pyridinyl) hexahydropyrrolo[3,4-c]pyrrole-2(1H)-carboxylate The product from Example 1D (864 mg, 4.1 mmol) and the product from Example 10C (1.0 g, 4.5 mmol) were processed as described in Example 1E to provide the title compound (480 mg, 34% yield). MS (DCI/NH$_3$) m/z 354/356 (M+H)$^+$.

Example 10E cis-2-(6-chloro-5-methoxy-3-pyridinyl)octahydropyrrolo[3,4-c]pyrrole dihydrochloride The product from Example 10D (480 mg, 1.36 mmol) was processed as described in Example 5B to provide the title compound as a white solid (325 mg, 73%). $^1$H NMR (CD$_3$OD, 300 MHz) δ 3.28 (m, 4H), 3.51 (m, 4H), 3.63 (m, 2H), 3.98 (s, 3H), 6.96 (d, J=3 Hz, 1H), 7.47 (d, J=3 Hz, 1H); MS (DCI/NH$_3$) m/z 254/256 (M+H)$^+$; Anal. calculated for C$_{12}$H$_{16}$N$_3$OCl.2HCl: C, 44.12; H, 5.55; N, 12.86. Found: C, 44.01; H, 5.69; N, 12.72.

Example 11 cis-2-(6-chloro-5-methyl-3-pyridinyl)octahydropyrrolo[3,4-c]pyrrole dihydrochloride

Example 11A 5-bromo-2-hydroxy-3-methylpyridine

2-Amino-5-bromo-3-methylpyridine (5.0 g, 26.7 mmol) in 2.6M H$_2$SO$_4$ (70 mL) was treated with sodium nitrite (5.0 g, 72.5 mmol) in water (10 mL) dropwise at 0° C. The mixture was allowed to warm to ambient temperature and stir for 1.5 hours. The mixture was filtered and the filtercake washed with cold water. The filtercake was dissolved in dichloromethane (100 mL), dried (MgSO$_4$), and concentrated to provide the title compound (4.2 g, 84% yield). MS (DCI/NH$_3$) m/z 188/190 (M+H)$^+$.

Example 11B 5-bromo-2-chloro-3-methylpyridine

The product from Example 11A (4.1 g, 221.8 mmol) in DMF (40 mL) was treated with phosphorus oxychloride (10 g, 65.4 mmol) dropwise at 0° C. After heating at 120° C. for 2 hours, the mixture was cooled and poured onto ice/water. The mixture was made basic with NH$_4$OH, filtered, and the filtercake washed with ice water. The obtained solid was dissolved in dichloromethane (100 mL), washed with brine, and dried (MgSO$_4$). The dried solution was filtered through a pad of silica using dichloromethane and the filtrate concentrated to provide the title compound as a white solid (3.48 g, 78% yield): $^1$H NMR (CDCl$_3$, 300 MHz) δ 2.39 (s, 3H), 7.70 (m, 1H), 8.31, d, J.=3 Hz, 1H).

Example 11C tert-butyl cis-5-(6-chloro-5-methyl-3-pyridinyl) hexahydropyrrolo[3,4-c]pyrrole-2(1H)-carboxylate The product from Example 1D (320 mg, 1.5 mmol) and the product from Example 11B (340 mg, 1.7 mmol) were processed as described in Example 1E to provide the title compound (190 mg, 37% yield). MS (DCI/NH$_3$) m/z 338/340 (M+H)$^+$.

Example 11D cis-2-(6-chloro-5-methyl-3-pyridinyl)octahydropyrrolo[3,4-c]pyrrole dihydrochloride The product from Example 11C (190 mg, 0.56 mmol) was processed as described in Example 8C to provide, after crystallization from ethyl acetate/methanol, the title compound (135 mg, 77% yield). $^1$H NMR (CD$_3$OD, 300 MHz) δ 2.42 (s, 3H), 3.28 (m, 4H), 3.50 (m, 4H), 3.62 (m, 2H), 7.46 (br s, 1H), 7.78 (br d. J=3 Hz, 1H); MS (DCI/NH$_3$) m/z 338/340 (M+H)$^+$; Anal. calculated for C$_{12}$H$_{16}$N$_3$Cl.2 HCl: C, 46.40; H, 5.84; N, 13.53. Found: C, 46.55; H, 5.93; N, 13.54.

Example 12 cis-2-[5-(2,2,2-trifluoroethoxy)-3-pyridinyl]octahydropyrrolo[3,4-c]pyrrole dihydrochloride

Example 12A 3-bromo-5-(2,2,2-trifluoroethoxy)pyridine 2,2,2-Trifluoroethanol and 3,5-dibromopyridine were processed as described in Example 7A except that the heating time was extended to 20 hours at 100° C. The reaction was quenched onto ice/water, extracted with ethyl ether, and concentrated. The residue was purified on silica gel (hexanes: ethyl acetate, 8:2) to provide the title compound as a colorless oil (70% yield). MS (DCI/NH$_3$) m/z 256/258 (M+H)$^+$.

Example 12B tert-butyl cis-5-[5-(2,2,2-trifluoroethoxy)-3-pyridinyl]hexahydropyrrolo[3,4-c]pyrrole-2(1H)-carboxylate The product from Example 1D (300 mg, 1.4 mmol) and the product from Example 12A (397 mg, 1.5 mmol) were processed as described in Example 1E to provide the title compound (480 mg, 88% yield).

Example 12C cis-2-[5-(2,2,2-trifluoroethoxy)-3-pyridinyl]octahydropyrrolo[3,4-c]pyrrole dihydrochloride The product from Example 12B (480 mg, 1.24 mmol) was processed as described in Example 8C to provide, after crystallization from ethyl acetate/methanol, the title compound (240 mg, 54% yield). mp 233-234° C. (dec); $^1$H NMR (CD$_3$OD, 300 MHz) δ 3.32 (m, 4H), 3.63 (m, 6H), 4.85 (q, J=8 Hz, 2H), 7.34 (t, J=3 Hz, 1H), 7.89 (d, J=3 Hz, 1H), 7.97 (d, J=3 Hz, 1H); MS (DCI/NH$_3$) m/z 288 (M+H)$^+$: Anal. calculated for C$_{13}$H$_{16}$N$_3$OF$_3$.2HCl: C, 43.35; H, 5.04; N, 11.67. Found: C, 43.27; H, 5.23; N, 11.46.

Example 13 cis-5-(6-chloro-3-pyridinyl)octahydropyrrolo[3,4-b]pyrrole hydrochloride

Example 13A cis-1-benzyl-5-(6-chloro-3-pyridinyl)octahydropyrrolo[3,4-b]pyrrole cis-1-Benzyloctahydropyrrolo[3,4-b]pyrrole (500 mg, 2.48 mmol), prepared as described in (U.S. Pat. No. 5,071,999), and 2-chloro-5-iodopyridine (643 mg, 2.69 mmol), prepared as described in (Tetrahedron Lett. (1993), 34, 7493-7496), were processed as described in Example 1E to provide the title compound as a tan solid (508 mg, 65% yield). MS (DCI/NH$_3$) m/z 314, 316 (M+H)$^+$.

Example 13B cis-7-(6-chloro-3-pyridinyl)-2,7-diazabicyclo[3.3.0]octane

The product from Example 13A (506 mg, 1.62 mmol) in chloroform (10 mL) was treated with 1-chloroethyl chloroformate (Aldrich; 1.35 mL, 12.5 mmol) at ambient temperature for 15 minutes and then warmed to reflux for 1 hour. The mixture was concentrated under reduced pressure, and the residue was stirred with methanol (10 mL) for 60 hours. Following concentration of the solution under reduced pressure, the residue was purified by chromatography (SiO$_2$, 95:5:0.5 CH$_2$Cl$_2$:MeOH:NH$_4$OH) to yield the title compound as an oil that solidified upon standing (222 mg, 61% yield). MS (DCI/NH$_3$) m/z 224, 226 (M+H)$^+$.

Example 13C cis-5-(6-chloro-3-pyridinyl)octahydropyrrolo[3,4-b]pyrrole hydrochloride

The product from Example 13B (202 mg, 0.906 mmol) was treated with a solution of HCl in 1,4-dioxane (Aldrich; 4 M, 240 μL, 0.96 mmol) as described in Example 1F to provide the title compound as a white solid (151 mg, 64% yield). $^1$H NMR (CD$_3$OD, 300 MHz) δ 2.05 (m, 1H), 2.36 (m, 1H), 3.37 (m, 6H), 3.86 (d, J=12 Hz, 1H), 4.42 (t, J=6 Hz, 1H), 7.23 (dd, J=9, 3 Hz, 1H), 7.29 (d, J=9 Hz, 1H), 7.83 (d, J=3 Hz, 1H); MS (DCI/NH$_3$) m/z 224, 226 (M−H)$^+$; Anal. Calculated for C$_{11}$H$_{14}$ClN$_3$.HCl: C, 50.78; H, 5.81; N, 16.15. Found: C, 50.73; H, 5.86; N, 16.12.

Example 14

(3aR,6aR)-5-(6-chloro-3-pyridinyl)octahydropyrrolo[3,4-b]pyrrole dihydrochloride

Example 14A ethyl {[(1R)-1-phenylethyl]amino}acetate

Ethyl bromoacetate (4.14 g; 24.8 mmol) was treated with (R) α-methylbenzylamine (3 g, 24.8 mmol) and ethyldiisopropylamine (3.2 g; 24.8 mmol) in toluene (100 mL). After heating at reflux for 18 hours, the mixture was cooled to room temperature and concentrated under reduced pressure. The residue was purified by flash chromatography (SiO$_2$, 20% ethyl acetate/pentane) to provide the title compound (3.2 g, 63% yield). MS (DCI/NH$_3$) m/z 208 (M+H)$^+$.

Example 14B

{[(1R)-1-phenylethyl]amino}acetic acid

The product from Example 14A (4.5 g; 15.6 mmol) in water (100 mL) was heated to reflux for 18 hours. The mixture was cooled to 30° C. and concentrated under reduced pressure to provide the title compounds as a white solid (2.7 g; 80% yield). MS (DCI/NH$_3$) m/z 180 (M+H)$^+$.

Example 14C ethyl cis-1-[(1R)-1-phenylethyl]hexahydropyrrolo[3,4-b]pyrrole-5(1H)-carboxylate The product from Example 14B (27.5 g, 154 mmol) and ethyl allyl(2-oxoethyl)carbamate (26.3 g, 154 mmol), prepared as described in (U.S. Pat. No. 5,071,999), in toluene (500 mL) were heated at reflux for 17 hours. The solvent was evaporated under reduced pressure to provide the crude product (45 g) as a nearly 1:1 mixture of diastereomers. These were separated by flash chromatography on silica gel, eluting with 30% ethyl acetate in pentane.

The more mobile diastereomer was obtained as a thick syrup (R$_f$=0.42, pentane:ethyl acetate (3:7) 17 g, 38% yield). The stereocenters were determined to be (R,R) using X-Ray diffraction as described in Example 14E. MS (DCI/NH$_3$) m/z 289 (M+H)$^+$.

The less mobile diastereomer was obtained as a thick syrup (R$_f$=0.21, pentane:ethyl acetate (3:7) 17.8 g, 40% yield). The stereocenters were determined to be (S,S) using X-Ray diffraction as described in Example 15B. MS (DCI/NH$_3$) m/z 289 (M+H)$^+$.

Example 14D

(3aR,6aR)-1-[(1R)-1-phenylethyl]octahydropyrrolo[3,4-b]pyrrole

The more mobile diastereomer from Example 14C (17 g, 59.0 mmol) in hydrochloric acid (12N, 200 mL) was heated in an oil bath at 120° C. for 20 hours. The mixture was cooled to 20° C. and concentrated under reduced pressure to remove excess HCl. The residue was taken in 10% Na$_2$CO$_3$ (100 mL) and extracted with CH$_2$Cl$_2$ (3×200 mL). The organic layers were combined, washed with brine, dried (Na$_2$CO$_3$), and concentrated. The residue was purified by chromatography (SiO$_2$, eluted with CH$_2$C$_2$:MeOH:NH$_4$OH; 90:10:1) to afford the title compound as a brownish oil (11.4 g, 89% yield). MS (DCI/NH$_3$) m/z 217 (M+H)$^+$.

Example 14E

(3aR,6aR)-5-[(4-nitrophenyl)sulfonyl]-1-[(1R)-1-phenylethyl]octahydropyrrolo[3,4-b]pyrrole The product from Example 14D was processed as described in Example 15B to provide the title compound. The stereocenters were determined to be (R,R) using X-ray diffraction as described in Example 15B.

Example 14F (3aR,6aR)-1-[(1R)-1-phenylethyl]-5-(trifluoroacetyl) octahydropyrrolo[3,4-b]pyrrole The product from Example 14D (11.3 g, 52 mmol) and triethylamine (6.8 g, 68 mmol) in anhydrous THF (200 mL) at 0-5° C. was treated with trifluoroacetic anhydride (25.2 g, 63 mmol) dropwise. The reaction mixture was allowed to warm to room temperature overnight. The THF was removed under reduced pressure and replaced with $CH_2Cl_2$ (200 mL). The methylene chloride was washed with brine, dried ($MgSO_4$), and concentrated. The residue was purified using chromatography ($SiO_2$, eluting with 5-15% ethyl acetate/hexanes) to provide the title compound as a light yellow oil (13.7 g, 84% yield). MS (DCI/$NH_3$) m/z 313 $(M+H)^+$.

Example 14G tert-butyl (3aR,6aR)-5-(trifluoroacetyl)hexahydropyrrolo[3,4-b]pyrrole-1(2H)-carboxylate The product from Example 14F (11.2 g; 35.8 mmol) and di-tert-butyl dicarbonate (8.58 g, 39.4 mmol) in methanol (400 mL) was treated with 10% Pd/C (0.6 g). The mixture was shaken under an atmosphere of hydrogen (4 atm) at 25° C. for 18 hours. After filtration, the solution was concentrated under reduced pressure and the residue was purified by chromatography ($SiO_2$, 2:1 ethyl acetate:hexanes) to provide the title compound as a crystalline solid (9.88 g, 89% yield). MS (DCI/$NH_3$) m/z 326 $(M+NH_4)^+$.

Example 14H tert-butyl (3aR,6aR)-hexahydropyrrolo[3,4-b]pyrrole-1(2H)-carboxylate The product from Example 14G (9.88 g, 32 mmol) in methanol (200 mL) and water (40 mL) was treated with solid potassium carbonate (4.86 g; 35 mmol). After stirring at 20° C. for 18 hours, the solvent was removed under reduced pressure. The residue was azeotroped with ethyl acetate (50 mL) twice and finally with toluene (100 mL). The dry powder was stirred with 20% MeOH/$CH_2Cl_2$ (100 mL), filtered, and the filtercake was rinsed with 20% MeOH/$CH_2Cl_2$ (100 mL). The filtrate was concentrated to provide the title compound as a white solid. MS (DCI/$NH_3$) m/z 213 $(M+H)^+$.

Example 14I tert-butyl (3aR,6aR)-5-(6-chloro-3-pyridinyl)hexahydropyrrolo[3,4-b]pyrrole-1(2H)-carboxylate The product from example 14H (2 g, 4.9 mmol) and 2-chloro-5-iodopyridine (1.55 g, 6.5 mmol) were processed as described in Example 1E except that a larger amount of sodium tert-butoxide (1.24 g, 12.9 mmol) was used. The crude product was purified by chromatography ($SiO_2$, 20% ethyl acetate in pentane) to provide the title compound (600 mg, 38% yield). MS (DCI/$NH_3$) m/z 324/326 $(M+H)^+$.

Example 14J (3aR,6aR)-5-(6-chloro-3-pyridinyl)octahydropyrrolo [3,4-b]pyrrole dihydrochloride The product from Example 14I (211 mg, 0.65 mmol) in ethanol (5 mL) was treated with HCl in 1,4-dioxane (4M, 2 mL, 8 mmol). After stirring at ambient temperature for 4 hours, the solution was concentrated under reduced pressure and the residue crystallized from ethanol:ethyl acetate (1:5) to provide the title compound as a white solid (165 mg, 85% yield). $^1$H NMR (CD$_3$OD, 300 MHz) δ 2.05 (m, 1H), 2.35 (m, 1H), 3.4 (m, 6H), 3.89 (dd, J=12, 1.5 Hz, 1H), 4.45 (t, J=6 Hz, 1H), 7.36 (dd, J=9.3 Hz, 1H), 7.45 (d, J=9 Hz, 1H), 7.9 (d, J=3 Hz, 1H); MS (DCI/$NH_3$) m/z 224/226 $(M+H)^+$; Anal. calculated for $C_{11}H_{14}ClN_3$.2 HCl: C, 44.48; H, 5.39; N, 14.15. Found: C, 44.18; H, 5.35; N, 14.05.

Example 15

(3aS,6aS)-5-(6-chloro-3-pyridinyl)octahydropyrrolo [3,4-b]pyrrole dihydrochloride

Example 15A (3aS,6aS)-1-[(1R)-1-phenylethyl]octahydropyrrolo [3,4-b]pyrrole

The less mobile diastereomer from Example 14C was processed as described in Example 14D to provide the title compound as a brownish oil (11.3 g, 76% yield). MS (DCI/$NH_3$) m/z 217 $(M+H)^+$.

Example 15B (3aS,6aS)-5-[(4-nitrophenyl)sulfonyl]-1-[(1R)-1-phenylethyl]octahydropyrrolo[3,4-b]pyrrole The product from Example 15A (148 mg, 0.68 mmol) and triethyl amine (0.15 mL, 1.08 mmol) in dichloromethane (5 mL) at 0° C. was treated with 4-nitrobenzenesulfonyl chloride (166 mg, 0.75 mmol) in dichloromethane (2 mL) over 1 minute. The reaction mixture was allowed to warm to room temperature. After 1 hour, the mixture was diluted with dichloromethane (20 mL) and washed with 5% NaHCO$_3$ (10 mL), brine (10 mL), dried (MgSO$_4$) and concentrated under reduced pressure to provide the title compound as a light yellow solid (270 mg, 98%). Single crystals suitable for x-ray diffraction were grown by slow evaporation from ethyl acetate solution. Crystal data: MW=401.48, $C_{20}H_{23}N_3O_4S$, crystal dimensions 0.60×0.10×0.10 mm, orthorhombic, $P2_12_12_1$ (#19), a=5.4031(5), b=16.168(2), c=22.687(2) Å, V=1981.8(3) Å$^3$, Z=4, $D_{calc}$=1.345 g/cm$^{-3}$. Crystallographic data were collected using Mo K α radiation (λ=0.71069 Å). Refinement of the structure using full matrix least squares refinement of 253 parameters on 2005 reflections with I>3.00σ(I) gave R=0.117, R$_w$=0.123.

Example 15C (3aS,6aS)-1-[(1R)-1-phenylethyl]-5-(trifluoroacetyl) octahydropyrrolo[3,4-b]pyrrole The product from Example 15A (11.3 g, 52 mmol) was processed as described in Example 14F to provide the title compound (11.2 g, 69% yield). MS (DCI/$NH_3$) m/z 313 $(M+H)^+$.

Example 15D tert-butyl (3aS,6aS)-5-(trifluoroacetyl)hexahydropyrrolo[3,4-b]pyrrole-1(2H)-carboxylate The product from example 15C was processed as described in Example 14G to provide the title compound (97% yield). MS (DCI/NH$_3$) m/z 326 (M+NH$_4$)$^+$.

Example 15E tert-butyl (3aS,6aS)-hexahydropyrrolo[3,4-b]pyrrole-1(2H)-carboxylate The product from Example 15D was processed as described in the Example 14H to provide the title compound.

Example 15F tert-butyl (3aS,6aS)-5-(6-chloro-3-pyridinyl)hexahydropyrrolo[3,4-b]pyrrole-1(2H)-carboxylate The product from Example 15E was processed as described in the Example 14I to provide the title compound (49% yield). MS (DCI/NH$_3$) m/z 324/326 (M+H)$^+$.

Example 15G (3aS,6aS)-5-(6-chloro-3-pyridinyl)octahydropyrrolo[3,4-b]pyrrole dihydrochloride The product from example 15F was processed as described in the example 14J to provide the title compound (45% yield). $^1$H NMR (CD$_3$OD, 300 MHz) δ 2.05 (m, 1H), 2.35 (m, 1H), 3.4 (m, 6H), 3.89 (d, J=12 Hz, 1H), 4.45 (t, J=6 Hz, 1H), 7.4 (m, 2H), 7.9 (d, J=3 Hz, 1H); MS (DCI/NH$_3$) m/z 224 (M+H)$^+$; Anal. calculated for C$_{11}$H$_{14}$ClN$_3$.1.7 HCl: C, 46.19; H, 5.59; N, 14.69. Found: C, 46.27; H, 5.66; N, 14.70.

Example 16 cis-1-(6-chloro-3-pyridinyl)octahydropyrrolo[3,4-b]pyrrole hydrochloride

Example 16A tert-butyl cis-1-(6-chloro-3-pyridinyl)hexahydropyrrolo[3,4b]-pyrrole-5(1H)-carboxylate tert-Butyl cis-hexahydropyrrolo[3,4-b]pyrrole-5(1H)-carboxylate (550 mg, 2.60 mmol), prepared as described in (U.S. Pat. No. 5,071,999) and 2-chloro-5-iodopyridine (660 mg, 2.76 mmol), prepared as described in (Tetrahedron Lett. (1993), 34, 7493-7496), were processed as described in Example 1E to provide the title compound as a tan foam (750 mg, 89% yield). MS (DCI/NH$_3$) m/z 324, 326 (M+H)$^+$.

Example 16B cis-1-(6-chloro-3-pyridinyl)octahydropyrrolo[3,4-b]pyrrole

The product from Example 16A (745 mg, 2.31 mmol) in dichloromethane (10 mL) was cooled to 0° C. and treated with trifluoroacetic acid (10 mL). The mixture was stirred for 5 minutes, allowed to warm to ambient temperature and stirred for 2 hours. The mixture was evaporated under reduced pressure and the residue purified by chromatography (SiO$_2$, 95:5:0.5 CH$_2$Cl$_2$:MeOH:NH$_4$OH) to provide the title compound as a yellow oil (384 mg, 74% yield). MS (DCI/NH$_3$) m/z 224, 226 (M+H)$^+$.

Example 16C cis-1-(6-chloro-3-pyridinyl)octahydropyrrolo[3,4-b]pyrrole hydrochloride The product from Example 16B (368 mg, 1.65 mmol) was treated with a solution of HCl in 1,4-dioxane (Aldrich; 4 M, 0.43 mL, 1.72 mmol) as described in Example 1F to provide the title compound as a white solid (300 mg, 70% yield). $^1$H NMR (CD$_3$OD, 300 MHz) δ 2.02 (m, 1H), 2.31 (m, 1H), 3.33 (m, 4H), 3.52 (m, 2H), 3.69 (m, 1H), 4.41 (td, J=6, 2 Hz, 1H), 7.14 (dd, J=9, 3 Hz, 1H), 7.29 (d, J=9 Hz, 1H), 7.73 (d, J=3 Hz, 1H); MS (DCI/NH$_3$) m/z 224, 226 (M+H)$^+$; Anal. Calculated for C$_{11}$H$_{14}$ClN$_3$.HCl: C, 50.78; H, 5.81; N, 16.15. Found: C, 50.88; H, 5.78; N, 16.08.

Example 17 cis-1-(6-chloro-3-pyridinyl)-5-methyloctahydropyrrolo[3,4-b]pyrrole hydrochloride The product from Example 16C (114 mg, 0.44 mmol) in methanol (3 mL) was cooled to 0° C. and treated with sodium cyanoborohydride (70 mg, 1.1 mmol) and formalin (3 mL, 36 mmol). After stirring at ambient temperature for 16 hours, the mixture was quenched with aqueous sodium carbonate and extracted into dichloromethane (3×10 mL). The organic extracts were combined and dried over potassium carbonate. The residue was purified by chromatography (SiO$_2$, 95:5:0.5 CH$_2$Cl$_2$:MeOH:NH$_4$OH) to afford the free base of the title compound (80 mg, 77% yield). The free base was then treated with a solution of HCl in 1,4-dioxane (4 M, 88 μL, 0.35 mmol) as described in Example 1F to provide the title compound as a white solid (70 mg, 75% yield). $^1$H NMR (CD$_3$OD, 300 MHz) δ 2.04 (m, 1H), 2.33 (m, 1H), 2.95 (s, 3H), 3.30-3.80 (br m, 7H), 4.43 (m, 1H), 7.15 (dd, J=8, 3 Hz, 1H), 7.29 (d, J=8 Hz, 1H), 7.74 (d, J=3 Hz, 1H); MS (DCI/NH$_3$) m/z 238, 240 (M+H)$^+$; Anal. Calculated for C$_{12}$H$_{16}$ClN$_3$.HCl: C, 52.57; H, 6.25; N, 15.33. Found: C, 52.59; H, 6.29; N, 15.26.

Example 18

(1R,5R)-2-(3-pyridinyl)-2,6-diazabicyclo[3.2.0]heptane bis(4-methylbenzenesulfonate)

Example 18A (2S,3S)-1-(tert-butoxycarbonyl)-3-hydroxy-2-pyrrolidinecarboxylic acid trans-3-Hydroxy (L)-proline (10.0 g, 76.3 mmol) in THF (50 mL) was treated with sodium hydroxide (3.36 g, 84 mmol) in water (34 mL) at ambient temperature. After 10 minutes of stirring, the mixture was treated with di-tert-butyl dicarbonate (16.63 g, 76.3 mmol) portionwise. After stirring at ambient temperature for 10 hours, the mixture was concentrated under reduced pressure, acidified to pH 2-3 with saturated KHSO$_4$ (aq), and extracted with ethyl acetate (2×200 mL). The organic extracts were combined, washed with brine (2×30 mL), and concentrated to provide the title compound as a white solid (12.3 g, 70%, yield). mp 156-157° C.

Example 18B tert-butyl (2R,3S)-3-hydroxy-2-(hydroxymethyl)-1-pyrrolidinecarboxylate The product from Example 18A (7.73 g, 33.5 mmol) in dry THF (100 mL) was treated with borane-methyl sulfide complex (10M in THF, 7.4 mL, 74 mmol) dropwise over 10 minutes. The solution was warmed to reflux for 1 hour, then cooled to 10-20° C. Methanol was added cautiously at 10-20° C. until there was no obvious evolution of hydrogen. The mixture was concentrated under reduced pressure and the white residue stirred with water (50 mL) for 10 minutes and then extracted with ethyl acetate (3×100 mL). The combined extracts were washed with brine (2×10 mL), dried ($Na_2SO_4$), and concentrated to provide the title compound as a white solid (7.24 g, 99% yield). $^1$H NMR (MeOH-$d_4$, 300 MHz) δ 1.48 (s, 9H), 1.82 (m, 1H), 2.10 (m, 1H), 3.45 (m, 3H), 3.66 (m, 2H), 4.30 (m, 1H); MS (DCI/$NH_3$) m/z 218 (M+H)$^+$.

Example 18C tert-butyl (2R,3S)-3-[(methylsulfonyl)oxy]-2-{[(methylsulfonyl)oxy]methyl}-1-pyrrolidinecarboxylate The product from Example 18B (4.6 g, 21.2 mmol) and triethylamine (9.0 g, 89.0 mmol) in dichloromethane (100 mL) 0° C. was treated with methasulfonyl chloride (4.9 mL, 63.5 mmol) over 20 minutes. After stirring at ambient temperature overnight, the mixture was quenched with saturated sodium bicarbonate (50 mL) and extracted with dichloromethane (2×100 mL). The combined extracts were washed with brine (2×10 mL), dried ($Na_2SO_4$), and concentrated. The reside was purified by chromatography ($SiO_2$, hexanes:ethyl acetate 60:40) to provide the title compound as a pale yellow solid (4.6 g, 58% yield). $^1$H NMR ($CDCl_3$, 300 MHz) δ 1.48 (br s, 9H), 2.28 (m, 2H), 3.05 (br s, 3H), 3.08 (br s, 3H), 3.55 (m, 2H), 4.20-4.44 (m, 3H), 5.20 (m, 1H); MS (DCI/$NH_3$) m/z 374 (M+H)$^+$, 391 (M+$NH_4$)$^+$.

Example 18D tert-butyl (1R,5R)-6-benzyl-2,6-diazabicyclo[3.2.0]heptane-2-carboxylate The product from Example 18C (4.5 g, 12 mmol) in anhydrous toluene (100 mL) was treated with benzylamine (7.7 g, 36 mmol) and heated at reflux for 20 hours. After cooling to ambient temperature, the mixture was filtered off and the filtrate was concentrated. The residue was purified by chromatography ($SiO_2$, hexanes:ethyl acetate 40:60) to provide the title compound as a white solid (2.4 g, 70% yield). $^1$H NMR ($CD_3OD$, 300 MHz) δ 1.46 (s, 4.5H), 1.48 (s, 4.5H), 1.60 (m, 2H), 3.18 (m, 2H), 3.60-3.75 (m, 4H), 3.98 (m, 1H), 4.20 (m, 1H), 7.20-7.42 (m, 5H); MS (DCI/$NH_3$) m/z 289 (M+H)$^+$.

Example 18E (1R,5R)-6-benzyl-2,6-diazabicyclo[3.2.0]heptane

The product from Example 18D (1.00 g, 3.4 mmol) in ethanol (10 mL) was treated with 12M HCl (1 mL) and heated at 50° C. for 1 hour. After cooling to ambient temperature, the mixture was concentrated under reduced pressure and then azeotroped from isopropyl acetate. The residue was purified by recrystallization from isopropyl acetate:heptane (1:1) to provide a white solid (0.74 g, 84% yield). $^1$H NMR ($CD_3OD$, 300 MHz) δ 2.20 (m, 1H), 2.50 (m, 1H), 3.90 (m, 1H), 4.00 (m, 1H), 4.26 (m, 1H), 4.50 (m, 1H), 4.76 (m 3H), 5.10 (m, 1H), 7.40-7.60 (m, 5H); MS (DCI/$NH_3$) m/z 189 (M+H)$^+$.

Example 18F (1R,5R)-6-benzyl-2-(3-pyridinyl)-2,6-diazabicyclo[3.2.0]heptane

The product from Example 18E (260 mg, 1.0 mmol) and 3-bromopyridine were processed as described in Example 1E, except that a larger amount of sodium tert-butoxide (384 mg, 4.0 mmol) was used to neutralize the salt. The crude product was purified by chromatography ($SiO_2$, $CH_2Cl_2$:MeOH, 95:5, $R_f$ 0.3) to provide the title compound (0.26 g, 98% yield). $^1$H NMR ($CD_3OD$, 300 MHz) δ 2.40 (m, 2H), 3.20 (m, 2H), 3.50-3.80 (m, 4H), 4.10 (m, 1H), 4.50 (m, 1H), 7.00-7.60 (m, 9H); MS (DCI/$NH_3$) m/z 266 (M+H)$^+$.

Example 18G (1R,5R)-2-(3-pyridinyl)-2,6-diazabicyclo[3.2.0]heptane bis(4-methylbenzenesulfonate)

The product from Example 18F (0.26 g, 0.98 mmol) in ethanol (10 mL) was treated with 10% Pd/C (0.13 g) under a hydrogen atmosphere at 50° C. for 16 hours. After cooling to ambient temperature, the mixture was filtered through diatomaceous earth with an ethanol (2×10 mL) rinse. The filtrate was concentrated under reduced pressure and the brown residue in isopropyl alcohol (10 mL) was treated with 4-methylbenzenesulfonic acid monohydrate (558 mg, 2.94 mmol). The mixture was warmed until the solids dissolved and then allowed to cool to ambient temperature and stirred for 10 hours. The precipitate was isolated by filtration and dried under reduced pressure at 40-50° C. to provide the title compound (180 mg, 44% yield). $^1$H NMR ($CD_3OD$, 300 MHz) δ 2.40 (s, 6H), 2.45 (m, 1H), 2.55 (m, 1H), 3.70 (dd, J=11.8, 3.0 Hz, 1H), 3.85 (m, 1H), 4.08 (m, 1H), 4.46 (dd, J=11.8, 5.5 Hz, 1H), 4.85 (m, 1H), 5.30 (t, 6.6 Hz, 1H), 7.24 (d, J=7.8 Hz, 4H), 6.98 (br d. J=8.0 Hz, 4H), 7.84 (m, 2H), 8.15 (m, 1H), 8.22 (m, 1H); MS (DCI/$NH_3$) m/z 176 (M+H)$^+$; Anal. calculated for $C_{10}H_{13}N_3$.2 TsOH: C, 54.71; H, 5.70; N, 7.98. Found: C, 55.20; H, 5.51; N, 7.58.

Example 19

(1R,5R)-6-(6-chloro-3-pyridinyl)-2,6-diazabicyclo[3.2.0]heptane bis(4-methylbenzenesulfonate)

Example 19A tert-butyl (1R,5R)-2,6-diazabicyclo[3.2.0]heptane-2-carboxylate

The product from Example 18D (1.25 g, 4.3 mmol) in ethanol (25 mL) was treated with 10% Pd/C (0.25 g) under a hydrogen atmosphere at 60° C. for 16 hours. The mixture was filtered through diatomaceous earth with an ethanol rinse (2×10 mL). The filtrate was concentrated under reduced pressure to provide the title compound as a yellow oil (0.85 g, 99% yield). $^1$H NMR ($CD_3OD$, 300 MHz) δ 1.46 (s, 4.5H), 1.48 (s, 4.5H), 1.60 (m, 2H), 3.18 (m, 2H), 3.60-3.75 (m, 3H), 3.98 (m, 0.5H), 4.20 (m, 0.5H), 7.20-7.42 (m, 5H); MS (DCI/NH$_3$) m/z 199 (M+H)$^+$.

Example 19B tert-butyl (1R,5R)-6-(6-chloro-3-pyridinyl)-2,6-diazabicyclo[3.2.0]heptane-2-carboxylate The product from Example 19A (200 mg, 1.0 mmol) and 2-chloro-5-iodopyridine (288 mg, 1.2 mmol), prepared as described in (Tetrahedron Lett. (1993), 34, 7493-7496), were processed as described in Example 1E to provide the title compound (0.26 g, 84% yield). $^1$H NMR CD$_3$OD, 300 MHz) δ 1.48 (s, 9H), 1.95 (m, 1H), 2.20 (dd, J=13.5, 6.1 Hz, 1H), 3.62 (m, 1H), 3.70 (dd, J=8.5, 1.7 Hz, 1H), 3.90 (m, 2H), 4.50 (m, 1H), 4.78 (br t, J=5.1 Hz, 1H), 6.90 (dd, J=8.4, 3.1 Hz, 1H), 7.22 (dd, J=8.5, 0.7 Hz, 1H), 7.59 (d, J=3.1 Hz, 1H); MS (DCI/NH$_3$) m/z 310/312 (M+H)$^+$.

Example 19C (1R,5R)-6-(6-chloro-3-pyridinyl)-2,6-diazabicyclo[3.2.0]heptane bis(4-methylbenzenesulfonate)

The product from Example 19B (250 mg, 0.83 mmol) in ethanol (10 mL) was treated with 4-methylbenzenesulfonic acid monohydrate (480 mg, 2.49 mmol). The mixture was heated to reflux for 2 hours, cooled to 25° C., and concentrated under reduced pressure. The brown residue was azeotroped in isopropyl acetate (10 mL) several times and then crystallized from isopropyl acetate:heptane (1:1) to provide the title compound (0.17 g, 37% yield). $^1$H NMR (CD$_3$OD, 300 MHz) δ 2.00 (m, 1H), 2.40 (s, 6H), 2.45 (dd, J=14.5, 6.0 Hz, 1H), 3.65-3.80 (m, 2H), 3.98 dd, J=9.8, 2.2 Hz, 1H), 4.15 (dd, J=10.2, 2.3 Hz, 1H), 4.58 (m, 1H), 4.95 (m, 1H), 7.09 (m, 1H), 7.24 (d, J=8.1 Hz, 4H), 7.32 (d, J=8.8 Hz, 1H), 7.68 (d, J=3.3 Hz, 1H), 7.72 (d, J=8.3 Hz, 4H); MS (DCI/NH$_3$) m/z 210/212 (M+H)$^+$, Anal. calculated for C$_{10}$H$_{12}$N$_3$Cl.2 TsOH: C, 52.02; H, 5.09; N, 7.58. Found: C, 52.00; H, 5.27; N, 7.45.

Example 20

(1R,5R)-6-(3-pyridinyl)-2,6-diazabicyclo[3.2.0]heptane bis(4-methylbenzenesulfonate)

Example 20A tert-butyl (1R,5R)-6-(3-pyridinyl)-2,6-diazabicyclo[3.2.0]heptane-2-carboxylate The product from Example 19A (200 mg, 1.0 mmol) and 3-bromopyridine (190 mg, 1.2 mmol) were processed as described in Example 1E to provide the title compound (0.27 g, 99% yield). $^1$H NMR (CD$_3$OD, 300 MHz) δ 1.50 (s, 9H), 1.95 (m, 1H), 2.20 (dd, J=13.0, 6.1 Hz, 1H), 3.62 (m, 1H), 3.70 (dd, J=8.1, 1.7 Hz, 1H), 3.90 (m, 2H), 4.50 (m, 1H), 4.78 (br t, J=6.8 Hz, 1H), 6.90 (m, 1H), 7.22 (ddd, J=8.5, 4.7, 0.7 Hz, 1H), 7.80 (d, J=3.1 Hz, 1H), 7.88 (dd, J=4.7, 0.7 Hz, 1H); MS (DCI/NH$_3$) m/z 276 (M+H)$^+$.

Example 20B (1R,5R)-6-(3-pyridinyl)-2,6-diazabicyclo[3.2.0]heptane bis(4-methylbenzenesulfonate)

The product from Example 20A was processed as described in Example 19C to provide the title compound (0.32 g, 62% yield). $^1$H NMR (CD$_3$OD, 300 MHz) δ 2.10 (m, 1H), 2.49 (s, 6H), 2.50 (dd, J=14.7, 6.0 Hz, 1H), 3.65-3.85 (m, 2H), 4.14 (m, 1H), 4.34 (m, 1H), 4.68 (m, 1H), 5.10 (t, J=5.0 Hz, 1H), 7.24 (d, J=7.8 Hz, 4H), 7.70 (dd, J=8.0, 1.8 Hz, 4H), 7.82 (m, 2H), 8.12 (m, 2H); MS (DCI/NH$_3$) m/z 176 (M+H)$^+$; Anal. calculated for C$_{10}$H$_{13}$N$_3$.2 TsOH: C, 55.47; H, 5.63. Found: C, 55.81; H, 5.61.

Example 22 cis-6-(6-chloro-3-pyridinyl)octahydro-1H-pyrrolo[3,4-b]pyridine dihydrochloride

Example 22A tert-butyl cis-6-(6-chloro-3-pyridinyl)octahydro-1H-pyrrolo[3,4-b]pyridine-1-carboxylate tert-Butyl cis-octahydro-1H-pyrrolo[3,4-b]pyridine-1-carboxylate (374 mg, 1.65 mmol), prepared as described in (EP0603887A2) and 5-bromo-2-chloropyridine (314 mg, 1.65 mmol), prepared as described in (Tetrahedron Lett. (1998), 39, 2059-2062) were processed as described in Example 1E to provide the title compound (273 mg, 49% yield). MS (DCI/NH$_3$) m/z 338/340 (M+H)$^+$.

Example 22B cis-6-(6-chloro-3-pyridinyl)octahydro-1H-pyrrolo[3,4-b]pyridine dihydrochloride The product from Example 22A in methanol (1 mL) was treated with a solution of HCl in ether (1N, 4 mL, 4 mmol). The mixture was stirred at ambient temperature for 2 hours and then concentrated under reduced pressure. The resulting solid was crystallized from ethanol/diethyl ether to provide the title compound (191 mg, 76% yield). $^1$H NMR (CD$_3$OD, 300 MHz) δ 1.85 (m, 2H), 1.94 (m, 2H), 2.88 (m, 1H), 3.07 (m, 1H), 3.32-3.58 (m, 4H), 3.70 (dd, J=12, 5 Hz, 1H), 3.98 (t, J=5 Hz, 1H), 7.24 (dd, J=9, 3 Hz, 1H), 7.40 (d, J=9 Hz, 1H), 7.78 (d, J=3 Hz, 1H); MS (DCI/NH$_3$) m/z 238/240 (M+H)$^+$; Anal. Calculated for C$_{12}$H$_{16}$ClN$_3$.2.1 HCl: C, 45.86; H, 5.80; N, 13.37. Found: C, 45.53; H, 6.10; N, 12.99.

Example 23 cis-6-(3-pyridinyl)octahydro-1H-pyrrolo[3,4-b]pyridine dihydrochloride

Example 23A tert-butyl cis-6-(3-pyridinyl)octahydro-1H-pyrrolo[3,4-b]pyridine-1-carboxylate The product from Example 22A (232 mg, 1.03 mmol) and 3-bromopyridine (162 mg, 1.03 mmol) were processed as described in Example 1E to provide the title compound (220 mg, 70% yield). MS (DCI/NH$_3$) m/z 304 (M+H)$^+$.

Example 23B cis-6-(3-pyridinyl)octahydro-1H-pyrrolo[3,4-b]pyridine dihydrochloride The product from Example 23A in methanol (1 mL) was treated with a solution of HCl in ether (1N, 4 m L, 4 mmol). The mixture was stirred at ambient temperature for 3 hours and then concentrated under reduced pressure. The resulting solid was crystallized from ethanol/diethyl ether to provide the title compound (169 mg, 83% yield). $^1$H NMR (CD$_3$OD, 300 MHz) δ 1.88 (m, 2H), 1.97 (m, 2H), 2.95 (m, 1H), 3.10 (m, 1H), 3.34-3.70 (m, 4H), 3.83 (dd, J=12, 5 Hz, 1H), 4.06 (t, J=5 Hz, 1H), 7.75 (dd, J=9, 2 Hz, 1H), 7.85 (dd, J=9.5 Hz, 1H), 8.09 (d, J=5 Hz, 1H), 8.11 (d, J=2 Hz, 1H); MS (DCI/NH$_3$) m/z 204 (M−H)$^+$; Anal. Calculated for C$_{12}$H$_{17}$N$_3$.2.1 HCl: C, 51.50; H, 6.88; N, 15.02. Found: C, 51.25; H, 6.71; N, 14.91.

Example 24

(3aR,6aR)-5-(5,6-dichloro-3-pyridinyl)octahydropyrrolo[3,4-b]pyrrole hydrochloride Example 24A tert-butyl (3aR,6aR)-5-(5,6-dichloro-3-pyridinyl)hexahydropyrrolo[3,4-b]pyrrole-1(2H)-carboxylate The product from Example 14H and 2,3-dichloro-5-iodo pyridine, prepared as described in (U.S. Pat. No. 5,733,912), were processed as described in Example 1E to provide the title compound in 42% yield. MS (DCI/NH$_3$) m/z 358/360/362 (M+H)$^+$.

Example 24B (3aR,6aR)-5-(5,6-dichloro-3-pyridinyl)octahydropyrrolo[3,4-b]pyrrole hydrochloride The product from Example 24A was processed as described in Example 14J to provide the title compound (65% yield). $^1$H NMR (CD$_3$OD, 300 MHz) δ 2.05 (m, 1H), 2.35 (m, 1H), 3.35 (m, 6H), 3.82 (dd, J=12, 1.5 Hz, 1H), 4.42 (t, J=6 Hz, 1H), 7.35 (d, J=3 Hz, 1H), 7.8 (d, J=3 Hz, 1H); MS (DCI/NH$_3$) m/z 258/260/262 (M+H)$^+$; Anal. calculated for C$_{11}$H$_{13}$Cl$_2$N$_3$.HCl.0.5H$_2$O: C, 43.47; H, 4.93; N, 13.83. Found: C, 43.82; H, 4.86; N, 13.99.

Example 25

(3aS,6aS)-5-(5,6-dichloro-3-pyridinyl)octahydropyrrolo[3,4-b]pyrrole hydrochloride Example 25A tert-butyl (3aS,6aS)-5-(5,6-dichloro-3-pyridinyl)hexahydropyrrolo[3,4-b]pyrrole-1(2H)-carboxylate The product from Example 15E and 2,3-dichloro-5-iodopyridine, prepared as described in (U.S. Pat. No. 5,773,912), were processed as described in Example 1E (41% yield) to provide the title compound. MS (DCI/NH$_3$) m/z 358/360/362 (M+H)$^+$.

Example 25B (3aS,6aS)-5-(5,6-dichloro-3-pyridinyl)octahydropyrrolo[3,4-b]pyrrole hydrochloride The product from Example 25A was processed as described in Example 14J to provide the title compound (78% yield). $^1$H NMR (CD$_3$OD, 300 MHz) δ 2.05 (m, 1H), 2.35 (m, 1H), 3.36 (m, 6H), 3.85 (dd, J=12, 1.5 Hz, 1H), 4.42 (t, J=6 Hz, 1H), 7.35 (d, J=3 Hz, 1H), 7.8 (d, J=3 Hz, 1H); MS (DCI/NH$_3$) m/z 258/260/262 (M+H)$^+$; Anal. calculated for C$_{11}$H$_{13}$Cl$_2$N$_3$.HCl: C, 44.79; H, 4.75; N, 14.25. Found: C, 44.76; H, 4.79; N, 14.24.

Example 26

(3aS,6aS)-5-(6-chloro-5-methyl-3-pyridinyl)octahydropyrrolo[3,4-b]pyrrole hydrochloride Example 26A tert-butyl (3aS,6aS)-5-(6-chloro-5-methyl-3-pyridinyl)hexahydropyrrolo[3,4-b]pyrrole-1(2H)-carboxylate The product from Example 15E and 5-bromo-2-chloro-3-methylpyridine were processed as described in Example 1E to provide the title compound (41% yield). MS (DCI/NH$_3$) m/z 338/340 (M+H)$^+$.

Example 26B (3aS,6aS)-5-(6-chloro-5-methyl-3-pyridinyl)octahydropyrrolo[3,4-b]pyrrole hydrochloride The product from Example 26A was processed as described in Example 14J to provide the title compound (42% yield). $^1$H NMR (CD$_3$OD, 300 MHz) δ 2.05 (m, 1H), 2.35 (m, 1H), 2.45 (s, 3H), 3.45 (m, 6H), 3.95 (dd, J=12, 1.5 Hz, 1H), 4.45 (t, J=6 Hz, 1H), 7.55 (d, J=3 Hz, 1H), 7.85 (d, J=3 Hz, 1H); MS (DCI/NH$_3$) m/z 238/240 (M+H)$^+$; Anal. calculated for C$_{12}$H$_{16}$ClN$_3$.1.8HCl: C, 47.46; H, 5.93; N, 13.84. Found: C, 47.24; H, 5.91; N, 13.69.

Example 27

(3aR,6aR)-5-(6-chloro-5-methyl-3-pyridinyl)octahydropyrrolo[3,4-b]pyrrole hydrochloride Example 27A tert-butyl (3aR,6aR)-5-(6-chloro-5-methyl-3-pyridinyl)hexahydropyrrolo[3,4-b]pyrrole-1(2H)-carboxylate The product from Example 14H and 5-bromo-2-chloro-3-methyl pyridine were processed as described in Example 1E to provide the title compound (24% yield). MS (DCI/NH$_3$) m/z 338/340 (M+H)$^+$.

Example 27B (3aR,6aR)-5-(6-chloro-5-methyl-3-pyridinyl)octahydropyrrolo[3,4-b]pyrrole hydrochloride The product from Example 27A was processed as described in Example 14J to provide the title compound.

(40% yield). $^1$H NMR (CD$_3$OD, 300 MHz) δ 2.05 (m, 1H), 2.35 (m, 1H), 2.45 (s, 3H), 3.45 (m, 6H), 3.92 (dd, J=12, 1.5 Hz, 1H), 4.45 (t, J=6 Hz, 1H), 7.52 (d, J=3 Hz, 1H), 7.82 (d, J=3 Hz, 1H); MS (DCI/NH$_3$) m/z 238/240 (M+H)$^+$; Anal. calculated for C$_{12}$H$_{16}$ClN$_3$·1.75 HCl: C, 47.74; H, 5.96; N, 13.92. Found: C, 47.57; H, 5.89; N, 13.62.

Example 28

(3aR,6aR)-5-(3-pyridinyl)octahydropyrrolo[3,4-b]pyrrole dihydrochloride

Example 28A tert-butyl (3aR,6aR)-5-(3-pyridinyl)hexahydropyrrolo[3,4-b]pyrrole-1(2H)-carboxylate The product from Example 14H (800 mg, 1.96 mmol) and 3-bromopyridine (400 mg, 2.5 mmol) were processed as described in Example 1E (with the modification that 2.1 eq. of sodium tert-butoxide (390 mg, 4.1 mmol) was used). The crude product was purified by chromatography (SiO$_2$, 4% MeOH in CH$_2$Cl$_2$) to provide the title compound as a pale yellow solid (400 mg, 70%). MS (DCI/NH$_3$) m/z 290 (M+H)$^+$.

Example 28B (3aR,6aR)-5-(3-pyridinyl)octahydropyrrolo[3,4-b]pyrrole dihydrochloride The product from Example 28A (400 mg, 1.38 mmol) in ethanol (3' mL) was treated with HCl/1,4-dioxane (4 M, 4 mL). After stirring at 20° C. for 2 hours, the mixture was concentrated under reduced pressure. The yellow oily residue was purified by chromatography (SiO$_2$, 90:10:1 CH$_2$Cl$_2$:MeOH:NH$_4$OH) to provide the free base as a pale oil (208 mg). The free base in ethanol (3 mL) was treated with HCl/1,4-dioxane (4M, 3 mL). The solvents were removed under reduced pressure to leave a light yellow solid, which was crystallized from ethanol:ethyl acetate (1:4) to provide the title compound as a hygroscopic off-white solid (253 mg, 70% yield). $^1$H NMR (CD$_3$OD, 300 MHz) δ 2.11 (m, 1H), 2.40 (dq, J=14.8 Hz, 1H), 3.4 (m, 3H), 3.53 (dd, J=8, 5 Hz, 1H), 3.61 (m, 1H), 3.71 (dd, J=12, 7 Hz, 1H), 3.99 (dd, J=12, 2 Hz, 1H), 4.52 (br t, J=7 Hz, 1H), 7.85 (m, 2H), 8.13 (m, 1H), 8.18 (br s, 1H); MS (DCI/NH$_3$) m/z 190 (M+H)$^+$; Anal. calculated for C$_{11}$H$_{15}$N$_3$·2 HCl·0.2 H$_2$O: C, 49.71; H, 6.60; N, 15.81. Found: C, 49.80; H, 6.59; N, 15.64.

Example 29

(3aR,6aR)-5-(5-methoxy-3-pyridinyl)octahydropyrrolo[3,4-b]pyrrole dihydrochloride Example 29A tert-butyl (3aR,6aR)-5-(5-methoxy-3-pyridinyl)hexahydropyrrolo[3,4-b]pyrrole-1(2H)-carboxylate The product from Example 14H (0.80 g, 1.96 mmol) and 3-bromo-5-methoxypyridine (478 mg, 2.54 mmol) from Example 7A were processed as described in Example 1E (with the modification that 2.1 eq. of sodium t-butoxide (400 mg, 4.2 mmol) was used) to provide the title compound as a pale yellow oil (0.62 g, 100% yield). MS (DCI/NH$_3$) m/z 290 (M+H)$^+$.

Example 29B (3aR,6aR)-5-(5-methoxy-3-pyridinyl)octahydropyrrolo[3,4-b]pyrrole dihydrochloride The product from Example 29A (620 mg, 1.96 mmol) in dichloromethane (20 mL) was treated with trifluoroacetic acid (10 mL). After stirring at ambient temperature for 2 hours, the mixture was concentrated under reduced pressure. The resulting yellow oil was purified by flash chromatography (89:10:1 CH$_2$Cl$_2$:MeOH:NH$_4$OH) to provide the free base as a pale oil (210 mg). The freebase was dissolved in ethanol (3 mL) and treated with HCl in 1,4-dioxane (4M, 3 mL, 12 mmol). After stirring for 30 minutes, the mixture was concentrated under reduced pressure. The residue was crystallized from ethanol:ethyl acetate (3:1) to provide the title compound as an off-white solid (317 mg, 57% yield). $^1$H NMR (CD$_3$OD, 300 MHz) δ 2.10 (m, 1H), 2.39 (dq, J=13, 7 Hz, 1H), 3.35-3.45 (m, 3H), 3.52 (dd, J=7.5 Hz, 1H), 3.61 (m, 1H), 3.69 (m, 1H), 3.96 (br d, J=13 Hz, 1H), 4.00 (s, 3H), 4.49 (br t, J=7 Hz, 1H), 7.24 (m, 1H), 7.83 (d, J=2 Hz, 1H), 7.91 d, J=2 Hz, 1H); MS (DCI/NH$_3$) m/z 220 (M+H)$^+$; Anal. calculated for C$_{12}$H$_{17}$N$_3$O·2.6 HCl: C, 45.89; H, 6.29; N, 13.38. Found: C, 46.02; H, 6.23; N, 13.49.

Example 30

(3aS,6aS)-5-(3-pyridinyl)octahydropyrrolo[3,4-b]pyrrole 4-methylbenzenesulfonate Example 30A tert-butyl (3aS,6aS)-5-(3-pyridinyl)hexahydropyrrolo[3,4-b]pyrrole-1(2H)-carboxylate The product from Example 15E (0.71 g, 3.30 mmol) in toluene (33 mL) was treated with tris(dibenzylideneacetone)dipalladium(0) (Pd$_2$(dba)$_3$, available from Alfa Aesar) (61 mg, 0.10 mmol), 2,2'-bis(diphenylphosphino)-1,1'-binaphthyl (BINAP, available from Strem Chemicals) (83 mg, 0.10 mmol), 3-bromopyridine (available from Aldrich Chemical Co.,) (0.58 g, 3.70 mmol), and sodium tert-butoxide (available from Aldrich Chemical Co.,) (0.54 g, 5.60 mmol). After heating at 80° C. for 16 hours, the mixture was poured into diethyl ether (100 mL), washed with brine (100 mL), dried (MgSO$_4$) and concentrated under reduced pressure. The residue was purified by chromatography (SiO$_2$, 5% MeOH/CH$_2$Cl$_2$) to provide the title compound as a yellow oil (0.87 g, 91% yield). MS (DCI/NH$_3$) m/z 290 (M+H)$^+$.

Example 30B (3aS,6aS)-5-(3-pyridinyl)octahydropyrrolo[3,4b]-pyrrole 4-methylbenzenesulfonate The product from Example 30A (0.87 g, 3.0 mmol) in CH$_2$Cl$_2$ (10 mL) was treated with trifluoroacetic acid (10 mL). After stirring at ambient temperature for one hour, the mixture was concentrated under reduced pressure. The residue was purified by chromatography (SiO$_2$, 10% MeOH/CH$_2$Cl$_2$/1% NH$_4$OH) to provide the free base of the title compound as a colorless oil (0.45 g, 79% yield). The salt was formed by combination with 4-methylbenzenesulfonic acid, and crystallized from ethanol:ethyl acetate (1:7) to provide the title compound as a white solid. $^1$H NMR (CD$_3$OD, 300 MHz) δ 1.98-2.11 (m, 1H), 2.38-2.42 (m, 1H), 3.25-3.41 (m, 5H), 3.50 (dd, J=3.0, 9.0 Hz, 1H), 3.87 (dd, J=3.0, 12.0 Hz, 1H), 4.42 (t, J=6.0 Hz, 1H), 7.27 (dd, J=2.0, 11.0 Hz, 1H), 7.31 (dd, J=2.0, 9.0 Hz, 1H), 7.96 (dd, J=2.0, 5.0 Hz, 1H), 8.04 (d, J=3.0 Hz, 1H); MS (DCI/NH$_3$) m/z 190 (M+H)$^+$; Anal. Calculated for C$_{11}$H$_{15}$N$_3$.1.15 TsOH: C, 59.08; H, 6.30; N, 10.85. Found: C, 58.89; H, 6.41; N, 10.96.

Example 31

(3aS,6aS)-5-(5-bromo-3-pyridinyl)octahydropyrrolo[3,4-b]pyrrole 4-methylbenzenesulfonate Example 31A tert-butyl (3aS,6aS)-5-(5-bromo-3-pyridinyl)hexahydropyrrolo[3,4-b]pyrrole-1(2H)-carboxylate The product from Example 15E (0.56 g, 2.70 mmol) in toluene (27 mL) was treated with tris(dibenzylideneacetone)dipalladium(0) (Pd$_2$(dba)$_3$, available from Alfa Aesar) (50 mg, 0.10 mmol), 2,2'-bis(diphenylphosphino)-1,1'-binaphthyl (BINAP, available from Strem Chemicals) (68 mg, 0.10 mmol), 3,5-dibromopyridine (available from Aldrich Chemical Co.,) (0.69 g, 2.90 mmol) and sodium tert-butoxide (available from Aldrich Chemical Co.,) (0.44 g, 4.60 mmol). After heating at 80° C. for 16 hours, the reaction mixture was poured into diethyl ether (100 mL), washed with brine (100 mL), dried (MgSO$_4$) and concentrated under reduced pressure. The residue was purified by chromatography (SiO$_2$, 5% MeOH/CH$_2$Cl$_2$) to provide the title compound as a yellow oil (0.47 g, 47% yield). MS (DCI/NH$_3$) m/z 368/370 (M+H)$^+$.

Example 31B (3aS,6aS)-5-(5-bromo-3-pyridinyl)octahydropyrrolo[3,4-b]pyrrole 4-methylbenzenesulfonate The product from Example 31A (0.47 g, 1.30 mmol) in CH$_2$Cl$_2$ (10 mL) was treated with trifluoroacetic acid (10 mL). After stirring at ambient temperature for one hour, the mixture was concentrated under reduced pressure. The residue was purified by chromatography (SiO$_2$, 10% MeOH/CH$_2$Cl$_2$/1% NH$_4$OH) to provide the free base of the title compound as a colorless oil (0.32 g, 91% yield). The salt was formed by combination with 4-methylbenzenesulfonic acid and crystallized from ethanol:ethyl acetate (1:10) to provide the title compound as a light brown solid. $^1$H NMR (CD$_3$OD, 300 MHz) δ 1.98-2.14 (m, 1H), 2.30-2.42 (m, 1H), 3.25-3.52 (m, 6H), 3.85 (d, J=15.0 Hz, 1H), 4.43 (t, J=6.0 Hz, 1H), 7.42 (d, J=2.0 Hz, 1H), 8.00 (d, J=3.0, 1H), 8.05 (d, J=2.0 Hz, 1H); MS (DCI/NH$_3$) m/z 268/270 (M+H)$^+$; Anal. Calculated for C$_{11}$H$_{14}$N$_3$Br.1.0 TsOH.1.0EtOH: C, 49.38; H, 5.80; N, 8.64. Found: C, 49.60; H, 5.99; N, 8.83.

Example 32

(3aS,6aS)-5-(5-methoxy-3-pyridinyl)octahydropyrrolo[3,4-b]pyrrole 4-methylbenzenesulfonate Example 32A tert-butyl (3aS,6aS)-5-(5-methoxy-3-pyridinyl)hexahydropyrrolo[3,4-b]pyrrole-1(2H)-carboxylate The product from Example 15E (0.549 g, 2.30 mmol) in toluene (23 mL) was treated with tris(dibenzylideneacetone)dipalladium(0) (Pd$_2$(dba)$_3$, available from Alfa Aesar) (43 mg, 0.10 mmol), 2,2'-bis(diphenylphosphino)-1,1'-binaphthyl (BINAP, available from Strem Chemicals) (58 mg, 0.10 mmol), 3-bromo-5-methoxypyridine from Example 7A (0.43 g, 2.30 mmol) and sodium tert-butoxide (available from Aldrich Chemical Co.,) (0.38 g, 3.90 mmol). After heating at 80° C. for 16 hours, the mixture was poured into diethyl ether (100 mL), washed with brine (100 mL), dried (MgSO$_4$) and concentrated under reduced pressure. The residue was purified by chromatography (SiO$_2$, 5% MeOH/CH$_2$Cl$_2$) to provide the title compound as a yellow oil (0.42 g, 57% yield). MS (DCI/NH$_3$) m/z 320 (M+H)$^+$.

Example 32B (3aS,6aS)-5-(5-methoxy-3-pyridinyl)octahydropyrrolo[3,4-b]pyrrole 4-methylbenzenesulfonate The product from Example 32A (0.47 g, 1.50 mmol) in CH$_2$Cl$_2$ (10 mL) was treated with trifluoroacetic acid (10 mL). After stirring at ambient temperature for one hour, the mixture was concentrated under reduced pressure. The residue was purified by chromatography (SiO$_2$, 10% MeOH/CH$_2$Cl$_2$/1% NH$_4$OH) to provide the free base of the title compound as a colorless oil (0.22 g, 63% yield). The salt was formed by combination with 4-methylbenzenesulfonic acid and crystallized from ethanol:ethyl acetate (1:10) to provide the title compound as a yellow solid. $^1$H NMR (CD$_3$OD, 300 MHz) δ 2.09-2.12 (m, 1H), 2.30-2.42 (m, 1H), 3.32-3.55 (m, 6H), 3.85-3.93 (m, 4H), 4.43 (t, J=6.0 Hz, 1H), 6.89 (d, J=2.0 Hz, 1H), 7.70 (d, J=2.0, 1H), 7.75 (d, J=2.0 Hz, 1H); MS (DCI/NH$_3$) m/z 220 (M+H)$^+$; Anal. Calculated for C$_{12}$H$_{17}$N$_3$O.1.0 TsOH.1.0H$_2$O: C, 55.73; H, 6.65; N, 10.26. Found: C, 55.85; H, 6.89; N, 10.02.

Example 33

(cis)-3-(3-pyridinyl)-3,8-diazabicyclo[4.2.0]octane tris(4-methylbenzenesulfonate)

Example 33A 1-tert-butyl 4-ethyl 3-oxo-1,4-piperidinedicarboxylate

Ethyl 1-benzyl-3-oxopiperidine-4-carboxylate hydrochloride (24.16 g, 81.1 mmol) in ethanol (250 mL) was treated with triethyl amine (11.3 mL, 81.1 mmol), di-tert-butyl dicarbonate (18.6 g, 85.3 mmol) and 10% Pd/C (0.13 g). After stirring under H$_2$ (1 atm) at 50° C. for 1 hour, the mixture was allowed to cool to ambient temperature and filtered through diatomaceous earth with an ethanol (2×20 mL) rinse. The filtrate was concentrated under reduced pressure. The residue was treated with diethyl ether (200 mL) and refiltered with a diethyl ether rinse (2×30 mL). The filtrate was concentrated under reduced pressure to provide the title compound as a yellow oil (20.6 g, 94% yield). $^1$H NMR (CD$_3$OD, 300 MHz) δ 1.32 (t, J=6.9 Hz, 3H), 1.48 (s, 9H), 2.32-2.26 (m, 3H), 3.5 (t, J=5.7 Hz, 1H), 4.0 (br s, 1H), 4.24 (q, J=6.9 Hz, 2H); MS (DCI/NH$_3$) m/z 272 (M+H)$^+$. 289 (M+NH$_4$)$^+$.

Example 33B tert-butyl 3-hydroxy-4-(hydroxymethyl)-1-piperidinecarboxylate

The product from Example 33A (10.84 g, 40 mmol) in methanol (200 mL) was treated with sodium borohydride (9.12 g, 240 mmol) slowly over 20 minutes at 0-10° C. The mixture was allowed to warm to ambient temperature and stirred for 20 hours. The mixture was concentrated under reduced pressure, treated with water (50 mL), and extracted with chloroform (2×100 mL). The organic phase was concentrated under reduced pressure to provide the title compound (8.0 g, 86% yield). $^1$H NMR (CD$_3$OD, 300 MHz) δ 1.48 (s, 9H), 1.70-1.50 (m, 3H), 2.90-2.70 (m, 2H), 3.72-3.40 (m, 2H), 4.18-3.90 (m, 4H); MS (DCI/NH$_3$) m/z 232 (M+H)$^+$.

Example 33C tert-butyl 3-[(methylsulfonyl)oxy]-4-{[(methylsulfonyl)oxy]methyl}-1-piperidinecarboxylate The product from Example 33B (8.0 g, 34.6 mmol) and triethylamine (14.0 g, 138.4 mmol) in dichloromethane (200 mL) was treated with methanesulfonyl chloride (6.7 mL, 86.5 mmol) at 0° C. After stirring at ambient temperature overnight, the mixture was quenched with saturated sodium bicarbonate (50 mL) and extracted with dichloromethane (2×100 mL). The combined extracts were washed with brine (2×10 mL), dried (Na$_2$SO$_4$), and concentrated under reduced pressure. The residue was purified by chromatography (SiO$_2$, hexanes:ethyl acetate, 50:50) to provide the title compound as a brown oil (7.8 g, 58% yield). $^1$H NMR (CD$_3$OD, 300 MHz) δ 1.48 (s, 9H), 1.60 (m, 2H), 2.10-2.30 (m, 1H), 3.08-3.20 (m, 6H), 3.90-4.60 (m, 7H); MS (DCI/NH$_3$) m/z 405 (M+NH$_4$)$^+$.

Example 33D tert-butyl (cis)-8-benzyl-3,8-diazabicyclo[4.2.0]octane-3-carboxylate The product from Example 33C (5.8 g, 15 mmol) in anhydrous toluene (100 mL) was treated with benzylamine (4.8 g, 45 mmol). After heating at reflux for 20 hours, the mixture was allowed to cool to 25° C. and then filtered. The filtrate was concentrated and the residue purified by chromatography (SiO$_2$, hexanes:ethyl acetate, 40:60) to provide the title compound as a brown oil (0.73 g, 15% yield). MS (DCI/NH$_3$) m/z 303 (M+H)$^+$.

Example 33E (cis)-8-benzyl-3,8-diazabicyclo[4.2.0]octane 4-methylbenzenesulfonate The product from Example 33D (0.30 g, 1.0 mmol) in ethanol (10 mL) was treated with 4-methylbenzenesulfonic acid monohydrate (0.57 g, 3 mmol). After heating at 80° C. for 1 hour, the mixture was allowed to cool to ambient temperature and concentrated under reduced pressure. The residue was azeotroped from isopropyl acetate.

Example 33F (cis)-8-benzyl-3-(3-pyridinyl)-3,8-diazabicyclo[4.2.0]octane

The product from Example 33E and 3-bromopyridine were processed according to the procedure of Example 1E, except that a larger amount of sodium tert-butoxide (384 mg, 4.0 mmol) was used. The residue was purified by chromatography (SiO$_2$, hexanes:ethyl acetate, 20:80, R$_f$ 0.2) to provide the title compound (0.16 g, 57% yield). $^1$H NMR (CD$_3$OD, 300 MHz) δ 2.04 (m, 2H), 2.56 (m, 1H), 3.00 (m, 2H), 3.22 (m, 2H), 3.55 (m, 1H), 3.60 (d, J=12.5 Hz, 1H), 3.70 (d, J=12.5 Hz, 1H), 3.55 (m, 1H), 3.70 (m, 1H), 7.04 (ddd, J=8.8, 3.0, 1.3 Hz, 1H), 7.17 (d, J=4.8 Hz, 1H), 7.24 (m, 5H), 7.80 (dd, J=4.7, 1.3 Hz, 1H), 7.84 (d, J=3.0 Hz, 1H); MS (DCI/NH$_3$) m/z 280 (M+H)$^+$.

Example 33G (cis)-3-(3-pyridinyl)-3,8-diazabicyclo[4.2.0]octane tris(4-methylbenzenesulfonate)

The product from Example 33F (150 mg, 0.54 mmol) in methanol (10 mL) was treated with 4-methylbenzenesulfonic acid monohydrate (0.205 g 1.08 mmol) and 10% Pd/C (0.15 g). After stirring under H$_2$ (1 atm) at 60° C. for 20 hours, the mixture was allowed to cool to ambient temperature and filtered through diatomaceous earth with an ethanol (2×10 mL) rinse. The filtrate was concentrated under reduced pressure and the brown residue azeotroped from isopropanol (10 mL). The obtained solid was crystallized from isopropanol/isopropyl acetate to provide the title compound (35.0 mg, yield 9%). $^1$H NMR (CD$_3$OD, 300 MHz) δ 2.10 (m, 2H), 2.35 (m, 1H), 2.40 (s, 9H), 3.20 (m, 1H), 3.46 (m, 1H), 3.70 (dd, J=11.8, 3.0 Hz, 1H), 3.85 (m, 1H), 4.08 (m 1H), 4.46 (dd, J=15.0, 3.0 Hz, 1H), 4.00 (m, 2H), 4.20 (m, 1H), 4.95 (m, 1H), 7.24 (d, J=7.8 Hz, 6H), 7.70 (d, J=8.0 Hz, 6H), 7.84 (dd, J=9.0, 5.7 Hz, 1H), 8.00 (ddd, J=9.3, 3.3, 1.2 Hz, 1H), 8.10 (d, J=5.4 Hz, 1H), 8.30 (d, J=3.1 Hz, 1H); MS (DCI/NH$_3$) m/z 190 (M+H)$^+$; Anal. calculated for C$_{11}$H$_{15}$N$_3$O.3 TsOH: C, 54.45; H, 5.57; N, 5.95. Found: C, 54.10; H, 5.79; N, 5.58.

Example 35

(3aR,6aR)-5-(5-ethynyl-3-pyridinyl)octahydropyrrolo[3,4-b]pyrrole hydrochloride dihydrochloride Example 35A tert-butyl (3aR,6aR)-5-{5-[(trimethylsilyl)ethynyl]-3-pyridinyl}hexahydropyrrolo[3,4-b]pyrrole-1(2H)-carboxylate The product of Example 36A (980 mg, 2.66 mmol) was treated with ethynyltrimethylsilane (0.73 mL, 5.2 mmol) in dry DMF (15 mL) in the presence of PdCl$_2$(Ph$_3$P)$_2$ (93.4 mg, 0.133 mmol), cuprous iodide (25.3 mg, 0.133 mmol) and triethylamine (1.0 g, 9.9 mmol) at 56-60° C. for 1 hr. The mixture was diluted with water and extracted with ethyl acetate (3×100 mL). The organic layers were combined, dried (MgSO$_4$), filtered and the filtrate evaporated under reduced pressure. The residue was purified by chromatography (SiO$_2$, ethyl acetate:hexanes, 1:9) to provide the title compound (550 mg, 55% yield). MS (DCI/NH$_3$) m/z 386 (M+H)$^+$.

Example 35B tert-butyl (3aR,6aR)-5-(5-ethynyl-3-pyridinyl) hexahydropyrrolo[3,4-b]pyrrole-1(2H)-carboxylate The product of Example 35A (550 mg, 1.42 mmol) in dry tetrahydrofuran (10 mL) was treated with tetrabutyl ammonium fluoride (4 mL, 4 mmol, 1M solution in tetrahydrofuran) at room temp for 1 hour. The solution was concentrated under reduced pressure and the residue was purified by chromatography (SiO$_2$, ethyl acetate:hexanes, 1:4) to provide the title compound (280 mg, 63% yield).

Example 35C (3aR,6aR)-5-(5-ethynyl-3-pyridinyl)octahydropyrrolo[3,4-b]pyrrole hydrochloride dihydrochloride The product of Example 35B (280 mg, 0.89 mmol) was processed according to the procedure of the example 14J to provide the title compound (180 mg, 94% yield).
$^1$H NMR (CD$_3$OD, 300 MHz) δ 2.05 (m, 1H), 2.35 (m, 1H), 3.45 (m, 6H), 3.92 (dd, J=12, 1.5 Hz, 1H), 4.18 (s, 1H), 4.45 (t, J=6 Hz, 1H), 7.83 (m, 1H), 8.18 (d, J=3 Hz, 1H), 8.25 (s, 1H); MS (DCI/NH$_3$) m/z 214 (M+H)$^+$; Anal. calculated for C$_{13}$H$_{15}$N$_3$.2HCl.0.25 H$_2$O: C, 53.64; H, 5.80; N, 14.14. Found: C, 53.53; H, 6.06; N, 14.36.

Example 36

(3aR,6aR)-5-(5-bromo-3-pyridinyl)octahydropyrrolo[3,4-b]pyrrole dihydrochloride

Example 36A tert-butyl (3aR,6aR)-5-(5-bromo-3-pyridinyl)hexahydropyrrolo[3,4-b]pyrrole-1(2H)-carboxylate The product of Example 14H (910 mg, 4.3 mmol) and 3,5-dibromopyridine (1.0 g, 4.3 mmol) were processed according to the procedure of Example 1E to provide the title compound (520 mg, 33% yield). MS (DCI/NH$_3$) m/z 370 (M+H)$^+$.

Example 36B (3aR,6aR)-5-(5-bromo-3-pyridinyl)octahydropyrrolo[3,4-b]pyrrole dihydrochloride The product of Example 36A (210 mg, 0.57 mmol) was processed according to the procedure of Example 14J to provide the title compound (169 mg. (87% yield). $^1$H NMR (CD$_3$OD, 300 MHz) δ 2.05 (m, 1H), 2.35 (m, 1H), 3.45 (m, 6H), 3.92 (dd, J=12, 1.5 Hz, 1H), 4.45 (t, J=6 Hz, 1H), 7.95 (d, J=3 Hz, 1H), 8.18 (d, J=3 Hz, 1H), 8.32 (d, J=1 Hz, 1H); MS (DCI/NH$_3$) m/z 270 (M+H)$^+$: Anal. calculated for C$_{11}$H$_{14}$BrN$_3$.2HCl: C, 38.69; H, 4.69; N, 12.31. Found: C, 38.38; H, 4.73; N, 12.17.

Example 37

5-((3aR,6aR)-hexahydropyrrolo[3,4-b]pyrrol-5(1H)-yl)nicotinonitrile

Example 37A 3-bromo-5-cyanopyridine

Phosphorus oxychloride (5 ml) was added to 5-bromonicotinamide (2 g, 10 mmol. Avocado Research Chemicals, Ltd.) and the mixture was heated to gentle reflux for 3 hours. The mixture was allowed to cool to room temperature, poured onto ice (100 g) and extracted with ethyl acetate (3×100 mL). The combined extracts were washed successively with aqueous ammonium hydroxide and water, dried (MgSO$_4$), filtered and the filtrate concentrated under reduced pressure. The residue was purified by chromatography (SiO$_2$, ethyl acetate: hexanes, 1:1) to provide the title compound (1.5 g, 82% yield). MS (DCI/NH$_3$) m/z 184 (M+H)$^+$.

Example 37B tert-butyl (3aR,6aR)-5-(5-cyano-3-pyridinyl)hexahydropyrrolo[3,4-b]pyrrole-1(2H)-carboxylate The product of Example 14H (1.7 g, 8 mmol) and 3-bromo-5-cyanopyridine (1.46 g, 8 mmol, from Example 37A) were processed according to the procedure described for Example 1E, to provide the title compound (600 mg, 24% yield). MS (DCI/NH$_3$) m/z 315 (M+H)$^+$.

Example 37C 5-((3aR,6aR)-hexahydropyrrolo[3,4-b]pyrrol-5(1H)-yl)nicotinonitrile fumarate The product of Example 37B (300 mg 0.95 mmol) in ethanol (8 mL) was treated with 4N HCl in 1,4-dioxane (2 mL, 8 mmol) for 4 hours. The mixture was concentrated under reduced pressure and the residue was purified by chromatography (SiO$_2$, CH$_2$Cl$_2$:methanol:NH$_4$OH$_{(aq)}$, 94:5:1) to provide the free base (100 mg, 42% yield). The free base was dissolved in 10% methanol/diethyl ether (35 mL) and treated with a solution of fumaric acid (65 mg, 0.56 mmol) in 10% methanol/diethyl ether (10 mL). The mixture was stirred at room temperature for 16 hours and the precipitate was isolated by filtration and dried under reduced pressure to provide the title compound (154 mg, 83% yield). $^1$H NMR (CD$_3$OD, 300 MHz) δ 2.05 (m, 1H), 2.35 (m, 1H), 3.45 (m, 6H), 3.90 (dd, J=12, 1.5 Hz, 1H), 4.45 (t, J=6 Hz, 1H), 6.68 (s, 2H), 7.45 (m, 1H), 8.25 (d, J=1.5 Hz, 1H), 8.35 (d, J=3 Hz, 1H); MS (DCI/NH$_3$) m/z 214 (M+H)$^+$: Anal. calculated for C$_{12}$H$_{14}$N$_4$.C$_4$H$_4$O$_4$: C, 58.12; H, 5.44; N, 16.95. Found: C, 58.20; H, 5.49; N, 17.00.

Example 38

(cis)-3-(3-pyridinyl)-3,6-diazabicyclo[3.2.0]heptane bis(4-methylbenzenesulfonate)

Example 38A benzyl 2,2-dimethoxyethylcarbamate

Benzyl chloroformate (231.3 g, 1.3 mol) was added gradually to a mixture of aminoacetaldehyde dimethyl acetal (152.0 g, 1.3 mol) in toluene (750 mL) and aqueous NaOH (72.8 g, 1.82 mol, in 375 mL of water) at 10-20° C. After the addition was completed, the mixture was stirred at ambient temperature over 4 hours. The organic layer was separated, washed with brine (2×100 mL) and concentrated to provide the title compound as an oil (281.5 g 90% yield). $^1$H NMR (CDCl$_4$, 300 MHz) δ 3.33 (t, J=6.0 Hz, 2H), 3.39 (s, 6H), 4.37 (t, J=6.0 Hz, 1H), 5.11 (s, 2H), 7.30 (m, 5H); MS (DCI/NH$_3$) m/z 257 (M+NH$_4$)$^+$, 340 (M+H)$^+$.

Example 38B benzyl allyl(2,2-dimethoxyethyl)carbamate

The product of Example 38A (281.0 g, 1.18 mol) in dry toluene (1.0 L) was treated with powdered KOH (291.2 g, 5.20 mol) and triethylbenzylammonium chloride (4.4 g, 0.02 mol). A solution of allyl bromide (188.7 g, 1.56 mol) in toluene (300 mL) was then added dropwise over 1 hour at 20-30° C. The mixture was stirred overnight at room temperature and then water (300 mL) was added over 20 minutes at 20-30° C. The layers were separated and the aqueous phase was extracted with toluene (2×300 mL). The organic phases were combined, washed with brine (2×100 mL), dried (K$_2$CO$_3$), filtered and the filtrate concentrated to provide the title compound as oil (315.6 g, 96%, yield). $^1$H NMR (MeOH-d$_4$, 300 MHz) δ 3.32 (s, 3H) 3.37 (m, 5H), 3.97 (d, J=5.4 Hz, 2H), 4.50-4.40 (m, 1H), 5.15 (m, 4H), 5.75 (m, 1H), 7.23 (m, 5H); MS (DCI/NH$_3$) m/z 297 (M+NH$_4$)$^+$, 280 (M+H)$^+$.

Example 38C benzyl allyl(2-oxoethyl)carbamate

The product of Example 38B (314.0 g, 1.125 mol) was treated with formic acid (88%, 350 mL) at room temperature and allowed to stir for 15 hours. Most of the formic acid was removed by concentration under reduced pressure at 40-50° C. The residue was extracted with ethyl acetate (3×500 mL). The extracts were combined and washed with brine until the wash had a pH=6-7. The organic phase was concentrated to provide the title compound as a slightly yellow oil (260.0 g, 99% yield). $^1$H NMR (CDCl$_3$, 300 MHz) δ 3.20 (m, 1H), 3.97 (m, 2H), 4.10 (m, 1H), 5.10 (m, 4H), 5.75 (m, 1H), 7.45 (m, 5H), 9.50 (d, J=6.4 Hz, 1H); MS (DCI/NH$_3$) m/z 234 (M+H)$^+$.

Example 38D benzyl allyl[2-(hydroxyimino)ethyl]carbamate

The product of Example 38C (260 g, 1.115 mol) in acetonitrile (1.5 L) was treated with sodium acetate trihydrate (170.6 g, 4.41 mol, in 0.75 L distilled water) and NH$_2$OH hydrochloride (98.0 g, 4.41 mol) under N$_2$. The mixture was stirred at room temperature over 20 hours. The volatiles were removed under reduced pressure and the residue was extracted with ethyl acetate (2×750 mL). The combined organic phases were washed with brine until the wash has pH=7. The organic phase was concentrated to provide the title compound as an oil (271 g, 98% yield). $^1$H NMR (MeOH-d$_4$, 300 MHz) δ 3.94 (m, 2H), 3.98 (d, J=5.5 Hz, 1H), 4.17 (d, J=4.4 Hz, 1H), 5.30 (m, 4H), 5.60 (m, 1H), 7.40 (m, 5H), MS (DCI/NH$_3$) m/z 266M+NH$_4$)$^+$, 249 (M+H)$^+$.

Example 38E benzyl (cis)-3-amino-4-(hydroxymethyl)-1-pyrrolidinecarboxylate

A solution of the product of Example 38D (240 g, 0.97 mol) in xylene (1.0 L) was heated at reflux under N$_2$ over 10 hours. The resulting brown solution was cooled to 10-15° C. and acetic acid (1.0 L) was added under N$_2$. Zinc powder (100 g, 1.54 mol) was added gradually, and the gray mixture was stirred at room temperature for 3 hours. The mixture was filtered and water (1.0 L) was added to the filtrate. The filtrate was stirred for 10 minutes and the brown organic layer was separated. The aqueous phase was washed well with xylenes (4×400 mL) and then concentrated under reduced pressure to a volume of approximately 200 mL. This residue was basified to pH 9-10 by cautious addition of saturated aqueous Na$_2$CO$_3$. The precipitated white solid was removed by filtration and the filtrate was extracted with CHCl$_3$ (3×600 mL). The combined organic phases were washed with saturated Na$_2$CO$_3$ solution (2×50 mL) and dried over anhydrous Na$_2$CO$_3$. The mixture was filtered through a short column of diatomaceous earth and the filtrate was concentrated to provide the title compound as slightly yellow oil. (145 g, 60% yield). $^1$H NMR (MeOH-d$_4$, 300 MHz) δ 2.40 (m, 1H), 3.30 (m, 2H), 3.80-3.50 (m, 5H), 5.10 (s, 2H), 7.35 (m, 5H); MS (DCI/NH$_3$) m/z 251 (M+H)$^+$.

Example 38F benzyl (cis)-3-[(tert-butoxycarbonyl)amino]-4-(hydroxymethyl)-1-pyrrolidinecarboxylate The product of Example 38E (7.0 g, 28 mmol) in ethanol (50 mL) was treated with 5% NaOH$_{(aq)}$ solution (10 mL) and di-tert-butyl dicarbonate (10.9 g, 50 mmol) at room temperature and allowed to stir overnight. Most of the ethanol was removed under reduced pressure and the residue was extracted with ethyl acetate (2×100 mL). The extracts were combined, washed with brine (2×20 mL) and concentrated. The residue was purified by chromatography (SiO$_2$, CH$_2$Cl$_2$: MeOH, 95:5, R$_f$, 0.5) to provide the title compound (7.5 g, 77% yield). $^1$H NMR (MeOH-d$_4$, 300 MHz) δ 1.50 (brs, 9H), 2.50 (m, 1H), 3.25 (m, 1H), 3.40 (m, 1H), 3.60 (m, 4H), 4.32 (m, 1H), 5.10 (s, 2H), 7.30 (m, 5H); MS (DCI/NH$_3$) m/z 368 (M+NH$_4$)$^+$, 351 (M+H)$^+$.

Example 38G benzyl (cis)-3-[(tert-butoxycarbonyl)amino]-4-{[methylsulfonyl)oxy]methyl}-1-pyrrolidinecarboxylate The product of Example 38F (4.80 g, 13.7 mmol) in CH$_2$Cl$_2$ (60 mL) was treated with triethylamine (2.77 g, 27.4 mmol). The mixture was stirred at room temperature over 5 minutes, cooled down to −10° C. and then treated with methanesulfonyl chloride (1.73 g, 15.1 mmol) in CH$_2$Cl$_2$ (10 mL) dropwise over 10 minutes. The resultant brown solution was stirred for 1 hour at room temperature and quenched with water (10 mL). The layers were separated and the aqueous phase was extracted with CH$_2$Cl$_2$ (2×50 mL). The combined organic phases were washed with brine (2×20 mL), dried over Na$_2$SO$_4$, filtered and the filtrate concentrated to provide the title compound as a dark brown oil (4.38 g, 75% yield). $^1$H NMR (MeOH-d$_4$, 300 MHz) δ 1.48 (s, 9H), 2.80 (m, 1H), 3.08 (s, 3H), 3.30 (m, 1H), 3.42 (m, 1H), 3.70 (m, 2H), 4.20 (m, 1H), 4.40 (m, 2H), 5.10 (s, 2H), 7.30 (m, 5H); MS (DCI/NH$_3$) m/z 446 (M+NH$_4$)$^+$. 429 (M+H)$^+$.

Example 38H benzyl (cis)-3-amino-4-{[(methylsulfonyl)oxy]methyl}-1-pyrrolidinecarboxylate A solution of the product of Example 38G (4.30 g, 10.0 mmol) in CH$_2$Cl$_2$ (5 mL) was treated with trifluoroacetic acid (5 mL) at room temperature over 1 hour. The mixture was concentrated to provide the title compound as a dark brown oil which was used directly in the next step without further purification. $^1$H NMR (MeOH-d$_4$, 300 MHz) δ 3.05 (m, 1H), 3.15 (s, 3H), 3.44 (m, 1H), 3.85-3.62 (m, 3H), 3.70 (m, 2H), 4.05 (m, 1H), 4.46 (m, 2H), 5.15 (s, 2H), 7.36 (m, 5H); MS (DCI/NH$_3$) m/z 346 (M+NH$_4$)$^+$, 329 (M+H)$^+$.

Example 38I 3-benzyl (cis)-6-tert-butyl 3,6-diazabicyclo[3.2.0]heptane-3,6-dicarboxylate The product of Example 38I-1 in ethanol (25 mL) was treated with 5% aqueous NaOH (~25 mL, pH>10) at 60° C. for 10 hours. The mixture was allowed to cool to room temperature and then was treated with di-tert-butyl dicarbonate (2.40 g, 11 mmol). After stinting at overnight room temperature, the volatiles were removed under reduced pressure and the aqueous residue was extracted with CHCl$_3$ (3×50 mL). The combined organic phases were washed with brine (2×20 mL), concentrated and the residue was purified by chromatography (SiO$_2$, CH$_2$Cl$_2$:MeOH 95:5:1, R$_f$, 0.5) to provide the title compound (3.2 g, 96% for steps 38H and 38I). $^1$H NMR (MeOH-d$_4$, 300 MHz) δ 1.46 (s, 9H), 3.10 (m, 2H), 3.25 (m, 1H), 3.46 (m, 1H), 3.90 (d, J=11.9 Hz, 1H), 4.05 (m, 2H), 4.68 (dd, J=6.3, 4.4 Hz, 1H), 5.20 (s, 2H), 7.36 (m, 5H); MS (DCI/NH$_3$) m/z 350 (M+NH$_4$)$^+$, 333 (M+H)$^+$.

Example 38J tert-butyl (cis)-3,6-diazabicyclo[3.2.0]heptane-6-carboxylate

The product of Example 38I (2.3 g, 6.92 mmol) in methanol (30 mL) was treated with 10% palladium on carbon (0.23 g) and stirred at room temperature under H$_2$ (1 atm) for 10 hours. The catalyst was removed by filtration through diatomaceous earth and the filtrate was concentrated to provide the title compound as a yellow oil. (1.27 g, 92% yield). $^1$H NMR (MeOH-d$_4$, 300 MHz) δ 1.46 (s, 9H), 2.47 (dd, J=12.9, 3.7 Hz, 1H), 2.64 (dd, J=12.2, 5.7 Hz, 1H), 2.95 (m, 1H), 3.05 (d, J=12.2 Hz, 1H), 3.24 (d, J=12.5 Hz, 1H), 3.46 (m, 1H), 3.95 (m, 1H), 4.64 (dd, J=6.1, 3.8 Hz, 1H), MS (DCI/NH$_3$) m/z 216 (M+NH$_4$)$^+$, 199 (M+H)$^+$.

Example 38K tert-butyl (cis)-3-(3-pyridinyl)-3,6-diazabicyclo [3.2.0]heptane-6-carboxylate The product of Example 38J (150 mg, 0.75 mmol) and 3-bromopyridine were processed according to the procedure described in Example 1E. The crude product was purified by chromatography (SiO$_2$, CH$_2$Cl$_2$: MeOH, 95:5, R$_f$, 0.3) to provide the title compound (110 mg, 53% yield), which as used directly in the next step without further purification. $^1$H NMR (MeOH-d$_4$, 300 MHz) δ 1.50 (s, 9H), 2.88 (m, 1H), 3.00 (dd, J=10.2, 6.5 Hz, 1H), 3.25 (m, 1H), 3.60 (m, 1H), 3.82 (d, J=10.2 Hz, 1H), 3.97 (m, 1H), 4.08 (m, 1H), 4.84 (dd, J=6.8, 4.1 Hz, 1H), 7.30 (m, 2H), 7.82 (m, 1H), 8.10 (m, 1H). MS (DCI/NH$_3$) m/z 293 (M+NH$_4$)$^+$, 276 (M+H)$^+$.

Example 38L (cis)-3-(3-pyridinyl)-3,6-diazabicyclo[3.2.0]heptane bis(4-methylbenzenesulfonate)

The product of Example 38K (100 mg, 0.36 mmol) in ethanol (10 mL) was treated with 4-methylbenzenesulfonic acid monohydrate (144 mg, 0.76 mmol) at 80° C. and allowed to stir for 6 hours. The mixture was concentrated under reduced pressure and the residue was diluted with warm methyl tert-butyl ether (20 mL) and stirred at ambient temperature for 10 hours. The precipitate was isolated by filtration and dried under reduced pressure at 40-50° C. to provide the title compound (140 mg, 86% yield). $^1$H NMR (MeOH-d$_4$, 300 MHz) δ 2.40 (s, 6H), 3.28 (dd, J=10.9, 6.4 Hz, 1H), 3.40 (dd, J=12.9, 5.5 Hz, 1H), 3.60 (m, 1H), 3.78 (dd, J=11.1, 15.0 Hz, 1H), 4.04 (d, J=10.8 Hz, 1H), 4.28 (d, J=12.9 Hz, 1H), 4.30 (m, 1H), 5.14 (dd, J=7.1, 5.4 Hz, 1H), 7.24 (d, J=7.8 Hz, 4H), 7.68 (d, J=8.1 Hz, 4H), 7.88 (dd, J=8.8, 5.4 Hz, 1H), 8.02 (ddd, J=9.1, 2.7, 1.3 Hz, 1H), 8.20 (d, J=5.4 Hz, 1H), 8.34 (d, J=3.0 Hz, 1H); m/z 176 (M+H)$^+$; Anal. calculated for C$_{10}$H$_{13}$N$_3$.2.4TsOH.H$_2$O: C, 53.07; H, 5.68; N, 6.93. Found: C, 52.99; H, 5.23; N, 6.62.

348896 Example 39

(cis)-6-(3-pyridinyl)octahydro-1H-pyrrolo[2,3-c] pyridine dihydrochloride

Example 39A 3-amino-4-methylpyridine

2-Chloro-3-nitro-4-methylpyridine (4.0 g, 23.2 mmol) in methanol was treated with 10% palladium on carbon (2 g) and anhydrous sodium acetate (2.14 g, 26 mmol) and agitated under H$_2$ (4 atm) at room temperature for 45 minutes. The mixture was filtered and the filtrate concentrated under reduced pressure to provide the title compound (2.5 g, 100% yield). MS (DCI/NH$_3$) m/z 109 (M+H)$^+$.

Example 39B tert-butyl 4-methyl-3-pyridinylcarbamate

The product of Example 39A (300 mg, 2.8 mmol) in tetrahydrofuran (10 mL) was treated with sodium bis(trimethylsilyl)amide (5.5 mL, 1M solution in tetrahydrofuran) at room temperature followed by addition of di-tert-butyl dicarbonate (605 mg, 2.8 mmol). The mixture was stirred at room temperature for 3 hours and concentrated under reduced pressure. The residue was partitioned between ethyl acetate (100 mL) and water (20 mL). The organic layer was separated, dried (MgSO$_4$) and concentrated under reduced pressure. The residue was purified by chromatography (SiO$_2$, ethyl acetate: hexanes, 3:7) to provide the title compound (400 mg, 69% yield). MS (DCI/NH$_3$) m/z 209 (M+H)$^+$.

Example 39C tert-butyl 2-hydroxy-2,3-dihydro-1H-pyrrolo[2,3-c] pyridine-1-carboxylate The product of Example 39B (900 mg, 4.32 mmol) in tetrahydrofuran (20 mL) was cooled to −40° C. and treated with n-butyllithium (5.4 mL, 1.6M solution in hexane, 8.6 mmol) at −40° C. The mixture was allowed to warm to room temperature over 2 hours and then N,N-dimethylformamide (0.2 mL) was added. The reaction mixture was stirred for 0.5 hours, poured into water (20 mL) and extracted with ethyl acetate (100 mL). The organic layer was dried (MgSO$_4$) and concentrated under reduced pressure. The residue was purified by chromatography (SiO$_2$, ethyl acetate:hexanes, 1:4) to provide the title compound (600 mg, 60% yield). MS (DCI/NH$_3$) m/z 237 (M+H)$^+$.

Example 39D tert-butyl 1H-pyrrolo[2,3-c]pyridine-1-carboxylate

The product of Example 39C (1.5 g, 6.4 mmol) and triethylamine (1.6 g, 15.8 mmol) in methylene chloride (50 mL) were treated with methanesulfonyl chloride (0.54 ml, 7 mmol). After stirring at room temperature for 18 hours, the reaction mixture was quenched with water (20 mL) and extracted with ethyl acetate (3×100 mL). The organic layer was dried (MgSO$_4$) and concentrated under reduced pressure. The residue was purified by chromatography (SiO$_2$, ethyl acetate:hexanes, 1:4) to provide the title compound (1.05 g, 79% yield). MS (DCI/NH$_3$) m/z 219 (M+H)$^+$.

Example 39E tert-butyl 2,3-dihydro-1H-pyrrolo[2,3-c]pyridine-1-carboxylate

The product of Example 39D (360 mg, 1.65 mmol) in methanol (10 mL) was treated with 10% palladium on carbon (750 mg) and agitated under H$_2$ (4 atm) for 3 days. The mixture was filtered and the filtrate was concentrated under reduced pressure to provide the title compound (240 mg, 64% yield). MS (DCI/NH$_3$) m/z 227 (M+H)$^+$.

Example 39F tert-butyl 6-(3-pyridinyl)octahydro-1H-pyrrolo[2,3-c]pyridine-1-carboxylate The product of Example 39E (226 mg, 1.0 mmol) and 3-bromopyridine (158 mg, 1.0 mmol) were processed according to the procedure described in Example 1E to provide the title compound (60 mg, 20% yield). MS (DCI/NH$_3$) m/z 304 (M+H)$^+$.

Example 39G (cis)-6-(3-pyridinyl)octahydro-1H-pyrrolo[2,3-c]pyridine dihydrochloride The product of Example 39F (60 mg, 0.19 mmol) was processed according to the procedure of Example 14J to provide the title compound (37 mg, 71% yield). $^1$H NMR (CD$_3$OD, 300 MHz) δ 1.70 (m, 1H), 2.0 (m, 2H), 2.3 (m, 1H), 2.65 (m, 1H), 3.1-4.0 (m, 7H), 7.85 (dd, J=9, 6 Hz, 1H), 8.18 (dd, J=9, 3 Hz, 1H), 8.42 (d, J=3 Hz, 1H); MS (DCI/NH$_3$) m/z 204 (M+H)$^+$; Anal. calculated for C$_{12}$H$_{17}$N$_3$.2HCl: C, 52.12; H, 6.87; N, 15.20. Found: C, 51.87; H, 6.88; N, 15.04.

Example 40

(cis)-6-(3-pyridinyl)-3,6-diazabicyclo[3.2.0]heptane fumarate

Example 40A benzyl (cis)-3,6-diazabicyclo[3.2.0]heptane-3-carboxylate

The product of Example 38I (1.0 g, 6.92 mmol) in CH$_2$Cl$_2$ (5 mL) was treated with trifluoroacetic acid (5 mL) at room temperature for 1 hour. The mixture was concentrated and the residue was diluted with CHCl$_3$ (50 mL). The brown chloroform solution was washed with saturated aqueous NaHCO$_3$ (2×20 mL, pH=8-9) and brine (5 mL), dried (MgSO$_4$), filtered, and the filtrate concentrated to provide the title compound as a brown oil (0.64 g, 97% yield) which was used in the next step without purification. $^1$H NMR (MeOH-d$_4$, 300 MHz) δ 3.30-3.16 (m, 3H), 3.36 (m, 1H), 3.80 (m, 3H), 4.45 (dd, J=6.4 Hz, 4.8 Hz, 1H), 5.16 (s, 2H), 7.36 (m, 5H); MS (DCI/NH$_3$) m/z 250 (M+NH$_4$)$^+$. 233 (M+H)$^+$.

Example 40B benzyl (cis)-6-(3-pyridinyl)-3,6-diazabicyclo[3.2.0] heptane-3-carboxylate The product of Example 40A (230 mg, 1.0 mmol) and 3-bromopyridine were processed according to the procedure described in Example 1E. The crude product was purified by chromatography (SiO$_2$, CH$_2$Cl$_2$: MeOH, 95:5, R$_f$, 0.3) to provide the title compound (130 mg, 42% yield: $^1$H NMR (MeOH-d$_4$, 300 MHz) δ 3.24 (dd, J=12.6, 4.1 Hz, 1H), 3.30 (m, 1H), 3.40 (m, 1H), 3.65 (dd, J=7.8, 3.4 Hz, 1H), 4.08-3.92 (m, 3H), 4.70 (m, 1H), 5.10 (m, 2H), 6.90 (m, 1H), 7.24 (m, 3H), 7.35 (m, 2H), 7.73 (d, J=2.7 Hz, 1H), 7.86 (d, J=4.7 Hz, 1H); MS (DCI/NH$_3$) m/z 310 (M+H)$^+$.

Example 40C 6-(3-pyridinyl)-3,6-diazabicyclo[3.2.0]heptane

The product of Example 40B (120 mg, 0.39 mmol) in MeOH (10 mL) was treated with 10% palladium on carbon (120 mg) and stirred at ambient temperature under H$_2$ (1 atm) for 2 hours. The mixture was filtered and the filtrate was concentrated to provide the title compound as a brown oil (65 mg, 94% yield). $^1$H NMR (MeOH-d$_4$, 300 MHz) δ 2.55 (dd, J=12.9, 3.4 Hz, 1H), 2.72 (dd, J=12.6, 6.5 Hz, 1H), 3.20 (m, 2H), 3.63 (dd, J=7.5, 3.4 Hz, 1H), 3.90 (t, J=7.8 Hz, 1H), 4.65 (dd, J=6.1, 3.4 Hz, 1H), 6.88 (ddd, J=8.5, 3.1, 1.4 Hz, 1H), 7.18 (dd, J=8.4, 4.8 Hz, 1H), 7.73 (d, J=3.0 Hz, 1H), 7.83 (dd, J=4.7, 1.3 Hz, 1H) m/z 176 (M+H)$^+$.

Example 40D (cis)-6-(3-pyridinyl)-3,6-diazabicyclo[3.2.0]heptane fumarate

The product of Example 40C (65 mg, 0.37 mmol) was treated with fumaric acid (46.4 mg, 0.4 mmol) in methanol/isopropylacetate (1:10 v/v, 20 mL). The mixture was stirred at room temperature overnight. The precipitate was collected by filtration and dried under reduced pressure at 40-50° C. to provide the title compound (47 mg, 44% yield). $^1$H NMR (MeOH-d$_4$, 300 MHz) δ 3.18 (dd, J=12.6, 3.4 Hz, 1H), 3.35 (m, 1H), 3.46 (m, 1H), 3.75 (m, 3H), 4.04 (t, J=7.5 Hz, 1H), 4.90 (m, 1H), 6.58 (s, 2H), 7.04 (ddd, J=8.2, 2.7, 1.3 Hz, 1H), 7.27 (dd, J=8.2, 4.8 Hz, 1H), 7.87 (d, 2.7 Hz, 1H), 7.95 (dd, J=4.8, 1.1 Hz, 1H); m/z 176 (M+H)$^+$; Anal. calculated for C$_{10}$H$_{13}$N$_3$.1.25C$_4$H$_4$O$_4$.0.6H$_2$O: C, 54.41; H, 5.84; N, 12.69. Found: C, 54.96; H, 5.50; N, 12.10.

Example 41

(cis)-3-(6-chloro-3-pyridinyl)-3,6-diazabicyclo[3.2.0]heptane fumarate

Example 41A tert-butyl (cis)-3-(6-chloro-3-pyridinyl)-3,6-diazabicyclo[3.2.0]heptane-6-carboxylate The product of Example 38J (150 mg, 0.75 mmol) and 5-bromo-2-chloropyridine were processed according to the procedure described in Example 1E. The crude product was purified by chromatography (SiO$_2$, hexane:ethyl acetate, 50:50, R$_f$ 0.3) to provide the title compound (150 mg, 48% yield: $^1$H NMR (MeOH-d$_4$, 300 MHz) δ 1.48 (s, 9H), 2.90 (dd, J=10.2, 6, 4.1 Hz, 1H), 3.00 (dd, J=10.2, 6.4 Hz, 1H), 3.27 (m, 2H), 3.60 (m, 1H), 3.77 (d, J=10.2 Hz, 1H), 3.92 (m, 1H), 4.08 (m, 1H), 7.26 (d, J=1.7 Hz, 2H), 7.85 (t, J=1.8 Hz, 1H); MS (DCI/NH$_3$) m/z 329 (M+2+NH$_4$)$^+$, 327 (M+NH$_4$)$^+$.

Example 41B

(cis)-3-(6-chloro-3-pyridinyl)-3,6-diazabicyclo[3.2.0]heptane

The product of Example 41A (150 mg, 0.48 mmol) in CH$_2$Cl$_2$ (5 mL) was treated with trifluoroacetic acid (5 mL) at room temperature and allowed to stir for 1 hour. The mixture was concentrated and the brown residue was neutralized to pH=9 with 5% NaOH. The mixture was extracted with CHCl$_3$ (3×50 mL) and the combined organic phases were concentrated to provide the title compound as brown oil (90 mg, 90% yield). $^1$H NMR (MeOH-d$_4$, 300 MHz) δ 2.95 (dd, J=10.1, 5.1 Hz, 1H), 3.05 (dd, J=10.2, 6.8 Hz, 1H), 3.27 (m, 2H), 3.40 (m, 1H), 3.75 (d, J=10.2 Hz, 1H), 3.87 (t, J=8.1 Hz, 1H), 4.58 (dd, J=6.8, 4.7 Hz, 1H), 7.26 (d, J=1.7 Hz, 2H), 7.87 (t, J=1.7 Hz, 1H); MS (DCI/NH$_3$) m/z 229 (M+2+NH$_4$)$^+$, 227 (M+NH$_4$)$^+$.

Example 41C

(cis)-3-(6-chloro-3-pyridinyl)-3,6-diazabicyclo[3.2.0]heptane fumarate

The product of Example 41B (90 mg, 0.43 mmol) was treated with fumaric acid (53.0 mg, 0.47 mmol) according to the procedure described in Example 40D to provide the title compound (100.2 mg, 73% yield). $^1$H NMR (MeOH-d$_4$, 300 MHz) δ 3.05 (dd, J=10.1, 5.1 Hz, 1H), 3.15 (dd, J=12.2, 5.1 Hz, 1H), 3.50 (m, 1H), 3.75 (dd, J=9.9, 5.8 Hz, 1H), 3.90 (d, J=10.5 Hz, 1H), 4.16 (d, J=12.2 Hz, 1H), 4.46 (dd, J=11.2, 8.5 Hz, 1H), 5.00 (dd, J=6.1, 5.7 Hz, 1H), 6.68 (s, 2H), 7.34 (d, J=8.8 Hz, 1H), 7.38 (dd, J=8.8, 2.7 Hz, 1H), 7.96 (d, J=2.7 Hz, 1H); MS (DCI/NH$_3$) m/z 229 (M+2+NH$_4$)$^+$, 227 (M+NH$_4$)$^+$. Anal. calculated for C$_{10}$H$_{12}$ClN$_3$.0.5C$_4$H$_4$O$_4$.0.5H$_2$O: C, 52.09; H, 5.46; N, 15.18. Found: C, 50.31; H, 4.920; N, 14.41.

Example 42

(cis)-3-(6-chloro-3-pyridinyl)-3,8-diazabicyclo[4.2.0]octane bis(4-methylbenzenesulfonate)

Example 42A tert-butyl (cis)-3-(benzylamino)-4-(hydroxymethyl)-1-piperidinecarboxylate

Benzylamine (17.8 g, 0.166 mol) and the product of Example 33A (41.0 g, 0.151 mol) in a mixture of acetic acid (27.3 g, 0.454 mol) and CH$_2$Cl$_2$ (600 mL) were treated with solid NaBH$_3$CN (96.2 g, 0.454 mol) gradually over 30 minutes. The mixture was stirred for 18 hours at room temperature. Water (200 mL) was added and the organic phase was separated, dried (MgSO$_4$), filtered and the filtrate concentrated under reduced pressure to provide an oil (40 g). The obtained oil was dissolved in tetrahydrofuran (300 mL) and treated with LiAlH$_4$ (1 M in THF, 121 mL, 121 mmol) at 0° C. The mixture was allowed to warm to room temperature and stir for 2 hours and then quenched by cautious addition of excess Na$_2$SO$_4$.10H$_2$O. The mixture was filtered and the filtrate was concentrated to provide the title compound as an oil (28.2 g, 58% yield) which was used directly in the next step without further purification. MS (DCI/NH$_3$) m/z 321 (M+H)$^+$.

Example 42B tert-butyl (cis)-3-amino-4-(hydroxymethyl)-1-piperidinecarboxylate

The product of Example 42A (28.2 g 0.088 mol) in ethanol (400 mL) was treated with 10% palladium on carbon (2 g) and the mixture was stirred under H$_2$ at 50° C. for 4 hours. The catalyst was removed by filtration and the filtrate was concentrated under reduced pressure to provide the title compound (18.0 g, 89%). MS (DCI/NH$_3$) m/z 231 (M+H)$^+$.

Example 42C tert-butyl (cis)-8-[(2-nitrophenyl)sulfonyl]-3,8-diazabicyclo[4.2.0]octane-3-carboxylate A solution of the product of Example 42B (11.2 g 48.7 mmol) in triethylamine (14.8 g, 146 mmol) and CH$_2$Cl$_2$ (500 mL) was treated with 2-nitrobenzenesulfonyl chloride (23.6 g, 107 mmol) and the mixture was stirred at room temperature for 16 hours. The mixture was concentrated under reduced pressure and the residue was taken up in ethanol (150 mL) and treated with potassium carbonate (7.4 g, 53.6 mmol). After stirring at room temperature for 40 hours, the solids were removed by filtration and the filtrate was concentrated to provide the title compound (6.1 g, 30% yield). MS (DCI/NH$_3$) m/z 415 (M+NH$_4$)$^+$.

Example 42D benzyl (cis)-8-[(2-nitrophenyl)sulfonyl]-3,8-diazabicyclo[4.2.0]octane-3-carboxylate The product of Example 42C (1.25 g, 3.2 mmol) in CH$_2$Cl$_2$ (20 mL) was treated with trifluoroacetic acid (20 mL) and the solution was stirred at room temperature for 1 hour. The mixture was concentrated under reduced pressure and the residue was taken up in 5% NaOH (10 mL) and extracted thoroughly with CHCl$_3$ (10×10 mL). The combined organic phases were concentrated under reduced pressure. The residue was dissolved in CH$_2$Cl$_2$ (20 mL) and treated with triethylamine (0.26 g, 2.6 mmol) and benzyl chloroformate (0.41 g, 2.4 mmol) at 0° C. The mixture was stirred at room temperature for 2 hours and then washed successively with 1N HCl (10 mL) and saturated NaHCO$_3$ (10 mL). The organic phase was dried (MgSO$_4$), filtered and the filtrate concen-

Example 42E benzyl (cis)-8-(tert-butoxycarbonyl)-3,8-diazabicyclo[4.2.0]octane-3-carboxylate The product of Example 42D (3.1 g, 7.2 mmol) in DMF (25 mL) was treated with $K_2CO_3$ (2.98 g, 21.6 mmol) and thiophenol (0.95 g, 8.6 mmol) and allowed to stir at room temperature for 16 hours. The mixture was further treated with di-tert-butyl dicarbonate (3.14 g, 14.4 mmol) and allowed to stir for an additional 4 hours at room temperature. The mixture was diluted with diethyl ether (100 mL), washed with brine, dried ($MgSO_4$), filtered and the filtrate concentrated under reduced pressure. The residue was purified by chromatography ($SiO_2$, methanol:$CH_2Cl_2$, 3:97) to provide the title compound (1.45 g g, 58% yield). MS (DCI/$NH_3$) m/z 347 $(M+H)^+$.

Example 42F tert-butyl (cis)-3,8-diazabicyclo[4.2.0]octane-8-carboxylate

The product of Example 42E (190 mg, 0.50 mmol) in methanol (10 mL) was treated with 10% palladium on carbon and the mixture was stirred under $H_2$ (1 atm) at 40-45° C. for 4 hours. The mixture was filtered and the filtrate concentrated to provide the title compound (60 mg, 60% yield). MS (DCI/$NH_3$) m/z 213 $(M+H)^+$.

Example 42G tert-butyl (cis)-3-(6-chloro-3-pyridinyl)-3,8-diazabicyclo[4.2.0]octane-8-carboxylate A solution of the product of Example 42F (0.32 g, 1.50 mmol) in toluene (15 mL) was treated with 2-chloro-5-bromopyridine (0.319 g, 1.70 mmol), $Pd_2(dba)_3$ (0.22 g, 0.03 mmol), BINAP (0.038 g, 0.010 mmol) and sodium tert-butoxide (0.29 g, 3.0 mmol) and the reaction was heated at 80° C. for 6 hours. The reaction mixture was poured into diethyl ether (150 mL), washed with brine (100 mL), dried over $MgSO_4$ and concentrated under reduced pressure. The residue was purified by chromatography ($SiO_2$, 3% MeOH/$CH_2Cl_2$) to provide a yellow oil (0.257 g, 53%). MS (DCI/$NH_3$) m/z 324 $(M+H)^+$.

Example 42H (cis)-3-(6-chloro-3-pyridinyl)-3,8-diazabicyclo[4.2.0]octane bis(4-methylbenzenesulfonate)

The product of Example 42G (0.25 g, 0.8 mmol) in dichloromethane (10 mL) was treated with trifluoroacetic acid (10 mL), stirred at room temperature for 1 hour and concentrated under reduced pressure. The residue was purified by chromatography ($SiO_2$, 10% methanol/$CH_2Cl_2$/1% $NH_4OH$) to provide a yellow oil (0.185 g) in 83% yield. The bis(4-methylbenzenesulfonate) salt was formed to afford a yellow foam/oil. $^1H$ NMR (MeOH, 300 MHz) δ 1.88-1.98 (m, 1H), 2.04-2.19 (m, 1H), 2.83-2.96 (m, 1H), 3.21-3.48 (m, 4H), 3.76-3.87 (m, 2H), 4.25-4.33 (m, 1H), 7.18-7.29 (m, 2H), 7.86 (d, J=3.0 MHz, 1H); MS (DCI/$NH_3$) m/z 224 $(M+H)^+$; Anal. Calcd for $C_{11}H_{14}N_3Cl.1.2$ TsoH.1.2IPA: C, 55.18; H, 6.49; N, 7.60. Found: C, 55.07; H, 6.16; N, 7.23.

Example 43

(3aR,6aR)-5-(6-bromo-5-methoxy-3-pyridinyl)octahydropyrrolo[3,4-b]pyrrole

Example 43A tert-butyl (3aR,6aR)-5-(6-bromo-5-methoxy-3-pyridinyl)hexahydropyrrolo[3,4-b]pyrrole-1(2H)-carboxylate hydrochloride The product of Example 29A (260 mg, 0.81 mmol) at 0-5° C. in acetonitrile (8 mL) was treated with N-bromosuccinimide (215 mg, 1.2 mmol) precooled to 0-5° C. in acetonitrile (4 mL). The mixture was allowed to warm to room temperature over 1 hour and then concentrated under reduced pressure. The residue was purified by chromatography ($SiO_2$, diethyl ether:hexanes 3:7) to provide the title compound (200 mg, 63% yield). MS (DCI/$NH_3$) m/z 398 $(M+H)^+$.

Example 43B tert-butyl (3aR,6aR)-5-(6-bromo-5-methoxy-3-pyridinyl)hexahydropyrrolo[3,4-b]pyrrole-1(2H)-carboxylate hydrochloride The product of Example 43A (200 mg, 0.5 mmol) was processed according to the procedure described in Example 14J to provide the title compound (142.5 mg, 78% yield). $^1H$ NMR ($CD_3OD$, 300 MHz) δ 2.05 (m, 1H), 2.35 (m, 1H), 3.45 (m, 6H), 3.92 (dd, J=12, 1.5 Hz, 1H), 4.45 (t, J=6 Hz, 1H), 6.95 (d, J=3 Hz, 1H), 7.55 (d, J=3 Hz, 1H); MS (DCI/$NH_3$) m/z 300 $(M+H)^+$; Anal. calculated for $C_{12}H_{16}N_3OBr.1.75$ HCl: C, 39.77; H, 4.90; N, 11.60. Found: C, 39.93; H, 5.01; N, 11.64

Example 44

(cis)-8-(3-pyridinyl)-3,8-diazabicyclo[4.2.0]octane bis(4-methylbenzenesulfonate)

Example 44A tert-butyl (cis)-3,8-diazabicyclo[4.2.0]octane-3-carboxylate

The product of Example 42C (2.5 g, 6.3 mmol) in DMF (50 mL) was treated with $K_2CO_3$ (2.62 g, 18.9 mmol) and thiophenol (0.84 g, 7.6 mmol) and the mixture was allowed to stir at room temperature for 12 hours. The mixture was poured into diethyl ether (00 mL) and washed with brine (4×50 mL). The organic phase was dried ($MgSO_4$), filtered and the filtrate concentrated under reduced pressure. The residue was purified by chromatography ($SiO_2$, metlhanol:$CH_2Cl_2$:$NH_4OH$, 5:94:1) to provide the title compound (0.40 g, 30% yield). MS (DCI/$NH_3$) m/z 213 $(M+H)^+$.

Example 44B tert-butyl (cis)-8-(3-pyridinyl)-3,8-diazabicyclo[4.2.0]octane-3-carboxylate The product of Example 44A (0.090 g, 0.40 mmol) in toluene (14 mL) was treated with 3-bromopyridine (0.074 g, 0.50 mmol), Pd$_2$(dba)$_3$ (8.0 mg, 0.008 mmol), BINAP (11 mg, 0.010 mmol) and sodium tert-butoxide (0.70 g, 0.7 mmol) and heated at 80° C. for 12 hours. The reaction mixture was allowed to cool to room temperature and concentrated under reduced pressure. The residue was purified by chromatography (SiO$_2$, 5% MeOH/CH$_2$Cl$_2$) to provide a yellow oil (99%, 0.156 g). MS (DCI/NH$_3$) m/z 290 (M+H)$^+$.

Example 44C (cis)-8-(3-pyridinyl)-3,8-diazabicyclo[4.2.0]octane bis(4-methylbenzenesulfonate)

The product of Example 44B (0.15 g 0.5 mmol) in dichloromethane (10 mL) was treated with trifluoroacetic acid (10 mL), stirred at room temperature for 1 hour and concentrated under reduced pressure. The residue was purified by chromatography (SiO$_2$, 10% methanol/CH$_2$Cl$_2$/1% NH$_4$OH) to provide a yellow oil (0.09 g) in 99% yield. The bis(4-methylbenzenesulfonate) salt was formed to afford a white solid. $^1$H NMR (MeOH, 300 MHz) δ 2.0-2.10 (m, 1H), 2.25-2.35 (m, 1H), 2.93-3.07 (m, 1H), 3.19-3.30 (m, 1H), 3.38 (dd, J=3.0, 15.0 Hz, 1H), 3.53-3.67 (m, 1H), 3.73 (dd, J=3.0, 15.0 Hz, 1H), 3.94 (dd, J=3.0, 10.0 Hz, 1H), 4.04 (m, 1H), 4.60 (dt, J=2.0, 5.0 Hz, 1H), 7.71-7.85 (m, 2H), 8.14 (d, J=3.0 Hz, 1H), 8.18 (d, J=9.0 Hz, 1H); MS (DCI/NH$_3$) m/z 190 (M+H)$^+$: Anal. Calcd for C$_{25}$H$_{31}$N$_3$S$_2$O$_6$.2.0EtOH: C, 55.66; H, 6.93; N, 6.71. Found: C, 55.43; H, 6.76; N, 6.39.

Example 45

(cis)-8-(6-chloro-3-pyridinyl)-3,8-diazabicyclo[4.2.0]octane bis(4-methylbenzenesulfonate)

Example 45A tert-butyl (cis)-8-(6-chloro-3-pyridinyl)-3,8-diazabicyclo[4.2.0]octane-3-carboxylate The product of Example 44A (0.391 g, 1.8 mmol) in toluene (50 mL) was (0.391 g, 1.8 mmol) was treated with 2-chloro-5-bromopyridine (0.388 g, 2.0 mmol), Pd$_2$(dba)$_3$ (0.34 g, 0.04 mmol), BINAP (0.046 g, 0.010 mmol) and sodium tert-butoxide (0.30 g, 3.10 mmol) and heated at 80° C. for 6 hours. The reaction mixture allowed to cool to room temperature, poured into diethyl ether (125 mL), washed with brine (100 mL), dried over MgSO$_4$ and concentrated under reduced pressure. The residue was purified by chromatography (SiO$_2$, 5% MeOH/CH$_2$Cl$_2$) to provide a yellow oil (37% 0.215 g). MS (DCI/NH$_3$) m/z 324 (M+H)$^+$.

Example 45B (cis)-8-(6-chloro-3-pyridinyl)-3,8-diazabicyclo[4.2.0]octane bis(4-methylbenzenesulfonate)

The product of Example 45A (0.215 g, 0.7 mmol) in dichloromethane (20 mL) was treated with trifluoroacetic acid (20 mL), stirred at room temperature for 1 hour and concentrated under reduced pressure. The residue was purified by chromatography (SiO$_2$, 10% methanol/CH$_2$Cl$_2$/1% NH$_4$OH) to provide a yellow oil (0.100 g) in 67% yield. The bis(4-methylbenzenesulfonate) salt was formed to afford a yellow foam. $^1$H NMR (MeOH, 300 MHz) δ 1.81-1.98 (m, 1H), 2.09-2.23 (m, 1H), 2.67-2.80 (m, 2H), 3.04 (dd, J=3.0, 15.0 Hz, 1H), 3.17-3.27 (m, 1H), 3.34-3.42 (m, 1H), 3.68 (dd, J=2.0, 9.0 Hz, 1H), 3.72-3.84 (m, 1H), 4.07-4.15 (m, 1H), 7.05 (dd, J=3.0, 12.0 Hz, 1H), 7.22 (d, J=15.0 Hz, 1H), 7.68 (d, J=3.0 Hz, 1H); MS (DCI/NH$_3$) m/z 224 (M+H)$^+$; Anal. Calcd for C$_{25}$H$_{30}$N$_3$S$_2$O$_6$Cl: C, 52.85; H, 5.32; N, 7.40. Found: C, 52.47; H, 5.38; N, 7.61.

Example 46

(cis)-6-(6-chloro-3-pyridinyl)-3,6-diazabicyclo[3.2.0]heptane fumarate

Example 46A benzyl (cis)-6-(6-chloro-3-pyridinyl)-3,6-diazabicyclo[3.2.0]heptane-3-carboxylate The product of Example 40A (0.8 g, 3.4 mmol) and 2-chloro-5-bromopyridine (0.98 g, 5.1 mmol) was processed according to the procedure described in Example 1E. The crude product was purified by chromatography (SiO$_2$, hexane:ethyl acetate, 60:40, R$_f$ 0.3) to provide the title compound (0.59 g, 51% yield). $^1$H NMR (MeOH-d$_4$, 300 MHz) δ 3.24 (dd, J=12.9, 4.1 Hz, 1H), 3.30 (m, 1H), 3.40 (m, 1H), 3.65 (dd, J=7.8, 3.4 Hz, 1H), 4.08-3.92 (m, 3H), 4.70 (dd, J=5.7, 3.7 Hz, 1H), 5.10 (m, 2H), 6.90 (dd, J=8.5, 3.1 Hz, 1H), 7.20 (d, J=8.8 Hz, 1H), 7.25 (m, 3H), 7.35 (m, 2H), 7.54 (d, J=3.0 Hz, 1H); MS (DCI/NH$_3$) m/z 346 (M+2+H)$^+$, 344 (M+H)$^+$.

Example 46B 6-(6-chloro-3-pyridinyl)-3,6-diazabicyclo[3.2.0]heptane

The product of Example 46A (250 mg, 0.73 mmol) was treated with trifluoroacetic acid (10 mL) at ambient temperature and allowed to stir for 50 hours. The mixture was concentrated and the residue was purified by chromatography (SiO$_2$, CH$_2$Cl$_2$:methanol:NH$_3$.H$_2$O, 90:10:1, R$_f$ 0.4) to provide the title compound (140 mg, 86% yield). $^1$H NMR (MeOH-d$_4$, 300 MHz) δ 2.54 (dd, J=12.8, 3.4 Hz, 1H), 2.74 (dd, J=12.2, 6.1 Hz, 1H), 3.16 (m, 1H), 3.18 (d, J=12.2 Hz, 1H), 3.26 (d, J=12.9 Hz, 1H), 3.62 (dd, J=7.7, 3.3 Hz, 1H), 3.92 (t, J=7.8 Hz, 1H), 4.65 (dd, J=6.1, 3.4 Hz, 1H), 6.90 (dd, J=8.8, 3.1 Hz, 1H), 7.20 (d, J=8.1 Hz, 1H), 7.25 (d, J=2.7 Hz, 1H); MS (DCI/NH$_3$) m/z 212 (M+2+H)$^+$. 210 (M+H)$^+$.

Example 46C (cis)-6-(6-chloro-3-pyridinyl)-3,6-diazabicyclo[3.2.01]heptane fumarate The product of Example 46B (130 mg, 0.62 mmol) was treated with fumaric acid (78.4 mg, 0.70 mmol) according to the procedure described in Example 40D to provide the title compound (195 mg, 99% yield). $^1$H NMR (MeOH-d$_4$, 300 MHz) δ 3.15 (dd, J=12.9, 3.7 Hz, 1H), 3.35 (m, 1H), 3.40 (m, 1H), 3.45 (m, 1H), 3.76 (m, 3H), 4.04 (t, J=7.8 Hz, 1H), 4.88 (m, 1H), 6.68 (s, 1H), 7.20 (dd, J=8.5, 3.1 Hz, 1H), 7.28 (d, J=8.5 Hz, 1H), 7.65 (d, J=3.0 Hz, 1H); MS (DCI/NH$_3$) m/z 212 (M+2+H)$^+$, 210 (M+H)$^+$. Anal. calculated for C$_{10}$H$_{12}$ClN$_3$.1.0C$_4$H$_4$O$_4$: C, 51.62; H, 4.95; N, 12.90. Found: C, 51.40; H, 4.84; N, 12.65.

Example 47

(1S,6R)-8-(6-chloro-3-pyridinyl)-3,8-diazabicyclo[4.2.0]octane difumarate

Example 47A tert-butyl (1S,6R)-8-(6-chloro-3-pyridinyl)-3,8-diazabicyclo[4.2.0]octane-3-carboxylate The product of Example 61F (212 mg, 1.0 mmol) and 5-bromo-2-chloropyridine were processed according to theprocedure described in Example 1E. The crude product was purified by chromatography (SiO$_2$, hexane:ethyl acetate, 60:40, R$_f$ 0.45) to provide the title compound (220 mg, 68% yield). $^1$H NMR (MeOH-d$_4$, 300 MHz) δ 1.30 (s, 5H), 1.45 (s, 4H), 1.90 (m, 1H), 2.10 (m, 1H), 2.94 (m, 1H), 3.30-3.50 (m, 1H), 3.68-3.88 (m, 4H), 4.10-4.30 (m, 2H), 6.96 (m, 1H), 7.20 (m, 1H), 7.58 (d, J=3.1 Hz); MS (DCI/NH$_3$) m/z 326 (M+2+ NH$_4$)$^+$, 324 (M+NH$_4$)$^+$.

Example 47B (1S,6R)-8-(6-chloro-3-pyridinyl)-3,8-diazabicyclo [4.2.0]octane difumarate The product of Example 47A (210 mg, 0.65 mmol) in CH$_2$Cl$_2$ (2 mL) was treated with trifluoroacetic acid (2 mL) at room temperature for 1 hour. The mixture was concentrated and the brown residue was neutralized to pH=9 with 5% NaOH. The mixture was extracted with CHCl$_3$ (3×50 mL). The extracts were combined and concentrated. The residue was treated with fumaric acid according to the procedure described in Example 40D to provide the title compound (210 mg, 72% yield). $^1$H NMR (MeOH-d$_4$, 300 MHz) δ 2.08 (m, 1H), 2.30 (m, 1H), 2.85 (m, 1H), 3.15 (m, 1H), 3.30 (m, 1H), 3.50-3.68 (m, 2H), 3.80 (dd, J=7.5, 1.7 Hz, 1H), 3.88 (t, J=7.5 Hz, 1H), 4.38 (dt, J=7.8, 2.4 Hz, 1H), 6.70 (s, 4H), 7.14 (dd, J=8.8 Hz, 1H), 7.28 (d, J=8.8 Hz), 7.74 (d, J=3.1 Hz, 1H); MS (DCI/NH$_3$) m/z 226 (M+2+NH$_4$)$^+$, 224 (M+NH$_4$)$^+$. Anal. calculated for C$_{11}$H$_{14}$ClN$_3$.2.2C$_4$H$_4$O$_4$.1.1H$_2$O: C, 47.67; H, 5.05; N, 8.42. Found: C, 47.81; H, 4.35; N, 8.06.

Example 48

(1R,6S)-8-(6-chloro-3-pyridinyl)-3,8-diazabicyclo [4.2.0]octane fumarate

Example 48A tert-butyl (1R,6S)-8-(6-chloro-3-pyridinyl)-3,8-diazabicyclo[4.2.0]octane-3-carboxylate The product of Example 90C (0.310 g, 1.50 mmol) in toluene (15 mL) was treated with 2-chloro-5-bromopyridine (0.308 g, 1.60 mmol), Pd$_2$(dba)$_3$ (0.28 g, 0.03 mmol), BINAP (0.038 g, 0.010 mmol) and sodium tert-butoxide (0.246 g, 2.60 mmol) and heated at 80° C. for 4 hours. The reaction mixture was allowed to cool to room temperature and concentrated under reduced pressure. The residue was purified by chromatography (SiO$_2$, 3% MeOH/CH$_2$Cl$_2$) to provide a yellow oil (69%, 0.382 g). MS (DCI/NH$_3$) m/z 368 (M+H)$^+$.

Example 48B (1R,6S)-8-(6-chloro-3-pyridinyl)-3,8-diazabicyclo [4.2.0]octane fumarate The product from Example 48A (0.33 g, 1.0 mmol) in dichloromethane (10 mL) was treated with trifluoroacetic acid (10 mL), stirred at room temperature for 1 hour, concentrated under reduced pressure and neutralized with 3% aqueous NH$_4$OH in methanol. The residue was purified by chromatography (SiO$_2$, methanol:CH$_2$Cl$_2$:NH$_4$OH, 10:89:1) to provide a colorless oil (0.119 g) in 53% yield. The fumarate salt was formed to afford a white foam. $^1$H NMR (MeOH, 300 MHz) δ 1.98-2.11 (m, 1H), 2.25-2.38 (m, 1H), 2.81-2.93 (m, 1H), 3.12-3.23 (m, 1H), 3.27-3.35 (m, 1H), 3.53-3.67 (m, 2H), 3.76-3.89 (m, 2H), 4.35 (dt, J=2.0, 10.0 Hz, 1H), 7.11 (dd, J=3.0, 12.0 Hz, 1H), 7.27 (d, J=12.0 Hz, 1H), 7.32 (d, J=3.0 Hz, 1H); MS (DCI/NH$_3$) m/z 224 (M+H)$^+$; Anal. Calcd for C$_{11}$H$_{14}$N$_3$Cl.1.2C$_4$H$_4$O$_4$: C, 52.28; H, 5.22; N, 11.58. Found: C, 52.08; H, 5.25; N, 11.51.

Example 49

(1R,6S)-3-(6-chloro-3-pyridinyl)-3,8-diazabicyclo [4.2.0]octane fumarate

Example 49A tert-butyl (1R,6S)-3,8-diazabicyclo[4.2.0]octane-8-carboxylate

The product of Example 90B was processed according to the procedures of Examples 42D, 42E, and 42F to provide the title compound. MS (DCI/NH$_3$) m/z 213 (M+H)$^+$.

Example 49B tert-butyl (1R,6S)-3-(6-chloro-3-pyridinyl)-3,8-diazabicyclo[4.2.0]octane-8-carboxylate The product of Example 49A (0.265 g, 1.30 mmol) in toluene (13 mL) was treated with 2-chloro-5-bromopyridine (0.263 g, 1.40 mmol), Pd$_2$(dba)$_3$ (0.0.24 g, 0.03 mmol), BINAP (0.032 g, 0.010 mmol) and sodium tert-butoxide (0.204 g, 2.10 mmol) and heated at 80° C. for 16 hours. The reaction mixture was allowed to cool to room temperature and concentrated under reduced pressure. The residue was purified by chromatography (SiO$_2$, 3% MeOH/CH$_2$Cl$_2$) to provide a colorless oil (36%, 0.182 g). MS (DCI/NH$_3$) m/z 368 (M+H)$^+$.

Example 49C (1R,6S)-3-(6-chloro-3-pyridinyl)-3,8-diazabicyclo [4.2.0]octane fumarate The product of Example 49B (0.182 g, 0.60 mmol) in dichloromethane (7.5 mL) was treated with trifluoroacetic acid (7.5 mL), stirred at room temperature for 1 hour, concentrated under reduced pressure and neutralized with 3% aqueous NH$_4$OH in methanol. The residue was purified by chromatography (SiO$_2$, methanol:CH$_2$Cl$_2$:NH$_4$OH, 10:89:1) to provide a colorless oil (0.112 g) in 84% yield. The fumarate salt was formed to afford a white solid. $^1$H NMR (MeOH, 300 MHz) δ 1.97-2.09 (m, 1H), 2.15-2.30 (m, 1H), 3.09-3.23 (m, 1H), 3.25-3.47 (m, 1H), 3.51 (dd, J=3.0, 15.0 Hz, 1H), 3.81-3.98 (m, 3H), 4.12-4.22 (m, 1H), 4.70 (dt, J=3.0, 9.0 Hz, 1H), 7.30 (d, J=3.0, 12.0 Hz, 1H), 7.38 (dd, J=3.0, 9.0 Hz, 1H), 7.98 (d, J=3.0 Hz, 1H); MS (DCI/NH$_3$) m/z 224 (M+H); Anal. Calcd for C$_{11}$H$_{14}$N$_3$C$_{11}$H$_{14}$C$_4$H$_4$O$_4$.1.0IPA: C, 54.03; H, 6.31; N, 9.27. Found: C, 54.36; H, 5.82; N, 9.19.

Example 50

5-[(1R,6S)-3,8-diazabicyclo[4.2.0]oct-8-yl]nicotinonitrile fumarate

Example 50A tert-butyl (1R,6S)-8-(5-cyano-3-pyridinyl)-3,8-diazabicyclo[4.2.0]octane-3-carboxylate The product from Example 90C (0.726 g, 3.40 mmol) in toluene (34 mL) was treated with 3-cyano-5-bromopyridine (0.748 g, 4.10 mmol), Pd$_2$(dba)$_3$ (0.0.63 g, 0.10 mmol), BINAP (0.086 g, 0.010 mmol) and sodium tert-butoxide (0.56 g, 5.8 mmol) and heated at 80° C. for 16 hours. The reaction mixture was allowed to cool to room temperature and concentrated under reduced pressure. The residue was purified by chromatography (SiO$_2$, 5% MeOH/CH$_2$Cl$_2$) to provide a yellow oil (21%, 0.231 g). MS (DCI/NH$_3$) m/z 315 (M+H)$^+$.

Example 50B

5-[(1R,6S)-3,8-diazabicyclo[4.2.0]oct-8-yl]nicotinonitrile fumarate

The product of Example 50A (0.212 g, 0.70 mmol) in dichloromethane (10 mL) was treated with trifluoroacetic acid (10 mL), stirred at room temperature for 1 hour, concentrated under reduced pressure and neutralized with 3% aqueous NH$_4$OH in methanol. The reaction mixture was purified by chromatography (SiO$_2$, methanol:CH$_2$Cl$_2$:NH$_4$OH, 10:89:1) to provide a colorless oil (0.062 g) in 41% yield. The fumarate salt was formed to afford a white foam. $^1$H NMR (MeOH, 300 MHz) δ 1.98-2.11 (m, 1H), 2.25-2.39 (m, 1H), 2.85-2.97 (m, 1H), 3.13-3.22 (m, 1H), 3.35 (d, J=2.0 Hz, 1H), 3.53-3.62 (m, 1H), 3.68 (dd, J=2.0, 10.0 Hz, 1H), 3.75 (dd, J=2.0, 8.0 Hz, 1H), 3.94 (t, J=9.0 Hz, 1H), 4.45 (dt, J=2.0, 8.0 Hz, 1H), 7.42 (dd, J=2.0, 6.0 Hz, 1H), 8.18 (d, J=3.0 Hz, 1H), 8.31 (d, J=2.0 Hz, 1H); MS (DCI/NH$_3$) m/z 215 (M+H)$^+$; Anal. Calcd for C$_{16}$H$_{18}$N$_4$O$_4$.0.30C$_4$H$_4$O$_4$.0.35CH$_4$O: C, 56.01; H, 5.52; N, 14.89. Found: C, 55.93; H, 5.37; N, 14.61

Example 51

5-((3aR,6aR)-hexahydropyrrolo[3,4-b]pyrrol-5(1H)-yl)-2-bromonicotinonitrile fumarate

Example 51A tert-butyl (3aR,6aR)-5-(6-bromo-5-cyano-3-pyridinyl)hexahydropyrrolo[3,4-b]pyrrole-1(2H)-carboxylate The product of Example 37B (380 mg, 1.2 mmol) in acetonitrile (10 mL) at 0-5° C. was treated with N-bromosuccinimide (215 mg, 1.2 mmol) in acetonitrile (4 mL) precooled to 0-5° C. The mixture was allowed to warm to room temperature over 30 minutes and then concentrated under reduced pressure. The residue was purified by chromatography (SiO$_2$, ethyl acetate:hexanes 1:4) to provide the title compound (250 mg, 53% yield). MS (DCI/NH$_3$) m/z 393 (M+H)$^+$.

Example 51B

5-((3aR,6aR)-hexahydropyrrolo[3,4-b]pyrrol-5(1H)-yl)-2-bromonicotinonitrile fumarate The product of Example 51A (250 mg, 0.63 mmol) in methylene chloride (4 mL) was treated with trifluoroacetic acid (2 mL) at room temperature for 2 hours. The solution was concentrated under reduced pressure and the residue was purified by chromatography (SiO$_2$, CH$_2$Cl$_2$:methanol: NH$_4$OH$_{(aq)}$, 94:5:1) to provide the free base of the title compound (180 mg, 90% yield). The free base was treated with fumaric acid according to the procedure described in Example 37C to provide the title compound (242 mg, 96% yield). $^1$H NMR (CD$_3$OD, 300 MHz) δ 2.05 (m, 1H), 2.35 (m, 1H), 3.45 (m, 6H), 3.85 (dd, J=12, 1.5 Hz, 1H), 4.45 (t, J=6 Hz, 1H), 6.65 (s, 2H), 7.50 (d, J=3 Hz, 1H), 8.05 (d, J=3 Hz, 1H); MS (DCI/NH$_3$) m/z 294 (M+H)$^+$; Anal. calculated for C$_{12}$H$_{13}$BrN$_4$.C$_4$H$_4$O$_4$: C, 46.91; H, 4.15; N, 13.68. Found: C, 46.83; H, 3.97; N, 13.82.

Example 52

(1R,5S)-6-(3-pyridinyl)-3,6-diazabicyclo[3.2.0]heptane fumarate

Example 52A benzyl (cis)-2,2-dimethylhexahydropyrrolo[3,4-d][1,3]oxazine-6(4H)-carboxylate (R)-Mandelate The product of Example 38E (140 g, 0.56 mol) in dry acetone (150 mL) was treated with 2-methoxypropene (55 mL 0.57 mol) at room temperature overnight. The reaction mixture was concentrated under reduced pressure and the residue was dissolved in dry acetone (750 mL). (R)-Mandelic acid (85 g, 0.56 mol) was added and the brown solution was stirred at room temperature for 48 hours. The precipitate was isolated by filtration and dried under reduced pressure to provide the title compound as a white solid (57.0 g, yield, 23%). $^1$H NMR (MeOH-D$_4$, 300 MHz) mixture of the title compound and hydrolyzed compound (cis)-3-amino-4-hydroxymethyl-N-benzyloxycarbonyl-pyrrolidinyl (R)-mandelate δ 1.20-1.40 (m, 3H), 2.09 (s, 3H), 3.30 (m, 1H), 3.48-3.75 (m, 6H), 4.20 (m, 1H), 5.10 (m, 3H), 7.25-7.52 (m, 10H); MS (DCI/NH$_3$) m/z 291 (M+H)$^-$ (for the product of Example 52A); 251 (M+H)$^+$ (for the hydrolyzed product of Example 52A).

Example 52B benzyl (3S,4S)-3-[(tert-butoxycarbonyl)amino]-4-(hydroxymethyl)-1-pyrrolidinecarboxylate The product of Example 52A (56 g, 127 mmol) in ethanol (50 mL) was treated with 5% aqueous H$_2$SO$_4$ (100 mL) at room temperature and allowed to stir for 16 hours. The mixture was basified to pH ~10 with 20% aqueous NaOH (50 mL) and then the mixture was treated with di-t-butyl dicarbonate (41.5 g, 190 mmol) in ethanol (50 mL) 10-20° C. After stirring at room temperature for 4 hours the ethanol was removed under reduced pressure and the residue was extracted with ethyl acetate (3×500 mL). The combined organic phases were washed with brine (2×100 mL) and concentrated to provide the title compound (43.7 g, 98% yield). $^1$H NMR (MeOH-d$_4$, 300 MHz) δ 1.46 (s, 9H), 2.50 (m, 1H), 3.25 (m, 1H), 3.40 (m, 1H), 3.50-3.75 (m, 4H), 4.20 (m, 1H), 5.10 (s, 2H), 7.35 (m, 5H); MS (DCI/NH$_3$) m/z 368 (M+NH$_4$)$^+$, 351 (M+H)$^+$. The enantiopurity of the title compound was determined to be ≧99% ee by HPLC (HPLC conditions: Chiracel AD column; ethanol/hexanes=20/80, flow rate, 1.0 nL/min; uv 215 nm; Retention time for the title compound as the more mobile isomer: 10.8 minutes; Retention time for less mobile isomer: 13.9 minutes; reference JP 2000 026408.

Example 52C benzyl (3S,4S)-3-[(tert-butoxycarbonyl)amino]-4-{[(methylsulfonyl)oxy]methyl}-1-pyrrolidinecarboxylate The product of Example 52B (43.7 g, 125 mmol) and triethylamine (25.2 g, 250 mmol) in CH$_2$Cl$_2$ (600 mL) was treated with methanesulfonyl chloride (12.6 mL, 163 mmol) over 30 minutes at −10° C. The solution was allowed to warm to room temperature over 1 hour and then quenched with water (100 mL). The layers were separated and the aqueous phase was extracted with CH$_2$C$_2$ (2×400 mL). The combined organic phases were washed with brine (2×100 mL), dried over Na$_2$SO$_4$, filtered and the filtrate concentrated to provide the title compound as a brown dark brown oil (52.0 g, yield, 97%). $^1$H NMR (CDCl$_3$, 300 MHz) δ 1.46 (s, 9H), 2.80 (m, 1H), 3.08 (s, 3H), 3.40 (m, 2H), 3.70 (m, 2H), 4.10 (m, 1H), 4.40 (m, 2H), 4.75 (m, 1H), 5.16 (s, 2H), 7.30 m, 5H); MS (DCI/NH$_3$) m/z 446 (M+NH$_4$)$^+$, 429 (M+H)$^+$.

Example 52D benzyl (1S,5S)-3,6-diazabicyclo[3.2.0]heptane-3-carboxylate

The product of Example 52C (43.7 g, 125 mmol) in CH$_2$Cl$_2$ (150 mL) was treated with trifluoroacetic acid (50 mL) at room temperature and allowed to stir for 1 hour. The mixture was concentrated under reduced pressure and the residue was dissolved in ethanol (250 mL) and basified to pH ~10 with 10% aqueous NaOH. The mixture was warmed to 60° C. at 10 hours. The reaction was allowed to cool to room temperature and was concentrated under reduced pressure to remove most of the ethanol. The residue was extracted with CHCl$_3$ (2×500 mL). The extracts were combined, washed with brine (3×50 mL) and then passed through a short column of diatomaceous earth. The filtrate was concentrated to provide the title compound as a yellow oil (28.0 g, 97%) which was used in the next step without further purification. $^1$H NMR (MeOH-d$_4$, 300 MHz) δ 3.30-3.16 (m, 3H), 3.36 (m, 1H), 3.82 (m, 3H), 4.55 (m, 1H), 5.20 (s, 2H), 7.36 (m, 5H); MS (DCI/NH$_3$) m/z 250 (M+NH$_4$)$^+$, 233 (M+H)$^+$.

Example 52E benzyl (1S,5S)-6-(3-pyridinyl)-3,6-diazabicyclo[3.2.0]heptane-3-carboxylate The product of Example 52D (230 mg, 1.0 mmol) and 3-bromopyridine were processed according to the procedure described in Example 1E. The crude product was purified by chromatography (SiO$_2$, CH$_2$Cl$_2$:methanol, 95:5, R$_f$ 0.3) to provide the title compound (190 mg, 61% yield). $^1$H NMR (MeOH-d$_4$, 300 MHz) δ 3.24 (dd, J=12.6, 4.1 Hz, 1H), 3.30 (m, 1H), 3.40 (m, 1H), 3.64 (dd, J=7.8, 3.4 Hz, 1H), 3.92-4.08 (m, 3H), 4.70 (m, 1H), 5.10 (m, 2H), 6.90 (m, 1H), 7.24 (m, 3H), 7.35 (m, 2H), 7.73 (d, J=2.7 Hz, 1H), 7.86 (d, J=4.7 Hz, 1H); MS (DCI/NH$_3$) m/z 310(M+H)$^+$.

Example 52F (1R,5S)-6-(3-pyridinyl)-3,6-diazabicyclo[3.2.0]heptane

The product of Example 52E (190 mg, 0.61 mmol) in methanol (10 mL) was treated with 10% palladium on carbon (100 mg) under H$_2$ according to the procedure described in Example 40C. The title compound was obtained as a yellow oil (100 mg, yield, 94%). $^1$H NMR (MeOH-d$_4$, 300 MHz) δ 2.53 (dd, J=12.5, 3.4 Hz, 1H), 2.72 (dd, J=12.5, 6.4 Hz, 1H), 3.20 (m, 2H), 3.63 (dd, J=7.8, 3.4 Hz, 1H), 3.90 (t, J=7.8 Hz, 1H), 4.65 (dd, J=6.1, 3.4 Hz, 1H), 6.88 (ddd, J=8.4, 3.0, 1.3 Hz, 1H), 7.18 (dd, J=8.5, 4.8 Hz, 1H), 7.73 (d, 3.1 Hz, 1H), 7.83 (dd, 4.7, 1.4 Hz, 1H) m/z 176 (M–H)$^+$.

Example 52G (1R,5S)-6-(3-pyridinyl)-3,6-diazabicyclo[3.2.0]heptane fumarate

The product (100 mg, 0.57 mmol) of Example 52F was treated with fumaric acid according to the procedure of Example 40D. The title compound was obtained as white solid (120 mg, 73% yield). $^1$H NMR (MeOH-d$_4$, 300 MHz) δ 3.18 (dd, J=12.6, 3.4 Hz, 1H), 3.35 (m, 1H), 3.46 (m, 1H), 3.75 (m, 3H), 4.04 (t, J=7.8 Hz, 1H), 4.90 (m, 1H), 6.58 (s, 2H), 7.04 (ddd, J=8.2, 2.7, 1.3 Hz, 1H), 7.27 (dd, J=8.2, 4.8 Hz, 1H), 7.87 (d, 2.7 Hz, 1H), 7.95 (dd, J=4.8, 1.1 Hz, 1H); m/z 176 (M+H)$^+$; Anal. calculated for C$_{11}$H$_{14}$ClN$_3$.1.25C$_4$H$_4$O$_4$.0.3H$_2$O: C, 55.31; H, 5.76. Found: C, 54.97; H, 5.47.

Example 53

(1R,5S)-6-(5-bromo-3-pyridinyl)-3,6-diazabicyclo[3.2.0]heptane fumarate

Example 53A benzyl (1S,5S)-6-(5-bromo-3-pyridinyl)-3,6-diazabicyclo[3.2.0]heptane-3-carboxylate The product of Example 52D (230 mg, 1.0 mmol) and 3,5-dibromopyridine were processed as described in Example 1E. The crude product was purified by chromatography (SiO$_2$, ethyl acetate, R$_f$ 0.2) to provide the title compound (180 mg, 47% yield). $^1$H NMR (MeOH-d$_4$, 300 MHz) δ 3.20 (dd, J=12.5, 4.0 Hz, 1H), 3.30 (m, 2H), 3.40 (m, 1H), 3.64 (dd, J=7.8, 3.4 Hz, 1H), 3.95-4.10 (m, 3H), 4.75 (m, 1H), 5.15 (m, 2H), 7.05 (t, J=2.1 Hz, 1H), 7.24 (m, 3H), 7.35 (m, 2H), 7.70 (d, J=2.3 Hz, 1H), 7.93 (d, J=1.7 Hz, 1H); MS (DCI/NH$_3$) m/z 390 (M+2+H)$^+$, 388 (M+H)$^+$.

Example 53B (1R,5S)-6-(5-bromo-3-pyridinyl)-3,6-diazabicyclo[3.2.0]heptane

The product of Example 53A (180 mg, 0.46 mmol) was treated with trifluoroacetic acid according to the procedure described in Example 46B. The crude product was purified by chromatography (SiO$_2$, CH$_2$Cl$_2$:methanol:NH$_4$OH, 90:10:1, R$_f$ 0.4) to provide the title compound (80 mg, 69% yield). $^1$H NMR (MeOH-d$_4$, 300 MHz) δ 2.94 (dd, J=12.4, 3.3 Hz, 1H), 3.12 (dd, J=12.2, 6.8 Hz, 1H), 3.35 (m, 1H), 3.52 (d J=12.2 Hz, 1H), 3.56 (d, J=12.5 Hz, 1H), 3.74 (dd, J=8.2, 3.4 Hz, 1H), 4.00 (t, J=8.1 Hz, 1H), 4.88 (m, 1H), 7.15 (t, J=1.7 Hz, 1H), 7.78 (d, J=2.3 Hz, 1H), 7.96 (d. J=2.0 Hz, 1H); MS (DCI/NH$_3$) m/z 256 (M+2+H)$^+$, 254 (M+H)$^+$.

Example 53C (1R,5S)-6-(5-bromo-3-pyridinyl)-3,6-diazabicyclo[3.2.0]heptane fumarate The product of Example 53B (100 mg, 0.57 mmol) was treated with fumaric acid according to the procedure described in Example 40D. The title compound was obtained as a white solid (100 mg, 48% yield). $^1$H NMR (MeOH-d$_4$, 300 MHz) δ 3.15 (dd, J=12.6, 3.4 Hz, 1H), 3.30 (m, 1H), 3.45 (m, 1H), 3.67 (d, J=11.5 Hz, 1H), 3.75 (m, 2H), 4.06 (t, J=8.1 Hz, 1H), 4.94 (m, 1H), 6.30 (s, 2H), 7.22 (t, J=2.3 Hz, 1H), 7.84 (d, J=2.3 Hz, 1H), 8.04 (d, J=1.7 Hz, 1H); MS (DCI/NH$_3$) m/z 256 (M+2+H)$^+$, 254 (M+H)$^+$. Anal. calculated for C$_{10}$H$_{12}$BrN$_3$.1.0C$_4$H$_4$O$_4$: C, 45.42; H, 4.36; N, 11.35. Found: C, 45.50; H, 4.34; N, 10.22.

Example 54

(1S,5R)-6-(6-chloro-3-pyridinyl)-3,6-diazabicyclo[3.2.0]heptane fumarate

Example 54A benzyl (cis)-2,2-dimethylhexahydropyrrolo[3,4-d][1,3]oxazine-6(4H)-carboxylate (S)-Mandelate The product of Example 38E (110 g, 0.44 mol) in dry acetone (100 mL) was treated with 2-methoxypropene and (S)-mandelic acid according to the procedure of Example 52A. The title compound was obtained as a white solid (48.0 g, yield, 25%). $^1$H NMR (MeOH-D$_4$, 300 MHz) mixture of the title compound and hydrolyzed compound (cis)-3-amino-4-hydroxymethyl-N-benzyloxycarbonyl-pyrrolidinyl (S)-mandelate δ 1.20 (s, 2H), 1.40 (s, 2H), 2.09 (s, 2H), 3.30-3.75 (m, 7H), 4.10 (m, 1H), 5.00 (s, 1H), 5.10 (m, 2H), 7.25-7.52 (m, 10H); MS (DCI/NH$_3$) m/z 291 (M+H)$^+$ (for the product of Example 54A); 251 (M+H)$^+$ (for the hydrolyzed product of Example 54A).

Example 54B benzyl (3R,4R)-3-[(tert-butoxycarbonyl)amino]-4-(hydroxymethyl)-1-pyrrolidinecarboxylate The product of Example 54A (6.2 g, 14 mmol) was treated with 5% aqueous H$_2$SO$_4$ for 2 hours, then neutralized with 20% aqueous NaOH, and treated with di-tert-butyl dicarbonate according to the procedure described in Example 52B. The title compound was obtained as a slightly yellow oil (4.4 g, yield, 90%). $^1$H NMR (MeOH-d$_4$, 300 MHz) δ 1.46 (s, 9H), 2.50 (m, 1H), 3.25 (m, 1H), 3.40 (m, 1H), 3.50-3.75 (m, 4H), 4.20 (m, 1H), 5.10 (s, 2H), 5.10 (s, 2H), 7.35 (m, 5H); MS (DCI/NH$_3$) m/z 368 (M+NH$_4$)$^+$, 351 (M+H)$^+$. The enantiopurity of the title compound was determined as 98% ee by HPLC (HPLC conditions: Chiracel AD column: ethanol/hexane=20/80, flow rate, 1.0 mL/min; uv 215 nm; Retention time for the more mobile isomer: 10.8 minutes; Retention time for the title compound as the less mobile isomer: 13.9 minutes; reference: JP 2000 026408.

Example 54C benzyl (3R,4R)-3-[(tert-butoxycarbonyl)amino]-4-{[(methylsulfonyl)oxy]methyl}-1-pyrrolidinecarboxylate The product of Example 54B (4.2 g, 12 mmol) was treated with methanesulfonyl chloride according to the procedure described in Example 38G. The title compound was obtained as a brown oil (5.10, 99% yield). $^1$H NMR (MeOH-D$_4$, 300 MHz) δ 1.46 (s, 9H), 2.80 (m, 1H), 3.08 (s, 3H), 3.40 (m, 2H), 3.70 (m, 2H), 4.16 (m, 1H), 4.35 (m, 2H), 5.16 (s, 2H), 7.30 (m, 5H); MS (DCI/NH$_3$) m/z 446 (M+NH$_4$)$^+$, 429 (M+H)$^+$.

Example 54D benzyl (1R,5R)-3,6-diazabicyclo[3.2.0]heptane-3-carboxylate

The product of Example 54C (5.10 g, 11.9 mmol) was processed according to the procedure of Example 52D. The crude product was purified by chromatography (SiO$_2$, CH$_2$Cl$_2$:MeOH:NH$_4$OH, 90:10:1. R$_f$ 0.1) to provide the title compound (1.91 g, 69% yield). $^1$H NMR (MeOH-d$_4$, 300 MHz) δ δ 3.30-3.16 (m, 3H), 3.36 (m, 1H), 3.76 (m, 3H), 4.48 (m, 1H), 5.16 (s, 2H), 7.36 (m, 5H); MS (DCI/NH$_3$) m/z 250 (M+NH$_4$)$^+$, 233 (M+H)$^+$.

Example 54E benzyl (1R,5R)-6-(6-chloro-3-pyridinyl)-3,6-diazabicyclo[3.2.0]heptane-3-carboxylate The product of Example 54D (230 mg, 1.0 mmol) and 2-chloro-5-bromopyridine were processed according to the procedure described in Example 1E. The crude product was purified by chromatography (SiO$_2$, ethyl acetate:hexane, 50:50. R$_f$ 0.4) to provide the title compound (120 mg, 35% yield). $^1$H NMR (MeOH-d$_4$, 300 MHz) δ 3.20 (dd, J=12.6, 4.1 Hz, 1H), 3.30 (m, 1H), 3.40 (m, 1H), 3.65 (dd, J=7.7, 3.7 Hz, 1H), 3.92-4.10 (m, 3H), 4.70 (dd, J=6.4, 3.9 Hz, 1H), 5.10 (m, 2H), 6.90 (dd, J=8.9, 3.1 Hz, 1H), 7.20 (d, J=9.1 Hz, 1H), 7.25 (m, 31H), 7.35 (m, 2H), 7.54 (d. J=2.8 Hz, 1H); MS (DCI/NH$_3$) m/z 346 (M+2+H)$^+$, 344 (M+H)$^+$.

Example 54F (1S,5R)-6-(6-chloro-3-pyridinyl)-3,6-diazabicyclo[3.2.0]heptane

The product of Example 54E (120 mg, 0.35 mmol) was treated with trifluoroacetic acid according to the procedure of Example 46B. The crude product was purified by chromatography (SiO$_2$, CH$_2$Cl$_2$:MeOH:NH$_4$OH, 90:10:1, R$_f$ 0.2) to provide the title compound (70 mg, yield 94%). $^1$H NMR (MeOH-d$_4$, 300 MHz) δ 2.64 (dd, J=12.9, 3.4 Hz, 1H), 2.80 (dd, J=12.5, 6.8 Hz, 1H), 3.20 (m, 1H), 3.28 (m, 2H), 3.64 (dd, J=7.8, 3.4 Hz, 1H), 3.92 (t, J=8.2 Hz, 1H), 4.68 (dd, J=6.1, 3.4 Hz, 1H), 6.94 dd, J=8.4, 3.0 Hz, 1H), 7.20 (d, J=8.8 Hz, 1H), 7.25 (d, J=2.7 Hz, 1H); MS (DCI/NH$_3$) m/z 212 (M+2+H)$^+$, 210 (M+H)$^+$.

Example 54G (1S,5R)-6-(6-chloro-3-pyridinyl)-3,6-diazabicyclo[3.2.0]heptane fumarate The product of Example 54F (70 mg, 0.33 mmol) was treated with fumaric acid according to the procedure of Example 46C. The title compound was obtained as a yellow solid (95 mg, 90% yield): $^1$H NMR (MeOH-d$_4$, 300 MHz) δ 3.15 (dd, J=12.8, 3.7 Hz, 1H), 3.35 (m, 1H), 3.40 (m, 1H), 3.45 (m, 1H), 3.76 m, 3H), 4.00 t, J=7.8 Hz, 1H), 4.88 (m, 1H), 6.70 (s, 1H), 7.05 dd, J=8.8, 3.0 Hz, 1H), 7.28 (d, J=8.4 Hz, 1H), 7.68 (d, J=3.0 Hz, 1H); MS (DCI/NH$_3$) m/z 212 (M+2+H)$^+$, 210 (M+H)$^+$. Anal. calculated for C$_{10}$H$_{12}$ClN$_3$.1.25C$_4$H$_4$O$_4$.0.1H$_2$O: C, 50.53; H, 4.86; N, 11.78. Found: C, 50.07; H, 4.20; N, 11.10.

Example 55

(1S,5R)-6-(3-pyridinyl)-3,6-diazabicyclo[3.2.0]heptane fumarate

Example 55A benzyl (1R,5R)-6-(3-pyridinyl)-3,6-diazabicyclo[3.2.0]heptane-3-carboxylate The product of Example 54D (230 mg, 1.0 mmol) and 3-bromopyridine were processed according to the procedure described in Example 1E. The crude product was purified by chromatography (SiO$_2$, CH$_2$Cl$_2$:MeOH, 95:5, R$_f$ 0.2) to provide the title compound (210 mg, 68% yield). $^1$H NMR (MeOH-d$_4$, 300 MHz) δ 3.24 (dd, J=12.6, 4.1 Hz, 1H), 3.30 (m, 1H), 3.40 (m, 1H), 3.65 (dd, J=7.8, 3.4 Hz, 1H), 3.92-4.10 (m, 3H), 4.70 (m, 1H), 5.10 (m, 2H), 6.90 (m, 1H), 7.24 (m, 3H), 7.35 (m, 2H), 7.73 (d, J=2.7 Hz, 1H), 7.86 (d, J=4.7 Hz, 1H); MS (DCI/NH$_3$) m/z 310 (M+H)$^+$.

Example 55B (1S,5R)-6-(3-pyridinyl)-3,6-diazabicyclo[3.2.0]heptane

The product of Example 55A (210 mg, 0.68 mmol) in methanol (10 mL) was treated with palladium on carbon under H$_2$ according to the procedure described in Example 40C. The title compound was obtained as oil (110 mg, 92% yield). $^1$H NMR (MeOH-d$_4$, 300 MHz) δ 2.55 (dd, J=12.9, 3.4 Hz, 1H), 2.75 (dd, J=12.5, 6.5 Hz, 1H), 3.20 (m, 2H), 3.63 (dd, J=7.5, 3.4 Hz, 1H), 3.94 (t, J=7.8 Hz, 1H), 4.65 (dd, J=6.1, 3.4 Hz, 1H), 6.88 (ddd, J=8.5, 3.1, 1.4 Hz, 1H), 7.18 (dd, J=8.4, 4.8 Hz, 1H), 7.73 (d, J=3.0 Hz, 1H), 7.83 (dd, J=4.7, 1.3 Hz, 1H) m/z 176 (M+H)$^+$.

Example 55C (1S,5R)-6-(3-pyridinyl)-3,6-diazabicyclo[3.2.0]heptane fumarate

The product of Example 55B (105 mg, 0.60 mmol) was treated with fumaric acid according to the procedure described in Example 40D. The title compound was obtained as a white solid (155 mg, 90% yield). $^1$H NMR (MeOH-d$_4$, 300 MHz) δ 3.18 (dd, J=12.2, 3.4 Hz, 1H), 3.35 (m, 1H), 3.46 (m, 1H), 3.75 (m, 3H), 4.04 (t, J=7.5 Hz, 1H), 4.90 (m, 1H), 6.58 (s, 2H), 7.04 (ddd, J=8.2, 2.7, 1.3 Hz, 1H), 7.27 (dd, J=8.1, 4.8 Hz, 1H), 7.87 (d, 2.7 Hz, 1H), 7.95 (dd, J=4.8, 1.1 Hz, 1H); m/z 176 (M+H)$^+$; Anal. calculated for C$_{10}$H$_{13}$N$_3$·1.30C$_4$H$_4$O$_4$·0.5H$_2$O: C, 54.48; H, 5.77. Found: C, 54.61; H, 5.25.

Example 56

(3aR,6aR)-5-(5-vinyl-3-pyridinyl)octahydropyrrolo[3,4-b]pyrrole dihydrochloride

Example 56A tert-butyl (3aR,6aR)-5-(5-bromo-3-pyridinyl)hexahydropyrrolo[3,4-b]pyrrolo-1(2H)-carboxylate The product of Example 14H (4.50 g, 21.2 mmol) in toluene (200 mL) was refluxed with a Dean-Stark trap to remove any water. The solution was then cooled to below 50° C. and tris(dibenzylideneacetone)dipalladium(0) (Pd$_2$(dba)$_3$, Alfa Aesar) (0.194 g, 0.210 mmol) and 2,2'-bis(diphenylphosphino)-1,1'-binaphthyl (BINAP, Strem Chemicals) (0.396 g, 0.636 mmol) were added. The mixture was warmed to 90° C. and allowed to stir for 15 minutes then was again cooled to below 50° C. Sodium tert-butoxide (4.07 g, 42.0 mmol) and 3,5-dibromopyridine (5.50 g, 23.0 mmol) were added and the mixture was warmed to 95° C. and stirred for 2 hours. The reaction mixture was then allowed to cool to ambient temperature, filtered through Celite and the filtrate was concentrated under reduced pressure. The residue was purified by chromatography (SiO$_2$, 50% EtOAc/hexanes) to provide the title compound (5.85 g, 15.9 mmol, 75% yield). MS (DCI/NH$_3$) m/z 368 (M+H)$^+$.

Example 56B tert-butyl (3aR,6aR)-5-(5-vinyl-3-pyridinyl)hexahydropyrrolo[3,4-b]pyrrole-1(2H)-carboxylate The product of Example 56A (2.40 g, 6.52 mmol) and Pd(PPh$_3$)$_4$ (0.301 g, 0.261 mmol) in toluene (50 mL) were treated with tributylvinyltin (2.87 mL, 9.78 mmol). The solution was warmed to 100° C. and allowed to stir for 36 hours. The reaction mixture was allowed to cool to ambient temperature, filtered through Celite and concentrated under reduced pressure. The residue was purified via chromatography (SiO$_2$, 50% EtOAc/hexanes) to provide the title compound (2.00 g, 6.34 mmol, 97% yield). MS (DCI/NH$_3$) m/z 316 (M+H)$^+$.

Example 56C (3aR,6aR)-5-(5-vinyl-3-pyridinyl)octahydropyrrolo[3,4-b]pyrrole

The product of Example 56B (0.500 g, 1.59 mmol) in CH$_2$Cl$_2$ (5 mL) at 0° C. was treated with trifluoroacetic acid (1 mL) dropwise via syringe. The mixture stirred at 0° C. for 2 hours and then concentrated under reduced pressure. The residue was purified via chromatography (SiO$_2$, 9:1:0.1 CH$_2$Cl$_2$:CH$_3$OH:NH$_4$OH) to provide the title compound (0.180 g, 0.836 mmol, 52% yield). MS (DCI/NH$_3$) m/z 216 (M+H)$^+$.

Example 56D (3aR,6aR)-5-(5-vinyl-3-pyridinyl)octahydropyrrolo[3,4-b]pyrrole dihydrochloride The product of Example 56C (0.170 g, 0.790 mmol) in ethyl acetate (5 mL) was treated with 4N HCl in 1,4-dioxane (2 mL). The precipitate, which formed immediately upon addition of the acid, was isolated via filtration and was recrystallized from methanol and ethyl acetate to provide the title compound (0.190 g, 0.620 mmol, 79% yield). $^1$H NMR (CH$_3$OH-d$_4$, 300 MHz) δ 2.10 (m, 1H), 2.40 (m, 1H), 3.40 (m, 3H), 3.60 (m, 2H), 3.70 (dd, J=12.2, 6.4 Hz, 1H), 3.96 (dd, J=12.6, 1.7 Hz, 1H), 4.50 (m, 1H), 5.68 (d, J=11.2 Hz, 1H), 6.19 (d, J=17.9 Hz, 1H), 6.86 (dd, J=17.9, 11.2 Hz, 1H), 7.80 (m, 1H), 8.08 (m, 1H), 8.28 (m, 1H); MS (DCI/NH$_3$) m/z 216 (M+H−2HCl)$^+$; Anal. calculated for C$_{13}$H$_{17}$N$_3$·2HCl·2H$_2$O: C, 48.16; H, 7.15; N, 12.96. Found: C, 48.53; H, 6.69; N, 13.08.

Example 57

(1R,5S)-6-(6-chloro-3-pyridinyl)-3,6-diazabicyclo[3.2.0]heptane fumarate

Example 57A benzyl (1S,5S)-6-(6-chloro-3-pyridinyl)-3,6-diazabicyclo[3.2.0]heptane-3-carboxylate The product of Example 52D (0.23 g, 1.0 mmol) and 2-chloro-5-bromopyridine (0.29 g, 1.5 mmol) were processed according to the procedure described in Example 1E. The crude product was purified by chromatography (SiO$_2$, hexane:ethyl acetate, 60:40, R$_f$ 0.3) to provide the title compound (0.13 g, 38% yield). $^1$H NMR (MeOH-d$_4$, 300 MHz) δ 3.24 (dd, J=12.9, 4.1 Hz, 1H), 3.30 (m, 1H), 3.40 (m, 1H), 3.65 (dd, J=7.8, 3.4 Hz, 1H), 4.08-3.92 (m, 3H), 4.70 (dd, J=5.7, 3.7 Hz, 1H), 5.10 (m, 2H), 6.90 (dd, J=8.5, 3.1 Hz, 1H), 7.20 (d, J=8.8 Hz, 1H), 7.25 (m, 3H), 7.35 (m, 2H), 7.54 (d, J=3.0 Hz, 1H); MS (DCI/NH$_3$) m/z 346 (M+2+H)$^+$, 344 (M+H)$^+$.

Example 57B (1R,5S)-6-(6-chloro-3-pyridinyl)-3,6-diazabicyclo
[3.2.0]heptane The product of Example 57A (130 mg, 0.38 mmol) was treated with trifluoroacetic acid according to the procedure of Example 46B. The product was purified by chromatography ($SiO_2$, $CH_2Cl_2$:MeOH:$NH_4OH$, 90:10:1, $R_f$ 0.4) to provide the title compound (70 mg, 88% yield). $^1$H NMR (MeOH-$d_4$, 300 MHz) δ 2.54 (dd, J=12.8, 3.4 Hz, 1H), 2.74 (dd, J=12.2, 6.1 Hz, 1H), 3.16 (m, 1H), 3.18 (d, J=12.2 Hz, 1H), 3.26 (d, J=12.9 Hz, 1H), 3.62 (dd, J=7.7, 3.3 Hz, 1H), 3.92 (t, J=7.8 Hz, 1H), 4.65 (dd, J=6.1, 3.4 Hz, 1H), 6.90 (dd, J=8.8, 3.1 Hz, 1H), 7.20 (d, J=8.1 Hz, 1H), 7.25 (d, J=2.7 Hz, 1H); MS (DCI/$NH_3$) m/z 212 (M+2+H)$^+$. 210 (M+H)$^+$.

Example 57C (1R,5S)-6-(6-chloro-3-pyridinyl)-3,6-diazabicyclo
[3.2.0]heptane fumarate The product of Example 57B (70 mg, 0.33 mmol) was treated with fumaric acid according to the procedure described in Example 46C to provide the title compound (195 mg, 99% yield). $^1$H NMR (MeOH-$d_4$, 300 MHz) δ 3.15 (dd, J=12.5, 3.7 Hz, 1H), 3.35 (m, 1H), 3.40-3.48 (m, 2H), 3.76 (m, 3H), 4.00 (t, J=8.2 Hz, 1H), 4.88 (m, 1H), 6.68 (s, 1H), 7.05 (dd, J=8.8, 3.1 Hz, 1H), 7.28 (d, J=8.8 Hz, 1H), 7.65 (d, J=3.0 Hz, 1H); MS (DCI/$NH_3$) m/z 212 (M+2+H)$^+$, 210 (M+H)$^+$. Anal. calculated for $C_{10}H_{12}ClN_3 \cdot 1.25C_4H_4O_4 \cdot 0.3H_2O$: C, 50.02; H, 4.93; N, 11.67. Found: C, 50.07; H, 4.20; N, 11.10.

Example 58

(3aR,6aR)-5-(5-methyl-3-pyridinyl)octahydropyrrolo
[3,4-b]pyrrole trihydrochloride

Example 58A tert-butyl (3aR,6aR)-5-(6-chloro-5-methyl-3-pyridinyl)hexahydropyrrolo[3,4-b]pyrrole-1(2H)-carboxylate The title compound was prepared according to the procedure described in Example 56A using the product of Example 14H (1.50 g, 7.07 mmol), $Pd_2(dba)_3$ (64.7 mg, 0.0707 mmol), BINAP (0.132 g, 0.212 mmol), 5-bromo-2-chloro-3-methylpyridine (1.60 g, 7.77 mmol, from Example 11B), and sodium tert-butoxide (1.36 g, 14.1 mmol) to provide 1.76 g of the title compound (5.21 mmol, 74% yield). MS (DCI/$NH_3$) m/z 338 (M+H)$^+$.

Example 58B tert-butyl (3aR,6aR)-5-(5-methyl-3-pyridinyl)hexahydropyrrolo[3,4-b]pyrrole-1(2H)-carboxylate The product of Example 58A (0.880 g, 2.61 mmol) in ethanol (200 proof, 15 mL) was treated with 30 mg of Pd/C (10 wt %) and triethylamine (1.00 mL, 7.17 mmol) under 1 atmosphere of $H_2$. After stirring for 36 hours, the mixture was filtered through Celite and the filtrate was concentrated under reduced pressure. The residue was purified via chromatography ($SiO_2$, 25% EtOAc/hexanes) to provide the title compound (0.500 g, 1.65 mmol, 63% yield). MS (DCI/$NH_3$) m/z 304 (M+H)$^+$.

Example 58C (3aR,6aR)-5-(5-methyl-3-pyridinyl)octahydropyrrolo
[3,4-b]pyrrole The product of Example 58B (0.500 g, 1.65 mmol) in $CH_2Cl_2$ (7 mL) at 0° C. was treated with trifluoroacetic acid (1.50 mL) dropwise. The mixture was stirred at 0° C. for 3 hours and then was concentrated under reduced pressure. The residue was purified via chromatography ($SiO_2$, 9:1:0.1 $CH_2Cl_2$:$CH_3OH$:$NH_4OH$) to provide the title compound (0.300 g, 1.48 mmol 89% yield). MS (DCI/$NH_3$) m/z 204 (M+H)$^+$.

Example 58D (3aR,6aR)-5-(5-methyl-3-pyridinyl)octahydropyrrolo
[3,4-b]pyrrole trihydrochloride The product of Example 58C (0.300 g, 1.48 mmol) in ethyl acetate (5 mL) was treated with 4N HCl in 1,4-dioxane (1 mL). A precipitate formed immediately upon addition of the acid and was isolated via filtration to provide the title compound (0.385 g, 1.10 mmol, 75% yield). $^1$H NMR ($CH_3OH$-$d_4$, 300 MHz) δ 2.10 (m, 1H), 2.40 (m, 1H), 2.50 (s, 3H), 3.40 (m, 3H), 3.55 (m, 2H), 3.68 (dd, J=12.2, 6.4 Hz, 1H), 3.95 (dd, J=12.2, 2.0 Hz, 1H), 4.49 (m, 1H), 7.70 (m, 1H), 8.05 (m, 2H); MS (DCI/$NH_3$) m/z 204 (M+H−2HCl)$^+$: Anal. calculated for $C_{12}H_{17}N_3 \cdot 3HCl \cdot H_2O$: C, 43.59; H, 6.71; N, 12.71. Found: C, 43.93; H, 6.53; N, 12.35.

Example 59

(3aR,6aR)-5-(6-bromo-5-chloro-3-pyridinyl)octahydropyrrolo[3,4-b]pyrrole fumarate The product of Example 24A (330 mg, 0.92 mmol) in HBr (30% in AcOH, 5 mL) was heated at 110° C. for 3 hours. The mixture was allowed to cool to room temperature and concentrated to dryness under reduced pressure. The residue was purified by chromatography ($SiO_2$, $CH_2Cl_2$:methanol: $NH_4OH_{(aq)}$, 94:5:1) to provide the free base of the title compound (119 mg, 43% yield). The free base was treated with fumaric acid according to the procedure described in Example 37C to provide the title compound (160 mg, 98% yield). $^1$H NMR ($CD_3OD$, 300 MHz) δ 2.05 (m, 1H), 2.35 (m, 1H), 3.45 (m, 6H), 3.85 (dd, J=12, 1.5 Hz, 1H), 4.45 (t, J=6 Hz, 1H), 6.65 (s, 2H), 7.35 (d, J=3 Hz, 1H), 7.80 (d, J=3 Hz, 1H); MS (DCI/$NH_3$) m/z 303 (M+H)$^+$; Anal. calculated for $C_{11}H_{13}BrClN_3 \cdot C_4H_4O_4$: C, 42.99; H, 4.06; N, 10.03. Found: C, 42.74; H, 4.19; N, 9.87

Example 60

(3aR,6aR)-5-(6-bromo-5-methyl-3-pyridinyl)octahydropyrrolo[3,4-b]pyrrole dihydrochloride

Example 60A (3aR,6aR)-5-(6-bromo-5-methyl-3-pyridinyl)octahydropyrrolo[3,4-b]pyrrole The product of Example 58A (0.250 g, 0.740 mmol) in 30% HBr/acetic acid (20 mL) was warmed to 100° C. in a sealed tube for 4 hours. The mixture was cooled to 0° C., the contents were transferred to a separatory funnel and the layers were separated. The aqueous layer was concentrated under reduced pressure and the residue was purified via chromatography (SiO$_2$, 9:1:0.1 CH$_2$Cl$_2$:CH$_3$OH:NH$_4$OH) to provide the title compound (0.100 g, 0.355 mmol, 48% yield). MS (DCI/NH$_3$) m/z 282 (M+H)$^+$.

Example 60B (3aR,6aR)-5-(6-bromo-5-methyl-3-pyridinyl)octahydropyrrolo[3,4-b]pyrrole dihydrochloride The title compound was prepared according to the procedure of Example 58D using the product of Example 60A (0.100 g, 0.355 mmol) to provide the salt (0.129 g, 3.54 mmol, 99% yield). $^1$H NMR (CH$_3$OH-d$_4$, 300 MHz) δ 2.05 (m, 1H), 2.35 (m, 1H), 2.40 (s, 3H), 3.30 (m, 2H), 3.38 (m, 3H), 3.46 (m, 2H), 3.87 (dd, J=11.9, 1.0 Hz, 1H), 7.33 (d, J=2.7 Hz, 1H), 7.76 (d, J=2.7 Hz, 1H); MS (DCI/NH$_3$) m/z 282 (M+H–2HCl)$^+$; Anal. calculated for C$_{12}$H$_{16}$BrN$_3$.2HCl.0.5H$_2$O: C, 39.58; H, 5.26; N, 11.54. Found: C, 39.87; H, 5.43; N, 11.46.

Example 61

5-[(1S,6R)-3,8-diazabicyclo[4.2.0]oct-8-yl]nicotinonitrile fumarate

Example 61A 1-tert-butyl 4-ethyl 5-{[(1S)-1-phenylethyl]amino}-3,6-dihydro-1,4(2H)-pyridinedicarboxylate The product of Example 33A (90.4 g, 0.333 mol) in toluene (250 mL) was treated with (S)-α-methylbenzylamine (42.4 g, 0.350 mol). The mixture was warmed to reflux with a Dean-Stark trap until the distillate was clear (7 hours) and ~7 mL of H$_2$O had been collected. The mixture was concentrated under reduced pressure to provide the title compound which was carried on directly to the next step without further purification.

Example 61B 1-tert-butyl 4-ethyl (cis)-3-{[(1S)-1-phenylethyl]amino}-1,4-piperidinedicarboxylate The product of Example 61A (62.3 g, 0.167 mol). NaBH(OAc)$_3$ (150.0 g, 0.708 mol), and powdered 4 Å molecular sieves (133.0 g) in toluene (730 mL) in a 3-neck round bottom flask equipped with a mechanical stirrer, thermometer and addition funnel at 0° C. was treated with acetic acid (191 mL, 3.30 mol) dropwise. After the addition was complete, the ice-bath was removed and the mixture was stirred for 20 hours, filtered and the filtrate concentrated under reduced pressure. The residue was dissolved in ethyl acetate (1000 mL) and quenched by slow addition of saturated aqueous NaHCO$_3$. The layers were separated and the aqueous layer was extracted with ethyl acetate. The combined organics were dried over Na$_2$SO$_4$, filtered and the filtrate concentrated under reduced pressure to provide the product as a ~1:1.5 mixture of the two (cis) isomers (60.0 g, 0.159 mol, 94% yield). MS (DCI/NH$_3$) m/z 377 (M+H)$^+$.

Examples 61C tert-butyl (3S,4S)-4-(hydroxymethyl)-3-{[(1S)-1-phenylethyl]amino}-1-piperidinecarboxylate and tert-butyl (3R,4R)-4-(hydroxymethyl)-3-{[(1S)-1-phenylethyl]amino}-1-piperidinecarboxylate The product of Example 61B (60.0 g, 0.159 mol) in tetrahydrofuran (200 mL) was added dropwise to a mixture of lithium aluminum hydride (7.00 g, 0.175 mol, 95%) in tetrahydrofuran (300 mL) at 0° C. After the addition was complete, the mixture was allowed to warm to ambient temperature and was quenched by slow addition of Na$_2$SO$_4$.10H$_2$O (excess). The mixture was stirred for 16 hours, filtered and the filtrate concentrated under reduced pressure. The residue was purified by column chromatography (SiO$_2$, 50% ethyl acetate/hexanes) to provide two diastereomers, a more mobile diastereomer determined to be the (3S,4S) diastereomer R$_f$=0.27 in 75% ethyl acetate/hexanes, 15.0 g, 44.8 mmol, 28% yield and a less mobile diastereomer determined to be the (3R,4R) diastereomer (R$_f$=0.20 in 75% ethyl acetate/hexanes, 22.5 g, 67.3 mmol, 42% yield). MS (DCI/NH$_3$) m/z 335 (M+H)$^+$.

The more mobile diastereomer was subjected to X-ray analysis. Single crystals suitable for x-ray diffraction were grown by slow evaporation from ethyl acetate solution. Crystal data: MW=334.46, C$_{19}$H$_{30}$N$_2$O$_3$, crystal dimensions 0.40×0.20×0.05 mm, orthorhombic, P2$_1$2$_1$2$_1$ (#19), a=6.5862 (1), b=12.6216(2), c=23.5983(3) Å, V=1962.69(4) Å$^3$, Z=4, D$_{calc}$=1.13 cm$^{-3}$. Crystallographic data were collected using Mo K α radiation (λ=0.711069 Å). Refinement of the structure using full matrix least squares refinement of 217 parameters on 2349 reflections with I>3.00σ(1) gave R=0.067. R$_w$=0.087.

Example 61D tert-butyl (3S,4S)-3-amino-4-(hydroxymethyl)-1-piperidinecarboxylate The more mobile diastereomer of Example 61C (13.3 g, 39.8 mmol) in ethanol (200 mL) was treated with 10% Pd/C (1.95 g) under 1 atmosphere of H$_2$ at 50° C. After stirring for 20 hours, the mixture was allowed to cool to ambient temperature, filtered through Celite, and the filtrate concentrated under reduced pressure to provide the title compound which was carried on directly to the next step without further purification. MS (DCI/NH$_3$) m/z 231 (M+H)$^+$.

Example 61E tert-butyl (1S,6R)-8-[(2-nitrophenyl)sulfonyl]-3,8-diazabicyclo[4.2.0]octane-3-carboxylate The product of Example 61D (39.8 mmol) in CH$_2$Cl$_2$(200 mL) at 0° C. was treated with triethylamine (116.7 mL, 0.120 mol) followed by 2-nitrobenzenesulfonyl chloride (19.5 g, 88.0 mmol). The ice-bath was removed and the solution stirred at ambient temperature for 20 hours. The mixture was concentrated under reduced pressure and the residue dissolved in a mixture of ethanol and 5% aqueous NaOH (2:1, 200 mL). The mixture was stirred for 30 minutes, concentrated under reduced pressure, diluted with ethyl acetate (200 mL) and the layers were separated. The organic layer was dried over Na$_2$SO$_4$, filtered, and the filtrate concentrated under reduced pressure. The residue was purified via chromatography (SiO$_2$), 50% ethyl acetate/hexanes) to provide the title compound (111.0 g, 27.7 mmol, 70% yield for two steps). MS (DCI/NH$_3$) m/z 415 (M+NH$_4$)$^+$.

Example 61F tert-butyl (1S,6R)-3,8-diazabicyclo[4.2.0]octane-3-carboxylate

The product of Example 61E (111.0 g, 27.7 mmol) in N,N-dimethylfomamide (1100 mL) was treated with K$_2$CO$_3$ (11.8 g, 85.8 mmol) followed by thiophenol (3.70 mL, 36.0 mmol) at ambient temperature. The mixture stirred for 20 hours, filtered and the filtrate concentrated under reduced pressure. The residue was purified via chromatography (SiO$_2$, 9:1:0.1 CH$_2$Cl$_2$:CH$_3$OH:NH$_4$OH) to provide the title compound (2.50 g, 11.8 mmol, 43% yield). MS (DCI/NH$_3$) m/z 213 (M+H)$^+$.

Example 61G tert-butyl (1S,6R)-8-(5-cyano-3-pyridinyl)-3,8-diazabicyclo[4.2.0]octane-3-carboxylate The product of Example 61F (0.780 g, 3.68 mmol) was treated with Pd$_2$(dba)$_3$ (34 mg, 0.0368 mmol), BINAP (69 mg, 0.1101 mmol), 3-bromo-5-cyanopyridine (0.810 g 4.41 mmol), Cs$_2$CO$_3$ (2.60 g, 8.09 mmol) and processed according to the procedure described in Example 56A to provide the title compound (0.630 g, 2.01 mmol, 55% yield). MS (DCI/NH$_3$) m/z 315 (M+H)$^+$.

Example 61H

5-[(1S,6R)-3,8-diazabicyclo[4.2.0]oct-8-yl]nicotinonitrile

The product of Example 61G (0.630 g, 2.01 mmol) in CH$_2$Cl$_2$ (10 mL) was treated with trifluoroacetic acid (7 mL) according to the procedure described in Example 64C to provide the title compound (0.500 g, >100% yield). MS (DCI/NH$_3$) m/z 215 (M+H)$^+$.

Example 61I

5-[(1S,6R)-3,8-diazabicyclo[4.2.0]oct-8-yl]nicotinonitrile fumarate

The title compound was prepared according to the procedure described in Example 66D using the product of Example 61H (2.01 mmol) and 0.230 g fumaric acid (2.01 mmol) to provide the salt (0.325 g, 0.953 mmol, 47% yield for two steps). $^1$H NMR (CH$_3$OH-d$_4$, 300 MHz) δ 2.06 (m, 1H), 2.31 (m, 1H), 2.92 (m, 1H), 3.20 (ddd, J=11.9, 7.5, 4.4 Hz, 1H), 3.34 (d, J=3.1 Hz, 1H), 3.57 (ddd, J=13.2, 9.2, 4.4 Hz, 1H), 3.67 (dd, J=14.5, 2.0 Hz, 1H) 3.85 (dd, J=7.5, 2.7 Hz, 1H), 3.94 (t, J=7.5 Hz, 1H), 4.46 (dt, J=7.8, 2.0 Hz, 1H), 6.67 (s, 2H), 7.41 (dd, J=3.1, 1.7 Hz, 1H), 8.17 (d, J=3.1 Hz, 1H), 8.31 (d, J=1.7 Hz, 1H); MS (DCI/NH$_3$) m/z 215 (M+H–C$_4$H$_4$O$_4$)$^+$; Anal. calculated for C$_{12}$H$_{14}$N$_4$.C$_4$H$_4$O$_4$.0.6H$_2$O: C, 56.33; H, 5.67; N, 16.42. Found: C, 56.15; H, 5.39; N, 16.14.

Example 62

(cis)-5-[3,8-diazabicyclo[4.2.0]oct-3-yl]nicotinonitrile fumarate

Example 62A tert butyl (cis)-3-(5-cyano-3-pyridinyl)-3,8-diazabicyclo[4.2.0]octane-8-carboxylate The product of Example 42F (0.220 g, 1.0 mmol) in (0.220 g, 1.0 mmol) in toluene (10 mL) was treated with 3-cyano-5-bromopyridine (0.206 g, 1.10 mmol), Pd$_2$(dba)$_3$ (0.0.19 g, 0.02 mmol), BINAP (0.026 g, 0.040 mmol) and sodium tert-butoxide (0.170 g, 1.80 mmol) and heated at 80° C. for 4 hours. The mixture was allowed to cool to room temperature and concentrated under reduced pressure. The residue was purified by chromatography (SiO$_2$, 5% MeOH/CH$_2$Cl$_2$) to provide the title compound as a yellow oil (77%, 0.232 g). MS (DCI/NH$_3$) m/z 314 (M+H)$^+$.

Example 62B

(cis)-5-[3,8-diazabicyclo[4.2.0]oct-3-yl]nicotinonitrile fumarate

The product of Example 62A (0.212 g 0.70 mmol) in dichloromethane (10 mL) was treated with trifluoroacetic acid (10 mL). After stirring at room temperature for 1 hour, the reaction mixture was concentrated under reduced pressure. The residue was purified by chromatography (SiO$_2$, methanol:CH$_2$Cl$_2$:NH$_4$OH, 10:89:1) to provide a yellow oil (0.059 g) in 39% yield. The fumarate salt was formed to afford an off-white loam. $^1$H NMR (MeOH, 300 MHz) δ 2.01-2.12 (m, 1H), 2.37-2.48 (m, 1H), 2.87-2.96 (m, 1H), 3.15-3.35 (m, 1H), 3.47 (d, J=3.0 Hz, 1H), 3.52-3.63 (m, 1H) 3.68 (dd, J=2.0, 12.0 Hz, 1H), 3.86 (dd, J=2.0, 9.0 Hz, 1H), 3.45 (t, J=8.0 Hz, 1H), 4.47 (dt, J=2.0, 8.0 Hz, 1H), 7.43 (t, J=2.0 Hz, 1H), 8.18 (d, J=3.0 Hz, 1H), 8.32 (d, J=2.0 Hz, 1H); MS (DCI/NH$_3$) m/z 215 (M+H)$^+$; Anal. Calcd for C$_{12}$H$_{14}$N$_4$.1.50C$_4$H$_8$O$_4$.1.0H$_2$O: C, 53.20; H, 5.46; N, 13.79. Found: C, 53.21; H, 5.16; N, 13.38

Example 63

(3aR,6aR)-5-(5-ethyl-3-pyridinyl)octahydropyrrolo[3,4-b]pyrrole

Example 63A tert-butyl (3aR,6aR)-5-(5-ethyl-3-pyridinyl)hexahydropyrrolo[3,4-b]pyrrole-1(2H)-carboxylate The product of Example 56B (1.00 g, 3.17 mmol) and Pd/C (0.100 g, 10 wt %) in ethanol (20 mL) were placed under 1 atmosphere of hydrogen. After stirring at ambient temperature for 5 hours, the mixture was filtered through Celite and the filtrate concentrated under reduced pressure to provide the title compound (0.900 g, 2.84 mmol, 89% yield). MS (DCI/NH$_3$) m/z 318 (M+H)$^+$.

Example 63B

(3aR,6aR)-5-(5-ethyl-3-pyridinyl)octahydropyrrolo[3,4-b]pyrrole

The product of Example 63A (0.360 g, 1.13 mmol) in CH$_2$Cl$_2$ (10 mL) was treated with trifluoroacetic acid (3 mL)

dropwise at 0° C. The mixture was stirred at 0° C. for 1 hour, allowed to warm to ambient temperature and stirred an additional 3 hours. The solution was concentrated under reduced pressure and purified via chromatography (SiO$_2$, 9:1:0.1 CH$_2$Cl$_2$:CH$_3$OH:NH$_4$OH) to provide the title compound (0.176 g, 0.810 mmol, 72% yield). MS (DCI/NH$_3$) m/z 218 (M+H)$^+$.

Example 63C (3aR,6aR)-5-(5-ethyl-3-pyridinyl)octahydropyrrolo[3,4-b]pyrrole

A solution of fumaric acid (94.0 mg, 0.810 mmol) in 10% CH$_3$OH in diethyl ether (7 mL) was treated with the product of Example 63B (0.176 g, 0.810 mmol) in 10% CH$_3$OH in diethyl ether (5 mL). After stirring for 20 hours, a precipitate formed and was isolated via filtration to provide the title compound (0.220 g, 0.643 mmol, 79% yield). $^1$H NMR (CH$_3$OH-d$_4$, 300 MHz) δ 1.25 (t, J=7.8 Hz, 3H), 2.05 (m, 1H), 2.35 (m, 1H), 2.65 (q, J=7.8 Hz, 2H), 3.34 (m, 5H), 3.49 (m, 1H), 3.87 (dd, J=11.5, 1.1 Hz, 1H), 4.40 (m, 1H), 6.67 (s, 2H), 7.06 (m, 1H), 7.84 (d, J=1.4 Hz, 1H), 7.87 (d. J=2.7 Hz, 1H); MS (DCI/NH$_3$) m/z 218 (M+H−C$_4$H$_4$O$_4$)$^+$; Anal. calculated for C$_{13}$H$_{19}$N$_3$.C$_4$H$_4$O$_4$.0.5H$_2$O: C, 59.63; H, 7.07; N, 12.27. Found: C, 59.73; H, 6.91; N, 12.16.

Example 64

[5-((3aR,6aR)-hexahydropyrrolo[3,4-b]pyrrol-5(1H)-yl)-2-bromo-3-pyridinyl]methanol fumarate

Example 64A tert-butyl (3aR,6aR)-5-[5-(hydroxymethyl)-3-pyridinyl]hexahydropyrrolo[3,4-b]pyrrole-1(2H)-carboxylate The product of Example 56A (3.40 g, 9.23 mmol) and N,N-dimethylformamide (1.43 mL, 18.5 mmol) in THF (100 mL) was treated with tert-butyllithium in pentane (1.7 M, 15.2 mL) dropwise at −78° C. After complete addition, the mixture was stirred for 20 minutes and then transferred via cannula to a mixture of NaBH$_4$ (1.75 g, 46.0 mmol) in CH$_3$OH (100 mL). The solution was stirred for 30 minutes at ambient temperature and then ethyl acetate (100 mL) and H$_2$O (100 mL) were added. The layers were separated and the aqueous layer was extracted with ethyl acetate (100 mL). The combined organic layers were dried over NaSO$_4$, filtered and the filtrate concentrated under reduced pressure. The crude material showed unreduced aldehyde; therefore, the mixture was dissolved in CH$_3$OH (100 mL) and NaBH$_4$ (1.75 g, 46.0 mmol) was added. The mixture was stirred for 2 hours and then was worked up as before to give a crude oil which was purified via chromatography (SiO$_2$, 50% ethyl acetate/hexanes) to provide the title compound (2.10 g, 6.57 mmol, 71% yield). MS (DCI/NH$_3$) m/z 320 (M+H)$^+$.

Example 64B tert-butyl (3aR,6aR)-5-[6-bromo-5-(hydroxymethyl)-3-pyridinyl]hexahydropyrrolo[3,4-b]pyrrole-1(2H)-carboxylate The product of Example 64A (1.11 g, 3.48 mmol) in CH$_3$CN (30 mL) was treated with N-bromosuccinimide (0.606 g 3.41 mmol) in CH$_3$CN (10 mL) dropwise −10° C. The mixture was stirred for 1 hour at −10° C. and then was quenched with H$_2$O (10 mL). The layers were separated and the aqueous layer was extracted with CH$_2$Cl$_2$ (10 mL). The combined organics were dried over Na$_2$SO$_4$, filtered and the filtrate concentrated under reduced pressure. The residue was purified via chromatography (SiO$_2$, 50% ethyl acetate/hexanes) to provide the title compound (1.32 g, 3.31 mmol, 95% yield). MS (DCI/NH$_3$) m/z 398 (M+H)$^+$.

Example 64C

[5-((3aR,6aR)-hexahydropyrrolo[3,4-b]pyrrol-5(1H)-yl)-2-bromo-3-pyridinyl]methanol The product of Example 64B (0.143 g, 0.359 mmol) in CH$_2$Cl$_2$ (5 mL) was treated with trifluoroacetic acid (5 mL) dropwise at 0° C. After the addition, the mixture was allowed to warm to ambient temperature and stirred for 2 hours. The solution was then concentrated under reduced pressure and the residue purified via chromatography (SiO$_2$, 9:1:0.1 CH$_2$Cl$_2$:CH$_3$OH:NH$_4$OH) to provide the title compound (0.090 g, 0.302 mmol, 84% yield).

Example 64D

[5-((3aR,6aR)-hexahydropyrrolo[3,4-b]pyrrol-5(1H)-yl)-2-bromo-3-pyridinyl]methanol fumarate The product of Example 64C (90.0 mg, 0.302 mmol) in 20% CH$_3$OH in diethyl ether (10 mL) was treated with a solution of fumaric acid (35.0 mg, 0.302 mmol) in 10% CH$_3$OH in diethyl ether (5 mL). The mixture was stirred for 20 hours and the precipitate was isolated via filtration to provide the title compound (91.3 mg, 0.211 mmol, 70% yield). $^1$H NMR (CH$_3$OH-d$_4$, 300 MHz) δ 2.05 (in 1H), 2.35 (m, 1H), 3.32 (m, 5H), 3.45 (m, 2H), 3.84 (dd, J=11.5, 1.2 Hz, 1H), 4.39 (m, 1H), 4.57 (s, 2H), 6.67 (s, 2H), 7.33 (d, J=3.1 Hz, 1H), 7.72 (d, J=3.1 Hz, 1H); MS (DCI/NH$_3$) m/z 299 (M+H−C$_4$H$_4$O$_4$)$^+$; Anal. calculated for C$_{12}$H$_{16}$BrN$_3$O.C$_4$H$_4$O$_4$.H$_2$O: C, 44.46; H, 5.13; N, 9.72. Found: C, 44.39; H, 4.79; N, 9.66.

Example 65

(3aR,6aR)-5-(6-bromo-5-vinyl-3-pyridinyl)octahydropyrrolo[3,4-b]pyrrole dihydrochloride

Example 65A tert-butyl (3aR,6aR)-5-(6-bromo-5-vinyl-3-pyridinyl)hexahydropyrrolo[3,4-b]pyrrole-1(2H)-carboxylate The product of Example 56B (0.550 g, 1.74 mmol) in CH$_3$CN (10 mL) was treated with solid N-bromosuccinimide (0.330 g, 1.83 mmol). The mixture was stirred at ambient temperature for 1 hour, quenched with water and extracted with CH$_2$Cl$_2$. The organic phase was dried over Na$_2$SO$_4$, filtered and the filtrate concentrated under reduced pressure. The residue was purified via chromatography to provide the title compound (0.210 g, 0.533 mmol, 31% yield). MS (DCI/NH$_3$) m/z 394 (M+H)$^+$.

Example 65B (3aR,6aR)-5-(6-bromo-5-vinyl-3-pyridinyl)octahydropyrrolo[3,4-b]pyrrole The product of Example 65A (0.200 g, 0.507 mmol) in $CH_2Cl_2$ (5 mL) was treated with trifluoroacetic acid (2 mL) dropwise at 0° C. The mixture was stirred at 0° C. for 3 hours and then was concentrated under reduced pressure. The residue was purified via chromatography ($SiO_2$, 9:1:0.1 $CH_2Cl_2$: $CH_3OH:NH_4OH$) to provide the title compound (0.140 g, 0.476 mmol, 94% yield). MS ($DCI/NH_3$) m/z 295 (M+H)$^+$.

Example 65C (3aR,6aR)-5-(6-bromo-5-vinyl-3-pyridinyl)octahydropyrrolo[3,4-b]pyrrole dihydrochloride The product of Example 65B (0.140 g, 0.476 mmol) in ethyl acetate (10 mL) was treated with 4N HCl in 1,4-dioxane (1 mL). The mixture was stirred at ambient temperature for 15 minutes and then concentrated under reduced pressure. The crude material was crystallized from $CH_3OH$ and ethyl acetate to provide the title compound (50.0 mg, 0.130 mmol, 27% yield). $^1$H NMR ($CH_3OH-d_4$, 300 MHz) δ 2.07 (m, 1H), 2.36 (m, 1H), 3.40 (m, 7H), 3.88 (dd, J=11.9, 1.3 Hz, 1H), 5.50 (dd, J=11.5, 1.0 Hz, 1H), 5.87 (dd, J=17.3, 1.0 Hz, 1H), 6.94 (dd, J=17.3, 11.5 Hz, 1H), 7.33 (d, J=3.1 Hz, 1H), 7.77 (d, J=3.1 Hz, 1H); MS ($DCI/NH_3$) m/z 294 (M+H−2HCl)$^+$: Anal. calculated for $C_{13}H_{16}BrN_3.2HCl.H_2O$: C, 40.54; H, 5.23; N, 10.91. Found: C, 40.86; H, 5.17; N, 10.41.

Example 66

[5-((3aR,6aR)-hexahydropyrrolo[3,4-b]pyrrol-5 (1H)-yl)-2-bromo-3-pyridinyl]acetonitrile fumarate

Example 66A tert-butyl (3aR,6aR)-5-(6-bromo-5-{[(methylsulfonyl)oxy]methyl}-3-pyridinyl)hexahydropyrrolo[3,4-b]pyrrole-1(2H)-carboxylate The product of Example 64B (0.300 g, 0.753 mmol) and triethylamine (0.231 mL, 1.66 mmol) in $CH_2Cl_2$ (5 mL) were treated with methanesulfonyl chloride (0.0641 mL, 0.829 mmol) at ambient temperature. The mixture was stirred for 20 hours and then was quenched with water (5 mL). The layers were separated and the organic layer was dried over $Na_2SO_4$, filtered and the filtrate concentrated under reduced pressure. The residue was purified via chromatography ($SiO_2$, 50% ethyl acetate/hexanes) to provide the title compound (0.300 g, 0.630 mmol, 84% yield).

Example 66B tert-butyl (3aR,6aR)-5-[6-bromo-5-(cyanomethyl)-3-pyridinyl]hexahydropyrrolo[3,4-b]pyrrole-1(2H)-carboxylate The product of Example 66A (0.300 g, 0.630 mmol) in N,N-dimethylfomamide (5 mL) was treated with KCN (61 mg, 0.945 mmol). The mixture was warmed to 60° C. and allowed to stir for 20 hours. The mixture was then concentrated under reduced pressure and the residue purified via chromatography ($SiO_2$, 50% ethyl acetate/hexanes) to provide the title compound (0.100 g, 0.246 mmol, 39% yield). MS ($DCI/NH_3$) m/z 409 (M+H)$^+$.

Example 66C

[5-((3aR,6aR)-hexahydropyrrolo[3,4-b]pyrrol-5 (1H)-yl)-2-bromo-3-pyridinyl]acetonitrile The product of Example 66B (0.100 g, 0.246 mmol) was processed according to the procedure described in Example 64C to provide the free amine (70 mg, 93% yield).

Example 66D

[5-((3aR,6aR)-hexahydropyrrolo[3,4-b]pyrrol-5 (1H)-yl)-2-bromo-3-pyridinyl]acetonitrile fumarate The product of Example 66C (70.0 mg, 0.228 mmol) in 10% $CH_3OH$ in diethyl ether (5 mL) was treated with fumaric acid (26.4 mg, 0.228 mmol) in 10% $CH_3OH$ in diethyl ether (5 mL). The mixture was stirred for 20 hours and the precipitate was isolated via filtration to provide the title compound (15 mg, 0.0347 mmol, 15% yield). $^1$H NMR ($CH_3OH-d_4$, 300 MHz) δ 2.04 (m, 1H), 2.34 (m, 1H), 3.33 (m, 3H), 3.45 (m, 3H), 3.83 (dd, J=11.9, 1.7 Hz, 1H), 3.95 (s, 2H), 4.38 (m, 1H), 6.68 (s, 2H), 7.27 (d, J=3.1 Hz, 1H), 7.82 (d, J=3.1 Hz, 1H); MS ($DCI/NH_3$) m/z 307 (M+H−$C_4H_4O_4$)$^+$; Anal. calculated for $C_{13}F_{15}BrN_4.C_4H_4O_4.0.5H_2O$: C, 47.24; H, 4.66; N, 12.96. Found: C, 47.39; H, 4.37; N, 12.76.

Example 67

(3aR,6aR)-5-[6-bromo-5-(methoxymethyl)-3-pyridinyl]octahydropyrrolo[3,4-b]pyrrole fumarate

Example 67A tert-butyl (3aR,6aR)-5-[6-bromo-5-(methoxymethyl)-3-pyridinyl]hexahydropyrrolo[3,4-b]pyrrole-1 (2H)-carboxylate The product of Example 64B (0.251 g, 0.630 mmol) in N,N-dimethylformamide (3 mL) was cooled to 0° C. and treated with NaH (38 mg, 0.940 mmol). The ice-bath was removed and the mixture stirred for 20 minutes. The mixture was recooled to 0° C. and $CH_3I$ (41.0 µL, 0.660 mmol) was added. The ice-bath was removed and the reaction mixture was stirred for 1 hour, cooled to 0° C. and quenched with ice/water. The mixture was diluted with $CH_2Cl_2$ and the phases separated. The organic layer was dried over $Na_2SO_4$, filtered and the filtrate concentrated under reduced pressure. The residue was purified via chromatography ($SiO_2$, 50% Ethyl acetate-hexanes) to provide the title compound (0.200 g, 0.485 mmol, 77% yield). MS ($DCI/NH_3$) m/z 412 (M+H)$^+$.

Example 67B (3aR,6aR)-5-[6-bromo-5-(methoxymethyl)-3-pyridinyl]octahydropyrrolo[3,4-b]pyrrole The product of Example 67A (0.200 g, 0.485 mmol) and trifluoracetic acid were processed according to the procedure described in Example 64C to provide the title compound (0.145 g, 0.464 mmol, 96% yield).

Example 67C

(3aR,6aR)-5-[6-bromo-5-(methoxymethyl)-3-pyridinyl]octahydropyrrolo[3,4-b]pyrrole fumarate The product of Example 67B (0.145 g, 0.464 mmol) and fumaric acid (54 mg, 0.464 mmol) were processed according to the procedure described in Example 66D to provide the title compound (0.155 g, 0.362 mmol, 78% yield). $^1$H NMR (CH$_3$OH-d$_4$, 300 MHz) δ 2.05 (m, 1H), 2.35 (m, 1H), 3.26 (m, 1H), 3.35 (m, 3H), 3.43 (m, 2H), 3.50 (s, 3H), 3.84 (dd, J=11.5, 1.3 Hz, 1H), 4.39 (m, 1H), 4.44 (s, 2H), 6.68 (s, 2H), 7.26 (d, J=3.1 Hz, 1H), 7.74 (d, J=3.1 Hz, 1H); MS (DCI/NH$_3$) m/z 313 (M+H–C$_4$H$_4$O$_4$)$^+$; Anal. calculated for C$_{13}$H$_{18}$BrN$_3$O.C$_4$H$_4$O$_4$: C, 47.68; H, 5.18; N, 9.81. Found: C, 47.31; H, 4.93; N, 9.56.

Example 68

(1S,5R)-6-(5-ethynyl-3-pyridinyl)-3,6-diazabicyclo[3.2.0]heptane fumarate

Example 68A tert-butyl (1R,5R)-6-{5-[(trimethylsilyl)ethynyl]-3-pyridinyl}-3,6-diazabicyclo[3.2.0]heptane-3-carboxylate The product of Example 69A (140 mg, 0.40 mmol) was treated with ethynyltrimethyl silane (100 mg, 1 mmol), triethylamine (122 mg, 1.2 mmol), PdCl$_2$(PPh$_3$)$_2$ (5.6 mg, 0.008 mmol) and CuI (7.6 mg, 0.004 mmol) in N,N-dimethylformamide under N$_2$ at 60-70° C. and allowed to stir for 10 hours. The mixture was diluted with 10 mL of water and extracted with ethyl acetate (3×50 mL). The extracts were combined and concentrated. The residue was purified by chromatography (SiO$_2$, EtOAc:hexanes, 50:50:, R$_f$ 0.50) to provide the title compound (120 mg, 80% yield). $^1$H NMR (MeOH-d$_4$, 300 MHz) δ 0.05 (s, 9H), 1.40 (brs, 9H), 3.16-3.35 (m, 3H), 3.50 (m, 1H), 3.85-4.05 (m, 3H), 4.50 (m, 1H), 6.68 (m, 1H), 7.48 (d, J=2.7 Hz, 1H), 7.67 (m, J=1.7 Hz, 1H); MS (DCI/NH$_3$) m/z 372 (M+H)$^+$.

Example 68B tert-butyl (1R,5R)-6-(5-ethynyl-3-pyridinyl)-3,6-diazabicyclo[3.2.0]heptane-3-carboxylate The product of Example 68A (120 mg, 0.32 mmol) was treated with Bu$_4$N$^+$F$^-$ (1M in THF, 2 mL) at room temperature over 20 minutes. The volatiles were removed at reduced pressure and the residue was purified by chromatography (SiO$_2$. EtOAc:hexane, 50:50:, R$_f$ 0.50) to provide the title compound (90 mg, 94% yield). $^1$H NMR (MeOH-d$_4$, 300 MHz) δ 1.40 (brs, 9H), 3.16 (dd, J=12.5, 4.1 Hz, 1H), 3.20-3.35 (m, 2H), 3.60 (m, 1H), 3.65 (s, 1H), 3.85-4.05 (m, 3H), 4.70 (dd, J=6.1, 4.4 Hz, 1H), 6.95 (dd, J=2.7, 1.7 Hz, 1H), 7.73 (d, J=2.7 Hz, 1H), 7.94 (d, J=1.7 Hz, 1H); MS (DCI/NH$_3$) m/z 300 (M+H)$^+$.

Example 68C

(1S,5R)-6-(5-ethynyl-3-pyridinyl)-3,6-diazabicyclo[3.2.0]heptane

The product of Example 68B (90 mg, 0.30 mmol) was treated with trifluoroacetic acid according to the procedure of Example 69C. The product was purified by chromatography (SiO$_2$, CH$_2$Cl$_2$:MeOH:NH$_4$OH, 90:10:1, R$_f$ 0.2) to provide the title compound (60 mg, 99% yield). $^1$H NMR (MeOH-d$_4$, 300 MHz) δ 2.57 (dd, J=12.6, 4.1 Hz, 1H), 2.75 (dd, J=12.5, 6.4 Hz, 1H), 3.10-3.30 (m, 3H), 3.60 (dd J=7.8, 3.4 Hz, 1H), 3.70 (s, 1H), 3.96 (t, J=7.8 Hz, 1H) 4.70 (dd, J=6.1, 3.3 Hz, 1H), 6.94 (dd, J=2.7, 1.7 Hz, 1H), 7.72 (d, J=2.7 Hz, 1H), 7.90 (d, J=1.7 Hz, 1H); MS (DCI/NH$_3$) m/z 200 (M+H)$^+$.

Example 68D

(1S,5R)-6-(5-ethynyl-3-pyridinyl)-3,6-diazabicyclo[3.2.0]heptane fumarate

The product of Example 68C (60 mg, 0.30 mmol) was treated with fumaric acid according to the procedure of Example 46C. The title compound was obtained as a solid (86 mg, 92% yield). $^1$H NMR (MeOH-d$_4$, 300 MHz) δ 3.16 (dd, J=12.6, 3.4 Hz, 1H), 3.35-3.40 (m, 3H), 3.45 (m, 1H), 3.70-3.85 (m, 3H), 4.05 (t, J=7.8 Hz, 1H), 4.96 (dd, J=6.4, 3.3 Hz, 1H), 6.70 (s, 2H), 7.10 (dd, J=2.3, 1.7 Hz, 1H), 7.85 (d, J=2.7 Hz, 1H), 8.00 (d, J=1.7 Hz, 1H); MS (DCI/NH$_3$) m/z 200 (M+H)$^+$. Anal. calculated for C$_{12}$H$_{13}$N$_3$.1.20C$_4$H$_4$O$_4$.0.8H$_2$O: C, 57.17; H, 5.54; N, 11.91. Found: C, 57.69; H, 5.06; N, 11.03.

Example 69

(1S,5R)-6-(5-vinyl-3-pyridinyl)-3,6-diazabicyclo[3.2.0]heptane fumarate

Example 69A tert-butyl (1R,5R)-6-(5-bromo-3-pyridinyl)-3,6-diazabicyclo[3.2.0]heptane-3-carboxylate The product of Example 71B (510 mg, 2.0 mmol) was treated with di-tert-butyl dicarbonate (660 mg, 3.0 mmol) and triethylamine (404 mg, 4 mmol) in CH$_2$Cl$_2$ (20 mL) at room temperature and allowed to stir for 10 hours. The mixture was concentrated and the residue was purified by chromatography (SiO$_2$, EtOAc:hexane, 50:50, R$_f$ 0.5) to provide the title compound (700 mg, 98% yield). $^1$H NMR (MeOH-d$_4$, 300 MHz) δ 1.40 (brs, 9H), 3.14 (dd, J=12.9, 4.0 Hz, 1H), 3.20-3.35 (m, 2H), 3.65 (m, 1H), 3.85-4.05 (m, 3H), 4.74 (dd, J=5.4, 3.7 Hz, 1H), 7.07 (t, J=2.0 Hz, 1H), 7.68 (d. J=2.7 Hz, 1H), 7.90 (d, J=1.7 Hz, 1H); MS (DCI/NH$_3$) m/z 356 (M+2+H)$^+$, 354 (M+H)$^+$.

Example 69B tert-butyl (1R,5R)-6-(5-vinyl-3-pyridinyl)-3,6-diazabicyclo[3.2.0]heptane-3-carboxylate The product of Example 69A (600 mg, 1.7 mmol) was treated with tributylvinylstannane (1.1 g, 3.4 mmol) and Pd(PPh$_3$)$_4$ (79 mg, 0.068 mmol) in toluene (20 mL) and heated at 100° C. for 10 hours. The mixture was concentrated and the residue was purified by chromatography (SiO$_2$, EtOAc:hexane, 50:50, R$_f$ 0.45) to provide the title compound (280 mg, 55% yield). ¹H NMR (MeOH-$d_4$, 300 MHz) δ 1.40 (brs, 9H), 3.16 (dd, J=12.6, 3.8 Hz, 1H), 3.20-3.35 (m, 2H), 3.65 (m, 1H), 3.85-4.05 (m, 3H), 4.70 (dd, J=5.8, 4.1 Hz, 1H), 5.42 (d, J=10.8 Hz, 1H), 5.90 (d, J=17.6 Hz, 1H), 6.70 (dd, J=17.7, 10.9 Hz, 1H), 6.95 (t, J=2.0 hz, 1H), 7.65 (d, J=2.7 Hz, 1H), 7.92 (d, J=1.8 Hz, 1H); MS (DCI/NH$_3$) m/z 302 (M+H)⁺.

Example 69C (1S,5R)-6-(5-vinyl-3-pyridinyl)-3,6-diazabicyclo[3.2.0]heptane

The product of Example 69B (140 mg, 0.46 mmol) was treated with trifluoroacetic acid (2 mL) in CH$_2$Cl$_2$ (2 mL) at room temperature. After stirring for one hour, the mixture was concentrated and the residue was purified by chromatography (SiO$_2$, CH$_2$Cl$_2$:MeOH:NH$_4$OH, 90:10:1, R$_f$ 0.2) to provide the title compound (80 mg, 86% yield). ¹H NMR (MeOH-$d_4$, 300 MHz) δ 2.57 (dd, J=12.8, 3.7 Hz, 1H), 2.75 (dd, J=12.2, 6.1 Hz, 1H), 3.10-3.30 (m, 3H), 3.65 (dd, J=7.8, 3.4 Hz, 1H), 3.95 (t, J=8.1 Hz, 1H), 4.70 (m, 1H), 5.40 (d, J=11.5 Hz, 1H), 5.90 (d, J=17.6 Hz, 6.70 (dd, J=17.6, 11.2 Hz, 1H), 6.95 (t, J=2.4 Hz, 1H), 7.65 (d, J=2.7 Hz, 1H), 7.90 (d, J=1.7 Hz, 1H); MS (DCI/NH$_3$) m/z 202 (M+H)⁺.

Example 69D (1S,5R)-6-(5-vinyl-3-pyridinyl)-3,6-diazabicyclo[3.2.01]heptane fumarate The product of Example 69C (80 mg, 0.40 mmol) was treated with fumaric acid according to the procedure of Example 46C. The title compound was obtained as a solid (62 mg, 50% yield). ¹H NMR (MeOH-$d_4$, 300 MHz) δ 3.20 (dd, J=12.6, 3.4 Hz, 1H), 3.35-3.40 (m, 2H), 3.45 (m, 1H), 3.70-3.85 (m, 3H), 4.05 (t, J=7.8 Hz, 1H), 4.96 (did, J=6.1, 3.4 Hz, 1H), 5.40 (d, J=10.8 Hz, 1H), 5.90 ((, J=17.6 Hz, 1H), 6.70 (s, 1H), 6.76 (dd, J=17.9, 11.2 Hz, 1H), 7.10 (t, J=2.4 Hz, 1H), 7.75 (d, J=2.7 Hz, 1H), 8.00 (d, J=1.7 Hz, 1H); MS (DCI/NH$_3$) m/z 202 (M+H)⁺. Anal. calculated for C$_{10}$H$_{12}$BrN$_3$·1.60C$_4$H$_4$O$_4$·1.30H$_2$O: C, 42.52; H, 4.57. Found: C, 42.16; H, 4.60.

Example 70

5-[(1S,5R)-3,6-diazabicyclo[3.2.01]hept-6-yl]nicotinonitrile fumarate

Example 70A benzyl (1R,5R)-6-(5-cyano-3-pyridinyl)-3,6-diazabicyclo[3.2.0]heptane-3-carboxylate The product of Example 54D (930 mg, 4 mmol) and 3-bromo-5-cyano-pyridine were processed according to the procedure of Example 1E. The crude product was purified by chromatography (SiO$_2$, EtOAc:hexane, 50:50, R$_f$ 0.2) to provide the title compound (810 mg, 61% yield). ¹H NMR (MeOH-$d_4$, 300 MHz) δ 3.20 (dd, J=12.9, 4.1 Hz, 1H), 3.30-3.40 (m, 2H), 3.65 (dd, J=8.2, 3.4 Hz, 1H), 3.96-4.10 (m, 3H), 4.74 (dd, J=6.1, 4.0 Hz, 1H), 5.10 (m, 2H), 7.15 (d, J=2.7, 1.7 Hz, 1H), 7.25 (m, 3H), 7.35 (m, 2H), 7.96 (d, J=2.7 Hz, 1H), 8.15 (d, J=1.7 Hz, 1H); MS (DCI/NH$_3$) m/z 335 (M+H)⁺.

Example 70B tert-butyl (1R,5R)-6-(5-cyano-3-pyridinyl)-3,6-diazabicyclo[3.2.0]heptane-3-carboxylate A solution of the product from Example 70A (800 mg, 2.40 mmol) in ethanol (40 mL) was combined with 10% palladium on carbon (400 mg) and the suspension was stirred under H$_2$ (1 atm) at ambient temperature for 2 hours. The mixture was treated with di-tert-butyl dicarbonate (660 mg, 3 mmol) and stirred for an additional 6 hours. The mixture was filtered and the filtrate was concentrated. The residue was purified by chromatography (SiO$_2$, CH$_2$Cl$_2$:MeOH, 95:5, R$_f$ 0.6) to provide the title compound (300 mg, 41% yield). ¹H NMR (MeOH-$d_4$, 300 MHz) δ 1.40 (brs, 9H), 3.20 (dd, J=12.9, 4.1 Hz, 1H), 3.30-3.40 (m, 2H), 3.68 (m, 1H), 3.85-4.10 (m, 3H), 4.74 (dd, J=6.1, 4.0 Hz, 1H), 7.15 (dd, J=2.7, 1.7 Hz, 1H), 7.96 (d, J=2.7 Hz, 1H), 8.15 (d, J=1.7 Hz, 1H); MS (DCI/NH$_3$) m/z 301 (M+H)⁺.

Example 70C

5-[(1S,5R)-3,6-diazabicyclo[3.2.01]hept-6-yl]nicotinonitrile

The product of Example 70B (300 mg, 1.0 mmol) was treated with trifluoroacetic acid according to the procedure of Example 46B. The crude material was purified by chromatography (SiO$_2$, CH$_2$Cl$_2$:MeOH:NH$_4$OH, 90:10:1. R$_f$ 0.2) to provide the title compound (110 mg, 55% yield). ¹H NMR (MeOH-$d_4$, 300 MHz) δ 2.58 (dd, J=12.9, 3.0 Hz, 1H), 2.76 (dd, J=12.2, 6.1 Hz, 1H), 3.15-3.30 (m, 3H), 3.65 (dd, J=8.2, 3.8 Hz, 1H), 4.00 (t, J=7.8 Hz, 1H), 4.75 (dd, J=5.7, 3.4 Hz, 1H), 7.24 (m, 1H), 7.83 (d, J=2.3 Hz, 1H), 8.10 (d, J=1.7 Hz, 1H); MS (DCI/NH$_{13}$) m/z 201 (M+H)⁺. [α]$_D^{20}$: 20.6° (c, 0.335, MeOH).

Example 70D

5-[(1S,5R)-3,6-diazabicyclo[3.2.01]hept-6-yl]nicotinonitrile fumarate

The product of Example 70C (100 mg, 0.50 mmol) was treated with fumaric acid according to the procedure of Example 46C. The title compound was obtained as a solid (140 mg, 90% yield). ¹H NMR (MeOH-$d_4$, 300 MHz) δ 3.20 (dd, J=12.7, 3.7 Hz, 1H), 3.35-3.40 (m, 2H), 3.50 (m, 1H), 3.70-3.85 (m, 3H), 4.10 (t, J=8.1 Hz, 1H), 5.00 (dd, J=6.5, 3.8 Hz, 1H), 6.70 (s, 1H), 7.36 (d, J=2.7, 1.7 Hz, 1H), 8.10 (d, J=3.0 Hz, 1H), 8.26 (d, J=1.4 Hz, 1H); MS (DCI/NH$_3$) m/z 201 (M+H)⁺. Anal. calculated for C$_{11}$H$_2$N$_4$·2.00C$_4$H$_4$O$_4$·1.20H$_2$O: C, 50.27; H, 4.97. Found: C, 49.83; H, 4.30.

Example 71

(1S,5R)-6-(5-bromo-3-pyridinyl)-3,6-diazabicyclo[3.2.0]heptane

Example 71A benzyl (1R,5R)-6-(5-bromo-3-pyridinyl)-3,6-diazabicyclo[3.2.0]heptane-3-carboxylate The product of Example 54D (920 mg, 4 mmol) and 3,5-dibromopyridine were processed according to the procedure described in Example 1E. The crude product was purified by chromatography (SiO$_2$, EtOAc:hexane, 50:50, R$_f$ 0.4) to provide the title compound (1.03 g, 66% yield). ¹H NMR (MeOH-d₄, 300 MHz) δ 3.20 (dd, J=12.9, 4.1 Hz, 1H), 3.30-3.40 (m, 2H), 3.65 (dd, J=7.8, 3.7 Hz, 1H), 3.92-4.10 (m, 3H), 4.74 (dd, J=6.1, 4.0 Hz, 1H), 5.10 (m, 2H), 7.05 t, J=2.1 Hz, 1H), 7.25 (m, 3H), 7.35 (m, 2H), 7.68 (d, J=2.4 Hz, 1H), 7.90 (d, J=1.3 Hz, 1H); MS (DCI/NH₃) m/z 390 (M+2+H)⁺, 388 (M+H)⁺.

Example 71B (1S,5R)-6-(5-bromo-3-pyridinyl)-3,6-diazabicyclo[3.2.0]heptane

The product of Example 71A (1.00 g, 2.58 mmol) was treated with trifluoroacetic acid according to the procedure described in Example 46B. The crude material was purified by chromatography (SiO₂, CH₂Cl₂:MeOH:NH₃.H₂O, 90:10:1, R_f, 0.2) to provide the title compound (0.58 g, 89% yield): ¹H NMR (MeOH-d₄ 300 MHz) δ 3.18 (dd, J=12.5, 3.4 Hz, 1H), 3.30 (m, 2H), 3.50 (m, H), 3.75 (m, 2H), 4.09 (m, 1H), 4.68 (dd, J=6.1, 3.4 Hz, 1H), 7.24 (m, 1H), 7.83 (d, J=2.4 Hz, 1H), 8.04 (d, J=2.0 Hz, 1H); MS (DCI/NH₃) m/z 256 (M+2+H)⁺, 254 (M+H)⁺.

Example 71C (1S,5R)-6-(5-bromo-3-pyridinyl)-3,6-diazabicyclo[3.2.0]heptane fumarate The product of Example 71B (75 mg, 0.30 mmol) was treated with fumaric acid according to the procedure of Example 46C. The title compound was obtained as a solid (85 mg, 78% yield). ¹H NMR (MeOH-d₄, 300 MHz) δ 3.20 (dd, J=12.7, 3.7 Hz, 1H), 3.35-3.40 (m, 2H), 3.45 (m, 1H), 3.70-3.82 (m, 31-1), 4.05 (t, J=8.1 Hz, 1H), 4.96 (dd, J=6.6, 3.7 Hz, 1H), 6.70 (s, 1H), 7.22 (m, 1H), 7.84 (s, 1H), 8.04 (s, 1H); MS (DCI/NH₃) m/z 256 (M+2+H)⁺, 254 (M+H)⁺. Anal. calculated for $C_{10}H_{12}BrN_3 \cdot 2.45C_4H_4O_4 \cdot 1.00H_2O$: C, 42.46; H, 4.35; N, 7.50 Found: C, 42.16; H, 4.30; N, 7.74.

Example 72

(1S,5R)-6-(6-bromo-5-vinyl-3-pyridinyl)-3,6-diazabicyclo[3.2.0]heptane fumarate

Example 72A tert-butyl (1R,5R)-6-(6-bromo-5-vinyl-3-pyridinyl)-3,6-diazabicyclo[3.2.0]heptane-3-carboxylate The product of Example 69B (130 mg, 0.43 mmol) in acetonitrile (10 mL) at −20° C. was treated with N-bromosuccinimide (73 mg, 0.41 mmol) in acetonitrile precooled to −10 to −20° C. The reaction mixture was quenched with water (5 mL) and diluted with ethyl acetate (50 mL). The combined organic phases were washed with brine (2×10 mL), concentrated and the residue was purified by chromatography (SiO₂, EtOAc:hexane, 30:70:, R_f 0.60) to provide the title compound (100 mg, 61% yield). ¹H NMR (MeOH-d₄, 300 MHz) δ 1.40 (brs, 9H), 3.16 (dd, J=12.6, 3.8 Hz, 1H), 3.20-3.35 (m, 2H), 3.65 (m, 1H), 3.85-4.05 (m, 3H), 4.70 (m, 1H), 5.42 (d, J=10.8 Hz, 1H), 5.90 (d, J=17.6 Hz, 1H), 6.90 (dd, J=17.7, 10.9 Hz, 1H), 7.05 (d, J=3.1 Hz, 1H), 7.48 (d, J=3.0 Hz, 1H); MS (DCI/NH₃) m/z 382 (M+2+H)⁺, 380 (M+H)⁺.

Example 72B (1S,5R)-6-(6-bromo-5-vinyl-3-pyridinyl)-3,6-diazabicyclo[3.2.0]heptane The product of Example 72A (100 mg, 0.26 mmol) was treated with trifluoroacetic acid according to the procedure described in Example 69C. The crude material was purified by chromatography (SiO₂, CH₂Cl₂: MeOH:NH₄OH, 90:10:1, R_f 0.4) to provide the title compound (70 mg, 96% yield). ¹H NMR (MeOH-d₄, 300 MHz) δ 2.57 (dd, J=12.6, 4.1 Hz, 1H), 2.75 (dd, J=12.5, 6.4 Hz, 1H), 3.10-3.30 (m, 3H), 3.70 (dd, J=7.8, 3.4 Hz, 1H), 3.90 (t, J=7.8 Hz, 1H), 4.70 (dd, J=6.1, 3.3 Hz, 1H), 5.45 (d, J=11.9 Hz, 1H), 5.90 (d, J=17.3 Hz, 6.95 (dd, J=17.6, 11.2 Hz, 1H), 7.00 (d, J=3.0 Hz, 1H), 7.46 (d, J=3.0 Hz, 1H); MS (DCI/NH₃) m/z 282 (M+2+H)⁺, 280 (M+H)⁺.

Example 72C (1S,5R)-6-(6-bromo-5-vinyl-3-pyridinyl)-3,6-diazabicyclo[3.2.0]heptane fumarate The product of Example 72B (70 mg, 0.25 mmol) was treated with fumaric acid according to the procedure described in Example 46C. The title compound was obtained as a solid (85 mg, 87% yield). ¹H NMR (MeOH-d₄, 300 MHz) δ 3.16 (dd, J=12.6, 3.4 Hz, 1H), 3.35-3.40 (m, 2H), 3.45 (m, 1H), 3.70-3.85 (m, 3H), 4.05 (t, J=7.8 Hz, 1H), 4.96 (dd, J=6.1, 3.4 Hz, 1H), 5.50 (d, J=11.9 Hz, 1H), 5.90 d, J=17.6 Hz, 1H), 6.70 (s, 1H), 6.96 (dd, J=17.9, 10.9 Hz, 1H), 7.10 (t, J=2.4 Hz, 1H), 7.15 (d, J=3.1 Hz, 1H), 7.60 (d, J=3.1 Hz, 1H); MS (DCI/NH₃) m/z 282 (M+2+H)⁺, 282 (M+H)⁺. Anal. calculated for $C_{10}H_{12}BrN_3 \cdot 1.00C_4H_4O_4$: C, 8.50; H, 4.58. Found: C, 48.15; H, 4.14.

Example 73

(3aR,6aR)-1-(6-chloro-3-pyridinyl)octahydropyrrolo[3,4-b]pyrrole fumarate

Example 73A tert-butyl (3aR,6aR)-1-[(R)-1-phenylethyl]hexahydropyrrolo[3,4-b]pyrrole-5(1H)-carboxylate The product of Example 14D (3.53 g, 16.3 mmol) in tetrahydrofuran (50 mL) and water (10 mL) was treated with di-tert-butyl dicarbonate (3.60 g, 16.3 mmol), The mixture was stirred for 15 minutes and then diluted with diethyl ether (30 mL). The organic layer was washed with water (10 mL), dried over Na₂SO₄, filtered and the filtrate concentrated under reduced pressure. The residue was purified via chromatography (SiO₂, 50% ethyl acetate-hexanes) to provide the title compound (4.70 g, 14.9 mmol 91% yield). MS (DCI/NH₃) m/z 317 (M+H)⁺.

Example 73B tert-butyl (3aR,6aR)-hexahydropyrrolo[3,4-b]pyrrole-5(1H)-carboxylate The product of Example 73A (4.70 g, 14.9 mmol) and 20% Pd(OH)₂/C (wet, 1.01 g) in CH₃OH (50 mL) were stirred at 50° C. under 60 psi of H₂. When H₂ absorption ceased, the reaction mixture was allowed to cool to ambient temperature, filtered and the filtrate was concentrated under reduced pressure. The residue was purified via chromatography (SiO$_2$, 9:1:0.1 CH$_2$Cl$_2$:CH$_3$OH:NH$_4$OH) to provide the title compound (2.19 g, 10.3 mmol, 69% yield). MS (DCI/NH$_3$) m/z 213 (M+H)$^+$.

Example 73C tert-butyl (3aR,6aR)-1-(6-chloro-3-pyridinyl)hexahydropyrrolo[3,4-b]pyrrole-5(1H)-carboxylate The product of Example 73B (0.510 g, 2.40 mmol), Pd$_2$(dba)$_3$ (22 mg, 0.0240 mmol), BINAP (45 mg, 0.0720 mmol), 3-bromo-5-chloropyridine (0.510 g, 2.60 mmol), and sodium tert-butoxide (0.460 g, 4.80 mmol) were processed according to the procedure described in Example 56A to provide the title compound (0.450 g, 1.39 mmol, 58% yield). MS (DCI/NH$_3$) m/z 324 (M+H)$^+$.

Example 73D (3aR,6aR)-1-(6-chloro-3-pyridinyl)octahydropyrrolo[3,4-b]pyrrole

The product of Example 73C (0.450 g, 1.39 mmol) and trifluoroacetic acid were processed according to the procedure described in Example 64C to provide the title compound (0.300 g, 1.34 mmol, 96% yield). MS (DCI/NH$_3$) m/z 224 (M+H)$^+$.

Example 73E (3aR,6aR)-1-(6-chloro-3-pyridinyl)octahydropyrrolo[3,4-b]pyrrole fumarate The product of Example 73D (0.300 g, 1.34 mmol) and fumaric acid (0.156 g, 1.34 mmol) were processed according to the procedure of Example 66D to provide the title compound (0.380 g, 1.12 mmol, 83% yield). $^1$H NMR (CH$_3$OH-d$_4$, 300 MHz) δ 2.00 (m, 1H), 2.30 (m, 1H), 3.30 (m, 4H), 3.47 (m, 2H), 3.66 (m, 1H), 4.38 (m, 1H), 6.68 (s, 2H), 7.13 (dd, J=8.5, 3.1 Hz, 1H), 7.28 (d, J=8.5 Hz, 1H), 7.73 (d, J=3.1 Hz, 1H); MS (DCI/NH$_3$) m/z 224 (M+H−C$_4$H$_4$O$_4$)$^+$: Anal. calculated for C$_{11}$H$_{14}$ClN$_3$.C$_4$H$_4$O$_4$: C, 53.02; H, 5.34; N, 12.37. Found: C, 52.84; H, 5.43; N, 12.22.

Example 74

5-[(1R,5S)-3,6-diazabicyclo[3.2.0]hept-6-yl]nicotinonitrile bis(4-methylbenzenesulfonate)

Example 74A benzyl (1S,5S)-6-(5-cyano-3-pyridinyl)-3,6-diazabicyclo[3.2.0]heptane-3-carboxylate The product of Example 52D (830 mg, 3.58 mmol) in toluene (20 mL) was treated with Pd$_2$(dba)$_3$ (71.0 mg, 0.072 mmol), BINAP (134 mg, 0.214 mmol), Cs$_2$CO$_3$ (2.32 g, 7.16 mmol) and 3-bromo-5-cyanopyridine (0.98 g, 5.37 mmol). The mixture was heated at 100° C. under N$_2$ for 10 hours and then allowed to cool to room temperature and diluted with ethyl acetate (100 mL). The brown solution was washed with water (2×10 mL) and concentrated under reduced pressure. The residue was purified by chromatography (SiO$_2$, EtOAc:hexane, 50:50. R$_f$ 0.3) to provide the title compound (770 mg, 64% yield). $^1$H NMR (MeOH-d$_4$, 300 MHz) δ 3.2 (dd, J=12.9, 4 Hz, 1H), 3.30-3.4 (m, 2H), 3.6 (dd, J=8.2, 3 Hz, 1H), 3.96-4.10 (m, 3H), 4.74 (dd, J=6.1, 4.0 Hz, 1H), 5.10 (m, 2H), 7.15 (dd, J=2.7, 1.7 Hz, 1H), 7.25 (m, 3H), 7.35 (m, 2H), 7.96 (d J=2.7 Hz, 1H), 8.15 (d, J=1.7 Hz, 1H); MS (DCI/NH$_3$) m/z 335 (M+H)$^+$.

Example 74B

5-[(1R,5S)-3,6-diazabicyclo[3.2.0]hept-6-yl]nicotinonitrile

The product of Example 74A (600 mg, 1.8 mmol) was treated with trifluoroacetic acid (5 mL) at 65-70° C. for 1.5 hours. The mixture was allowed to cool to room temperature and concentrated under reduced pressure. The residue was basified to pH ~10 with 10% NaOH and stirred at room temperature for 10 minutes. The mixture was extracted with CHCl$_3$ (3×50 mL). The combined organic phases were washed with brine (2×10 mL) and concentrated under reduced pressure. The residue was purified by chromatography (SiO$_2$, CH$_2$C$_2$:MeOH:NH$_4$OH, 90:10:1, R$_f$ 0.2) to provide the title compound (290 mg, 80% yield). $^1$H NMR (MeOH-d$_4$, 300 MHz) δ 2.55 (dd, J=12.9, 3.0 Hz, 1H), 2.74 (dd, J=12.2, 6.1 Hz, 1H), 3.15-3.30 (m, 3H), 3.65 (dd, J=8.2, 3.8 Hz, 1H), 4.00 (t, J=7.8 Hz, 1H), 4.75 (dd, J=5.4, 3.7 Hz, 1H), 7.24 (m, 1H), 7.83 (d, J=2.3 Hz, 1H), 8.10 (d, J=1.7 Hz, 1H); MS (DCI/NH$_3$) m/z 201 (M+H)$^+$. α$_{[D]}^{20}$: −20.0° (c, 0.520. MeOH).

Example 74C

5-[(1R,5S)-3,6-diazabicyclo[3.2.0]hept-6-yl]nicotinonitrile bis(4-methylbenzenesulfonate)

The product of Example 74B (250 mg, 1.25 mmol) was treated with 4-methylbenzenesulfonic acid monohydrate (450 mg, 2.5 mmol) in a mixture of 2-propanol (10 mL) and ethyl acetate (10 mL). The mixture was stirred at room temperature overnight. The precipitate was isolated by filtration and dried under reduced pressure at 40-50° C. to provide the title compound (565 mg, 83% yield), $^1$H NMR (MeOH-d$_4$, 300 MHz) δ 2.40 (s, 6H), 3.20 (dd, J=12.6, 3.7 Hz, 1H), 3.35 (m, 1H), 3.55 (m, 1H), 3.72 (d, J=12.5 Hz, 1H), 3.85 (d, J=12.9 Hz, 1H), 3.90 (dd, J=8.5, 3.4 Hz, 1H), 4.16 (t, J=8.2 Hz, 1H), 5.10 (dd, J=6.5, 3.8 Hz, 1H), 7.22 (d, J=8.1 Hz, 4H), 7.68 (d, J=8.1 Hz, 1H), 7.74 (dd, J=2.8, 1.6 Hz, 1H), 8.24 (d, J=2.7 Hz, 1H), 8.44 (d, J=1.4 Hz, 1H); MS (DCI/NH$_3$) m/z 201 (M+H)$^+$. Anal. calculated for C$_{11}$H$_{12}$N$_4$.2.00TsOH: C, 55.13; H, 5.18; N, 10.29. Found: C, 54.90; H, 5.12; N, 9.96.

Example 74D

5-[(1R,5S)-3,6-diazabicyclo[3.2.0]hept-6-yl]nicotinonitrile (D)-tartarate

The product of Example 74B (100 mg, 0.5 mmol) in methanol (5 mL) was treated with (D)-tartaric acid (75 mg, 0.5 mmol) and the mixture was stirred at room temperature overnight. The precipitate was isolated by filtration and dried under reduced pressure at 40-50° C. to provide the title compound (137 mg, 78% yield). mp 205-210° C.: $^1$H NMR (DMSO-d$_6$, 300 MHz) δ 2.74 (dd, J=12.9, 3.4 Hz, 1H), 2.86 (dd, J=12.2, 6.4 Hz, 1H), 3.20 (m, 1H), 3.30 (d, J=12.2 Hz, 1H), 3.45 (d, J=12.5 Hz, 1H), 3.65 (dd, J=8.2, 3.7 Hz, 1H), 3.96 (t, J=7.8 Hz, 1H), 4.80 (dd, J=6.4, 3.7 Hz, 1H), 7.34 (dd, J=2.8, 2.0 Hz, 1H), 8.08 (d, J=2.7 Hz, 1H), 8.24 (d, J=1.7 Hz, 1H); MS (DCI/NH$_3$) m/z 201(M+H)$^+$. Anal. calculated for C$_{11}$H$_{12}$N$_4$.0.5C$_4$H$_6$O$_6$.1.00H$_2$O: C, 53.24; H, 5.84; N, 19.10. Found: C, 53.76; H, 5.80; N, 17.81.

Example 75

(3aR,6aR)-1-(3-pyridinyl)octahydropyrrolo[4-b]pyrrole fumarate

Example 75A tert-butyl (3aR,6aR)-1-(3-pyridinyl)hexahydropyrrolo[3,4-b]pyrrole-5(1H)-carboxylate The product of Example 73B (0.500 g, 2.36 mmol), $Pd_2$(dba)$_3$ (22 mg, 0.0236 mmol) BINAP (45 mg, 0.0720 mmol), 3-bromopyridine (0.250 mL, 2.59 mmol), and sodium tert-butoxide (0.45 g 4.70 mmol) were processed according to the procedure described in Example 56A to provide the title compound (0.380 g, 1.31 mmol, 56% yield). MS (DCI/NH$_3$) m/z 290 (M+H)$^+$.

Example 75B

(3aR,6aR)-1-(3-pyridinyl)octahydropyrrolo[3,4-b]pyrrole

The product of Example 75A (0.380 g, 1.31 mmol) was processed according to the procedure described in Example 64C to provide the title compound (0.240 g, 1.28 mmol, 97% yield). MS (DCI/NH$_3$) m/z 190 (M+H)$^+$.

Example 75C

(3aR,6aR)-1-(3-pyridinyl)octahydropyrrolo[3,4-b]pyrrole fumarate

The product of Example 75B (0.240 g, 1.28 mmol) and fumaric acid (0.147 g, 1.28 mmol) were processed according to the procedure described in Example 66D to provide the title compound (0.130 g, 0.385 mmol, 30% yield). $^1$H NMR (CH$_3$OH-d$_4$, 300 MHz) δ 2.01 (m, 1H), 2.32 (m, 1H), 3.30 (m, 4H), 3.50 (dt, J=12.5, 5.7 Hz, 2H), 3.71 (dt, J=9.5, 7.1 Hz, 1H), 4.40 (m, 1H), 6.68 (s, 2H), 7.12 (ddd, J=8.5, 2.7, 1.0 Hz, 1H), 7.29 (ddd, J=8.5, 4.7, 0.7 Hz, 1H), 7.94 (m, 2H); MS (DCI/NH$_3$) m/z 190 (M+H–C$_4$H$_4$O$_4$)$^+$; Anal. calculated for C$_{11}$H$_{15}$N$_3$.C$_4$H$_4$O$_4$.0.5CH$_3$OH.H$_2$O: C, 56.44; H, 6.57; N, 12.74. Found: C, 56.71; H, 6.42; N, 12.46.

Example 76

2-bromo-5-[(1R,5S)-3,6-diazabicyclo[3.2.0]hept-6-yl]nicotinonitrile fumarate

Example 76A benzyl (1S,5S)-6-(5-cyano-3-pyridinyl)-3,6-diazabicyclo[3.2.0]heptane-3-carboxylate The product of Example 52D (0.800 g, 3.40 mmol) in toluene (34 mL) was treated with 3-cyano-5-bromopyridine (0.690 g, 3.8 mmol), Pd$_2$(dba)$_3$ (0.0.64 g, 0.10 mmol), BINAP (0.086 g, 0.010 mmol) and Cs$_2$CO$_3$ (0.221 g, 6.80 mmol) and the reaction was heated at 80° C. for 12 hours. The mixture was allowed to cool to room temperature and then concentrated under reduced pressure. The residue was purified by chromatography (SiO$_2$, 5% MeOH/CH$_2$Cl$_2$) to provide the title compound as a yellow oil (47%, 0.530 g). MS (DCI/NH$_3$) m/z 335 (M+H)$^+$.

Example 76B tert-butyl (1S,5S)-6-(5-cyano-3-pyridinyl)-3,6-diazabicyclo[3.2.0]heptane-3-carboxylate The product of Example 76A (0.312 g) in methanol (30 mL) was treated with 10% Pd/C (0.100 g) and the mixture was stirred at room temperature under 1 atmosphere of H$_2$ for 1 hour. The reaction was filtered and concentrated under reduced pressure. The residue was dissolved in methylene chloride (20 mL) and treated with di-tert-butyl dicarbonate (0.387 g, 1.80 mmol) and triethylamine (0.152 g, 1.50 mmol). The reaction was stirred at room temperature overnight. The material was concentrated under reduced pressure. The residue was purified by chromatography (SiO$_2$, ethyl acetate:hexane 1:1) to provide the title compound as a colorless oil (59%, 0.265 g). MS (DCI/NH$_3$) m/z 301 (M+H)$^+$.

Example 76C tert-butyl (1S,5S)-6-(6-bromo-5-cyano-3-pyridinyl)-3,6-diazabicyclo[3.2.0]heptane-3-carboxylate The product of Example 76B (0.263 g, 0.90 mmol) in acetonitrile (10 mL) was treated with N-bromosuccinimide (0.149 g, 0.80 mmol) at –20° C. After stirring for 10 minutes, the reaction mixture was quenched with water (5.0 mL) and extracted with methylene chloride (100 mL). The organic phase was dried (MgSO$_4$), filtered and the filtrate concentrated under reduced pressure. The residue was purified by chromatography (SiO$_2$, ethyl acetate:hexane 1:1) to provide the title compound as a white solid (29%, 0.098 g). MS (DCI/NH$_3$) m/z 379 (M+H)$^+$.

Example 76D

2-bromo-5-[(1R,5S)-3,6-diazabicyclo[3.2.0]hept-6-yl]nicotinonitrile fumarate The product of Example 76C (0.098 g, 0.30 mmol) in dichloromethane (5.0 mL) was treated with trifluoroacetic acid (5.0 mL). After stirring at room temperature for 1 hour, the reaction mixture was concentrated under reduced pressure. The residue was purified by chromatography (SiO$_2$, 10% methanol/CH$_2$Cl$_2$/1% NH$_4$OH) to provide the title compound as a colorless oil (0.051 g) in 61% yield. The fumarate salt was formed to afford an off white foam. $^1$H NMR (MeOH, 300 MHz) δ 3.17-3.28 (dd, J=3.0, 12.0 Hz, 1H), 3.28-3.38 (m, 2H), 3.43-3.52 (m, 1H), 3.68-3.72 (m, 2H), 4.08 (t, J=9.0 Hz, 1H), 4.93-4.98 (m, 1H), 7.40 (d, J=3.0 Hz, 1H), 7.90 (d, J=3.0 Hz, 1H). MS (DCI/NH$_{13}$) m/z 279 (M+H)$^+$; Anal. Calcd for C$_{19}$H$_{19}$N$_4$O$_8$Br: C, 44.63; H, 3.75; N, 10.96. Found: C, 44.26; H, 3.91; N, 10.68.

Example 77

(3aS,6aS)-1-(6-chloro-3-pyridinyl)octahydropyrrolo[3,4-b]pyrrole fumarate

Example 77A tert-butyl (3aS,6aS)-1-[(1R)-1-phenylethyl]hexahydropyrrolo[3,4-b]pyrrole-5(H)-carboxylate The product of Example 15A (4.33 g, 20.0 mmol) in tetrahydrofuran (60 mL) and water (15 mL) was treated with di-tert-butyl dicarbonate (4.15 g, 19.0 mmol), The reaction mixture was stirred at ambient temperature for 1 hour and then diluted with diethyl ether (50 mL). The organic layer was washed with water (20 mL). The combined aqueous layers were back-extracted with diethyl ether (30 mL), and the combined diethyl ether phases were dried over $Na_2SO_4$, filtered and the filtrate concentrated under reduced pressure. The residue was purified via chromatography ($SiO_2$, 50% ethyl acetate/hexanes) to provide the title compound (4.90 g, 15.5 mmol, 77% yield). MS ($DCI/NH_3$) m/z 317 $(M+H)_4$.

Example 77B tert-butyl (3aS,6aS)-hexahydropyrrolo[3,4-b]pyrrole-5(1H)-carboxylate The product of Example 77A (4.90 g, 15.5 mmol) was processed according to the procedure described in Example 73B to provide the title compound (3.24 g, 15.3 mmol, 99% yield). MS ($DCI/NH_3$) m/z 213 $(M+H)^+$.

Example 77C tert-butyl (3aS,6aS)-1-(6-chloro-3-pyridinyl)hexahydropyrrolo[3,4-b]pyrrole-5(1H)-carboxylate The product of Example 77B (0.520 g, 2.45 mmol), $Pd_2(dba)_3$ (22.4 mg, 0.0245 mmol), BINAP (46.0(mg, 0.0735 mmol), 5-bromo-2-chloropyridine (0.520 g, 2.69 mmol), and sodium tert-butoxide (0.470 g, 4.90 mmol) were processed according to the procedure described in Example 56A to provide the title compound (0.390 g, 1.20 mmol, 49% yield). MS ($DCI/NH_3$) m/z 324 $(M+H)^+$.

Example 77D (3aS,6aS)-1-(6-chloro-3-pyridinyl)octahydropyrrolo[3,4-b]pyrrole

The product of Example 77C (0.390 g, 1.20 mmol) and trifluoroacetic acid were processed according to the procedure described in Example 64C to provide the title compound (0.260 g, 1.16 mmol, 97% yield), carried on directly in the next step.

Example 77E (3aS,6aS)-1-(6-chloro-3-pyridinyl)octahydropyrrolo[3,4-b]pyrrole fumarate The product of Example 77D (0.260 g, 1.16 mmol) and fumaric acid (0.135 g, 1.16 mmol) were processed according to the procedure described in Example 66D to provide the title compound (0.310 g, 0.912 mmol, 79% yield). $^1H$ NMR ($CH_3OH$-$d_4$, 500 MHz) δ 2.00 (m, 1H), 2.30 (m, 1H), 3.32 (m, 4H), 3.50 (dt, J=12.5, 5.9 Hz, 2H), 3.67 (dt, J=9.7, 6.3 Hz, 1H), 4.39 (m, 1H), 6.67 (s, 2H), 7.12 (dd, J=8.8, 3.1 Hz, 1H) 7.27 (d, J=8.8 Hz, 1H), 7.73 (d, J=3.1 Hz, 1H); MS (DCI/$NH_3$) m/z 224 $(M+H-C_4H_4O_4)^+$; Anal. calculated for $C_{11}H_{14}ClN_3 \cdot C_4H_4O_4$: C, 53.02; H, 5.34; N, 12.37. Found: C, 52.86; H, 5.31; N, 12.30.

Example 78

(3aS,6aS)-1-(3-pyridinyl)octahydropyrrolo[3,4-b]pyrrole dihydrochloride

Example 78A tert-butyl (3aS,6aS)-1-(3-pyridinyl)hexahydropyrrolo[3,4-b]pyrrole-5(1H)-carboxylate The product of Example 77B (0.560 g, 2.64 mmol), $Pd_2(dba)_3$ (24 mg, 0.0262 mmol), BINAP (49 mg, 0.0787 mmol), 3-bromopyridine (0.28 mL, 2.90 mmol), and sodium tert-butoxide (0.510 g, 5.30 mmol) were processed according to the procedure described in Example 56A to provide the title compound (0.600 g, 2.07 mmol, 79% yield). MS ($DCI/NH_3$) m/z 290 $(M+H)^+$.

Example 78B (3aS,6aS)-1-(3-pyridinyl)octahydropyrrolo[3,4-b]pyrrole

The product of Example 78A (0.600 g, 2.07 mmol) and trifluoroacetic acid were processed according to the procedure described in Example 64C to provide the title compound (0.390 g, 2.06 mmol, 99% yield). MS ($DCI/NH_3$) m/z 190 $(M+H)^+$.

Example 78C (3aS,6aS)-1-(3-pyridinyl)octahydropyrrolo[3,4-b]pyrrole dihydrochloride The product of Example 78B (0.390 g, 2.06 mmol) was processed according to the procedure described in Example 58D to provide the title compound (0.362 g, 1.36 mmol, 66% yield). $^1H$ NMR ($CH_3OH$-$d_4$, 300 MHz) δ 2.11 (m, 1H), 2.35 (m, 1H), 3.40 (m, 3H), 3.55 (m, 2H), 3.65 (dt, J=12.9, 6.1 Hz, 1H), 3.77 (dt, J=10.2, 7.4 Hz, 1H), 4.60 (m, 1H), 7.84 (m, 2H), 8.12 (d, J=5.1 Hz, 1H), 8.17 (d, J=2.4 Hz, 1H); MS (DCI/$NH_3$) m/z 190 $(M+H-2HCl)^+$; Anal. calculated for $C_{11}H_{15}N_3 \cdot 2HCl \cdot 0.25H_2O$: C, 49.54; H, 6.61; N, 15.76. Found: C, 49.46; H, 6.65; N, 15.76.

Example 79

5-[(1R,5R)-3,6-diazabicyclo[3.2.0]hept-3-yl]nicotinonitrile fumarate

Example 79A tert-butyl (1S,5R)-3-(5-cyano-3-pyridinyl)-3,6-diazabicyclo[3.2.0]heptane-6-carboxylate The product of Example 80A (198 mg, 1.0 mmol) and 5-bromo-3-cyanopyridine were processed according to the procedure of Example 1E. The crude product was purified by chromatography ($SiO_2$, hexane: EtOAc, 50:50, $R_f$ 0.3) to provide the title compound (120 mg, 40% yield). $^1H$ NMR (MeOH-$d_4$, 300 MHz) δ 1.48 (s, 9H), 3.00 (dd, J=11.2, 4.4 Hz, 1H), 3.10 (dd, J=10.5, 6.8 Hz, 1H), 3.27 (m, 2H), 3.60 (m, 1H), 3.85 (d, J=10.2 Hz, 1H), 3.97 (d, J=12.2 Hz, in, 1H), 4.10 (m, 1H), 7.55 (m, 1H), 8.20 (d, J=1.7 Hz, 1H), 8.34 (d, J=1.7 Hz, 1H); MS ($DCI/NH_{13}$) m/z 301 $(M+H)^+$.

Example 79B

5-[(1R,5R)-3,6-diazabicyclo[3.2.0]hept-3-yl]nicotinonitrile fumarate

The product of Example 79A (120 mg, 0.40 mmol) in $CH_2C_2$(2 mL) was treated with trifluoroacetic acid (2 mL) at room temperature and allowed to stir for 1 hour. The mixture was concentrated and the residue was neutralized to pH ~9 with 5% NaOH. The mixture was then extracted with $CHCl_3$ (3×50 mL) and the combined organic phases concentrated. The residue was treated with fumaric acid according to the procedure of Example 46C to provide the title compound (84 mg, 67% yield). $^1$H NMR (MeOH-d$_4$, 300 MHz) δ 3.14 (dd, J=10.6, 6.2 Hz, 1H), 3.24 (dd, J=12.8, 5.0 Hz, 1H), 3.55 (m, 1H), 3.75 (dd, J=11.0, 5.0 Hz, 1H), 3.96 (d, J=10.6 Hz, 1H), 4.18 (d, J=12.2 Hz, 1H), 4.28 (dd, J=10.9, 8.4 Hz, 1H), 6.40 (s, 2H), 7.65 dd, J=2.9, 1. Hz, 1H), 8.33 (d, J=1.2 Hz, 1H), 8.45 (d, J=2.8 Hz, 1H); MS (DCI/NH$_3$) m/z 201 (M+H)$^+$. Anal. calculated for C$_{11}$H$_{12}$N$_4$.1.0C$_4$H$_4$O$_4$. 0.5H$_2$O: C, 55.38; H, 5.27; N, 17.22. Found: C, 55.00; H, 5.27; N, 17.00.

Example 80

(1R,5R)-3-(6-chloro-3-pyridinyl)-3,6-diazabicyclo[3.2.0]heptane fumarate

Example 80A tert-butyl (1S,5R)-3,6-diazabicyclo[3.2.0]heptane-6-carboxylate

The product of Example 54D (2.32 g, 10 mol) was treated with di-tert-butyl dicarbonate according to the procedure described in Example of 381, then hydrogenated over palladium on carbon according to the procedure described in Example 38J to provide the title compound (1.52 g, 76% yield). $^1$H NMR (MeOH-d$_4$, 300 MHz) δ 1.46 (s, 9H), 2.47 (dd, J=19.9, 3.7 Hz, 1H), 2.64 (dd J=12.2, 5.7 Hz, 1H), 2.95 (m, 1H), 3.05 d, J=12.2 Hz, 1H), 3.24 (d, J=12.5 Hz, 1H), 3.46 (m, 1H), 3.95 (m, 1H), 4.64 (dd, J=6.1, 3.8 Hz, 1H), MS (DCI/NH$_3$) m/z 216 (M+NH$_4$)$^+$, 199 M+H)$^+$.

Example 80B tert-butyl (1S,5R)-3-(6-chloro-3-pyridinyl)-3,6-diazabicyclo[3.2.0]heptane-6-carboxylate The product of Example 80A (198 mg, 1.0 mmol) and 5-bromo-2-chloropyridine were processed according to the procedure described in Example 1E. The crude product was purified by chromatography (SiO$_2$, hexane: EtOAc, 50:50, R$_f$ 0.3) to provide the title compound (80 mg, 25% yield). $^1$H NMR (MeOH-d$_4$, 300 MHz) δ 1.48 (s, 9H), 2.90 (dd, J=10.6, 4.1 Hz, 1H), 3.00 (dd, J=10.2, 6.4 Hz, 1H), 3.27 (m, 2H), 3.60 (m, 1H), 3.77 (d, J=10.2 Hz, 1H), 3.92 (m, 1H), 4.08 (m, 1H), 7.26 (d, J=1.7 Hz, 2H), 7.85 (t, J=1.8 Hz, 1H); MS (DCI/NH$_3$) m/z 329 M+2+NH$_4$)$^+$, 327 (M+NH$_4$)$^+$.

Example 80C (1R,5R)-3-(6-chloro-3-pyridinyl)-3,6-diazabicyclo[3.2.0]heptane fumarate The product of Example 80B (80 mg, 0.26 mmol) in CH$_2$Cl$_2$ (2 mL) was treated with trifluoroacetic acid (2 mL) at room temperature and allowed to stir for 1 hour. The mixture was concentrated and the residue neutralized to pH ~9 with 5% NaOH. The mixture was extracted with CHCl$_3$ (3×50 mL) and the combined organic phases were concentrated under reduced pressure. The residue was treated with fumaric acid according to the procedure of Example 46C to provide the title compound (26.0 mg, 31% yield). $^1$H NMR (MeOH-d$_4$, 300 MHz) δ 3.05 (dd, J=10.1, 5.1 Hz, 1H), 3.15 (dd, J=12.6, 5.1 Hz, 1H), 3.50 (m, 1H), 3.75 (dd, J=11.2, 3.1 Hz, 1H), 3.90 (d, J=10.5 Hz, 1H), 4.10 (d, J=12.2 Hz, 1H), 4.25 (dd, J=11.2, 8.8 Hz, 1H), 5.05 (dd, J=6.8, 4.8 Hz, 1H), 6.68 (s, 2H), 7.34 (d, J=8.5 Hz, 1H), 7.38 (dd, J=8.9, 3.1 Hz, 1H), 7.96 (d, J=2.7 Hz, 1H); MS (DCI/NH$_3$) m/z 229 (M+2+NH$_4$)$^+$, 227 (M+NH$_4$)$^+$. Anal. calculated for C$_{10}$H$_{12}$ClN$_3$.1.1C$_4$H$_6$O$_6$.0.30H$_2$O: C, 50.46; H, 12.26; N, 19.10. Found: C, 50.25; H, 4.65; N, 11.73.

Example 81

5-((3aR,6aR)-hexahydropyrrolo[3,4-b]pyrrol-1(2H)-yl)nicotinonitrile

Example 81A tert-butyl (3aR,6aR)-1-(5-cyano-3-pyridinyl)hexahydropyrrolo[3,4-b]pyrrole-5(1H)-carboxylate The product of Example 73B (0.570 g, 2.69 mmol), Pd$_2$(dba)$_3$ (25 mg, 0.0269 mmol), BINAP (50 mg, 0.0810 mmol), 3-bromo-5-cyanopyridine (0.540 g, 2.95 mmol), and sodium tert-butoxide (0.520 g, 5.40 mmol) were processed according to the procedure described in Example 56A to provide the title compound (0.400 g, 1.27 mmol, 47% yield). MS (DCI/NH$_3$) m/z 315 (M+H)$^+$.

Example 81B 5-((3aR,6aR)-hexahydropyrrolo[3,4-b]pyrrol-1(2H)-yl)nicotinonitrile The product of Example 81A (0.400 g, 1.27 mmol) and trifluoroacetic acid were processed according to the procedure described in Example 64C to provide the title compound (97 mg, 0.450 mmol, 35% yield) which was carried on directly to the next reaction.

Example 81C 5-((3aR,6aR)-hexahydropyrrolo[3,4-b]pyrrol-1(2H)-yl)nicotinonitrile fumarate The product of Example 81B (97 mg, 0.450 mmol) and fumaric acid (53 mg, 0.450 mmol) were processed according to the procedure described in Example 66D to provide the title compound (110 mg, 0.301 mmol, 67% yield). $^1$H NMR (CH$_3$OH-d$_4$, 300 MHz) δ 2.04 (m, 1H), 2.31 (m, 1H), 3.40 (m, 4H), 3.55 (dt, J=12.5, 5.7 Hz, 2H), 3.70 (dt, J=9.8, 7.1 Hz, 1H), 4.47 (ddd, J=7.8, 7.2, 2.4 Hz, 1H), 6.66 (s, 2H), 7.38 (dd, J=2.7, 1.4 Hz, 1H), 8.20 (m, 2H); MS (DCI/NH$_3$) m/z 215 (M+H−C$_4$H$_4$O$_4$)$^+$; Anal. calculated for C$_{12}$H$_{14}$N$_4$.1.3C$_4$H$_4$O$_4$: C, 56.57; H, 5.30; N, 15.34. Found: C, 56.63; H, 5.32; N, 14.99.

Example 82

(3aS,6aS)-1-(5-hydroxy-3-pyridinyl)octahydropyrrolo[3,4-b]pyrrole dihydrochloride

Example 82A tert-butyl (3aS,6aS)-1-[5-(benzyloxy)-3-pyridinyl]hexahydropyrrolo[3,4-b]pyrrole-5(1H)-carboxylate The product of Example 77B (1.05 g, 4.95 mmol), Pd$_2$(dba)$_3$ (45 mg, 0.0495 mmol), BINAP (92 mg, 0.148 mmol), 3-benzyloxy-5-bromopyridine (1.44 g, 5.40 mmol), and sodium tert-butoxide (0.950 g, 9.89 mmol) were processed according to the procedure described in Example 56A to provide the title compound (1.27 g, 3.21 mmol, 65% yield).

Example 82B tert-butyl (3aS,6aS)-1-(5-hydroxy-3-pyridinyl) hexahydropyrrolo[3,4-b]pyrrole-5(1H)-carboxylate The product of Example 82A (1.27 g, 3.21 mmol) in methanol (25 mL) was treated with ammonium formate (2.00 g, 30.2 mmol) and 10% Pd/C (0.27 g, wet). The mixture was warmed to reflux and allowed to stir for 20 hours. The reaction mixture was then allowed to cool to ambient temperature, filtered through Celite and the filtrate was concentrated under reduced pressure to provide the crude title compound which was taken on directly to the next step without further purification. MS (DCI/NH$_3$) m/z 306 (M+H)$^+$.

Example 82C (3aS,6aS)-1-(5-hydroxy-3-pyridinyl)octahydropyrrolo[3,4-b]pyrrole The product of Example 82B (3.21 mmol) and trifluoroacetic acid was processed according to the procedure described in Example 64C to provide the title compound (0.250 g, 1.22 mmol, 38% yield over two steps). MS (DCI/NH$_3$) m/z 206 (M+H)$^+$.

Example 82D (3aS,6aS)-1-(5-hydroxy-3-pyridinyl)octahydropyrrolo[3,4-b]pyrrole dihydrochloride The product of Example 82C (0.250 g, 1.22 mmol) was processed according to the procedure described in Example 58D to provide the title compound (0.320 g, 0.793 mmol, 65% yield). $^1$H NMR (CH$_3$OH-d$_4$, 300 MHz) δ 2.08 (m, 1H), 2.33 (m, 1H), 3.40 (m, 4H), 3.53 (m, 2H), 3.62 (m, 1H), 3.72 (dt, J=9.5, 6.8 Hz, 1H), 4.55 (ddd, J=7.8, 6.8, 2.4 Hz, 1H), 7.04 (dd, J=2.3, 1.7 Hz, 1H), 7.65 (d, J=1.7 Hz, 1H), 7.73 (d, J=2.3 Hz, 1H); MS (DCI/NH$_3$) m/z 206 (M+H−2HCl)$^+$; Anal. calculated for C$_{11}$H$_{15}$N$_3$O.2.5HCl.2NH$_4$Cl: C, 32.75; H, 6.37; N, 17.36. Found: C, 33.11; H, 6.71; N, 17.77.

Example 83

5-((3aS,6aS)-hexahydropyrrolo[3,4-b]pyrrol-1(2H)-yl)nicotinonitrile fumarate

Example 83A tert-butyl (3aS,6aS)-1-(5-cyano-3-pyridinyl)hexahydropyrrolo[3,4-b]pyrrole-5(1H)-carboxylate The product of Example 77B (1.15 g, 5.42 mmol), Pd$_2$(dba)$_3$ (55 mg, 0.0596 mmol), BINAP (101 mg, 0.160 mmol), 3-bromo-5-cyanopyridine (1.09 g, 5.96 mmol), and sodium tert-butoxide (1.04 g, 10.8 mmol) were processed according to the procedure described in Example 56A to provide the title compound (1.35 g, 4.29 mmol, 79% yield).

Example 83B 5-((3aS,6aS)-hexahydropyrrolo[3,4-b]pyrrol-1(2H)-yl)nicotinonitrile The product of Example 83A (1.35 g, 4.29 mmol) and trifluoroacetic acid were processed according to the procedure described in Example 64C to provide the crude title compound (>100%) which was carried directly to the next step without further purification.

Example 83C 5-((3aS,6aS)-hexahydropyrrolo[3,4-b]pyrrol-1(2H)-yl)nicotinonitrile fumarate The crude product of Example 83B (~4.29 mmol) and fumaric acid (0.501 g, 4.29 mmol) were processed according to the procedure described in Example 66D to provide the title compound (0.510 g, 1.54 mmol, 36% yield over two steps). $^1$H NMR (CH$_3$OH-d$_4$, 300 MHz) δ 2.03 (m, 1H), 2.31 (m, 1H), 3.26 (m, 1H), 3.35 (m, 1H), 3.42 (dd, J=5.7, 4.0 Hz, 1H), 3.46 (m, 2H), 3.52 (dd, J=12.5, 5.7 Hz, 1H), 3.70 (dt, J=9.9, 6.8 Hz, 1H), 4.46 (m, 1H), 6.67 (s, 2H), 7.38 (dd, J=3.1, 1.7 Hz, 1H), 8.21 (d, J=3.1 Hz, 1H), 8.23 (d, J=1.7 Hz, 1H); MS (DCI/NH$_3$) m/z 215 (M+H−C$_4$H$_4$O$_4$)$^+$; Anal. calculated for C$_{12}$H$_{14}$N$_4$.C$_4$H$_4$O$_4$: C, 58.17; H, 5.49; N, 16.96. Found: C, 58.17; H, 5.73; N, 17.32.

Example 84

(1R,5S)-6-(5-ethynyl-3-pyridinyl)-3,6-diazabicyclo[3.2.0]heptane fumarate

Example 84A tert-butyl (1S,5S)-6-{5-[(trimethylsilyl)ethynyl]-3-pyridinyl}-3,6-diazabicyclo[3.2.0]heptane-3-carboxylate The product of Example 96A (120 mg, 0.34 mmol) was treated with ethynyltrimethylsilane according to the procedure described in Example 68A. The title compound was purified by chromatography (SiO$_2$, EtOAc:hexane, 50:50, R$_f$ 0.50) to provide the title compound (90 mg, 71% yield). $^1$H NMR (MeOH-d$_4$, 300 MHz) δ 0.05 (s, 9H), 1.40 (brs, 9H), 3.16 (dd, J=12.6, 3.6 Hz, 1H), 3.20-3.35 m, 2H), 3.65 (m, 1H), 3.85-4.05 (m, 3H), 4.70 (m, 1H), 6.68 (m, 1H), 7.48 (d, J=2.7 Hz, 1H), 7.67 (m, J=1.7 Hz, 1H); MS (DCI/NH$_3$) m/z 372 (M+H)$^+$.

Example 84B (1R,5S)-6-(5-ethynyl-3-pyridinyl)-3,6-diazabicyclo[3.2.0]heptane The product of Example 84A (90 mg, 0.24 mmol) was treated with Bu$_4$N$^+$F$^-$ solution (1M in THF, 2 mL) at room temperature. After stirring for 20 minutes, the mixture was diluted with ethyl acetate (50 mL), washed with water (2×5 mL) and concentrated under reduced pressure. The residue was treated with trifluoroacetic acid (2.5 mL) in CH$_2$Cl$_2$ (2.5 mL) at room temperature. After stirring for 1 hour, the mixture was concentrated and the residue was purified by chromatography (SiO$_2$. CH$_2$Cl$_2$:MeOH:NH$_4$OH, 90:10:1, R$_f$ 0.2) to provide the title compound (45 mg, 94% yield). $^1$H NMR (MeOH-d$_4$, 300 MHz) δ 2.75 (dd, J=12.9, 3.4 Hz, 1H), 2.90

(dd, J=12.2, 6.5 Hz, 1H), 3.10 (m, 1H), 3.30 (d, J=12.6 Hz, 1H), 3.40 (d, J=12.9 Hz, 1H), 3.70 (dd, J=7.8, 3.3 Hz, 1H), 3.76 (s, 1H), 3.96 (t, J=7.8 Hz, 1H) 4.70 (dd, J=6.1, 3.3 Hz, 1H), 6.94 (dd, J=2.7, 1.7 Hz, 1H), 7.77 (d, J=2.7 Hz, 1H), 7.94 (d, J=1.7 Hz, 1H); MS (DCI/NH$_3$) m/z 200 (M+H)$^+$.

Example 84C (1R,5S)-6-(5-ethynyl-3-pyridinyl)-3,6-diazabicyclo[3.2.0]heptane fumarate The product of Example 84B (45 mg, 0.226 mmol) was treated with fumaric acid according to the procedure of Example 46C. The title compound was obtained as a solid (51.0 mg, 73% yield). $^1$H NMR (MeOH-d$_4$, 300 MHz) δ 3.16 (dd, J=12.6, 3.7 Hz, 1H), 3.35-3.40 (m, 3H), 3.45 (m, 1H), 3.70-3.85 (m, 3H), 3.95 (t, J=7.8 Hz, 1H), 4.96 (dd, J=6.1, 3.4 Hz, 1H), 6.70 (s, 2H), 7.10 (dd, J=2.4, 2.0 Hz, 1H), 7.85 (d, J=3.0 Hz, 1H), 7.96 (d J=1.7 Hz, 1H); MS (DCI/NH$_3$) m/z 200 (M+H)$^+$. Anal. calculated for C$_{12}$H$_{13}$N$_3$.1.2C$_4$H$_6$O$_6$.1.00H$_2$O: C, 56.59; H, 5.60; N, 11.78. Found: C, 56.92; H, 4.98; N, 11.18.

Example 85

(1R,5S)-6-(5,6-dichloro-3-pyridinyl)-3,6-diazabicyclo[3.2.0]heptane fumarate

Example 85A benzyl (1S,5S)-6-(5,6-dichloro-3-pyridinyl)-3,6-diazabicyclo[3.2.0]heptane-3-carboxylate The product of Example 52D (451 mg, 1.94 mmol) was coupled with 2,3-dichloro-5-iodopyridine (805 mg, 2.94 mmol: U.S. Pat. No. 7,733,912) using tris(dibenzylideneacetone)dipalladium (Pd$_2$(dba)$_3$, 36 mg, 0.039 mmol; Alfa Aesar), 2,2'-bis(diphenylphosphino)-1,1'-binaphthyl (BINAP, 82 mg, 0.13 mmol; Strem), and sodium tert-butoxide (360 mg, 3.75 mmol; Aldrich) according to the procedure described in Example 1E to provide the title compound (184 mg, 25% yield). MS (DCI/NH$_3$) m/z 378, 380 (M+H)$^+$.

Example 85B (1R,5S)-6-(5,6-dichloro-3-pyridinyl)-3,6-diazabicyclo[3.2.0]heptane

The product from Example 85A (184 mg, 0.49 mmol) in trifluoroacetic acid (10 mL) was heated at 65° C. for 3 hours, allowed to cool to room temperature, concentrated, and the residue purified by chromatography on silica gel (10-50% A-CH$_2$Cl$_2$, A=CH$_2$Cl$_2$-MeOH—NH$_4$OH, 75:22.5:2.5) to afford the title compound as an oil (112 mg, 94%). MS (DCI/NH$_3$) m/z 244, 246 (M+H)$^+$.

Example 85C (1R,5S)-6-(5,6-dichloro-3-pyridinyl)-3,6-diazabicyclo[3.2.0]heptane fumarate The product from Example 85B (110 mg, 0.45 mmol) in ethanol was treated with a solution of fumaric acid (52 mg, 0.45 mmol. Aldrich) in ethanol and stirred for 2 hours. The precipitate was collected by filtration to provide the title compound as an off-white solid (105 mg, 65% yield). $^1$H NMR(CD$_3$OD, 300 MHz) δ 3.12 (dd, J=13, 4 Hz, 1H), 3.28 (m, 1H), 3.44 (ddd, J=14, 7, 3 Hz, 1H), 3.68 (dd, J=12, 12 Hz, 2H), 3.75 (dd, J=8, 3 Hz, 1H), 4.04 (dd, J=8, 8 Hz, 1H), 4.92 (dd, J=6, 3 Hz, 1H), 6.68 (s, 2H), 7.20 (d, J=3 Hz, 1H), 7.62 (d, J=3 Hz, 1H); MS (DCI/NH$_3$) m/z 244, 246 (M+H)$^+$; Anal. Calculated for C$_{10}$H$_{11}$Cl$_2$N$_3$.C$_4$H$_4$O$_4$: C, 46.68; H, 4.20; N, 11.67. Found: C, 46.61; H, 4.19; N, 11.59.

Example 86

(1R,5S)-6-(5-methoxy-3-pyridinyl)-3,6-diazabicyclo[3.2.0]heptane 4-methylbenzenesulfonate Example 86A benzyl (1S,5S)-6-(5-methoxy-3-pyridinyl)-3,6-diazabicyclo[3.2.0]heptane-3-carboxylate The product of Example 52D (940 mg, 4.05 mmol) and 3-bromo-5-methoxypyridine (1.13 g, 6.07 mmol) were processed according to the procedure described in Example 1E. The crude product was purified by chromatography (SiO$_2$, ethyl acetate:hexane, 1:1) to provide the title compound (0.50 g, 37% yield). MS (DCI/NH$_3$) m/z 340 (M+H)$^+$.

Example 86B (1R,5S)-6-(5-methoxy-3-pyridinyl)-3,6-diazabicyclo[3.2.0]heptane

The product from Example 86A (300 mg, 0.88 mmol) in trifluoroacetic acid (10 mL) was heated at 60° C. for 2 hours, cooled to room temperature, concentrated, and the residue was purified by chromatography on silica gel (CH$_2$Cl$_2$: MeOH:NH$_4$OH, 90:10:1) to provide the title compound (150 mg, 83%). MS (DCI/NH$_3$) m/z 206 (M+H)$^+$.

Example 86C (1R,5S)-6-(5-methoxy-3-pyridinyl)-3,6-diazabicyclo[3.2.0]heptane 4-methylbenzenesulfonate The product of Example 86B (150 mg, 0.73 mmol) was treated with 4-methylbenzenesulfonic acid monohydrate (153 mg, 0.84 mmol) in ethanol (4 mL) and ethyl acetate (16 mL). The mixture was stirred at room temperature overnight. The precipitate was isolated by filtration and dried under reduced pressure at 40-50° C. to provide the title compound (182 mg, 67% yield). $^1$H NMR (MeOH-d$_4$, 300 MHz) δ 2.37 (s, 3H), 3.20 (dd, J=12.6, 3.7 Hz, 1H), 3.35 (m, 1H), 3.45 (m, 1H), 3.72 (m, 3H), 3.83 (s, 3H), 4.16 (t, J=8.2 Hz, 1H), 4.90 (dd, J=6.5, 3.8 Hz, 1H), 6.54 (t, J=2.4 Hz, 1H), 7.22 (d, J=6.0 Hz, 2H), 7.47 (d, J=2.8 Hz, 1H), 7.67 (d, J=2.8 Hz, 1H), 7.69 (d, J=6.0 Hz, 2H); MS (DCI/NH$_3$) m/z 206 (M+H)$^+$. Anal. calculated for C$_{11}$H$_{15}$N$_3$O.C$_7$H$_8$O$_3$S: C, 57.28; H, 6.14; N, 11.13. Found: C, 57.16; H, 6.15; N, 11.0.

Example 87

(1R,5S)-6-(6-chloro-5-methyl-3-pyridinyl)-3,6-diazabicyclo[3.2.0]heptane 4-methylbenzenesulfonate Example 87A benzyl (1S,5S)-6-(6-chloro-5-methyl-3-pyridinyl)-3,6-diazabicyclo[3.2.0]heptane-3-carboxylate The product of Example 52D (1.30 g, 5.60 mmol) and 5-bromo-2-chloro-3-methylpyridine (1.73 g, 8.39 mmol) were processed according to the procedure described in Example 1E. The crude product was purified by chromatography (SiO$_2$, ethyl acetate:hexane, 1:1) to provide the title compound (0.22 g, 11% yield) which was used directly in the next step without further purification. MS (DCI/NH$_3$) m/z 358, 360 (M+H)$^+$.

Example 87B (1R,5S)-6-(6-chloro-5-(ethyl-3-pyridinyl)-3,6-diazabicyclo[3.2.0]heptane The product from Example 87A (220 mg, 0.61 mmol) in trifluoroacetic acid (6 mL) was heated at 60° C. for 2 hours, cooled to room temperature, concentrated, and purified by chromatography on silica gel (CH$_2$Cl$_2$:MeOH:NH$_4$OH, 90:10:1) to afford the title compound as an oil (100 mg, 80% yield). MS (DCI/NH$_3$) m/z 224, 226 (M+H)$^+$.

Example 87C (1R,5S)-6-(6-chloro-5-methyl-3-pyridinyl)-3,6-diazabicyclo[3.2.0]heptane 4-methylbenzenesulfonate The product of Example 87B (100 mg, 0.47 mmol) was treated with p-toluenesulfonic acid monohydrate (85 mg, 0.47 mmol) in ethanol:ethyl acetate (1:4, mL). The mixture was stirred at room temperature overnight. The precipitate was isolated by filtration and dried under reduced pressure at 40-50° C. to provide the title compound (133 mg, 72% yield). $^1$H NMR (MeOH-d$_4$, 300 MHz) δ 2.31 (s, 3H), 2.36 (s 3H), 3.18 (dd, J=12.6, 3.7 Hz, 1H), 3.41 (m, 2H), 3.72 (dd, J=12.6, 3.7 Hz, 2H), 3.76 (d, 3.7 Hz, 1H), 3.98 (t, J=8.2 Hz, 1H), 4.87 (dd, J=6.5, 3.8 Hz, 1H), 6.97 (d, J=2.4 Hz, 1H), 7.22 (d, J=6.0 Hz, 2H), 7.48 (d, J=2.8 Hz, 1H), 7.68 (d, J=2.8 Hz, 1H); MS (DCI/NH$_3$) m/z 224, 226 (M+H)$^+$. Anal. calculated for C$_{11}$H$_4$N$_3$Cl.C$_7$H$_8$O$_3$S: C, 54.61; H, 5.60; N, 10.61. Found: C, 54.47; H, 5.51; N, 10.46.

Example 88

(1S,6R)-8-(5-methoxy-3-pyridinyl)-3,8-diazabicyclo[4.2.0]octane fumarate

Example 88A tert-butyl (1S,6R)-8-(5-methoxy-3-pyridinyl)-3,8-diazabicyclo[4.2.0]octane-3-carboxylate The product of Example 61F (0.780 g, 3.68 mmol) was treated with Pd$_2$(dba)$_3$ (34 mg, 0.0368 mmol), BINAP (69 mg, 0.110 mmol), 3-bromo-5-methoxypyridine (1.03 g, 5.50 mmol), and Cs$_2$CO$_3$ (3.60 g, 11.0 mmol) according to the procedure described in Example 56A to provide the title compound (0.548 g, 1.72 mmol, 47% yield).

Example 88B (1S,6R)-8-(5-methoxy-3-pyridinyl)-3,8-diazabicyclo[4.2.0]octane

The product of Example 88A (0.540 g, 1.70 mmol) and trifluoroacetic acid were processed according to the procedure described in Example 64C to provide the title compound (0.340 g, 1.55 mmol, 91% yield).

Example 88C (1S,6R)-8-(5-methoxy-3-pyridinyl)-3,8-diazabicyclo[4.2.0]octane fumarate The product of Example 88B (1.55 g, 0.710 mmol) and fumaric acid (83 mg, 0.710 mmol) were processed according to the procedure described in Example 66D to provide the title compound (116 mg, 0.346 mmol, 49% yield). $^1$H NMR (CH$_3$OH-d$_4$, 300 MHz) δ 2.31 (m, 1H), 2.85 (m, 1H), 3.15 (ddd, J=12.6, 8.2, 4.5 Hz, 1H), 3.34 (m, 2H), 3.56 (m, 1H), 3.64 (dd, J=14.2, 1.7 Hz, 1H), 3.79 (dd, J=7.8, 2.7 Hz, 1H), 3.85 (s, 3H), 3.86 (m, 1H), 4.36 (dt, J=8.1, 2.7 Hz, 1H), 6.62 (dd, J=2.2, 2.2 Hz, 1H), 6.68 (s, 2H), 7.55 (d, J=2.2 Hz, 1H), 7.72 (d, J=2.2 Hz, 1H); MS (DCI/NH$_3$) m/z 220 (M+H–C$_4$H$_4$O$_4$)$^+$; Anal. calculated for C$_{12}$H$_{17}$N$_3$O.C$_4$H$_4$O$_4$.0.5H$_2$O: C, 55.81; H, 6.44; N, 12.20. Found: C, 55.69; H, 6.10; N, 11.95.

Example 89

(1S,6R)-8-(6-chloro-5-methyl-3-pyridinyl)-3,8-diazabicyclo[4.2.0]octane fumarate

Example 89A tert-butyl (1S,6R)-(6-chloro-5-methyl-3-pyridinyl)-3,8-diazabicyclo[4.2.0]octane-3-carboxylate The product of Example 61F (0.35 g, 1.65 mmol), Pd$_2$(dba)$_3$ (30 mg, 0.0330 mmol), BINAP (41 mg, 0.0660 mmol), 5-bromo-2-chloro-3-methylpyridine (0.372 g, 1.82 mmol), and Cs$_2$CO$_3$ (0.860 g, 2.64 mmol) were processed according to the procedure described in Example 56A to provide the title compound (141 mg, 0.418 mmol, 25% yield). MS (DCI/NH$_3$) m/z 338 (M+H)$^+$.

Example 89B (1S,6R)-8-(6-chloro-5-methyl-3-pyridinyl)-3,8-diazabicyclo[4.2.0]octane The product of Example 89A (0.140 g, 0.418 mmol) and trifluoroacetic acid were processed according to the procedure described in Example 64C to provide the title compound (85 mg, 0.359 mmol, 86% yield).

Example 89C (1S,6R)-8-(6-chloro-5-methyl-3-pyridinyl-3,8-diazabicyclo[4.2.0]octane fumarate The product of Example 89B (0.850 g, 0.359 mmol) and fumaric acid (42 mg, 0.359 mmol) were processed according to the procedure described in Example 66D to provide the title compound (97 mg, 0.250 mmol, 70% yield). $^1$H NMR (CH$_3$OH-d$_4$, 300 MHz) δ 2.05 (m, 1H), 2.30 (m, 1H), 2.32 (s, 3H), 2.85 (m, 1H), 3.15 (ddd, J=12.5, 8.1, 4.4 Hz, 1H), 3.31 (m, 1H), 3.57 (ddd, J=12.5, 8.5, 4.1 Hz, 1H), 3.64 (dd, J=14.6, 2.0 Hz, 1H), 3.77 (dd, J=7.1, 2.3 Hz, 1H), 3.83 (t, J=7.4 Hz, 1H), 4.34 (dt, J=7.8, 2.3 Hz, 1H), 6.69 (s, 2H), 7.04 (d, J=2.8 Hz, 1H), 7.57 (d, J=2.8 Hz, 1H); MS (DCI/NH$_3$) m/z 238

(M+H−C$_4$H$_4$O$_4$)$^+$; Anal. calculated for C$_{12}$H$_{16}$ClN$_3$.1.3C$_4$H$_4$O$_4$: C, 53.16; H, 5.50; N, 10.81. Found: C, 52.91; H, 5.62; N, 10.86.

Example 90

(1R,6S)-8-(6-chloro-5-ethyl-3-pyridinyl)-3,8-diazabicyclo[4.2.0]octane fumarate

Example 90A tert-butyl (3S,4S)-3-amino-4-(hydroxymethyl)-1-piperidinecarboxylate The less mobile diastereomer of Example 61C (14.4 g, 43.4 mmol) in absolute ethanol (200 mL) was treated with 10% palladium on carbon (1.50 g) and stirred under 1 atmosphere of H$_2$ (1 atm) at 50° C. for 20 hours. The mixture was allowed to cool to ambient temperature, filtered through Celite, and the filtrate concentrated under reduced pressure to provide the title compound (9.90 g, 43.0 mmol, 99% yield). MS (DCI/NH$_3$) m/z 231 (M+H)$^+$.

Example 90B tert-butyl (1R,6S)-8-[(2-nitrophenyl)sulfonyl]-3,8-diazabicyclo[4.2.0]octane-3-carboxylate The product of Example 90A (9.90 g, 43.0 mmol), triethylamine (17.9 mL, 0.129 mol) and 2-nitrobenzenesulfonyl chloride (20.9 g, 94.3 mmol) were processed according to the procedure described in Example 61E to provide the title compound (7.84 g, 19.7 mmol, 46% yield). MS (DCI/NH$_3$) m/z 415 (M+NH$_4$)$^+$.

Example 90C tert-butyl (1R,6S)-3,8-diazabicyclo[4.2.0]octane-3-carboxylate

The product of Example 90B (7.80 g, 19.7 mmol), K$_2$CO$_3$ (8.40 g, 60.8 mmol) and thiophenol (2.60 mL, 25.5 mmol) were processed according to the procedure described in Example 61F to provide the title compound (2.80 g, 13.2 mmol, 67% yield). MS (DCI/NH$_3$) m/z 213 (M+H)$^+$.

Example 90D tert-butyl (1R,6S)-8-(6-chloro-5-methyl-3-pyridinyl)-3,8-diazabicyclo[4.2.0]octane-3-carboxylate The product of Example 90C (365 mg, 1.72 mmol), Pd$_2$(dba)$_3$ (30 mg, 0.0330 mmol), BINAP (41 mg, 0.0660 mmol), 5-bromo-2-chloro-3-methylpyridine (388 mg, 1.89 mmol), and Cs$_2$CO$_3$ (897 mg, 2.75 mmol) were processed according to the procedure described in Example 56A to provide the title compound (190 mg, 0.564 mmol, 33% yield). MS (DCI/NH$_3$) m/z 338 (M+H)$^+$.

Example 90E (1R,6S)-8-(6-chloro-5-methyl-3-pyridinyl)-3,8-diazabicyclo[4.2.0]octane The product of Example 90D (0.190 g, 0.564 mmol) and trifluoroacetic acid were processed according to the procedure described in Example 64C to provide the title compound (133 mg, 0.561 mmol, 99% yield).

Example 90F (1R,6S)-8-(6-chloro-5-methyl-3-pyridinyl)-3,8-diazabicyclo[4.2.0]octane fumarate The product of Example 90E (0.130 g, 0.548 mmol) and fumaric acid (64 mg, 0.548 mmol) were processed according to the procedure described in Example 66D to provide the title compound (77 mg, 0.182 mmol, 33% yield). $^1$H NMR (CH$_3$OH-d$_4$, 300 MHz) δ 2.08 (m, 1H), 2.30 (m, 1H), 2.33 (s, 3H), 2.85 (m, 1H), 3.15 (ddd, J=12.6, 8.2, 4.4 Hz, 1H), 3.30 (m, 1H), 3.57 (ddd, J=12.8, 8.4, 4.0 Hz, 1H), 3.64 (dd, J=14.2, 1.7 Hz, 1H), 3.76 (dd, J=7.1, 2.3 Hz, 1H), 3.84 (t, J=7.4 Hz, 1H), 4.34 (dt, J=8.1, 2.4 Hz, 1H), 6.70 (s, 2H), 7.05 (d, J=2.7 Hz, 1H), 7.57 (d, J=2.7 Hz, 1H); MS (DCI/NH$_3$) m/z 238 (M+H−C$_4$H$_4$O$_4$)$^+$; Anal. calculated for C$_{12}$H$_{16}$ClN$_3$.1.6C$_4$H$_4$O$_4$: C, 52.19; H, 5.33; N, 9.92. Found: C, 52.09; H, 5.22; N, 10.10.

Example 91

(1S,6R)-8-(3-pyridinyl)-3,8-diazabicyclo[4.2.0]octane 4-methylbenzenesulfonate

Example 91A tert-butyl (1S,6R)-8-(3-pyridinyl)-3,8-diazabicyclo[4.2.0]octane-3-carboxylate The product of Example 61F (390 mg, 1.84 mmol), Pd$_2$(dba)$_3$ (34 mg, 0.0368 mmol) BINAP (46 mg, 0.0736 mmol), 3-bromopyridine (320 mg, 2.02 mmol), and sodium tert-butoxide (283 mg, 2.94 mmol) were processed according to the procedure described in Example 56A to provide the title compound (360 mg, 1.25 mmol, 68% yield). MS (DCI/NH$_3$) m/z 290 (M+H)$^+$.

Example 91B (1S,6R)-8-(3-pyridinyl)-3,8-diazabicyclo[4.2.0]octane

The product of Example 91A (0.360 g, 1.25 mmol) and trifluoroacetic acid were processed according to the procedure described in Example 64C to provide the title compound (230 mg, 1.22 mmol, 97% yield). MS (DCI/NH$_3$) m/z 190 (M+H)$^+$.

Example 91C (1S,6R)-8-(3-pyridinyl)-3,8-diazabicyclo[4.2.0]octane 4-methylbenzenesulfonate The product of Example 91B (60.0 mg, 0.317 mmol) in ethyl acetate (10 mL) and ethanol (2 mL) was treated with 4-methylbenzenesulfonic acid monohydrate (61 mg, 0.317 mmol) in ethyl acetate (2 mL) dropwise. After the addition was complete, the mixture was refrigerated for 16 hours. The resulting precipitate was isolated by filtration to provide the title compound (110 mg, 0.304 mmol, 96% yield). $^1$H NMR (CH$_3$OH-d$_4$, 300 MHz) δ 2.06 (m, 1H), 2.33 (m, 1H), 2.37 (s, 3H), 2.86 (m, 1H), 3.16 (ddd, J=12.5, 8.1, 4.4 Hz, 1H), 3.35 (d, J=2.7 Hz, 1H), 3.57 (ddd, J=12.9, 8.9, 4.5 Hz, 1H), 3.65 (dd, J=14.6, 2.4 Hz, 1H), 3.79 (dd, J=7.1, 2.7 Hz, 1H), 3.85 (t, J=7.4 Hz, 1H), 4.35 (dt, J=8.1, 2.7 Hz, 1H), 7.12 (ddd, J=8.3, 3.1, 1.4 Hz, 1H), 7.22 (m, 2H), 7.27 (ddd, J=8.3, 4.7, 0.7 Hz, 1H), 7.70 (m, 2H), 7.95 (dd, J=3.1, 0.7 Hz, 1H), 8.01 (dd, J=4.7, 1.3 Hz, 1H); MS (DCI/NH$_3$) m/z 190 (M+H)$^+$; Anal. calculated for C$_{11}$H$_{15}$N$_3$.C$_7$H$_8$O$_3$S: C, 59.81; H, 6.41; N, 11.62. Found: C, 59.68; H, 6.40; N, 11.47.

Example 92

(1R,6S)-8-(3-pyridinyl)-3,8-diazabicyclo[4.2.0]octane 4-methylbenzenesulfonate

Example 92A tert-butyl (1R,6S)-8-(3-pyridinyl)-3,8-diazabicyclo[4.2.0]octane-3-carboxylate The product of Example 90C (400 mg, 1.89 mmol), Pd$_2$(dba)$_3$ (35 mg, 0.0378 mmol), BINAP (47 mg, 0.0755 mmol), 3-bromopyridine (328 mg, 2.08 mmol), and sodium tert-butoxide (290 mg, 3.02 mmol) were processed according to the procedure described in Example 56A to provide the title compound (325 mg, 1.12 mmol, 60% yield). MS (DCI/NH$_3$) m/z 290 (M+H)$^+$.

Example 92B (1R,6S)-8-(3-pyridinyl)-3,8-diazabicyclo[4.2.0]octane

The product of Example 92A (0.325 g, 1.12 mmol) and trifluoroacetic acid were processed according to the procedure described in Example 64C to provide the title compound (188 mg, 0.995 mmol, 89% yield). MS (DCI/NH$_3$) m/z 190 (M+H)$^+$.

Example 92C (1R,6S)-8-(3-pyridinyl)-3,8-diazabicyclo[4.2.0]octane 4-methylbenzenesulfonate The product of Example 92B (0.120 g, 0.634 mmol) and 4-methylbenzenesulfonate acid monohydrate (121 mg, 0.634 mmol) were combined according to the procedure described in Example 91C to provide the title compound (200 mg, 0.553 mmol, 87% yield). $^1$H NMR (CH$_3$OH-d$_4$, 300 MHz) δ 2.05 (m, 1H), 2.31 (m, 1H), 2.37 (s, 3H), 2.85 (m, 1H), 3.15 (ddd, J=12.2, 7.8, 4.1 Hz, 1H), 3.32 (d, J=2.7 Hz, 1H), 3.56 (ddd, J=12.9, 8.8, 4.4 Hz, 1H), 3.64 (dd, J=14.5, 2.0 Hz, 1H), 3.79 (dd, J=7.1, 2.4 Hz, 1H), 3.86 (t, J=7.1 Hz, 1H), 4.35 (dt, J=8.1, 2.4 Hz, 1H), 7.12 (ddd, J=8.1, 3.1, 1.3 Hz, 1H), 7.23 (m, 2H), 7.28 (ddd, J=8.4, 4.8, 0.7 Hz, 1H), 7.69 (m, 2H), 7.93 (dd, J=3.1, 0.7 Hz, 1H), 8.02 (dd, J=4.8, 1.3 Hz, 1H); MS (DCI/NH$_3$) m/z 190 (M+H)$^+$; Anal. calculated for C$_{11}$H$_{15}$N$_3$.C$_7$H$_8$O$_3$S: C, 59.81; H, 6.41; N, 11.62. Found: C, 59.58; H, 6.39; N, 11.59.

Example 93

(1S,6R)-8-(5,6-dichloro-3-pyridinyl)-3,8-diazabicyclo[4.2.0]octane 4-methylbenzenesulfonate Example 93A tert-butyl (1S,6R)-8-(5,6-dichloro-3-pyridinyl)-3,8-diazabicyclo[4.2.0]octane-3-carboxylate The product of Example 61F (392 mg, 1.84 mmol), Pd$_2$(dba)$_3$ (34 mg, 0.0368 mmol), BINAP (46 mg, 0.0736 mmol), 2,3-dichloro-5-iodopyridine (554 mg, 2.02 mmol), and sodium tert-butoxide (283 mg, 2.94 mmol) were processed according to the procedure described in Example 56A to provide the title compound (80 mg, 0.224 mmol, 12% yield). MS (DCI/NH$_3$) m/z 358 (M+H)$^+$.

Example 93B (1S,6R)-8-(5,6-dichloro-3-pyridinyl)-3,8-diazabicyclo[4.2.0]octane

The product of Example 93A (80 mg, 0.224 mmol) and trifluoroacetic acid were processed according to the procedure described in Example 64C to provide the title compound (45 mg, 0.175 mmol, 78% yield).

Example 93C (1S,6R)-8-(5,6-dichloro-3-pyridinyl)-3,8-diazabicyclo[4.2.0]octane 4-methylbenzenesulfonate The product of Example 93B (45.0 mg, 0.175 mmol) and 4-methylbenzenesulfonic acid monohydrate (33.3 mg, 0.175 mmol) were processed according to the procedure described in Example 91C to provide the title compound (58 mg, 0.135 mmol, 77% yield). $^1$H NMR (CH$_3$OH-d$_4$, 300 MHz) δ 2.04 (m, 1H), 2.30 (m, 1H), 2.39 (s, 3H), 2.89 (m, 1H), 3.16 (ddd, J=12.2, 7.4, 4.1 Hz, 1H), 3.28 (m, 1H), 3.57 (ddd, J=12.9, 8.8, 4.1 Hz, 1H), 3.64 (dd, J=14.6, 2.0 Hz, 1H), 3.79 (dd, J=7.5, 2.7 Hz, 1H), 3.90 (t, J=7.5 Hz, 1H), 4.41 (dt, J=8.1, 2.4 Hz, 1H), 7.22 (m, 2H), 7.27 (d, J=2.7 Hz, 1H), 7.70 (m, 3H); MS (DCI/NH$_3$) m/z 258 (M+H)$^+$; Anal. calculated for C$_{11}$H$_{13}$Cl$_2$N3.C$_7$H$_8$O$_3$S: C, 50.24; H, 4.92; N, 9.76. Found: C, 50.14; H, 4.88; N, 9.67.

Example 94

(1R,6S)-8-(5,6-dichloro-3-pyridinyl)-3,8-diazabicyclo[4.2.0]octane 4-methylbenzenesulfonate Example 94A tert-butyl (1R,6S)-8-(5,6-dichloro-3-pyridinyl)-3,8-diazabicyclo[4.2.0]octane-3-carboxylate The product of Example 90C (390 mg, 1.84 mmol), Pd$_2$(dba)$_3$ (34 mg, 0.0368 mmol), BINAP (46 mg, 0.0736 mmol), 2,3-dichloro-5-iodopyridine (554 mg, 2.02 mmol), and sodium tert-butoxide (283 mg, 2.94 mmol) were processed according to the procedure described in Example 56A to provide the title compound (110 mg, 0.308 mmol, 17% yield). MS (DCI/NH$_3$) m/z 358 (M+H)$^+$.

Example 94B (1R,6S)-8-(5,6-dichloro-3-pyridinyl)-3,8-diazabicyclo[4.2.0]octane

The product of Example 94A (110.0 mg, 0.308 mmol) and trifluoroacetic acid were processed according to the procedure of Example 64C to provide the title compound (74 mg, 0.288 mmol, 93% yield).

Example 94C (1R,6S)-8-(5,6-dichloro-3-pyridinyl)-3,8-diazabicyclo[4.2.0]octane 4-methylbenzenesulfonate The product of Example 94B (74 mg, 0.288 mmol) and 4-methylbenzenesulfonic acid monohydrate (55 mg, 0.288 mmol) were combined according to the procedure described in Example 91C to provide the title compound (83 mg, 0.193 mmol, 67% yield). $^1$H NMR (CH$_3$OH-d$_4$, 300 MHz) δ 2.04 (m, 1H), 2.31 (m, 1H), 2.36 (S, 2H), 2.88 (m, 1H), 3.17 (ddd, J=11.8, 7.8, 4.0 Hz, 1H), 3.29 (m, 1H), 3.56 (ddd, J=13.2, 9.1, 4.4 Hz, 1H), 3.64 (dd, J=14.6, 2.0 Hz, 1H) 3.80 (dd, J=7.4, 2.7 Hz, 1H), 3.89 (t, J=7.4 Hz, 1H), 4.41 (dt, J=8.1, 2.4 Hz, 1H), 7.23 (m, 2H), 7.27 (d, J=2.7 Hz, 1H), 7.69 (m, 2H), 7.71 (d, J=2.7 Hz, 1H); MS (DCI/NH$_3$) m/z 258 (M+H)$^+$; Anal. calculated for C$_{11}$H$_{13}$Cl$_2$N$_3$.C$_7$H$_8$O$_3$S: C, 50.24; H, 4.92; N, 9.76. Found: C, 50.09; H, 4.94; N, 9.64.

Example 95

(1R,5S)-6-(6-bromo-5-methoxy-3-pyridinyl)-3,6-diazabicyclo[3.2.0]heptane 4-methylbenzenesulfonate

Example 95A benzyl (1S,5S)-6-(6-bromo-5-methoxy-3-pyridinyl)-3,6-diazabicyclo[3.2.0]heptane-3-carboxylate The product of Example 86A (330 mg, 0.99 mmol) in acetonitrile (8 mL) was treated with N-bromosuccinimide (176 mg, 0.99 mmol) in acetonitrile (4 mL) at −42° C. After 20 minutes, the mixture was allowed to warm to ambient temperature and then was concentrated under reduced pressure. The residue was purified by chromatography (SiO$_2$, ethyl acetate:hexane, 30:70) to provide the title compound (110 mg, 26% yield). MS (DCI/NH$_3$) m/z 218, 220 (M+H)$^+$.

Example 95B (1R,5S)-6-(6-bromo-5-methoxy-3-pyridinyl)-3,6-diazabicyclo[3.2.0]heptane The product from Example 95A (110 mg, 0.26 mmol) in trifluoroacetic acid (6 mL) was heated at 60° C. for 2 hours, cooled to room temperature, concentrated, and the residue was purified by chromatography on silica gel (CH$_2$Cl$_2$:MeOH:NH$_4$OH, 90:10:1) to provide the title compound (60 mg, 83% yield). MS (DCI/NH$_3$) m/z 284, 286 (M+H)$^+$.

Example 95C (1R,5S)-6-(6-bromo-5-methoxy-3-pyridinyl)-3,6-diazabicyclo[3.2.0]heptane 4-methylbenzenesulfonate The product of Example 95B (60 mg, 0.26 mmol) was treated with 4-methylbenzenesulfonic acid monohydrate (40 mg, 0.26 mmol) in ethanol (4 mL) and ethyl acetate (16 mL). The mixture was stirred at room temperature overnight. The precipitate was isolated by filtration and dried under reduced pressure at 40-50° C. to provide the title compound (61 mg, 52% yield). $^1$H NMR (MeOH-d$_4$, 300 MHz) δ 2.37 (s, 3H), 3.20 (dd, J=12.6, 3.7 Hz, 1H), 3.35 (m, 1H), 3.45 (m, 1H), 3.72 (m, 3H), 3.90 (s, 3H), 4.06 (t, J=8.2 Hz, 1H), 4.95 (dd, J=6.5, 3.8 Hz, 1H), 6.61 (d J=2.4 Hz, 1H), 7.22 (d, J=6.0 Hz, 2H), 7.27 (d, J=2.8 Hz, 1H), 7.70 (d, J=6.0 Hz, 2H); MS (DCI/NH$_3$) m/Z 284, 286 (M+H)$^+$. Anal. calculated for C$_{11}$H$_{15}$N$_3$O.1.33C$_7$H$_8$S.0.33H$_2$O: C, 46.99; H, 4.91; N, 8.09. Found: C, 46.93; H, 4.88; N, 8.07.

Example 96

(1R,5S)-6-(5-azido-3-pyridinyl)-3,6-diazabicyclo[3.2.0]heptane fumarate

Example 96A tert-butyl (1S,5S)-6-(5-bromo-3-pyridinyl)-3,6-diazabicyclo[3.2.0]heptane-3-carboxylate The product of Example 53B (360 mg, 1.42 mmol) in dichloromethane (10 mL) was treated with di-tert-butyl dicarbonate (463 mg, 2.13 mmol; Aldrich). The reaction mixture was stirred at ambient temperature for 3 hours and then concentrated under reduced pressure. The residue was purified by chromatography (SiO$_2$, 10-50% ethyl acetate/hexanes) to provide the title compound (475 mg, 94% yield). MS (DCI/NH$_3$) m/z 354, 356 (M+H)$^+$.

Example 96B tert-butyl (1S,5S)-6-(5-azido-3-pyridinyl)-3,6-diazabicyclo[3.2.0]heptane-3-carboxylate The product from Example 96A (475 mg, 1.34 mmol) in anhydrous tetrahydrofuran (10 mL) was treated with n-butyllithium (1.6 M in hexanes, 0.900 mL, 1.44 mmol: Aldrich) dropwise over 10 minutes at −78° C. under a nitrogen atmosphere. The deep burgundy solution was stirred at −78° C. for 15 minutes and then a solution of trisyl azide (673 mg, 2.18 mmol; prepared according to Org. Synth. coll. vol. V, 179) in tetrahydrofuran (5 mL) was added via cannula over 5 minutes. The color rapidly faded to light orange. After stirring for an additional 30 minutes, the reaction mixture was quenched by the addition of acetic acid (0.4 mL) and then allowed to warm slowly to room temperature. The mixture was treated with saturated aqueous sodium bicarbonate and extracted twice with ethyl acetate. The combined organic phases were dried over magnesium sulfate, filtered and the filtrate concentrated. The residue was purified by chromatography (SiO$_2$, 10-100% ethyl acetate/hexanes) to afford the title compound (275 mg, 65% yield). MS (DCI/NH$_3$) m/z 317 (M+H)$^+$.

Example 96C (1R,5S)-6-(5-azido-3-pyridinyl)-3,6-diazabicyclo[3.2.0]heptane fumarate A solution of the product from Example 96B (134 mg, 0.42 mmol) in anhydrous dichloromethane (2 mL) at 0° C. was treated with trifluoroacetic acid (1 mL). The mixture was allowed to warm slowly to room temperature, then concentrated in vacuo and purified by chromatography on silica gel (10-50% A/CH$_2$Cl$_2$, A=CH$_2$Cl$_2$:MeOH:NH$_4$OH, 75:22.5:2.5) to afford the free base of the title compound (77 mg, 0.36 mmol, 84% yield). The free base in ethanol (1 mL) was treated with a solution of fumaric acid (40 mg, 0.34 mmol: Aldrich) in ethanol/ethyl acetate (4 mL) and stirred for 12 hours. The precipitate was collected by filtration to provide the title compound (60 mg, 51% yield) as a tan solid. $^1$H NMR (CD$_3$OD, 300 MHz) δ 3.15 (dd, J=13.3 Hz, 1H), 3.30 (m, 1H), 3.45 (ddd, J=14, 7, 3 Hz, 1H), 3.71 (dd, J=13, 12 Hz, 2H), 3.78 (dd, J=8, 3 Hz, 1H), 4.05 (t, J=8 Hz, 1H), 4.94 (dd, J=6, 4 Hz, 1H), 6.67 (m, 1H), 6.68 (s, 2H), 7.66 (d, J=3 Hz, 1H), 7.72 (d, J=2 Hz, 1H); MS (DCI/NH$_3$) m/z 217 (M+H)$^+$: Anal. Calculated for $C_{10}H_{12}N_6 \cdot 1.08\ C_4H_4O_4$: C, 50.35; H, 4.82; N, 24.60. Found: C, 50.75; H, 4.96; N, 24.23.

The foregoing description is merely illustrative and is not intended to limit the invention to the disclosed compounds. Variations and changes which are obvious to one skilled in the art of organic and/or medicinal chemistry are to be within the scope and nature of the invention which are defined in the appended claims.

We claim:

1. A compound of formula I

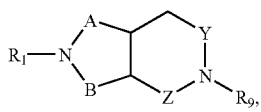

or pharmaceutically acceptable salts thereof, wherein
A is a covalent bond;
B is $CH_2$;
Y is selected from the group consisting of a covalent bond, $CH_2$, and $CH_2CH_2$;
Z is selected from the group consisting of a covalent bond, $CH_2$, and $CH_2CH_2$, provided that when Y is $CH_2CH_2$, then Z is a covalent bond and further provided that when Z is $CH_2CH_2$, then Y is a covalent bond;
$R_1$ is selected from the group consisting of

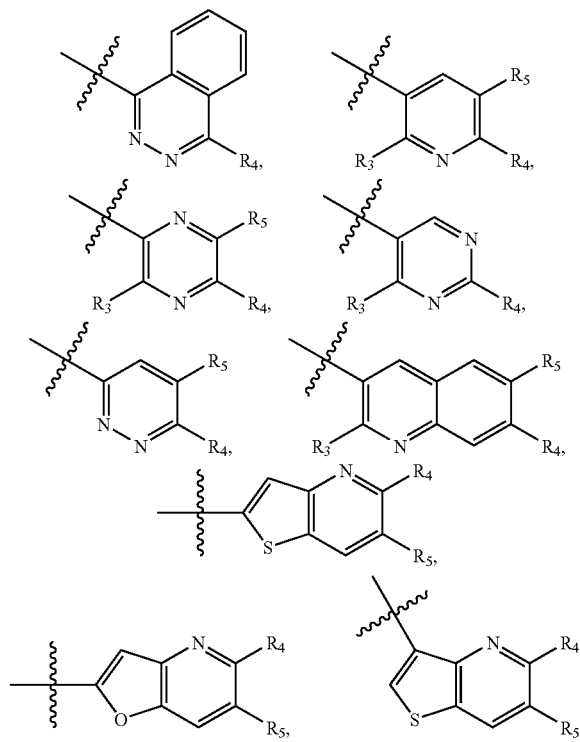

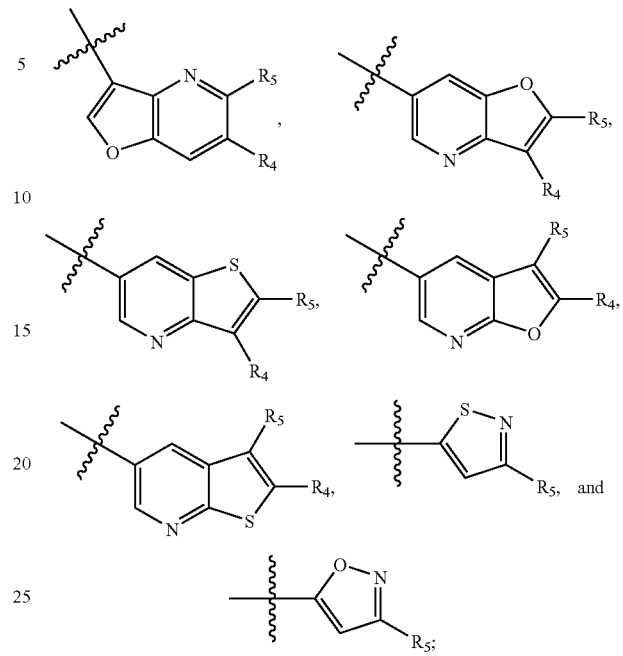

$R_3$ is selected from the group consisting of hydrogen, alkyl, and halogen;

$R_4$ is selected from the group consisting of hydrogen, alkoxy, alkyl, amino, halogen, and nitro;

$R_5$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, antinocarbonylalkyl, aminosulfonyl, carboxy, carboxyalkyl, cyano, cyanoalkyl, formyl, formylalkyl, haloalkoxy, halo alkyl, halogen, hydroxy, hydroxyalkyl, mercapto, mercaptoalkyl, nitro, 5-tetrazolyl, —NR$_6$S(O)$_2$R$_7$, —C(NR$_6$)NR$_7$R$_8$, —CH$_2$C(NR$_6$)NR$_7$R$_8$, —C(NOR$_6$)R$_7$, —C(NCN)R$_6$, —C(NNR$_6$R$_7$)R$_8$, —S(O)$_2$OR$_6$, and —S(O)$_2$R$_6$;

$R_6$, $R_7$, and $R_8$ are independently selected from the group consisting of hydrogen and alkyl; and $R_9$ is selected from the group consisting of hydrogen, alkoxycarbonyl, alkyl, amino, aminoalkyl, aminocarbonylalkyl, benzyloxycarbonyl, cyanoalkyl, dihydro-3-pyridinylcarbonyl, hydroxy, hydroxyalkyl, and phenoxycarbonyl.

2. A compound according to claim 1 wherein
$R_1$ is selected from the group consisting of

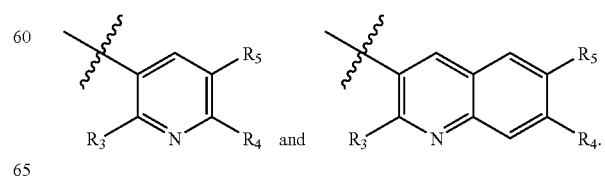

3. A compound according to claim 1 of formula II

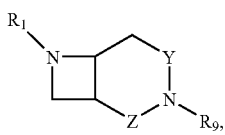

or pharmaceutically acceptable salts thereof.

4. A compound according to claim 3 wherein Y is a covalent bond and Z is CH$_2$.

5. A compound according to claim 3 wherein
Y is a covalent bond;
Z is CH$_2$; and
R$_1$ is

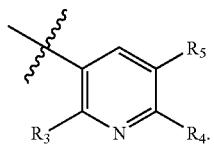

6. A compound according to claim 5 selected from the group consisting of
(cis)-6-(3-pyridinyl)-3,6-diazabicyclo[3.2.0]heptane;
(cis)-6-(6-chloro-3-pyridinyl)-3,6-diazabicyclo[3.2.0]heptane;
(1R,5S)-6-(3-pyridinyl)-3,6-diazabicyclo[3.2.0]heptane;
(1R,5S)-6-(5-bromo-3-pyridinyl)-3,6-diazabicyclo[3.2.0]heptane;
(1S,5R)-6-(6-chloro-3-pyridinyl)-3,6-diazabicyclo[3.2.0]heptane;
(1S,5R)-6-(3-pyridinyl)-3,6-diazabicyclo[3.2.0]heptane;
(1R,5S)-6-(6-chloro-3-pyridinyl)-3,6-diazabicyclo[3.2.0]heptane;
(1S,5R)-6-(5-ethynyl-3-pyridinyl)-3,6-diazabicyclo[3.2.0]heptane;
(1S,5R)-6-(5-vinyl-3-pyridinyl)-3,6-diazabicyclo[3.2.0]heptane;
5-[(1S,5R)-3,6-diazabicyclo[3.2.0]hept-6-yl]nicotinonitrile;
(–) (cis)-6-(5-bromo-3-pyridinyl)-3,6-diazabicyclo[3.2.0]heptane;
(cis)-6-(5-bromo-3-pyridinyl)-3,6-diazabicyclo[3.2.0]heptane;
(1S,5R)-6-(6-bromo-5-vinyl-3-pyridinyl)-3,6-diazabicyclo[3.2.0]heptane;
2-bromo-5-[(1R,5S)-3,6-diazabicyclo[3.2.0]hept-6-yl]nicotinonitrile;
(1R,5S)-6-(5-ethynyl-3-pyridinyl)-3,6-diazabicyclo[3.2.0]heptane;
(1R,5S)-6-(5,6-dichloro-3-pyridinyl)-3,6-diazabicyclo[3.2.0]heptane;
(1S,5R)-6-(5,6-dichloro-3-pyridinyl)-3,6-diazabicyclo[3.2.0]heptane;
(cis)-6-(5,6-dichloro-3-pyridinyl)-3,6-diazabicyclo[3.2.0]heptane;
(1R,5S)-6-(5-methoxy-3-pyridinyl)-3,6-diazabicyclo[3.2.0]heptane;
(1S,5R)-6-(5-methoxy-3-pyridinyl)-3,6-diazabicyclo[3.2.0]heptane;
(cis)-6-(6-bromo-5-methoxy-3-pyridinyl)-3,6-diazabicyclo[3.2.0]heptane;
(1R,5S)-6-(6-chloro-5-methyl-3-pyridinyl)-3,6-diazabicyclo[3.2.0]heptane;
(1S,5R)-6-(6-chloro-5-methyl-3-pyridinyl)-3,6-diazabicyclo[3.2.0]heptane;
(cis)-6-(6-chloro-5-methyl-3-pyridinyl)-3,6-diazabicyclo[3.2.0]heptane;
(1R,5S)-6-(6-bromo-5-methoxy-3-pyridinyl)-3,6-diazabicyclo[3.2.0]heptane;
(1S,5R)-6-(6-bromo-5-methoxy-3-pyridinyl)-3,6-diazabicyclo[3.2.0]heptane;
(cis)-6-(5-azido-3-pyridinyl)-3,6-diazabicyclo[3.2.0]heptane;
(1R,5S)-6-(5-azido-3-pyridinyl)-3,6-diazabicyclo[3.2.0]heptane; and
(1R,5S)-6-(5-azido-3-pyridinyl)-3,6-diazabicyclo[3.2.0]heptane.

7. A compound according to claim 5 that is 5-[(1R,5S)-3,6-diazabicyclo[3.2.0]hept-6-yl]nicotinonitrile.

8. A compound according to claim 3 wherein Y is CH$_2$ and Z is a covalent bond.

9. A compound according to claim 3 wherein
Y is CH$_2$;
Z is a covalent bond; and
R$_1$ is

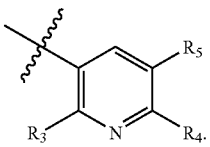

10. A compound according to claim 9 selected from the group consisting of
(1R,5R)-6-(6-chloro-3-pyridinyl)-2,6-diazabicyclo[3.2.0]heptane and
(1R,5R)-6-(3-pyridinyl)-2,6-diazabicyclo[3.2.0]heptane.

11. A compound according to claim 3 wherein Y is CH$_2$CH$_2$ and Z is a covalent bond.

12. A compound according to claim 3 wherein Y is CH$_2$ and Z is CH$_2$.

13. A compound according to claim 3 wherein Y is a covalent bond and Z is CH$_2$CH$_2$.

14. A compound according to claim 3 wherein
Y is a covalent bond;
Z is CH$_2$CH$_2$; and
R$_1$ is

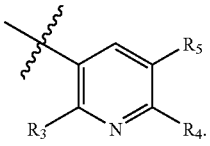

15. A compound according to claim 14 selected from the group consisting of
(cis)-8-(3-pyridinyl)-3,8-diazabicyclo[4.2.0]octane;
(cis)-8-(6-chloro-3-pyridinyl)-3,8-diazabicyclo[4.2.0]octane;
(1S,6R)-(cis)-8-(6-chloro-3-pyridinyl)-3,8-diazabicyclo[4.2.0]octane;
(–) (cis)-8-(6-chloro-3-pyridinyl)-3,8-diazabicyclo[4.2.0]octane;

5-[(1R,6S)-3,8-diazabicyclo[4.2.0]oct-8-yl]nicotinonitrile;
(1S,6R)-5-[3,8-diazabicyclo[4.2.0]oct-8-yl]nicotinonitrile;
(1S,6R)-8-(5-methoxy-3-pyridinyl)-3,8-diazabicyclo[4.2.0]octane;
(cis)-8-(5-methoxy-3-pyridinyl)-3,8-diazabicyclo[4.2.0]octane;
(1R,6S)-8-(5-methoxy-3-pyridinyl)-3,8-diazabicyclo[4.2.0]octane;
(cis)-8-(6-chloro-5-methyl-3-pyridinyl)-3,8-diazabicyclo[4.2.0]octane;
(1S,6R)-8-(6-chloro-5-methyl-3-pyridinyl)-3,8-diazabicyclo[4.2.0]octane;
(1R,6S)-8-(6-chloro-5-methyl-3-pyridinyl)-3,8-diazabicyclo[4.2.0]octane;
(1S,6R)-8-(3-pyridinyl)-3,8-diazabicyclo[4.2.0]octane;
(1R,6S)-8-(3-pyridinyl)-3,8-diazabicyclo[4.2.0]octane;
(cis)-8-(5,6-dichloro-3-pyridinyl)-3,8-diazabicyclo[4.2.0]octane;
(1S,6R)-8-(5,6-dichloro-3-pyridinyl)-3,8-diazabicyclo[4.2.0]octane; and
(1R,6S)-8-(5,6-dichloro-3-pyridinyl)-3,8-diazabicyclo[4.2.0]octane.

16. A pharmaceutical composition comprising a therapeutically effective amount of a compound of claim 1 in combination with a pharmaceutically acceptable carrier.

17. A method of treating a disorder in a mammal in need of such treatment, comprising administering a therapeutically effective amount of a compound of claim 1, wherein the disorder is selected from the group consisting of Alzheimer's disease, Parkinson's disease, memory dysfunction, Tourette's syndrome, sleep disorders, attention deficit hyperactivity disorder, neurodegeneration, inflammation, neuroprotection, amyotrophic lateral sclerosis, anxiety depression, mania, schizophrenia, eating disorders, AIDS-induced dementia, epilepsy, urinary incontinence, Crohn's disease, migraines, pain, PMS, erectile dysfunction, substance abuse, smoking cessation, and inflammatory bowel syndrome.

18. The method of claim 17 wherein the disorder is selected from the group consisting of Alzheimer's disease, Parkinson's disease, attention deficit hyperactivity disorder, depression, nicotinic withdrawal syndrome, Tourette's syndrome, and schizophrenia.

19. The method of claim 17 wherein the disorder is pain.

* * * * *